US008586326B2

(12) United States Patent
El-Gewely

(10) Patent No.: US 8,586,326 B2
(45) Date of Patent: Nov. 19, 2013

(54) MOLECULES INVOLVED IN PROTEIN FOLDING

(76) Inventor: Raafat El-Gewely, Tomasjoro (NO)

( * ) Notice: Subject to any disclaimer, the term of this patent is extended or adjusted under 35 U.S.C. 154(b) by 1417 days.

(21) Appl. No.: 11/569,304

(22) PCT Filed: May 17, 2005

(86) PCT No.: PCT/GB2005/001907
§ 371 (c)(1),
(2), (4) Date: Aug. 9, 2007

(87) PCT Pub. No.: WO2005/111060
PCT Pub. Date: Nov. 24, 2005

(65) Prior Publication Data
US 2007/0298418 A1 Dec. 27, 2007

(30) Foreign Application Priority Data

May 17, 2004 (GB) .................................. 0410983.1

(51) Int. Cl.
*C12P 21/06* (2006.01)
(52) U.S. Cl.
USPC ...................................................... 435/69.1
(58) Field of Classification Search
USPC ...................................................... 435/69.1
See application file for complete search history.

(56) References Cited

FOREIGN PATENT DOCUMENTS

WO WO 02/077183 * 10/2002

OTHER PUBLICATIONS

Wang et al., 1998, Enzymes as chaperones and chaperones as enzymes, FEBS Letters, 425: 382-384.*
Hesterkamp et al., 1998, The EMBO Journal, 17(16): 4818-4828.*
Perna et al., Genome sequence of enterohaemorrhagic *Escherichia coli* 0157:H7, Nature, 409: 529-533, 2001.*
Hayashi et al., Complete Genome Sequence of Enterohemorrhagic *Eshelichia coli* 0157:H7 and Genomic Comparison with a Laboratory Strain K-12, DNA Res., 8:11-22, 2001.*
Arimilli, S. et al., "Refolding and reconsitution of functionally active complexes of human leukocyte antigen DR2 and myelin basic protein peptide from recombinant alpha and beta polypeptide chains," J. Biol. Chem. (1995) 270(2):971-977.
Baneyx, F., "Recombinant protein expression in *Escherichia coli*," Curr. Opin. Biotech. (1999) 10:411-421.
Beutin, L. et al., "Genetical and functional investigation of fliC genes encoding flagellar serotype H4 in wildtype strains of *Escherichia coli* and in a laboratory *E. coli* K-12 strain expressing flagellar antigen type H48," BMC Microbiology (2005) 5(4):1-11.
Bolivar, F. et al., "Construction and characterization of new cloning vehicles. II. A multipurpose cloning system," Gene (1977) 2:95-113.
Boyer, H. et al., "A complementation analysis of the restriction and modification of DNA in *Escherichia coli*," J. Mol. Biol. (1969) 41:459-472.

Bukau, B. et al., "Getting newly synthesized proteins into shape," Cell (2000) 101:119-122.
Cazorla, D. et al., "Variable specific activity of *Escherichia coli* beta-galactosidase in bacterial cells," Biotechnol. Bioeng. (2001) 72:255-260.
Cho, Y. et al., "Crystal structure of a p53 tumor suppressor-DNA complex: understanding tumorigenic mutations," Science (1994) 265:346-355.
Dobson, C.M. et al., "Protein folding and misfolding inside and outside the cell," The EMBO Journal (1998) 17(18):5251-5254.
El-Gewely, M.R., "Shorter is better" Nature Biotech. (1999) 17:210.
Ellis, R.J., "Chaperonins," Curr. Biol. (1999) 9(10):R362.
Ellis, R.J., "Molecular chaperones: avoiding the crowd," Current Biol. (1997) 7:R631-R633.
Ellis, R.J., "Molecular chaperones: inside and outside the Anfinsen cage," Curr. Biol. (2001) 11:R1038-R1040.
Ellis, R.J., "The general concept of molecular chaperones," Phil. Trans. R. Soc. Lond. B. (1993) 350:257-261.
Ewalt, K.L. et al., "In vivo observation of polypeptide flux through the bacterial chaperonin system," Cell (1997) 90:491-500.
Fradkov, A.F. et al., "Novel fluorescent protein from discosoma coral and its mutants possesses a unique far-red fluorescence," FEBS Lett. (2000) 479:127-130.
Gilbert, H.F., "Protein disulfide isomerase and assisted protein folding," J. Biol. Chem. (1997) 272(47):29399-29402.
Guzman, L-M. et al., "Tight regulation, modulation, and high-level expression by vectors containing the arabinose $P_{BAD}$ promoter," J. Bacteriol. (1995) 177(14):4121-4130.
Hesterkamp, T. et al., "Role of the DnaK and HscA homologs of Hsp70 chaperones in protein folding in *E.coli*," The EMBO Journal (1998) 17(16):4818-4828.
Hockney, R.C., "Recent developments in heterologous protein production in *Escherichia coli*," TIBTECH (1994) 12:456-463.
Jakobs, S. et al., "EGFP and DsRed expressing cultures of *Escherichia coli* imaged by confocal, two-photon and fluorescence lifetime microscopy," FEBS Lett. (2000) 479:131-135.
Jeffrey, P.D. et al., "Crystal structure of the tetramerization domain of the p53 tumor suppressor at 1.7 angstroms," Science (1995) 267:1498-1502.
Kim, E.K. et al., "Lipase and its modulator from *Pseudomonas sp.* strain KFCC 10818: proline-to-glutamine substitution at position 112 induces formation of enzymatically active lipase in the absence of the modulator," J. Bacteriol. (2001) 183(20):5937-5941.
Lawhon, S.D. et al., "Global regulation by CsrA in *Salmonella typhimurium*," Mol. Microbiol. (2003) 48(6):1633-1645.

(Continued)

*Primary Examiner* — Amber D Steele
(74) *Attorney, Agent, or Firm* — Michael Best & Friedrich LLP

(57) ABSTRACT

The present invention provides a method of identifying a molecule which functions as a catalyst of protein folding in a cell, which comprises: (a) transforming a library of cells with a gene encoding a reporter protein; (b) selecting those cells which contain said gene but wherein said reporter protein has reduced activity; (c) transforming the selected cells with a genomic library and then selecting those cells wherein the activity of the reporter protein has. been restored; and (d) for those cells selected at (c) above, analyzing the nucleic acid sequence that was introduced during the second transformation event as part of step (c), molecules identified thereby and methods of protein production which employ said molecules.

2 Claims, 12 Drawing Sheets

(56) References Cited

OTHER PUBLICATIONS

Lund, P.A., "Microbial molecular chaperones," Adv. Microbial Physiol. (2001) 44:93-140.

Ma, B. et al., "Binding and folding: in search of intramolecular chaperone-like building block fragments," Protein Eng. (2000) 13(9):617-627.

Martin, G.A. et al., "High-yield, in vitro protein expression using a continuous-exchange, coupled transcription/translation system," BioTechniques (2001) 31(4):948-953.

Maurer, L.M. et al., "pH regulates genes for glafellar motility, catabolism, and oxidative stress in Escherichia coli K-12," J. Bacteriol. (2005) 187(1):304-319.

Miller, H.I. et al., "An E coli gene product required for λ site-specific recombination," Cell (1980) 20:711-719.

Miller, W.G. et al., "An improved GFP cloning cassette designed for prokaryotic transcriptional fusions," Gene (1997) 191:149-153.

Rossignol, M. et al., "NKBOR, a mini-tn10-based transposon for random insertion in the chromosome of Gram-negative bacteria and the rapid recovery of sequences flanking the insertion sites in Escherichia coli," Res. Microbiol. (2001) 152:481-485.

Sankar, P. et al., "Expression analysis of cloned chromosomal segments of Escherichia coli," J. Bacteriol. (1993) 175(16):5145-5152.

Sideraki, V. et al., "Mechanisms of the antichaperone activity of protein disulfide isomerase: facilitated assembly of large, insoluble aggregates of denatured lysozyme and PDI," Biochem. (2000) 39:1180-1188.

Sperandio, V. et al., "Quorum sensing escherichia coli regulators B and C (QseBC): a novel two-component regulatory system involved in the regulation of flagella and motility by quorum sensing in E. coli," Mol. Microbiol. (2002) 43(3):809-821.

Soutourina, O.A. et al., "Regulation cascade of flagellar expression in gram-negative bacteria," FEMS Microbiology Reviews (2003) 27:505-523.

Varshavsky, A., "The N-end rule: functions, mysteries, uses," Proc. Natl. Acad. Sci. USA (1996) 93:12142-12149.

Wall, J.G. et al., "Effects of overexpressing folding modulators on the in vivo folding of heterologous proteins in Escherichia coli," Curr. Opin. Biotech. (1995) 6:507-516.

Wang, C-C. et al., "Enzymes as chaperones and chaperones as enzymes," FEBS Lett. (1998) 425:382-384.

Weickert, M.J. et al., "Optimization of heterologous protein production in Escherichia coli," Curr. Opin. Biotech. (1996) 7:494-499.

* cited by examiner

MOLECULES INVOLVED IN PROTEIN FOLDING

CROSS-REFERENCE TO RELATED APPLICATIONS

This patent application is a national stage filing under 35 U.S.C. 371 of International Application No. PCT/GB2005/001907, filed May 17, 2005, which claims priority to Great Britain Application No. 0410983.1, which was filed May 17, 2004, the disclosures of which are incorporated by reference herein in their entireties.

The present invention relates to a new class of molecules, referred to herein as conformases. This class consists of naturally occurring protein molecules, or derivatives of such naturally occurring molecules, which are involved in the production of functionally active proteins. These molecules can be considered protein catalysts which assist in protein folding in vivo. Various applications of these conformase molecules are also within the scope of the present invention, in particular their use in methods of improving heterologous expression of target proteins in host cells.

The existence of this class of molecules goes against the generally accepted principles of protein folding. Current Molecular Biology and Biotechnology is based on the widely accepted notion that the primary structure of proteins dictates their tertiary structure. As shown by the following statement in the standard undergraduate Biochemistry textbook by Voet & Voet, $2^{nd}$ Ed. 1995, John Wiley & Sons Inc. " . . . , the three-dimensional structure of a native (physiologically folded) protein is specified by its primary structure . . . ". Even after the recombinant DNA era, the Nobel Prize Laureate Dr. Christian Anfinsen stated that "I think that most of us are by this time convinced that three-dimensional structure is completely determined by the primary sequence and that the folding process proceeds spontaneously" (Anfinsen, C. (1986) in Protein Engineering: Applications in Science and Industry. Edited by Inouye and Sarma. Academic Press Inc. Florida).

Scientists that want to express heterologous genes in order to produce recombinant therapeutic proteins or recombinant proteins to be used as targets for drug discovery are often disappointed. Often such recombinant proteins do not have the proper conformation although they retain the correct amino acid sequence. The recombinant proteins in many cases maintain the same primary structure (amino acid sequence), but are present in the cell in aggregated forms known as inclusion bodies.

We have analyzed the relationship between the primary structure of protein (amino acid sequence) and the Tertiary/quaternary structure of protein (Conformation) Only proteins with the correct conformation will be biologically active as the three-dimensional protein will provide binding pockets and surfaces which allow more or less specific interactions with other three-dimensional molecules. Our work led us to conclude that the primary structure of protein is not the only factor determining the final tertiary/quaternary structure of the expressed protein. As the final structure-function of proteins depends on the folding environment, protein primary structure does not necessary guarantee a unique tertiary-structure, functionality, or even solubility (El-Gewely, (1999) M. R. Nature Biotechnology 17, 210).

Primary structure plays an important role in shaping the tertiary structure of a given protein, but there are other factors in addition to the genetic code, which affect the tertiary structure of proteins.

We believe one of the main problems in heterologous gene expression is that factors assisting in protein folding are absent in the host cell or not present in sufficiently large amounts, e.g. when the target protein is being over-expressed from a high copy number plasmid and/or a strong promoter is used for expression. This usually leads either to the formation of inclusion bodies (aggregates of misfolded proteins) or to the rapid degradation of the expressed protein.

The problem of aggregation of recombinantly produced proteins has been discussed in the literature (e.g. a review by Gilbert, H. F. 1994, Current Opinion in Biotechnology 5: 534-539) and it has been suggested that the situation may be improved by using molecules from one or two different classes, known as chaperones and foldases. 'Foldases' are catalysts involved in the formation of covalent bonds and increase the rate of folding, examples include protein disulfide isomerase (PDI) and peptidyl prolyl isomerase (PPI). 'Chaperones' are generally thought to decrease aggregation by interacting specifically with the unfolded protein and indeed many chaperones have been identified through investigation of aggregated proteins with which the chaperones were associated. Almost all chaperones require ATP to perform their anti-aggregation function and many are stress-proteins, not ubiquitously present but produced when the cell is subjected to certain environmental pressures, e.g. in response to heat-shock. Analysis of over-expressed proteins following heat-shock treatment has been an alternative way in which these chaperone molecules have been identified.

However, the conclusions in the above-mentioned review by Gilbert are that no universal strategy is available for over-expression of a given protein and that the process is still largely one of trial and error.

Moreover, in our experience, the presently available molecules which can assist in correct protein folding are unable to facilitate recombinant expression of certain heterologous proteins in bacterial hosts. Particularly problematic proteins include β-galactosidase and members of the human peroxisome proliferating enzyme family, members of the human phosphodiesterase family and human interleukin-2.

Attempts to overcome these problems have been made by testing different hosts (*E. coli*, yeast, *Pichia*, insect cells, mammalian cells etc) in the hope that one host will be better than another in producing a more active recombinant protein. However, it is generally recognised that a simple bacterial expression system, e.g. one based in *E. coli*, is the most convenient. Thus there is a real need to improve the yields of active eukaryotic proteins in *E. coli* and other bacterial or yeast cells.

It is almost a standard practice to focus on purifying the aggregated recombinant protein as inclusion bodies and then to attempt to solubilize it in vitro, by using strong denaturating agents such as 6M guanidinium chloride. Subsequent slow renaturation and purification steps are required with often low recovery in the end. However several expressed recombinant proteins could not be denturated and renaturated at all in this way and each protein requires much optimization work to generate an acceptable protocol. The problems of aggregation mean that many proteins, such as cystic fibrosis transmembrane conductance regulator and p53 have to be expressed as individual domains and then analysed separately or combined in vitro to measure activity.

A new class of molecules involved in the production of functionally active proteins, i.e. proteins with a correct tertiary structure, has now been identified and characterised and a strategy developed for isolating these proteins and the genes which encode them. Several genes/proteins that play a significant role in producing functionally active proteins in *E*.

*coli* have been identified and these molecules and the class of compounds which they represent are termed 'conformases' because of their ability to encourage a given target protein to adopt its correct conformation and thus its native activity.

Unlike the foldases discussed above, this class of molecule is not involved in catalysing the formation of covalent bonds, e.g. di-sulphide bridges, within the target molecule. Nor is this class of molecule homologous to any protein involved in such catalysis. Although more than 20 different conformases have been identified in *E. coli* this number is dwarfed by the total number of genes in *E. coli* and it has been shown that each conformase is not specific for a given target protein. Without wishing to be bound by theory it is believed that the mode of action of each conformase is a non-specific catalytic role in generating correctly folded and therefore active proteins. This is supported by the observation of an additive effect, whereby the addition of a first conformase to a partly active expression system will improve expression of the target protein, and addition of a second and further conformase will further improve yields of active target protein. Moreover, the bacterial conformases identified can enhance the yield of a eukaryotic target protein which is being expressed in a bacterial host system, confirming a non-specific action. This is in contrast to a previously identified class of molecules, chaperones, which do not have such a general ability to assist folding of many different proteins and which generally do not exhibit such an additive effect.

Sequence analysis also highlights the differences between the new conformases and molecules previously identified which play a part in protein folding in certain circumstances. The identified conformases have no known significant homology with nor share any of the characteristic signatures of known chaperones and heat shock proteins such as GroEL, GroES, Hsp70 (and its *E. coli* homologues DnaK and HscA) and DnaJ. Nor do they have signatures in common with peptide isomerase or thioredoxin which further confirms their separate status and role in vivo. The PROSITE database was used to perform protein signature analysis of all the conformases identified herein and an equivalent analysis was performed for chaperones, DNAK, DNAJ, DSB and cis-trans peptide isomerase (PDI). The results of this analysis are shown in Example 6. None of the molecules of the invention (conformases) have any of the signature nos 10-19 of Table 6.

New strategies has been developed which may conveniently be used to identify conformase molecules in a given cell type. The ability to be identified by one of these strategies is one of the defining characteristics of the class of molecule referred to herein as conformases.

According to a particularly preferred strategy, the ability of a cell to fold proteins is compromised, e.g. by transposition-mutagenesis; the cells are transformed with a gene encoding a reporter protein and colonies are selected which contain the reporter protein but in inactive or poorly active form. A second transformation event using, e.g. the host cell genome is then performed and colonies wherein the activity of the reporter protein has been restored are identified. In this way gene sequences are identified which can complement the defect in the mutation repertoire. This technique is further described and exemplified below in relation to *E. coli* but it will be appreciated that the same approach may be used to isolate conformases from other cells, e.g. other hosts used in the expression of recombinant DNA, including other bacteria, yeasts, mammalian and insect cells etc.

Thus, according to one aspect, the present invention provides a method of identifying a molecule which functions as a catalyst of protein folding in a cell, which comprises:

(a) transforming a library of cells with a gene encoding a reporter protein;
(b) selecting those cells which contain said gene but wherein said reporter protein has reduced activity;
(c) transforming the selected cells with a genomic library and then selecting those cells wherein the activity of the reporter protein has been restored; and
(d) for those cells selected at (c) above, analysing the nucleic acid sequence that was introduced during the second transformation event as part of step (c).

The library of cells will typically be a mutant library as is discussed in more detail below. Alternatively it may be a cell population which is, or which is suspected to be, folding compromised or to contain folding compromised cells. In that cells are fully or partially deficient in one or more conformases and, at least for some types of protein, have a reduced ability to express active protein molecules. Typically this ability is reduced as compared to wild type strains or other strains of that same species. Any cell sample can be transformed in step (a), with folding compromised cells being selected in step (b).

According to a preferred embodiment, the present invention provides a method of identifying a molecule which functions as a catalyst of protein folding in a target cell (a conformase) which comprises:

(a) transforming a library of mutated target cells with a gene encoding a reporter protein;
(b) selecting those cells that contain the reporter protein but wherein said reporter protein has reduced activity;
(c) transforming the selected cells with a genomic library of the target cell and then selecting those cells wherein the activity of the reporter protein has been restored; and
(d) for those cells selected at (c) above, analysing the nucleic acid sequence that was introduced during the second transformation event as part of step (c).

Thus, a conformase is a molecule which functions as a catalyst of protein folding but is not involved in catalysing the formation of covalent bonds. Typically they have a catalytic activity which is not specific to a particular protein and are expressed constitutively. They may not require ATP to perform their folding function. These molecules are identifiable by the method defined herein. Preferably these conformases are not species specific, so a conformase from one species can assist folding of a protein from another species.

The mutated library of target cells is preferably generated by transposition-mutagenesis but may also be generated by exposure to a mutagen such as UV light or chemical mutagens such as methyl methanesulfonate and ethyl methanesulfonate which cause random mutagenesis. Other techniques such as random mutagenesis with a mini-transposon suicide vector such as NKBOR (Rossignol, M. et al. (2001) Res. Microbiol. 152, 481-485). Where a transposon is used, it will randomly insert throughout the genome. The term 'transposon' as used herein refers to any nucleic acid molecule which can be used in transposition mutagenesis and thus includes any suitable variants of traditional transposons such as mini-transposons, plasposons and the like. Cells selected at (b) above which do not exhibit reporter protein activity may have a transposon inserted in or nearby a gene responsible for protein folding/activity, i.e. a conformase as described herein. The target cell population can be considered a library as it comprises a series of substantially identical cells which differ only in the presence and position of mutations. These mutations giving rise to a range of different genotypes and phenotypes which may then be investigated, in particular by an assay which determines the ability of a given cell to generate an active (i.e. correctly folded) target protein.

Thus the cells of (a) may be true library in that the total cell population contains a number of different types of cell, e.g. a mutant library where different cells contain different mutations. Alternatively, as in the case of a folding compromised strain, the cells may be substantially homogeneous.

The gene identified at step (d) above may be further investigated by cloning in an expression vector and testing its activity in vivo. Also, after step (c) the character of the nucleic acid used to transform the cells in step (c) may, for those cells demonstrating restored activity of the reporter protein, be verified by re-transforming the corresponding mutated strain with said nucleic acid. This step is preferably performed as cells with the corrected phenotype can habour more than one of the vectors (e.g. plasmids) used in the transformation step (c). After testing the phenotypic manifestation of each rescued plasmid, the plasmid that is itself able to restore activity can then be analysed as described at (d) above. Step (d) will preferably involve a nucleic acid sequencing step and in this way the nucleic acid and amino acid sequence of a conformase molecule is obtained and thus a functioning conformase is identified.

For identification of bacterial conformases, suitable reporter proteins will be those whose absence does not lead to cell death but which give a readily identifiable phenotype, e.g. β-gal, Green Fluorescent Protein (GFP) or a Red Fluorescent protein (RFP), such as the newly identified protein dsFP593 from *Discosoma* coral (Jakobs et al. FEBS Letters 479 (2000) 131-135). These reporter proteins may also be used in other cell types, e.g. yeast or mammalian cells etc.

β-galactosidase, as encoded by the LacZ gene, was selected as a convenient reporter protein for *E. coli* and therefore, as described in the Examples, the starting strain for the method of the invention described above lacked a fully functional LacZ gene. This well known reporter system utilises a stain to give white colonies where there is little or no β-galactosidase activity and blue colonies where there is β-galactosidase activity. Thus, according to the method described above, the cells selected at step (b) will be white and those selected at (c) will be blue. Preferably, the colonies selected at (b) are clearly white not pale blue and the colonies selected at (c) are dark blue.

The above method of the invention refers to selection of cells wherein the reporter protein has 'reduced activity' and 'restored' activity. It will be understood that even in cells which lack one or more native conformases, some of the reporter protein may be present in its proper active conformation and likewise even if through complementarity the folding ability of the cell in respect of the target protein is restored, there will be some molecules of reporter protein which do not have a functional conformation. The selection will be based on the average activity of the reporter protein in a given cell or cell colony and a positive or negative result may depend on the sensitivity of the selection criteria. Thus 'reduced activity' implies that the activity of the reporter protein fails to meet a predetermined threshold, which may be a point in a continuous scale, e.g. a level of fluorescence where GFP is used as reporter protein, or a negative result where there are only two discrete results possible, positive or negative, e.g. white or blue colonies when the reporter protein is β-gal. Similarly, a 'restored' activity will be determined according to the criteria set by the method and indicates that a significantly greater proportion of the reporter proteins have an active conformation indicative of correct folding. The Examples herein describe suitable tests and it is within the competence of the skilled addressee to make necessary modifications to the selection criteria for other reporter proteins/ target cells.

The reporter protein is typically introduced by transformation with a plasmid which encodes the reporter protein. This plasmid also conveniently carries a marker, e.g. a gene for antibiotic resistance, which facilitates identification of those cells which have been successfully transformed with the gene encoding the reporter protein. From this group, those cells which exhibit reduced reporter protein activity are then identified, e.g. by colony colour. The non-specific nature of the conformases means that many can be identified using a single reporter protein system but a further reporter protein may be used to isolate even more conformases.

Preferably the genomic library used in step (c) is a library of the target cell's genome. Methods for the construction of a cell's genomic library are known in the art and for *E. coli* are described in the Examples and Figures hereto. This library is then used in step (c) to transform the cells which exhibit reduced reporter protein activity. The transformation of the selected cells is expected to be essentially random, with each cell typically receiving one or more plasmids each containing a digested fragment of the full genome. Although not every individual cell will be transformed.

In an alternative to the method described above where the sequences which can complement the loss of folding activity are identified, a conformase may be identified with reference to the mutation, i.e. the compromised gene is identified directly (in the first described method, genes capable of compensating for the compromised gene are identified). Thus according to a further aspect, the present invention provides a method of identifying a molecule which functions as a catalyst of protein folding in a (target) cell, a conformase, which comprises:

(a) transforming a library of (target) cells which have undergone transposition mutagenesis with a gene encoding a reporter protein;

(b) selecting those cells that contain the reporter protein (or the reporter gene) but wherein said reporter protein has reduced activity;

(c) for those cells selected at step (b), identifying the gene disrupted by the transposon used to perform transposition mutagenesis of the (target) cells.

The gene identified at (c) above is then preferably further investigated by cloning in an expression vector and testing its ability to restore folding ability in a cell in which that same gene is compromised. In this way the conformase status is verified.

The transposon can act as a marker to identify disrupted genes and probes to regions of the transposon sequence can be used to pin-point the affected gene. Typically, regions adjacent to the transposon are sequenced and cloned in an expression vector in order to verify the function of the disrupted gene as a conformase. Such techniques are known in the art and described, for example, in Rossignol 2001, supra, where self-cloning transposons are used. The inclusion of a conditional origin of replication within the transposed sequences allows for the rapid cloning of DNA flanking the insertion site of the transposon. The transposon may have inserted in the coding or regulatory region of the conformase gene. Thus, any reference herein to disruption of a gene by a transposon is not limited to insertion of the trasposon within the gene but includes events where the transposon has disrupted the normal expression of a gene e.g. by insertion into a regulatory sequence. Comparisons with gene databanks may conveniently be used during the cloning process to confirm the sequence of the gene of interest and to provide information about whether the discovered gene is a member of an operon or only appears to act as a single cistron.

The above methods do not identify known heat-shock or other chaperones or foldases described in the prior art; instead they specifically identify the new class of molecules which assist in protein folding and are referred to herein as conformases. This new class of molecule constitutes a further aspect of the present invention as do functionally active fragments and derivatives thereof. Thus in one aspect, the present invention provides an isolated molecule which functions as a catalyst of protein folding, a "conformase", identifiable by a method described herein. *E. coli* conformases are a preferred aspect of the invention in particular those *E. coli* conformases whose nucleic acid and amino acid sequences are provided herein. Although it will be appreciated that the identification methods described herein provide the skilled man with the necessary tools to identify further *E. coli* conformases and conformases in other species.

Thus, preferred embodiments of this aspect of the invention are isolated nucleic acid or protein molecules which comprise any one of the sequences described in the Examples hereto, as well as functionally active fragments and derivatives thereof. The nucleic acid molecules of the invention will preferably be synthetic or recombinant. Functional activity of fragments and derivatives can readily be determined by analysing the ability of the test molecule to increase folding of a reporter protein e.g. β-galactosidase or green fluorescent protein (GFP) according to a co-expression method as described herein. By 'isolated' it is meant that the molecules are not in their normal cellular environment, free of substantially all other native cellular components; organelles, proteins, nucleic acids etc. Nucleic acid molecules having the sequence of one of the 23 conformases identified herein (or an active fragment thereof) will typically form part of an expression vector and such vectors constitute further aspects of the present invention. Conformase molecules preferably exist in purified form, i.e. a preparation is at least 60%, preferably at least 70%, more preferably at least 80% e.g. at least 90% pure.

The work described herein led to the positive identification of 23 conformases and these molecules constitute a particularly preferred aspect of the invention. Thus in a preferred aspect, there is provided a conformase which comprises the amino acid sequence of any one of SEQ ID Nos 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68 or 70 or a functionally active fragment or variant thereof. Preferably, the conformase is encoded by a nucleic acid molecule having the sequence of any one of SEQ ID Nos 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67 or 69 or by any other gene located on the same operon of *Escherichia coli* as any of said sequences, or a functionally active variant of any of these sequences.

Molecules comprising and/or consisting of the nucleic acid or amino acid sequences of these 23 conformases are per se a preferred aspect of the present invention. The use of all these molecules in a method of protein production (particularly heterologous protein production in a bacterial host) constitutes a further preferred aspect of the invention. Use of a recombinant conformase in a method of protein production is particularly preferred. None of these molecules have previously been ascribed a role in protein folding or the generation of active protein molecules in vivo.

In addition, as described herein, many of these 23 conformases are part of operons with other genes and given the way organisms generally have genes of common or related function linked as operons, we believe the other genes of these operons would also be likely to exhibit conformase activity. The statements above regarding nucleic acid and protein molecules of the invention thus also extend to genes present on operons with one of the 23 identified conformases. This is particularly so for those linked genes for which no other function has yet been ascribed. The methods described herein can be used or readily adapted for confirmation of the conformase activity of genes within these operons. Relevant operons and particular genes within them are listed in Table 2 herein.

In addition to the above described assay for functionality, fragments will typically comprise at least 40%, preferably at least 50%, more preferably at least 60% of the full length sequence as set out herein.

Derivatives or variants of the precise sequences given herein (or fragments thereof) must also be functionally active as conformases and this may be tested as described above in relation to fragments. In addition the variants will have at least 60%, preferably at least 70%, more preferably at least 80%, e.g. at least 90% sequence identity with one of the nucleic acid or protein sequences described herein. Computer programs for calculating sequence identity are well known in the art and these may allow for insertions or deletions in the sequence. Amino acid sequence homology may conveniently be determined using the BestFit program of the Genetics Computer Group (CGC) Version 10 Software package from the University of Wisconsin. The program uses the local homology algorithm of Smith and Waterman with the default values: Gap creation penalty=8, Gap extension penalty=2, Average match=2.912, Average mismatch=−2.003. Nucleic acid homology may conveniently be analysed using NCBI (National Center for Biotechnology Information) online programs.

Derivatives may also be defined in terms of their ability to hybridise to a molecule comprising one of the nucleic acid sequences defined herein or the complement thereof. Of course, defining proteins/polypeptides in this way requires an assessment of whether the nucleic acid which encodes that protein/polypeptide is able to hybridise to a molecule comprising one of the nucleic acid sequences defined herein or the complement thereof. Derivatives which "hybridise" are those binding (hybridising under non-stringent conditions (e.g. 6×SSC, 50% formamide at room temperature) and washed under conditions of low stringency (e.g. 2×SSC, room temperature, more preferably 2×SSC, 42° C.) or conditions of higher stringency (e.g. 2×SSC, 65° C.) (where SSC=0.15M NaCl, 0.015M sodium citrate, pH 7.2). Preferably, the variants will hybridise under conditions of higher stringency as defined above.

A particularly preferred set of derivatives are those incorporating N-terminal modifications to obviate problems with in vivo degradation associated with certain N-terminal residues. As discussed by Varshavsky in PNAS (1996) Vol. 93, pp 12142-12419, the N-End Rule defines the relationship between the metabolic stability of a protein and the identity of its N-terminal residue. In *E. coli* F, L, W and Y (single letter code) are particularly destabilising. The problems of degradation may be overcome by introducing (adding or substituting) one of the other residues at the N-terminus, e.g. for conformase 1 herein which begins MY . . . , the sequence may be engineered to begin MMY . . . and so the half-life and thus efficacy is increased.

As mentioned above, there is a need to improve current systems for expression of heterologous proteins and in a further aspect the present invention provides a method which meets this need. Thus, the present invention also provides a method of enhancing production of an active conformation of a target protein in a host cell which comprises introducing a conformase as defined and exemplified herein into said host cell. This introduction will typically involve transformation of the host cell with a vector encoding one or more conformases, although the conformase protein itself may be introduced into the host cell. Alternatively viewed, there is provided a method of producing a target protein in a host cell wherein a conformase or a nucleic acid molecule encoding a conformase is introduced into said host cell. Preferably, the conformase used in these methods is a conformase of the present invention. These methods of protein production may preferably involve a bacterial cell as a host cell. Preferably, the host cell comprises a recombinant nucleic acid molecule encoding said target protein. Thus, alternatively viewed, there is provided a method of producing a target protein in a host cell, said cell comprising a recombinant nucleic acid molecule encoding a conformase.

Other methods of protein expression are also contemplated in the context of the present invention. For example, protein production may involve cell lysates. These lysates may be prepared from cells which express a conformase of the present invention. Alternatively, a vector encoding a conformase or purified conformase protein may be added to the lysate.

By 'enhancing production' is meant that the total activity of the produced target protein is increased. In other words, the transcription and translation mechanisms may be no less efficient but the amount of active, correctly folded target protein is increased. The conformases used in this method of improving production of active protein in a host cell are obtainable (i.e. identifiable) by one of the identification methods described herein. An 'active conformation' is one which enables the molecule to perform its native function under normal cellular conditions, such a conformation will be one which renders the protein soluble in the normal intra-cellular environment. The 'active', conformation will generally be the conformation in which the molecule is at its most soluble. An 'active conformation', will have the correct tertiary/quaternary structure.

Alternatively viewed, the invention provides a method of producing a target protein in a host cell characterised in that a conformase (as defined and exemplified herein) is introduced into said host cell. Typically, a recombinant nucleic acid molecule, e.g. a plasmid encoding said target protein is also introduced (has been introduced) into said host cell. After a culturing step, suitable methods of cell culturing being well known in the art, the target protein may then be harvested from the host cells and isolated in the normal way. Because of the ability of the conformase molecules the subject of the present invention to assist in correct protein folding, the introduction of a conformase into the host cell provides a method of increasing the proportion of target cell molecules produced which have their active conformation.

Preferably, the conformase is recombinant, i.e. it is not produced from any endogenous gene of the host cell used for protein production, but from an exogenous gene. More preferably, the conformase is heterologous, i.e. it is not naturally present in the host cell. In one embodiment the conformase is from the same species as the target protein to be produced. Nevertheless, a conformase from a given species can increase expression of a protein in cells of that species, for example because the increased concentration of that conformase is helpful when a target protein is over-expressed.

Conformases according to the present invention include the 23 active molecules from *E. coli* already identified and, where appropriate, the other molecules encoded by genes on their operons. The other genes on these operons are identified in the Examples and Tables herein, for all genes lacking a previously ascribed function, full sequence information is provided herein.

Fragments, derivatives and homologues of these molecules which also exhibit this newly identified non-specific folding ability are also included, in particular homologues from other species. Appropriate percentages of sequence identity for derivatives and homologues are discussed herein. The present invention also provides clear direction as to how to identify and test further conformases, both in *E. coli* and other species. Specifically, a C-terminally truncated version of conformase 1 as identified herein has been shown to restore folding function. Therefore the scope of the present invention extends to all members of this new class (referred to herein as conformases) which are defined by the properties discussed herein and in particular through an ability to be identified by one of the identification methods described herein, especially the methods incorporating double transformation of mutated or inherently folding-compromised cell populations.

Although the conformase may be introduced into the host cell directly as a protein, typically the conformase will be introduced into the cell by transforming (bacterial cells) or transfecting (eukaryotic cells) (although the terms are used interchangeably for convenience herein) the cells with a nucleic acid molecule which contains a gene encoding said conformase operably linked to suitable promoter regions. The nucleic acid molecule will preferably make up a plasmid and suitable plasmids and promoter regions for different host cells are well known in the literature.

Expression vectors incorporating nucleic acid which encodes a conformase according to the present invention constitutes a further preferred aspect of the present invention, as such vectors constitute the preferred vehicle for introduction of a conformase into a host cell. Suitable expression vectors (typically plasmids) which are capable of directing expression of a conformase in the host cell are well known in the art and the skilled man is aware of host-cell specific modifications to the plasmids described in the present Examples which may be required. These vectors will preferably be constitutive (i.e. allow for expression of the conformase gene without regulation and have a strong constitutive promoter) and/or have a replication origin compatible with a wide range of plasmids which may conveniently be used for co-expression of the target protein in the host cell. The use of such vectors in a method of production of a target protein constitutes a particularly preferred aspect of the present invention.

Particularly preferred plasmids are those based on pConst-Ex4 and pMRE101, details of which are provided herein. For pMRE101 the TIR sequence (fragment from phage T7 gene 10 translational enhancer) is preferably introduced upstream of a reporter (e.g. lacZ) gene and downstream of the Tet constitutive promoter in order to increase transcription. More cloning sites may be inserted downstream of the BamHI site and the lacZ sequence removed; such a plasmid is suitable for cloning conformases. The construction of a vector which allows constitutive expression of a protein of interest is described in Example 7. This describes the construction of pMRE200 in which lacO, the binding site for the lacZ repressor, is deleted to allow constitutive expression.

In a further preferred embodiment the host cells are co-transfected with a tRNA gene such as for ArgA, ArgU or Ilex, as these genes compensate for the low level of these tRNAs in *E. coli*, thus facilitating the expression of heterologous proteins that have a high frequency of these codes (e.g. human proteins). These tRNA genes may conveniently be inserted in the plasmid vectors discussed above, e.g. in the SacII site of pMRE101. The construction of suitable vectors such as pMRE403 and pMRE103 is described in Example 8. The particular features of the plasmids described herein are of general utility and these plasmids, with or without an inserted conformase gene, constitute a further aspect of the present invention.

Thus in a further aspect, the present invention provides a vector, e.g. a vector suitable for expression of a conformase molecule as defined herein, wherein said vector comprises at least one of the features selected from:
 (a) a deletion of the LacO sequence of lacI to allow constitutive expression of a target protein;
 (b) one or more of tRNA genes ArgU, ArgW and IleX;
 (c) an origin of replication which is compatible with most other origins of replication; and
 (d) a canamycin resistance gene Preferably, the vector comprises at least (a) and (b). According to one preferred embodiment, the vector comprises at least features (a) and (b). In another preferred embodiment, the vector comprises at least features (a) and (c). In another preferred embodiment, the vector comprises at least features (a) and (d). In another preferred embodiment, the vector comprises at least features (b) and (c). In another preferred embodiment, the vector comprises at least features (b) and (d). More preferably, the vector also contains a nucleic acid sequence encoding a conformase.

Preferably, in methods of target protein production more than one conformase will be introduced into the host cell, e.g. 2-4 different conformases will be introduced.

Generally nucleic acid encoding the target protein will also be introduced into the host cells by transformation, with the aim of over-expressing a protein which is native to the host cell or, more usually, a heterologous protein.

Thus, target proteins include any proteins it is desired to harvest for therapeutic, diagnostic, analytical or other reasons. Preferably the target proteins are eukaryotic, e.g. mammalian, especially preferably human proteins of therapeutic interest. As demonstrated in the Examples, such proteins can be expressed in bacterial host cells and have their yields enhanced by bacterial conformases.

The host cell may be any cell type which can be used in the production of target proteins, e.g. bacteria, yeast mammalian or insect cells but the host cells are preferably bacterial, most preferably *E. coli*. The introduced conformase may be native to the host cell, as discussed previously bacterial conformases are able to facilitate protein folding of eukaryotic proteins and this is a particularly advantageous feature of this aspect of the present invention. If a non-native conformase is introduced the promoter controlling it should be specific to the host cell type. Non-native conformases will typically be from the same species as the target protein. The host cell may be poor at expressing a target protein but even if it is one of the better host cell types/lines for heterologous gene expression, it may still have its performance significantly enhanced by the introduction of one or more of the conformases described herein or obtained according to a method described herein.

It is known that different strains or cell lines from the same host cell species may vary in their ability to generate useful yields of a target protein. It is now believed that such variances are due, at least in part, to the presence, absence or relative concentration of different conformases. Example 3 herein shows how some strains of *E. coli*, even those routinely used in protein expression, indicated a poor yield of the active reporter protein GFP. This can be attributed to poor folding of the reporter protein and this points to a new method of testing a host cell for its suitability in recombinant protein production. Thus, in a further aspect, the present invention provides a method for determining the suitability of a cell for use in a method of protein production which comprises assaying for the presence of one or more conformases as defined and exemplified herein.

A conformase may be assayed directly, e.g. by an immunoassay utilising antibodies or antibody fragments which specifically bind to the conformase or by utilising a reporter protein (e.g. GFP) and determining the yield of functionally active reporter protein which can be equated to the cell's conformase activity and thus its suitability in protein engineering. Antibodies to conformases, in particular to the conformases exemplified herein may be readily prepared by techniques well known in the art and comprise a further aspect of the present invention.

Just as cell lines may be evaluated for their suitability in protein production so existing cell lines may be a useful starting point in the identification of further conformases. Identified strains which have a low folding ability can be considered equivalent to the cells selected at step (b) in the identification methods described above. Such strains can then be subjected to the transformation step (c) and the analysis step (d) so that genes from the genomic library which are capable of restoring protein folding activity can be identified. The strains can be identified as folding compromised by the use of one of the reporter proteins described herein.

Thus a method analogous to the first identification method described herein is performed but instead of transforming a library of cells incorporating different mutations, a homogeneous cell population is investigated by transforming that population with a gene encoding a reporter protein. If the cell population overall indicates reduced reporter protein activity (e.g. white colonies where the reporter protein is β-gal) then it can be assumed that it is deficient in one or more conformases and through transformation of the cells with the cell's genomic library, sequences capable of restoring protein folding ability (i.e. conformase sequences) may be identified. Such a method, wherein step (a) comprises transforming a sample of target cells with a gene encoding a reporter protein, constitutes a further aspect of the present invention.

If a strain is already known to have compromised folding activity then step (a) is performed in order to introduce a reporter protein and step (b) is also performed, although in this case the primary function of this step is to confirm successful transformation with the reporter. Steps (c) and (d) are then performed as described above to identify conformases through functional complementation. As well as identifying new conformases per se, this method helps in identifying suitable conformases which may be used to improve the folding ability of particular weak strains.

As used herein, 'low folding ability', and 'compromised folding activity', etc. may be used interchangeably.

Some of the conformase identification methods described herein result in the generation of mutant cells (e.g. mutant bacterial strains) which have a mutation, typically caused by a transposon, in one or more of their conformase genes resulting in a reduced ability to produce the active conformation of a target protein. Such cells constitute a further aspect of the present invention. A preferred aspect of the present invention is the use of a mutant strain of *Escherichia coli* in a method as described herein, wherein the mutant strain has a transposon insertion in any one of the genes represented by SEQ ID NOs 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67 or 69.

The invention will now be further described in the following Examples and with reference to the Figures in which:

FIG. 1 is a schematic representation of the reporter-1 plasmid which expresses complete lacZ. The LacZ gene is expressed from the Tet promoter. pMRE101 has the p15A replication origin, which is compatible with plasmids with other replication origins such as pMB1 and ColE1.

FIG. 2 provides schematic representation of the reporter-2 plasmid and α-complementation of β-galactosidase. Transposon mutants were selected in such a way that the described α-complementation strategy is no longer functional.

FIG. 3 is a schematic representation of the construction of the E. coli genomic library. Partially digested E. coli DNA (Sau3A) was ligated to BAMHI, CIAP-treated pGEM-Ex1 plasmid DNA.

FIG. 4 is a graph showing the effect of conformases on the activity of rHP1. Conformases were cloned in vectors pBAD33, or pAltEx2. The activity of rHP1 was compared to the activity of purified rHP1 (without conformases). Presented are 7 groups of histograms. In the first group from the left, note that amount of purified rHP1 protein in 10 μl protein preparation was significantly higher than that in 10 μl cell lysate judged by western analysis. In the presence of 0M of an inhibitor lead compound, the full activity of rHP1 can be observed. The activity is reduced as the concentration of the lead compound is increased (e.g. 50 μM). In the next 3 sets of histograms, coexpression of conformase F1 or F2 cloned in pBAD33 vector together with the vector expressing rHP1 using the E. coli host BL21 (Novagen, now affiliate of Merck Germany) is presented. The level of expression was compared to the empty vector (no conformases) control. F1 as well as F2 conformases in pBAD33 were not properly induced with Arabinose in this experiment compared to the empty vector.

In the following 3 sets of histograms demonstrating the coexpression of rHP1 with pALTEx2 (empty vector control), pF2-ALTEx2 (F2 conformase), pF2-1-3ALTEx2 (F2, F1, F3 Conformases). Significant increase in activity was observed using conformers 2 alone over the empty vector, however coexpression of F2, F1 and F3 conformases simultaneously have a drastic effect in increasing the activity of rHP1. These activities were inhibited with increasing amounts of the lead compound, indicating that the increase in activity was real.

FIG. 5 Is a graph showing the effect of the coexpression of conformases on the activity of recombinant human protein 2 (rHP2). As the percentage of lysate in the reaction mixture increased (from $1 \times 10^{-6}$-0.1%) so the activity increased. The activity of rHP2 increased over 100 fold in the presence of conformase 2 (F2) relative to the empty vector control (pBAD33). o/n=overnight, F1=conformase 1.

Figure 8:
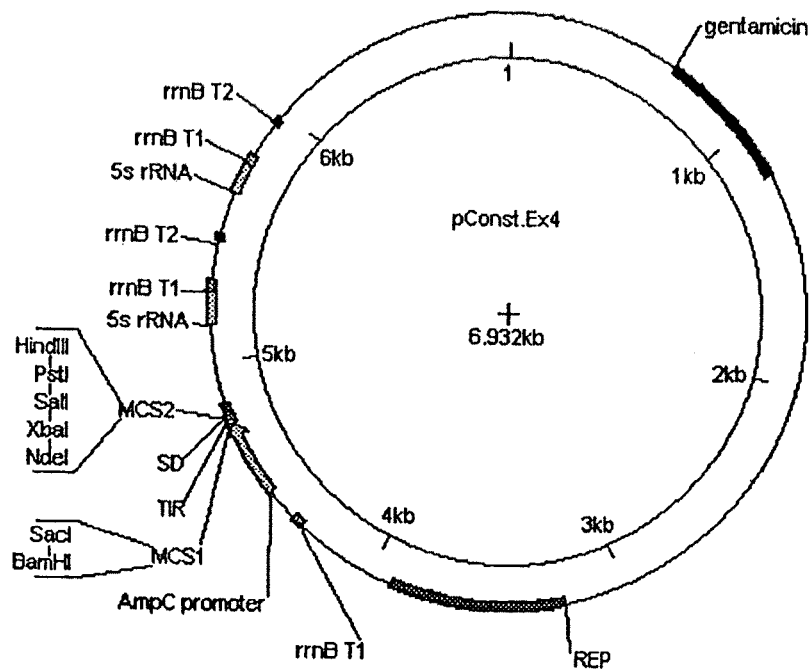

FIG. 8 is a diagrammatic representation of the pConstEx4 plasmid. AmpC promoter is a strong constitutive promoter; TIR is a fragment from phage T7 gene 10 translational enhancer; SD is the ribosomal binding site; rrnB T1 and T2 are transcription terminators; genes to be expressed can be cloned in MCS2 sites; genes with their own SD sequence and ATG start codon can also be cloned using the MCS1 site (there is an ATG in the Nde1 site).

Figure 9:
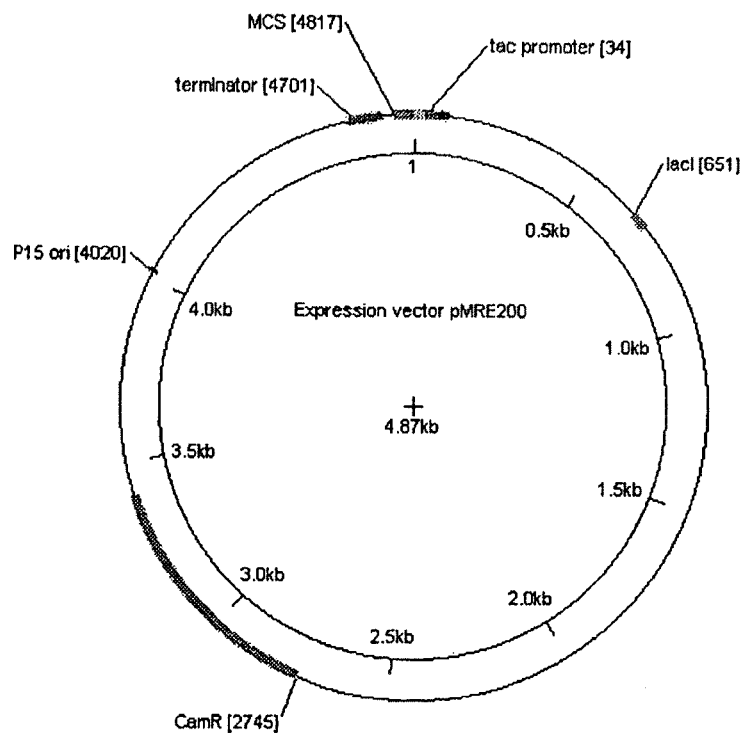

FIG. 9 is a schematic representation of expression vector pMRE200. It has a P15 origin of replication from pACYC184 (P15 ori) and encodes canamycin resistance (CamR). It contains a multiple cloning site (MCS) and a mutated lacZ expression system which allows constitutive expression of any gene inserted into the MCS.

Figure 10:
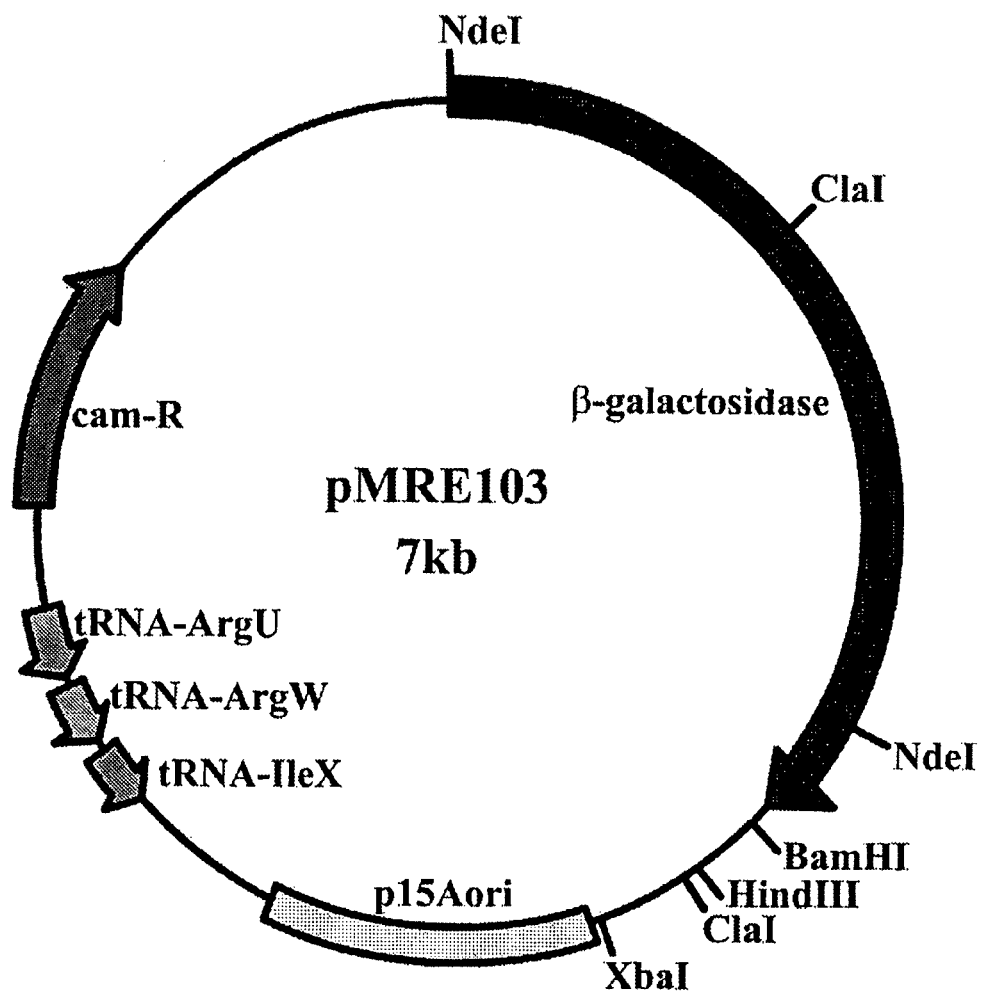

FIG. 10 is a schematic representation of expression vector pMRE103. It contains a beta-galactosidase reporter gene and the rare tRNA genes ArgU, ArgW and IleX. It has a P15 origin of replication from pACYC184 (P15 ori) and encodes canamycin resistance (CamR).

Figure 11:
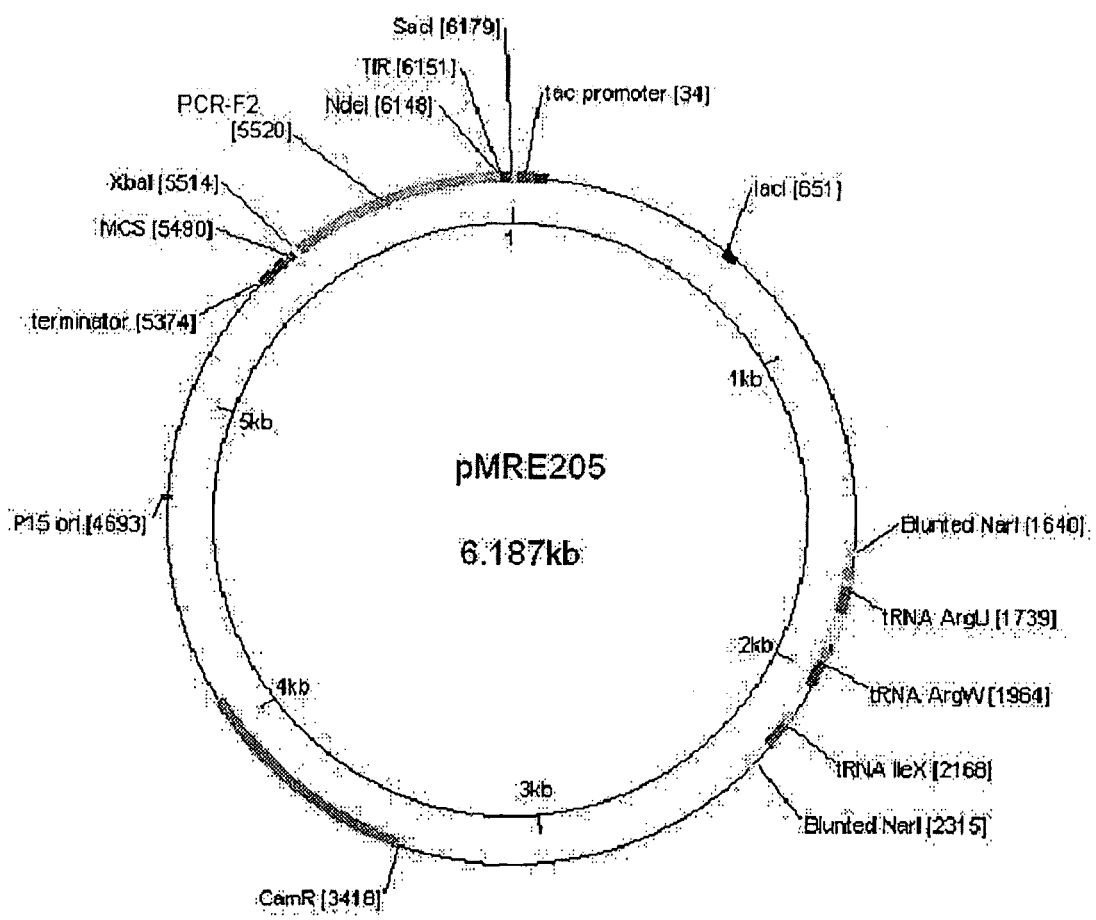

FIG. 11 is a schematic representation of expression vector pMRE205 which carried a gene that encodes conformase 2 under the modified constitutive promoter from the lacZ system. It contains the rare tRNA genes ArgU, ArgW and IleX. It has a P15 origin of replication from pACYC184 (P15 ori) and encodes canamycin resistance (CamR).

Figure 12:
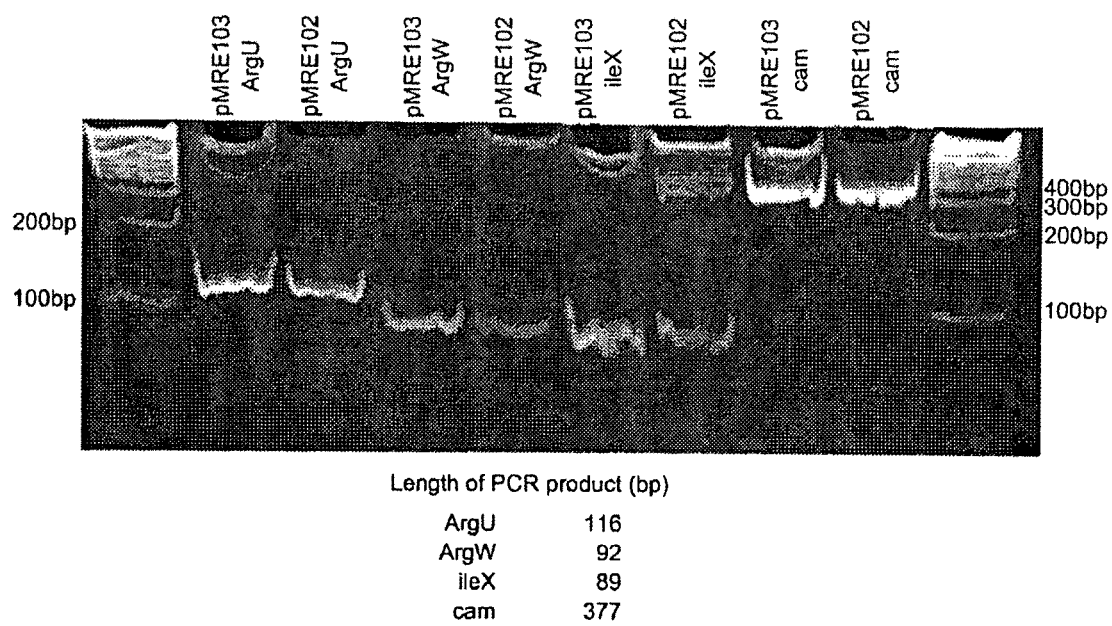

FIG. 12 is a photograph of an acrylamide gel following gel electrophoresis which shows that cells containing heterologous tRNA gene clusters expressed higher amounts of ArgU, ArgW and IleX than control cells.

EXAMPLES

Example 1

Identification of Conformases

Materials and Methods

In order to identify Conformases the following reporters were designed.

Figure 1:
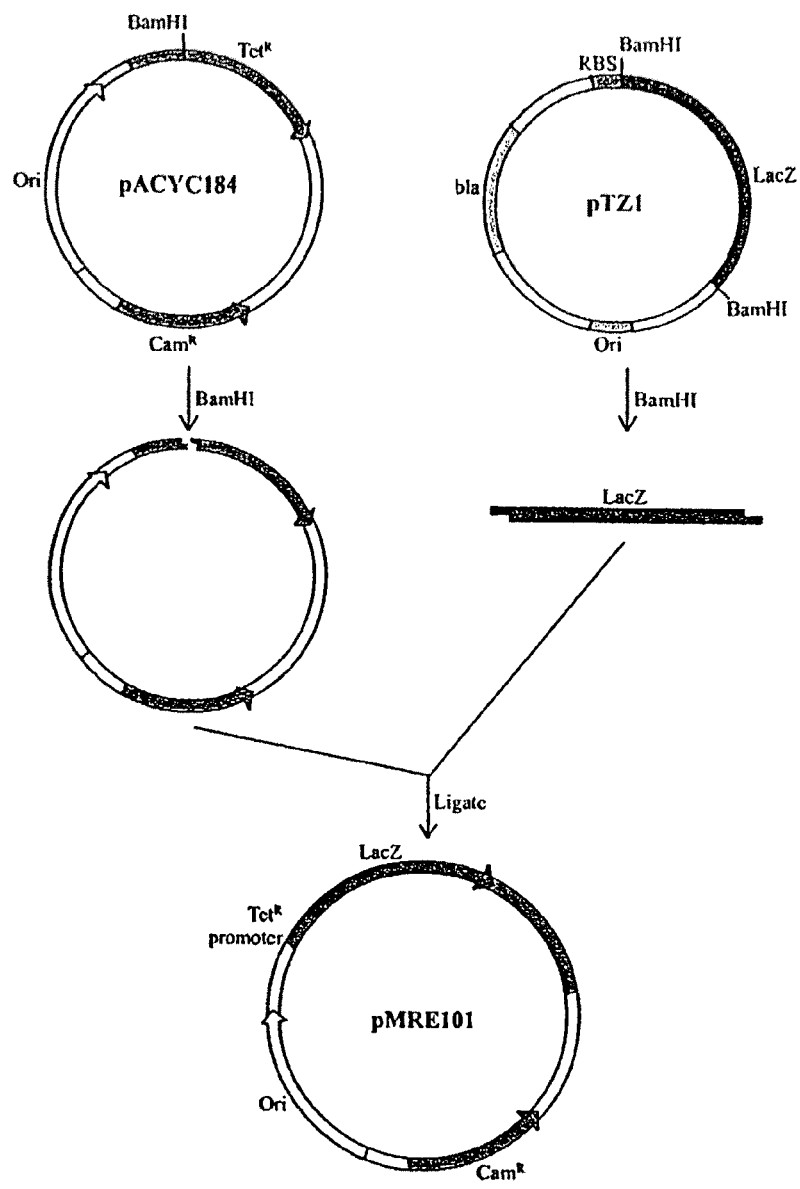

Protein Reporters:

Reporter-1. Complete Beta-Glactosidase as encoded by the complete (LacZ) gene, was chosen as a reporter protein in this study. Since we needed the complete lacZ gene sequence, a special lacZ expression plasmid was designed and made (pMRE101) (FIG. 1). It has the complete LacZ gene as a BamHI fragment from pTZ1(Su T Z, et al., Gene. 1990 May 31; 90(1): 129-33). This fragment was cloned in the correct orientation from the Tet promoter in the pACYC184 (Chang and Cohen, 1978) giving rise to pMRE101 (FIG. 1). This plasmid has a Chloramphenicol resistance gene and p15A origin of replication. This replication origin is compatible with other replication origins such as (pMB1 and ColE1). The complete lacZ fragment is expressed constitutively from the tet promoter. This would be important when two different plasmids are combined in vivo in the same cell.

Figure 2:
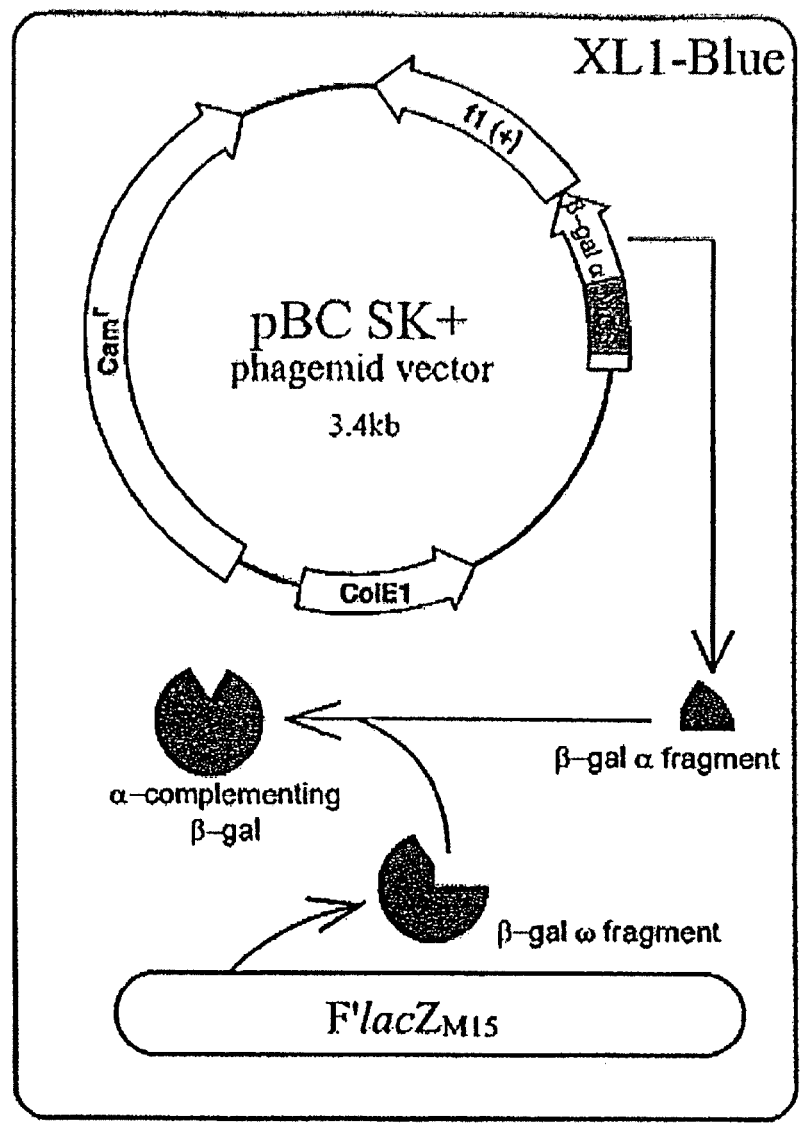

Reporter-2. Alpha-complementation of β-gal. This reporter was designed to monitor reconstituted β-galactosidase activity as a measure of conformation catalysis (conformase activity) that requires different domains of proteins to fold together. Alpha complementation of β-galactosidase is a standard technique in molecular biology. When an Escherichia coli strain with a deletion in Lac to encode only for the M fragment of β-galactosidase, such as XL1blue is transformed with a plasmid containing only the α-fragment of lacZ, reconstituted active β-galactosidase activity can be monitored in plates and in spectrophotometric assays. The aim is to generate E. coli transposon-mutants that fail in this type of alpha-complementation (See FIG. 2). In this way additional conformases that could be required for the proper function and conformation optimization of proteins were found. A standard commercially available plasmid (pBCSK+: Stratagene) encoding the α-fragment was used as the reporter for alpha-complementation proficiency (FIG. 2).

Transposon-Mutagenesis:

Transposon mutagenesis was performed to construct a comprehensive E. coli gene insertion mutation library. The transposon, "λTn5seq1" was used in this study. This transposon was from Nag et al., Gene 1988 Apr. 15; 64(1): 135-45.

Standard methods of transpositions was followed, in particular that described by Way et al., Gene 1984 December; 32(3): 369-79 but with some modifications to suit our objectives as outlined above these modifications are described in the procedure below.

Transposition Procedures:

An E. coli strain with a deletion of the α-fragment of LacZ such as strain XL1-blue (Stratagene) was inoculated in 10 ml LB media (bacto-tryptone 10 g/liter, yeast extract 10 g/liter, NaCl 5 g/liter), supplemented with 0.2% maltose, 10 mM $MgCl_2$ and tetracycline was added to 15 µg/ml. This was shaken at 37° C. overnight.

1—3 ml of the overnight culture was used to inoculate 100 ml LB media supplemented as above.
2—Culture was incubated at 37° C., with continuous shaking.
3—When the OD at 600 nm reached 0.8-1.0, culture was centrifuged at 8,000 g for 10 min. at 4° C.
4—Bacterial cells were resuspended in 10 ml fresh media (as above).
5—2 ml of this culture was used and cell number calculated by the following equation: 1 OD (A600 nm)=$8 \times 10^8$ cells.
6—Phage was added from a stock λTn5seq1 at MOI (multiplicity of infection) equal/less than 0.3/cell.
7—This was incubated at room temperature for 30 min to allow phage absorption.
8—2.5 ml fresh media was added and incubated at 37° C. for 90 min to allow transposition and to give time for the gene expression of the drug-resistant marker (Kanamycin) encoded in the transposon.
9—25 ml LB containing kanamycin (25 µg/ml) and tetracycline (15 µg/ml) was added. The media also contained 1.25 mM sodium pyrophosphate, to inhibit growth of any replication-proficient phages. Incubated with shaking at 30° C. overnight. (30° C. was chosen in order not to screen-out any temperature sensitive mutant.)
10—Plated on LB-Agar plates containing kanamycin (50 µg/ml) and tetracycline (30 µg/ml) and 1.25 mM sodium pyrophosphate at 30° C.
11—Colonies were pooled in 30 ml LB with kanamycin (25 µg/ml) and tetracycline (15 µg/ml).
12—Aliquots of the pooled mutation-library were used for transformation using the appropriate reporter. The remaining culture was brought to 30% glycerol, divided in portions of 1 to 2 ml and subsequently frozen at –70° C.

Transformation with Reporter Encoded Plasmids:

1—An aliquote of $2-3 \times 10^8$ cells of the E. coli tranposon-mutation library was used to inoculate 40-50 ml LB supplemented with kanamycin (25 µg/ml) and tetracycline (15 µg/ml) in order to prepare transformation-competent cells.
2—Culture was shaken at 25-30° C. until OD between 0.6-0.8 (A600 nm), chilled on ice then centrifuged at 8000 g for 5 min at 4° C.
3—Cells were resuspended in 1 volume (original culture) of cold 0.1 M $MgCl_2$. Centrifuged as above.
4—Cells were resuspended in ¼ volume (original culture) of Transformation buffer (75 mM $CaCl_2$, 6 mM $MgCl_2$), then chilled for 20 min on ice.
5—Centrifuged as above. Cells were resuspended in 2.5 ml Transformation buffer (0.75M $CaCl_2$, 6 mM $MgCl_2$). Aliquots of cells can be frozen at –70° C. after adjusting glycerol to 30%.
6—About 2-3 µg DNA of the appropriate reporter (see protein reporters 1&2 above) were used to transform about 200-300 µl competent cells. After adding DNA to cells, they were incubated on ice for 30 min. Heat shock at 37° C. for 3 min and then back on ice.
7—3-5 ml LB supplemented with kanamycin (25 µg/ml) and tetracycline (15 µg/ml) was added and incubated at 30° C. for 90-120 minutes to allow the expression of the chloramphenicol resistant gene encoded in the reporters.
8—Plated on LB plates containing kanamycin (50 µg/ml), tetracycline (30 µg/ml), chloramphenicol (30 µg/ml) and X-Gal (60 µg/ml). For the inducible reporter 2, IPTG (60 µg/ml) was also added.
9—Plates were incubated at 30 or 37° C. as required.

Selection of colonies that contain plasmid-encoded reporter protein, but exhibit a noticeably reduced activity (e.g. white colonies).

After plating on the screening media indicted above (Transformation, point 8). A few colonies were white using either of the reporter systems. These colonies were streaked several times on selective media to ensure their phenotype and genetic stability. This clearly indicates that these mutants are defective in a gene that is needed for the proper folding of the reporter protein.

Moving the mutants into a wild-type background strain to confirm phenotype and genotype.

Frozen stocks of the selected mutants were stored at –70° C. In order to move any mutated gene into a new bacterial strain with wt background, the standard P1 lysate transduction method was followed (Sternberg and Maurer, 1991 in Methods in Enzymology Vol 204, pp 18-43, Ed. Miller. Academic Press).

Transduction of the Mutants:

1—A small overnight culture (10 ml) of a given selected mutant was inoculated. LB media was supplemented with kanamycin (25 µg/ml), tetracycline (15 µg/ml) and chloramphenicol (15 µg/ml).
2—100 µl overnight culture was added to 10 ml LB media as above, but the media also contained 5 mM $CaCl_2$. This was shaken at 37° C. for 1 hr.
3—100 µl P1 (phage lysate) was added and culture shaken at 37° C. until cells lysed.
4—100 µl chloroform was added to ensure lysis of cells.
5—Lysates were centrifuged at 10,000 g to remove cell debris.
6—Clear lysates were stored with 100 µl chloroform at 4° C.
7—A small LB culture (5-10 ml) was inoculated with the wild type strain K37 (Olson E R, et al., 1984. J. Mol. Biol.; 180(4): 1053-63).
8—2 ml culture was centrifuged for 10 min at 5,000 g.
9—Cells were suspended in 1 ml Tris-buffer (5 mM Tris, 10 mM $MgCl_2$, 5 mM $CaCl_2$).
10—0.5 ml P1 phage lysate (from the mutants) was added, and incubated at 32° C. for 30 min without shaking.
11—0.5 1M Na-Citrate was added and mixed well.
12—5 ml LB containing 0.05M Citrate was added and incubated at 32° C. for 1 hr without shaking.
13—Cells spun down at 5000 g for 10 min. The supernatant was poured off and cells resuspended in 1 ml LB (0.05M Citrate).
14—The cells were plated on selective LB plates, containing kanamycin (50 µg/ml), tetracycline (15 µg/ml), Xgal (60 µg/ml) and IPTG (60 µg/ml). Control WT K37 strain without P1 was used as control. Another control was made using XL1blue to prepare P1 lysates in comparison with lysates prepared from mutants.

Figure 3:
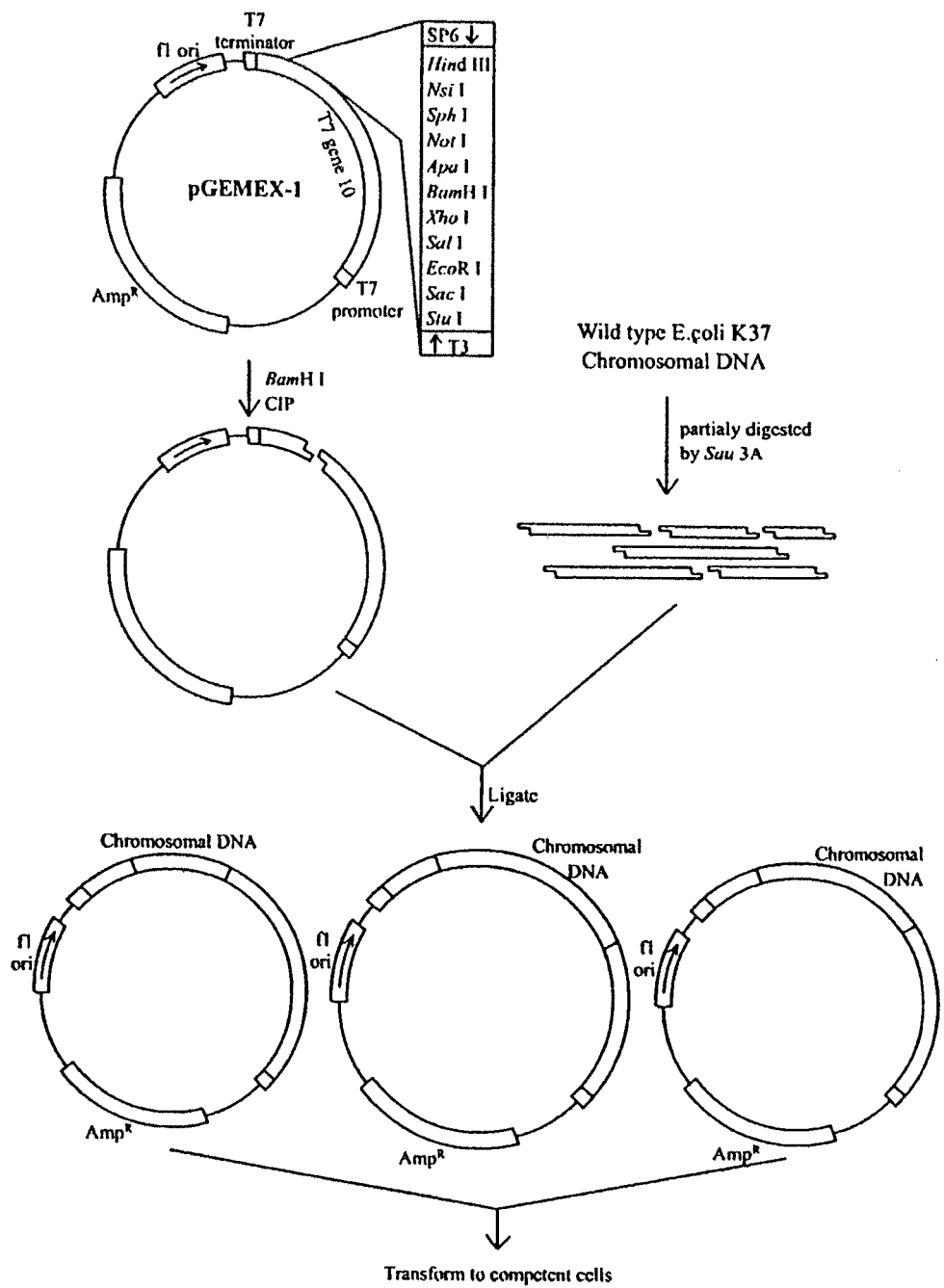

Construction of *Escherichia coli* Genomic Library:

A genomic library of *Escherichia coli* was prepared using DNA isolated from the WT strain K37 (Olson E. R., et al., 1984. J. Mol. Biol.; 180(4): 1053-63). The outline of the library construction is set out in FIG. 3. The plasmid pGE-MEX1 (Promega) was used because:
1—it does not have lacZ sequences.
2—it is a high copy number plasmid.
3—Gene expression will be from cloned fragment own promoter.
4—T3 and SPS primers can be used for the initial DNA sequencing of any identified fragment that can restore function.

Standard methods were used as described, for example in Sambrook et al, 1989 Molecular cloning: A Laboratory Manual and Ausubel et al., 1994 Current Protocols in Molecular Biology.

Genomic DNA Library Construction:
1—Small culture LB (10 ml) of wild type strain such as K37 (Olson E. R., et al., 1984. J. Mol. Biol.; 180(4): 1053-63) was prepared. This was shaken at 37° C. overnight.
2—DNA was isolated using standard methods.
3—*E. coli* DNA (15 µg) was subjected to partial digestion by Sau3A, then tested by gel electrophoresis for partial digestion. Diluted Sau3A was added as needed. When generated fragments were in the range between 2-12 kb, the enzyme was inactivated, DNA was treated by phenol-chloroform and precipitated by 2 Vol. of Ethanol and the pellet washed by 70% ETOH.
4—About 15 µg pGEMEX-1 DNA was digested by BamHI and treated with (CIAP) calf intestine alkaline phosphatase. When the cutting was complete as judged by electrophoresis, the enzymes were heat inactivated, the DNA was treated with phenol-chloroform and precipitated by 2 Vol. of Ethanol and the pellet washed by 70% ETOH.
5—Digested DNA from *E. coli*, and plasmid was resuspended in 160 µl H$_2$O, adding 40 µl 5× ligase buffer. Then heated at 75° C. for 15 min and cooled slowly until room temperature and placed on ice. 5 µl ligase (5 Units) was added thereto and the mix incubated at 19° C. overnight.
6—The ligation Mix was diluted to 1 ml using 1× ligase buffer and 2 U ligase was added. Incubated at 19° C. for 2 hours.
7—Transformation was performed using 50 µl ligation mix and 200 µl competent DH5α. Plated on LB plates containing 200 µg/ml Ampicilin.
8—All colonies (over 30,000) were pooled using LB with 100 µg/ml ampicillin. Small 2 ml portions were frozen in media containing glycerol and stored at −70° C.
9—DNA plasmid isolation was made using 2 ml genomic library aliquots to inoculate 1 liter LB culture containing 100 µg/ml ampicillin. DNA isolation protocol was according to standard procedures (Sambrook, J. et al, 1988, A Laboratory Manual, Cold Spring Harbor Laboratory Press, Cold Spring Harbor, N.Y.; Ausubel F M., et al., John Wiley & Sons 1994).

Phenotype Complementation of Folding Impaired Mutants, by Genomic Libraries:
1—A few transposon-mutants of *E. coli* strains which were unable to produce active β-galactosidase were moved to a wild type background (K37).
2—Transformation of such mutant strains was made using the established *E. coli* library DNA. Transformation protocol was performed as described above.
3—Colonies exhibiting folding restoration phenotype were screened on selective LB plates containing, Ampicillin (200 g/ml), kanamycin (50 µg/ml), X-Gal (60 µg/ml) and IPTG (60 µg/ml).
4—Colonies with blue color were picked as indicating restoration of reporter protein function. Small plasmid DNA preparation was made using Qiagen Plasmid preparation kit.
5—The same transposon-mutant strain was re-transformed with the isolated plasmid DNA. Cells were plated on selective plates, LB plates containing, Ampicillin (200 µg/ml), kanamycin (50 µg/ml), X-Gal (60 µg/ml) and IPTG (60 µg/ml). It has been noticed that cells with corrected phenotype can harbour more than one plasmid. After testing the phenotypic manifestation of each rescued plasmid, only the plasmid that confirms the phenotype restored reporter protein activity is pursued further.
6—If all transformants with the rescued plasmid have the corrected phenotype (blue), confirming the complementation of the function, the plasmid DNA was subjected to DNA sequence analysis.

DNA Sequence Analysis

Standard Sanger's method (Sanger et al., 1977 PNAS USA 74(12): 5463-7) was used manually or by using ALF Plus, or ALF Express automatic DNA sequencers (Pharmacia).

In Vitro Transcription Translation of the First Discovered Conformase:

When it was first identified in 1993, this conformase was mapped to a region that was not yet sequenced. It was therefore necessary firstly to prove that this open reading-frame existed. An in vitro translation of this plasmid was done using commercially available *E. coli* S30 extract (Promega, Cat # L48880). As controls, plasmid pGEMEX-1 DNA as well as plasmid pGEMβGal DNA were used. The Supplier protocol was essentially followed using about 2 µg DNA, and the provided pGEMβGal DNA. The in vitro transcription translation is summarized in the Table 1. below:

TABLE 1

In vitro transcription/translation of Conformase 1a

| No. | Plasmid | DNA µl | H2O µl | Premix (−M) µl | $^{35}$S-M µl | S30-Extract µl |
|---|---|---|---|---|---|---|
| 1 | pF1e-pGEMEX-1 | 14 | 0 | 20 | 1 | 15 |
| 2 | pGEMβGal | 4 | 10 | 20 | 1 | 15 |
| 3 | pGEMEX-1 | 2 | 12 | 20 | 1 | 15 |

In Vitro Transcription/Translation Protocol:
1—The above three mirofuge tubes were placed on ice
2—Mixed gently and then centrifuged for 1 min.
3—Incubated at 37° C. for 1 hr.
4—The reaction was stopped by placing on ice then it was frozen until used.
5—For gel electrophoresis 10 µl of each sample was taken and 40 µl sample buffer (Mellipore, reducing buffer) added thereto. 5-10 µl was applied to gel
6—Film was exposed as required to detect protein synthesis signals.

Fluorescence Spectrophotometer
1. An overnight culture of 12-15 ml LB+ medium was started with 10 mM Mg and appropriate antibiotics.
2. The bacteria cells were harvested by centrifugation of 10 ml of the culture at 3500 rpm (2330 g) for 10 min.

3. The pellet was resuspended in 4 ml potassium phosphate buffer pH 7.
4. The fluorescence was measured after heating the test sample at 30° C.
   Excitation wavelength: 490
   Emission wavelength: 510
5. Fluorescence was calculated according to Miller W G. et al., Gene 191(2): 149-53 (1997).

Similar genes from yeast, mammalian cells, and insect cells with potential conformase activity can be identified in an analogous manner to the strategies described herein.

Results

Identified Mutants:

Initially three mutants with compromised ability to fold/conform protein correctly were characterised. These mutants now in K37 wild type background are referred to herein as follows:

BG1=MRE401 (isolated using complete lacZ; pMRE101, reporter-1)
BG2=MRE402 (isolated using complete lacZ; pMRE101, reporter-1)
Alpha-2=MRE414 (isolated using the alpha fragment of Lac; pBCSK+, reporter-2)

Initially Discovered Conformases

Among the genes that early-on corrected the folding defects in the mutants are the genes coding for the conformases referred to herein as:
Conformase-1a,
Conformase-2, and
Conformase-3.

These genes were mapped and were completely sequenced, sequence information is provided below. The ability of these conformases to help in heterologous gene expression was also tested and these experiments are described in detail below. This was done by first cloning these genes in appropriate expression vectors and then introducing these genes into an appropriate host. Bacterial hosts were transformed by the conformases together with the target protein whose solubility/activity is in question. The expression of combinations of these conformases worked in most tested cases in an additive manner.

Initially BG1 was used for screening and enabled the identification of the above 3 conformases. Conformase 2 was the compromised gene (knocked out by transposon mutagenesis) but the other two conformases were identified through their ability to functionally complement conformase 2. This highlights the additive effect.

Although the complete lacZ is expressed in the mutant BG1, as well as the wild type, to a similar level after induction with IPTG, the phenotype is clearly different giving rise to reduced β-gal activity due to the specific conformation/folding-mutation(s) in BG1. Protein gel electrophoresis showed the presence of the complete β-gal protein band in both the wild type strain K37, and the mutant BG1/(K37), for example. Complete β-gal protein is not detected in the XL1 strain (has a Lac deletion) or before gene expression induction with IPTG.

β-galactosidase activity as observed through blue staining on plates demonstrated that a vector containing the DNA fragment of conformase 1 was able to correct the phenotype of the folding compromised mutant BG1 as observed by β-gal activity on plates. An empty vector gave no such phenotype correction.

Plasmid DNA from BG1 colonies with confirmed restored phenotype were isolated and subjected to restriction enzyme analysis.

Mapping the Rescued DNA Fragments that Complement Mutants on *Esherichia coli* Physical Map Using Kohara Genomic Library:

Kohara minimized Filters containing the arrayed *Escherichia coli* genomic library (Kohara Y., et al., Cell. 1987 Jul. 31; 50(3):495-508 and Takara Shuzo Co. Ltd., Kyoto 600-91, Japan) were used to map identified gene sequences that complement selected mutants. The filter helped us identify the exact λ-clone containing the specific *Escherichia coli* genomic region. The Kohara *Escherichia coli* genomic library helped us pick-up the clone and isolate the DNA of the entire region for confirmation, restriction mapping and also for some of the sequence data.

The result of hybridization with a DNA fragment from conformase-1 gave the strongest signal with Kohara clone λ-238. A similar experiment with conformase-2 gave the strongest hybridization signal with the λ-625 Kohara clone. Clones λ-626 and λ-627 also gave a fairly strong signal indicating overlap in some of the sequences.

Data Mining Before and after the Completion of the Complete *Escherichia coli* Genome Sequence.

Prior to the completion of the *Escherichia coli* genome sequence in 1997, any homology study remained difficult with conformase-1 due to the fact that large sections of the genome were not yet completed. Today the gene in the database is without a tested function. Therefore for some of the early DNA fragment identification/mapping, we relied on mapping the fragment using Kohara et al (1987 supra) arrayed *E. coli* genomic library cloned in λ vector. Non-radioactive labeling of the cloned fragment or non-radioactive labeling of RNA transcripts from the SP6 promoter sequence in λTn5seq1 were used to 'probe' the arrayed genomic library. The method of labeling and detection was performed according to the supplier of the non-radioactive detection kits, Boehringer Mannheim Biochemicals, Germany).

For conformase-1, back in March 1993, we wanted to verify that the open reading frame does actually exist as reflected by transcription and translation. In vitro protein transcription/translation using the rescued cloned DNA fragment (pGEM-EX1) that complemented a conformation compromised mutant (BG1) was performed. The identified open reading-frame gave rise to a translated protein of about 30 KD as observed by gel electrophoresis and is as expected from the DNA sequence data.

The DNA sequence of the first three identified Conformases:

1—Conformase-1a

The current Name of the Gene in the database NCBI is: Ycfu

The gene accession no. is AE005321 (SEQ ID No. 1). All accession and protein ID numbers are from the NCBI database.

The encoded protein is 399 amino acid with previously unknown function (Protein ID-AAG55862.1) (SEQ ID NO. 2).

```
Deduced Protein Sequence (SEQ ID NO 2):
   1 myqpvalfig lrymrgraad rfgrfvswls tigitlgvma
     lvtvlsvmng ferelqnnil 61 glmpqailss ehgslnpqql petavkldgv nrvapittgd
     vvlqsarsva vgvmlgidpa 121 qkdpltpylv nvkqtdlepg kynvilgeql asqlgvnrgd
     qirvmvpsas qftpmgrips
```

```
181 qrlfnvigtf aansevdgye mlvniedasr lmrypagnit
    gwrlwldepl kvdslsqqkl 241 pegskwqdwr drkgelfqav rmeknmmgll lslivavaaf
    niitslglmv mekqgevail 301 qtqgltprqi mmvftnvqgs agiigailga algallasql
    nnlmpiigvl ldgaalpvai 361 eplqvivial vamalallst lypswraaat qpaealrye Gene Sequence (SEQ ID NO 1):
   1 atgtaccaac ctgtcgctct atttattggc ctgcgttaca
     tgcgtgggcg tgcagcggat 61 cgcttcggtc gtttcgtctc ctggctttct accatcggca
     ttaccctcgg ggtgatggcg 121 ctggtcacag tattgtcagt gatgaacggc tttgagcgcg
     agctgcaaaa caacatccct 181 ggcctgatgc cacaggcaat tctctcttct gagcatggct
     ctcttaaccc gcagcaactc 241 ccggaaacgc cagtcaaact ggacggcgtt aatcgcgtcg
     cacctattac taccggtgat 301 gtggtactga aaagcgcgcg cagcgtggcg gtcggggtga
     tgctgggtat cgatccggcg 361 caaaaagatc cactaacgcc gtatctggtc aatgtgaaac
     aaactgacct cgagccgggg 421 aaatataatg tcatcctcgg cgaacaactt gcctcacagc
     taggcgttaa tcgcggtgat 481 caaatccgcg tgatggtgcc atctgccagc cagttcacgc
     cgatgggcg tattccaagt 541 cagcgcctgt tcaatgtgat tggtactttt gccgcta&ca
     gtgaagtcgd tggctatgaa 601 atgctggtga atattgagga tgcctcgcgt ctgatgcgtt
     atccggcagg caatattacc 661 ggctggcgtt tgtggctgga tgagccgctg aaagttgact
     ctttaagtca gcaaaaactg 721 cctgaaggca gcaaatggca ggactggcgt gatcgtaaag
     gcgagctgtt ccaggccgta 781 cgcatggaaa aaaatatgat gggcttactg ctgagcctga
     ttgtcgccgt tgcggcgttt 841 aacattatta cctcgctggg gctgatggtg atggagaagc
     agggcgaagt agcgatcctg 901 caaacgcaag gcttaactcc gcgacaaatc atgatggtct
     ttatggtgca aggggccagc 961 gccgggatta tcggtgcgat cctcggagcg gcgcttggcg
     cactgcttgc cagccagtta 1021 aataatctga tgccgataat cggcgtcctg cttgatggcg
     cggcgctgcc ggtggctatc 1081 gaaccttac aggtcattgt tattgcgctg gtggcgatgg
     ctatcgcgct gctgtctacg 1141 ctttacccc tt catggcgcgc tgccgccaca caacccgctg
     aggctttacg ttatgaataa
```

Our early DNA sequence data indicated that the gene has close proximity (without new promoter) to another open reading frame. Initially we focused on testing the biological activity of the first member of this "operon" on protein folding but it is anticipated that the other genes in this operon would have conformase activity.

After completing the *Escherichia coli* genome sequence, this gene was assigned the name ycfu. The rest of the operon has the following linked genes ycfv, ycfw, ycfx, cobB. The sequence information for these linked genes is given below:

Ycfv
function: Putative transport and putative ATP-binding component of a transport system.

```
Deduced protein (228 aa) (SEQ ID NO 4):
mqcdnlckry qegsvqtdvl hnvsfsvgeg emmaivgssg         60
sgkstllhll ggldtptsgd vifngqpmsk lssaakaelr nqklgfiyqf hhllpdftal        120
envampllig kkkpaeinsr alemlkavgl ehranhrpse lsggerqrva iaralvnnpw        180
lvladeptgn ldarnadsif qllgelnrlq gtaflvvthd lqlakrmsrq lemrdgrlta
elslmgae Gene Sequence (SEQ ID NO 3):
ttgcaatgcg acaacctgtg caaacgctat caggaaggca         60
gtgtgcaaac cgatgtactg cacaatgtca gtttcagcgt gggcgaaggt gaaatgatgg        120
cgatcgtcgg tagctctggt tccggtaaaa gtaccttgct gcacctgctg ggcgggctgg        180
atacaccaac ctccggcgat gtgatcttta acggtcaacc gatgagcaaa ctgtcttcgg        240
cggcgaaagc agaactgcgc aaccagaagc tgggctttat ttatcagttt caccacctgc        300
tgccggattt tactgccctg gaaaacgtgg ctatgccgct gctgattggc aagaaaaagc        360
ccgctgaaat caacagccgt gcacttgaga tgttaaaagc ggtgggggctg gagcatcgtg        420
cgaatcaccg cccatctgaa ctttctggcg gcgaacgcca gcgtgtggcg attgcccgtg        480
cgctggtcaa taacccgtgg ctggtactgg cggatgaacc taccggtaac ctcgatgcgc        540
gtaacgcaga cagcatcttc cagttgcttg gggaattgaa tcgcttgcag ggcaccgcct        600
tcctggtggt tactcacgac ctgcaactgg cgaaacgtat gagccgccaa ctggagatgc        660
gtgatggtcg tctgacggcg gaactgagcc tgatgggggc ggagtaa Ycfw
Function: putative enzyme: putative kinase.

Deduced protein (414 aa) (SEQ ID NO 6):
mamplsllig lrfsrgrrrg gmvslisvis tigialgvav         60
livglsamng ferelanril avvphgeiea vdqpwtnwqe aldnvqkvpg iaaaapyinf        120
tglvesganl raiqvkgvnp qqeqrlsalp sfvqgdawrn fkageqqiii gkgvadalkv        180
kqgdwvsimi pnsnpehklm qpkrvrlhva gilqlsgqld hsfamiplad aqqyldmgss        240
vsgialkmtd vfnanklvrd agevtnsyvy ikswigtygy myrdiqmira imylamvlvi        300
gvacfnivst lvmavkdksg diavlrtlga kdgliraifv wygllaglfg slcgviigvv        360
vslqltpiie rieklighqf lssdiyfidf lpselhwldv fyvlvtalll sllaswypar
rasnidparc lsgq
```

Gene Sequence (SEQ ID NO 5):
```
atggcgatgc ctttatcgtt attgattggc ctgcgtttta      60
gccgcggacg gcgacgcggc ggcatggtgt cgctgatctc cgtcatttct accattggca     120
ttgcccttgg cgtggcggta ttgatcgtcg gcttaagcgc gatgaacggc tttgaacgcg     180
aactgaataa ccgcattctg gcggtggtgc cgcatggcga aatagaggcg gtggatcaac     240
cgtggactaa ctggcaggaa gcactggata cgtgcaaaa agtgccaggt attgccgccg      300
ctgcgccgta tatcaatttc accgggctgg tggaaagtgg agcgaatctg cgcgcaatcc     360
aggtgaaggg cgttaacccg caacaggaac agcgtctgag cgcattaccc tcgtttgttc     420
aggggatgc ctggcgcaat tttaaagcgg cgaacagca aattatcatc ggcaaaggcg      480
tggcggatgc gctgaaagtg aagcagggcg attgggtgtc gattatgatc cccaactcga     540
atcctgagca taaactgatg cagccaaaac gtgtgcgttt gcacgttgcc ggtattttgc     600
agttgagtgg tcaactcgat cacagttttg ccatgatccc gctggcggat gcccaacaat     660
atcttgatat gggttccagc gtgtcaggta ttgcccttaa aatgacggat gttttcaacg     720
ccaataagct ggtacgcgat gcgggtgaag tgaccaacag ctatgtttat attaaaagct     780
ggattggtac ttacggctat atgtatcgcg atatccagat gatccgcgcc attatgtatc     840
tggcgatggt actggtgatt ggcgtggcct gtttcaacat cgtctccacc ttagtgatgg     900
cggtgaaaga caagagtggc gatatcgcag tattaagaac gctggggcg aaagatggtt       960
taattcgcgc catctttgtc tggtatggat tgctggcagg gctattcggt agcctgtgtg    1020
gtgtgattat cggcgtagtt gtttcactgc aacttacccc gattattgag cggattgaaa    1080
agctgatcgg tcatcagttc ctctccagcg atatctatt tattgacttc ctgccatcgg     1140
aattgcactg gctggacgtc ttctacgtac tggtcacagc attgttgctg agtcttttgg    1200
caagttggta tccggcgcgg cgcgccagta atattgaccc tgcgcgagtc cttagcggcc
agtaa
```

Ycfx
function = putative regulator;
putative NAGC-like transcriptional regulator Deduced protein (303 aa) (SEQ ID NO 8):
```
myygfdiggt kialgvfdsg rqlqwekrvp tprdsydafl      60
davcelvaea dqrfgckgsv gigipgmpet edgtlyaanv paasgkplra dlsarldrdv     120
rldndancfa lseawddeft qyplvmglil gtgvgglif ngkpitgksy itgefghmrl      180
pvdaltmmgl dfplrrcgcg qhgcienyls grgfawlyqh yyhqplpape iialydqgde     240
qarahveryl dllavclgni
```

```
ltivdpdlvv igggslsnfpa ittqladrlp rhllpvarvp    300
rierarhgda ggmrgaaflh ltd
```

Gene Sequence (SEQ ID NO 7):
```
atgtattacg ggtttgatat tggtggaaca aaaattgcgc      60
ttggcgtgtt tgatagcggt cggcagttgc agtgggaaaa gcgggtgccg acaccgcgtg     120
acagctatga cgcatttta gatgcagtgt gcgagctggt agccgaagct gatcaacgtt     180
ttggctgtaa aggctctgtc ggcatcggta ttccgggaat gccggaaaca gaagatggta     240
cgctgtatgc cgccaatgtc cctgctgcca gcggtaaacc gctgcgtgcc gacctgagcg     300
cacgtcttga tcgcgatgta cgccttgata cgatgccaa ctgttttgcc ctttcagaag       360
cctgggatga cgaatttacg caatatccgt tggtgatggg gttgattctc ggcaccggcg     420
ttggcggcgg gctgatttc aacggcaaac cgattaccgg gaaaagctac attaccggcg     480
agtttggcca tatgcgtctg ccggttgatg cgttaaccat gatggggctg gatttcccgt     540
tacgccgctg cggctgtggt cagcatggct gcattgaaaa ttatctgtct ggtcgcggtt     600
ttgcgtggct gtatcaacac tattatcatc aaccgttgcc ggctcccgaa attattgcgc     660
tttatgatca aggcgatgag caggcaaggg cgcacgttga gcgttatctg gatttattag     720
cggtttgtct gggaaatatc ctgaccattg ttgacccctga cctggtcgtc attggtggtg    780
gcttatcgaa tttccccggca atcacaacgc aactggcgga caggctgcct cgtcatctct     840
tacctgtagc tcgtgttccg cgcattgaac gcgcgcgcca ggtgatgcg ggaggaatgc      900
gtggtgcggc cttcctacat ctaaccgatt aa
``` cobB
Function: putative enzyme Biosynthesis of cofactors,
carriers: Cobalamin (Putative nicotinic acid
mononucleotide: 5,6-dimethylbenzimidazole (DMB)
phosphoribosyltransferase).

Deduced protein (273 aa) (SEQ ID NO 10):
```
mlsrrghrls rfrknkrrlr erlrqriffr dkvvpeamek      60
prvlvltgag isaesgirtf raadglweeh rvedvatpeg fdrdpelvqa fynarrrqlq     120
qpeiqpnaah lalaklqdal gdrfllvtqn idnlheragn tnvihmhgel lkvrcsqsgq     180
vldwtgdvtp edkchccqfp aplrphvvwf gemplgmdei ymalsmadif iaigtsghvy     240
paagfvheak lhgahtveln lepsqvgnef aekyygpasq vvpefvekll kgl
```

Gene Sequence (SEQ ID NO 9):
```
atgctgtcgc gtcggggtca tcggttaagt cgttttcgta      60
aaaataaacg ccgcctgcgc
```

-continued

```
gagcgtttgc gtcagcgtat ttttttcaga gataaagtgg      120
tgccggaagc aatggaaaaa ccaagagtac tcgtactgac aggggcagga atttctgcgg      180
aatcaggtat tcgtacctttt cgcgccgcag atggcctgtg ggaagaacat cgggttgaag      240
atgtggcaac gccggaaggt ttcgatcgcg atcctgaact ggtgcaagcg ttttataacg      300
cccgtcgtcg acagctgcag cagccagaaa ttcagcctaa cgccgcgcat cttgcgctgg      360
ctaaactgca agatgctctc ggcgatcgct ttttgctggt gacgcagaat atagacaacc      420
tgcatgaacg cgcaggtaat accaatgtga ttcatatgca tggggaactg ctgaaagttc      480
gttgttcaca aagtggtcag gttctcgact ggaccggaga cgttacccca gaagataaat      540
gccattgctg ccagttcccg gcccccttgc gcccacacgt agtatggttt ggcgaaatgc      600
cactcggcat ggatgaaatt tatatgccgt tgtcgatggc cgatattttc attgccattg      660
gtacttccgg gcatgtttat ccggcggctg ggtttgttca cgaagcgaaa ctgcatggcg      720
cgcacaccgt ggagctgaat cttgaaccaa gtcaggtcgg taatgaattt gccgagaaat      780
attacggccc ggcaagccag gtggtgccag aatttgttga aaagttgctg aagggattat aa
```

Conformase-2

Our data suggests that Conformase-2 is the gene that was compromised in our selected mutant BG1 (K37). After extensive sequence analysis we clearly found out that Conformase-2 is the E. coli gene Crp(Cyclic AMP Receptor Protein). This new function has never been assigned to this gene before. When we over express this protein, we observed significant increase in the co-expressed "recombinant protein" activity as shown herein.
The Gene Accession No. is AP002564 (SEQ ID NO 11). This Gene is Part of a 2 Gene Operon with YhfK.

The gene codes for a protein of 210 amino acids (protein ID=AAG68465.1) (SEQ ID NO 12).

```
Deduced Protein (SEQ ID NO 12):
   1 mvlgkpqtdp tlewflshch ihkypskstl ihqgekaetl
     yyivkgsvav likdeegkem 61 ilsylnqgdf igelgifeeg qersawvrak tacevaeisy
     kkfrqliqvn pdilmrlsaq 122 marrlqvtse kvgnlafldv tgriaqtlln lakqpdamth
     pdgmqikitr qeigqivgcs 181 retvgrilkm ledqnlisah gktivvygtr Gene Sequence (SEQ ID NO 11):
   1 atggtgcttg gcaaaccgca aacagacccg actctcgaat
     ggttcttgtc tcattgccac 61 attcataagt acccatccaa gagcacgctt attcaccagg
     gtgaaaaagc ggaaacgctg 121 tactacatcg ttaaaggctc tgtggctgtg ctgatcaaag
     acgaagaggg taaagaaatg
```

```
 181 atcctctcct atctgaatca gggtgatttt attggcgaac
     tgggcctgtt tgaagagggc 241 caggaacgta gcgcatgggt acgtgcgaaa accgcctgtg
     aagtggctga aatttcgtac 301 aaaaaatttc gccaattgat tcaggtaaac ccggacattc
     tgatgcgtct gtctgcacag 361 atggcgcgtc gtctgcaagt cacttcagag aaagtgggca
     acctggcgtt cctcgacgtg 421 acgggccgca ttgcacagac tctgctcaat ctggcaaaac
     aaccagacgc tatgactcac 481 ccggacggta tgcaaatcaa aattacccgt caggaaatcg
     gtcagattgt cggctgttct 541 cgtgaaaccg tgggacgcat tctgaagatg cttgaagatc
     agaacctgat ctccgcacac 601 ggtaaaacca tcgtcgttta cggcactcgt taa
```

Yhfk
Unknown function
hypothetical protein.

```
Deduced protein (696 aa) (SEQ ID NO 14):
mwrrliyhpd inyalrqtlv lclpvavglm lgelrfgllf      60
slvpaccnia gldtphkrff krliigaslf atcslltqll lakdvplpfl ltgltlvlgv     120
taelgplhak llpasllaai ftlslagymp vweplliyal gtlwyglfnw fwfwiwreqp     180
lreslsllyr eladyceaky slltqhtdpe kalppllvrq qkavdlitqc yqqmhmlsaq     240
nntdykrmlr ifqealdlqe hisvslhqpe evqklversh aeevirwnaq tvaarlrvla     300
ddilyhrlpt rftmekqiga lekiarqhpd npvgqfcywh fsriarvlrt qkplyardll     360
adkqrrmpll palksylslk spalrnagrl svmlsvaslm gtalhlpksy wilmtvllvt     420
qngygatrlr ivnrsvgtvv gliiagvalh fkipegytlt lmlittlasy lilrknygwa     480
tvgftitavy tlqllwlnge qyilprlidt iigcliafgg tvwlwpqwqs gllrknahda     540
leayqeairl ilsedpqptp lawqrmrvnq ahntlynsln qamqepafns hyladmklwv     600
thsqfivehi namttlareh ralppelaqe ylqsceiaiq rcqqrleyde pgssgdanim     660
dapemqpheg aagtleqhlq rvighlntmh tissmawrqr phhgiwlsrk lrdska Gene Sequence (SEQ ID NO 13):
   1 atgtggcgca gactgattta tcaccccgat atcaactatg      61
     cacttcgaca aacgctggtg ctatgtttgc ccgtgccgt tgggttaatg cttggcgaat     121
     tacgattcgg tctgctcttc tcccctcgttc ctgcctgttg caatattgcg ggccttgata    181
     cgcctcataa acgtttttc aaacgcttaa tcattggtgc gtcgctgttt gccacctgta    241
     gcttgctgac acagctacta ctggcaaaag atgttcccct gccctttttg ctgaccggat    301
     taacgctggt acttggcgtc
```

```
actgctgagc tggggccatt gcacgcaaaa ttgcttcctg    361
catcgctgct cgccgccatt tttaccctca gtttggcggg atacatgccg gtctgggaac    421
cgttgctcat ctatgcgttg ggcactctct ggtacggatt gtttaactgg ttttggttct    481
ggatctggcg cgaacaaccg ctgcgcgagt cactaagtct gctgtaccgt gaactggcag    541
attattgtga agccaaatac agcctgctta cccagcacac cgaccctgaa aaagcgctgc    601
cgccgctgct ggtgcgccag caaaaagcgg tcgatctaat tacccagtgc tatcagcaaa    661
tgcatatgct ttccgcgcaa aataatactg actacaagcg gatgctgcgt attttccagg    721
aggcgctgga tttacaggaa catatttcgg tcagtttgca tcagccggaa gaggtgcaaa    781
agctggtcga gcgtagccat gcggaagaag ttatccgctg gaatgcgcaa accgtcgccg    841
ctcgcctgcg cgtgctggct gatgacattc tttaccatcg cctgccaacg cgttttacga    901
tggaaaagca aattggcgca ctggaaaaaa tcgcccgcca gcatccggat aatccggttg    961
ggcaattctg ctactggcat ttcagccgca tcgcccgcgt gctgcgcacc caaaaaccgc   1021
tctatgcccg tgacttactg gccgataaac agcggcgaat gccattactt ccggcgctga   1081
aaagttatct gtcactaaag tctccggcgc tacgcaatgc cggacgactc agtgtgatgt   1141
taagcgttgc cagcctgatg ggcaccgcgc tgcatctgcc gaagtcgtac tggatcctga   1201
tgacggtatt gctggtgaca caaaatggct atggcgcaac ccgtctgagg attgtgaatc   1261
gctccgtggg aaccgtggtc gggttaatca ttgcgggcgt ggcgctgcac tttaaaattc   1321
ccgaaggtta caccctgacg ttgatgctga ttaccaccct cgccagctac ctgatattgc   1381
gcaaaaacta cggctgggcg acggtcggtt ttactattac cgcagtgtat accctgcaac   1441
tattgtggtt gaacggcgag caatacatcc ttccgcgtct tatcgatacc attattggtt   1501
gtttaattgc tttcggcggt actgtctggc tgtgccgca gtggcagagc gggttattgc    1561
gtaaaaacgc ccatgatgct ttagaagcct atcaggaagc gattcgcttg attcttagcg   1621
aggatccgca acctacgcca ctggcctggc agcgaatgcg ggtaaatcag gcacataaca   1681
ctctgtataa ctcattgaat caggcgatgc aggaaccgga gtttaacagc cattatctgg   1741
cagatatgaa actgtgggta acgcacagcc agtttattgt tgagcatatt aatgccatga   1801
ccacgctggc gcgggaacac cgggcattgc cacctgaact ggcacaagag tatttacagt   1861
cttgtgaaat cgccattcag cgttgtcagc agcgactgga gtatgacgaa ccgggtagtt   1921
ctggcgacgc caatatcatg
```

```
gatgcgccgg agatgcagcc gcacgaaggc gcggcaggta   1981
cgctggagca gcatttacag cgggttattg gtcatctgaa caccatgcac accatttcgt   2041
cgatggcatg gcgtcagcga ccgcatcacg ggatttggct gagtcgcaag ttgcgggatt
cgaaggcgta a
```

Conformase-3

=yjei (Accession No. AE005648) (SEQ ID NO 15). A very small open reading frame was found also to complemente the mutant BG1 (K37). This fragment was mapped to the Kohara A649 clone. After completing the *Escherichia coli* genome sequence, this gene was assigned the name yjei. According to current understanding, it remains a hypothetical protein in the *Escherichia coli* genome.

The gene codes for a protein of 128 amino acid of previously unknown function (protein ID=AAG59343.1) (SEQ ID NO 16).

```
Deduced Protein (SEQ ID NO 16):
   1 massslimgn nmhvkylagi vgaallmagc sssnelsaag
     qsvrivdeqp gaecqligta 61 tgkqsnwlsg qhgeeggsmr gaandlrnqa aamggnviyg
     isspsqgmls sfvptdsqii 121 gqvykcpn Gene Sequence (SEQ ID NO 15):
   1 gtggcgtcca gctcattgat tatgggaat aacatgcacg
     taaaatactt agcagggatt 61 gtcggtgccg cgctactgat ggcgggttgt agctccagca
     acgaattgag tgctgccggt 121 cagagtgtac gcattgtgga cgagcagcca ggcgcagagt
     gccagctgat tggtactgcg 181 acaggtaagc aaagcaactg gctttccggg caacacggag
     aagagggcgg ttctatgcgc 241 ggcgcagcaa acgatctgcg caaccaggcg gctgcaatgg
     gcggtaacgt gatttatggc 301 atcagtagcc cgtcgcaggg aatgttgtcc agttttgtcc
     cgacggatag ccagattatc 361 ggccaggtat ataagtgccc gaactga
```

Example 2

The Biological Activity of Conformases 1, 2 and 3 on Expressed Human Recombinant Proteins (rHPs)

When three of these genes are cloned and expressed using compatible plasmids to the ones often used in gene/protein expression, they helped in increasing the activity (solubility) of the expressed proteins in vivo, in an additive way. Some of the tested proteins that we recently co-expressed are key human proteins that are being used as targets for drug development. These include proteins of different functional classes such as hydrolysis enzymes (β-Gal), Energy transfer proteins (GFP), peroxisome proliferating enzymes and phosphodiesterases.

The following is a standard protocol for assaying rHP activity as an indicator of conformase efficiency.

1—Transform the plasmid encoding rHP into an appropriate host.

2—Transform the same host with a plasmid encoding appropriate conformase(s) or empty vector as control.

3—Replication origin of the plasmid used to clone the conformase(s) has to be compatible. If that is not the case, one of the plasmids will be diluted out very quickly. Additionally, each plasmid has to have a different selection marker (e.g. different antibiotic resistance gene).

4—Induce gene expression both from the plasmid coding rHP as well as the plasmid coding for the conformase(s).

5—Harvest and break the cell for total protein extraction.

6—Assay for rHP activity in the crude extract with the different conformase(s) and compare with an empty vector that was used to clone conformases.

Figure 4:
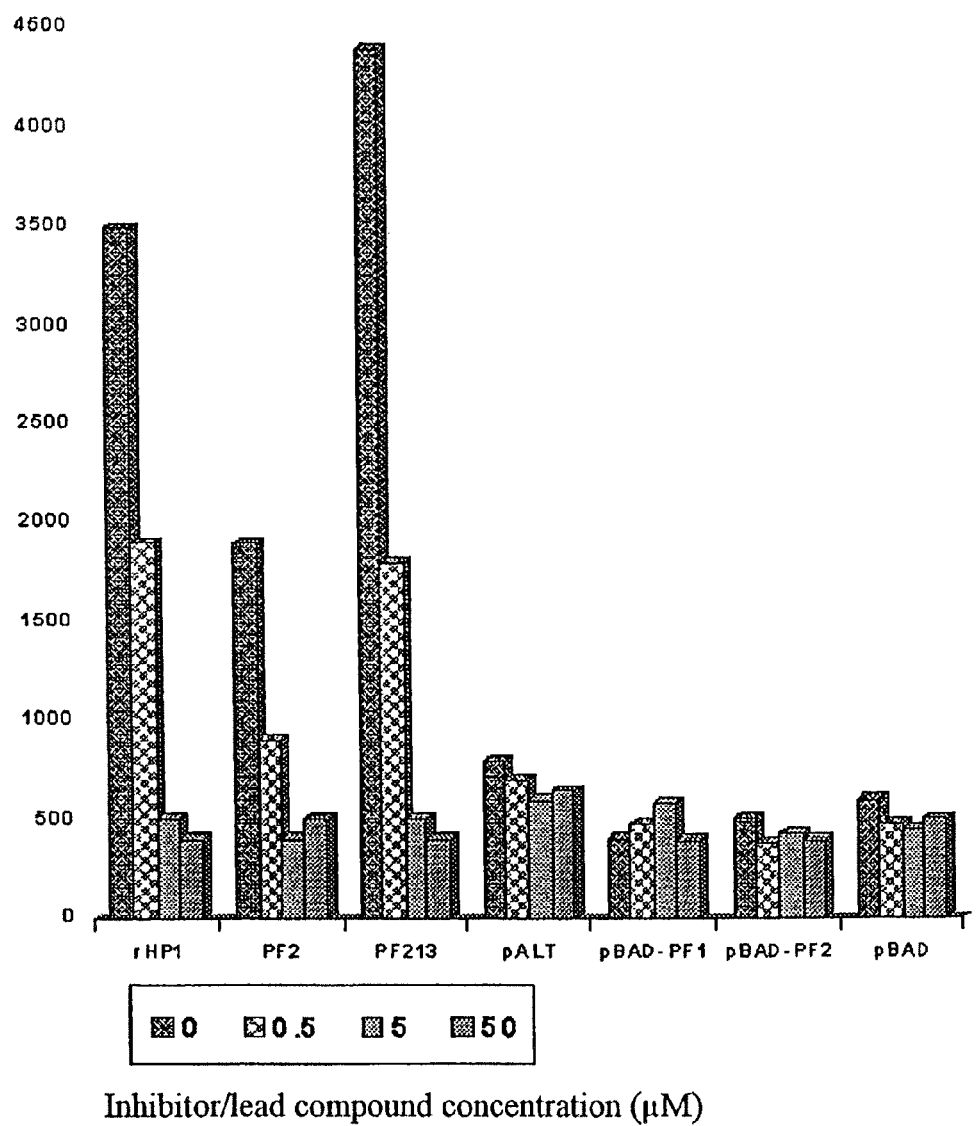

Testing Conformase Activities on Recombinant Human Proteins:

When combinations of these conformases are co-expressed together with a recombinant human protein (used as target for drug discovery) rhp1, their effect was clearly additive (FIG. 4). Conformases expressed from Tac promoter of pAltEx2 (Promega) were active in K37 cells. Protein activity of rHP1 expressed with empty vector pAltex2 was significantly lower than that expressed with the different Conformases (conformase-1, or with co-expressed conformases-1, 2, 3. "rHP1" was purified and concentrated, while in the case of the co-expressed rHP1 with conformases, only a 10 µl aliquot of supernatant lysates were used directly in the activity assay. These experiments are described in further detail in the legend to FIG. 4.

The activity of the rHP1 is inhibited by the lead compound depending on its concentration. In the absence of inhibitor (OM), the activity of rHP1 has been increased by the presence of conformases (relative to empty vector) as follows:

27 fold using conformase (F2)

62 fold using a combination of conformases 1, 2 & 3 (F213), see FIG. 4.

Figure 5:
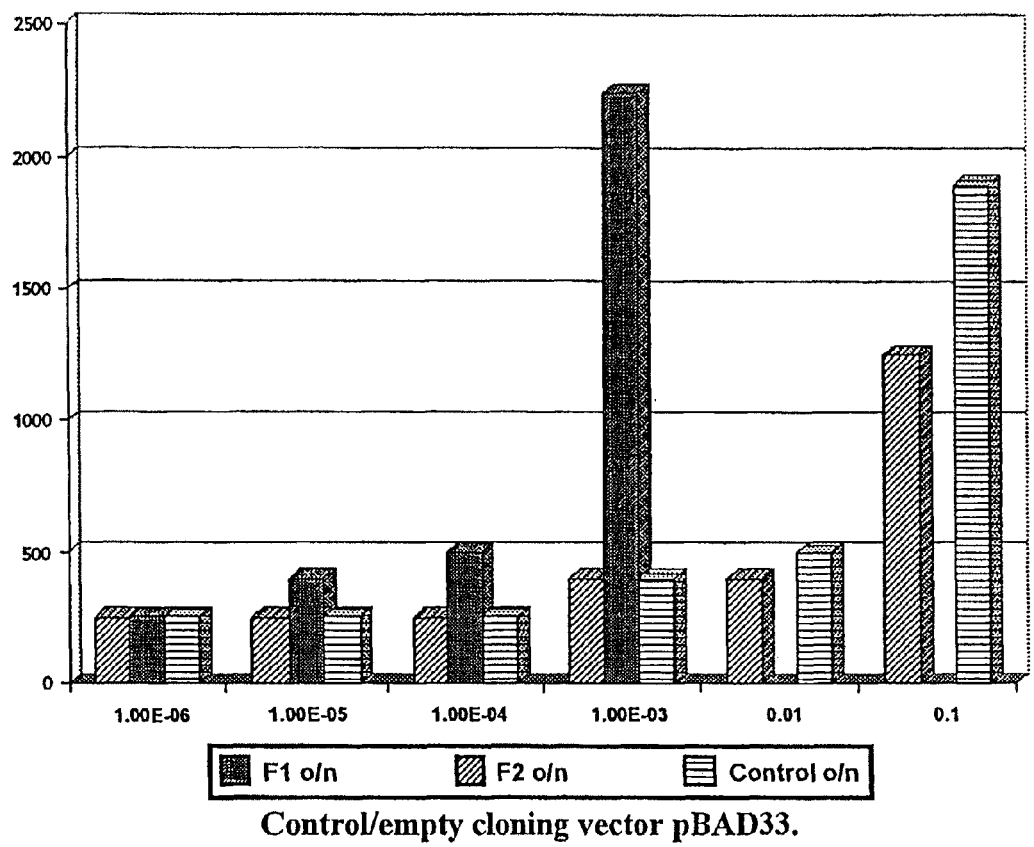

A further protein, recombinant human protein (rHP2) was investigated by co-expression with conformases 1 and 2, see FIG. 5. Plasmid pBAD33 (Guzman et al. July 1995 Journal of Bacteriology, Vol. 177, No. 14, pp 4121-4130 was used. Conformase 2 greatly enhanced the activity of rHP2 but activity was inhibited by conformase 1 which suggests some degree of specificity in conformase action.

Example 3

Further Identified Conformases

By complementing the BG2 (MRE402) and α-2 (MRE414) cell lines additional conformases were discovered and sequenced. Interestingly conformase 3 was rediscovered using α-2 (MRE414) mutant. Independent discoveries were made for gene members of the same operons, indicating involvement of the whole operon in the process of folding.

Summary of the new Conformases/Foldases are presented in Table 2 below and full sequence data follows.

TABLE 2

Further Conformases

| NO. | Putative name | How Strong | Possible gene name | Accession no. | Protein ID | Operon? (Judged by linkage/ co-transcription) | Possible Function | Observations |
|---|---|---|---|---|---|---|---|---|
| 1. | Pab-402 | v. strong | YicE | AE005593 (SEQ ID NO 17) | AAG58799.1 (SEQ ID NO 18) | (2) genes (+YicH) | Transport/ unknown | 463 aa |
| 2. | Pc-402 | v. strong | B2596 | AE000346.1 (SEQ ID NO 19) | AAC75645.1 (SEQ ID NO 20) | Yes (3) +B2596, B2597 | Unknown | 68 aa! small |
| 3 | Pd-402 | Med. | NuoG | AE000317 (SEQ ID NO 21) | AAC75343.1 (SEQ ID NO 22) | Yes (14) +Nuoa,b,c,d,e,f, h,i,j,k,l,m,n | NADH- dehydro- genase-G | Large 910 aa |
| 4. | PL-402 | Strong | NuoC | AE000317 (SEQ ID NO 23) | AAC75346.1 (SEQ ID NO 24) | Yes (13) Nuoa,b,d,e,f,g, h,i,j,k,l,m,n | NADH- dehydro- genase-CD | 600 aa |
| 5. | Pe-402 | v. strong | Hnr | AE000222 (SEQ ID NO 25) | AAC74317.1 (SEQ ID NO 26) | ? | Protein synthesis | 337 aa |
| 6. | Pf-402 | Strong | FlgH | AE000208 (SEQ ID NO 27) | AAC74163.1 (SEQ ID NO 28) | Yes (14) Flga,b,c,d,e,f, g,i,j,k,l,m,n | Flagellar- basal body | 232 aa |
| 7. | PU2-414 | Strong | flgI | AE000208.1 (SEQ ID NO 29) | AAC74164.1 (SEQ ID NO 30) | Yes (14) Flga,b,c,d,e,f, g,h,j,k,l,m,n | Flagellar basel body | 365 |
| 8. | Pg-402 | Strong | B0960 | AE000198 (SEQ ID NO 31) | AAC74046.1 (SEQ ID NO 32) | Yes (2) +YccF | Unknown | Large, 720 aa |
| 9. | Pi-402 | Strong | Ybdk | AE005237 (SEQ ID NO 33) | AAG54914.1 (SEQ ID NO 34) | ? 2-5 ? | Unknown | 372 aa |
| 10. | PA1-414 | Strong | Yjei | AE005648 (SEQ ID NO 35) | AAG59343.1 (SEQ ID NO 36) | No | Unknown | 128 aa; F-3! |
| 11. | PC1E2- 414 | Strong | B1728 | AE000268.1 (SEQ ID NO 37) | AAC74798.1 (SEQ ID NO 38) | No | Unknown | 200 aa |

TABLE 2-continued

Further Conformases

| NO. | Putative name | How Strong | Possible gene name | Accession no. | Protein ID | Operon? (Judged by linkage/ co-transcription) | Possible Function | Observations |
|---|---|---|---|---|---|---|---|---|
| 12. | PD1a-M2-414 | Strong | B2475 | AE000334.1 (SEQ ID NO 39) | AAC75528.1 (SEQ ID NO 40) | 2 genes ? YpfI | Unknown | 287 aa |
| 13. | PD1b-M2b-414 | Strong | YjfR ? | AE000491.1 (SEQ ID NO 41) | AAC77149.1 (SEQ ID NO 42) | No | Unknown | 356 aa |
| 14. | PML-414 | Strong | MdoH | AE000206.1 (SEQ ID NO 43) | AAC74133.1 (SEQ ID NO 44) | 2 genes MdoG | Osmotic adaptaion | 847 aa |
| 15. | PO1a414 | Strong | Yhft | AE000413.1 (SEQ ID NO 45) | AAC76402.1 (SEQ ID NO 46) | 15 genes + YhfL, m,n,o,p,q,r,s,u, v,w,x,y,z | Transport ? | 434 aa |
| 16. | PO1b414 | Strong | ArcA | AE000510.1 (SEQ ID NO 47) | AAC77354.1 (SEQ ID NO 48) | No | Negative resp. regul. | 238 aa |
| 17. | PQ1-414 | Strong | tolA | AE000177.1 (SEQ ID NO 49) | AAC73833.1 (SEQ ID NO 50) | 4 genes +tolQ,r,b | Outer membrane integrity | 421 aa |
| 18. | PB2-d2-414 | Strong | TorT | D90737.1 (SEQ ID NO 51) | BAA35761.1 (SEQ ID NO 52) | >3 genes +torR, torS | Periplasmic prot. Regul, CAD | 342 aa |
| 19. | PK2-414 | Strong | YeeX | AE000292.1 (SEQ ID NO 53) | AAC75068.1 (SEQ ID NO 54) | 2 ? +YeeA | Unknown | 131 aa |
| 20. | PK2b414 | Strong | YeeA | AE000292.1 (SEQ ID NO 55) | AAC75069.1 (SEQ ID NO 56) | 2 ? +YeeX | Unknown | 352 aa |

Gene Sequence and Amino Acid Sequence for Further Conformases:

1—pab-402.

Codes for a protein of 463 amino acids of unknown function. Part of a two-gene operon with YicH.

```
="yicE" (SEQ ID NO 18)
   1 msvstlesen aqpvaqtqns eliyrledrp plpqtlfaac
     qhllamfvav itpallicqa
  61 lqlpaqdtqh iismslfasg vasiiqikaw gpvgsgllsi
     qgtsfnfvap limggtalkt
 121 ggadvptmma alfgtlmlas ctemvisrvl hlarriitpl
     vsgvvvmiig lsliqvglts
 181 igggyaamsd ntfgapknll lagvvlalii llnrqrnpyl
     rvaslviama agyalawfmg
 241 mlpesnepmt qelimvptpl yyglgiewsl llplmlvfmi
     tsletigdit atsdvseqpv
 301 sgplymkrlk ggvlanglns fvsavfntfp nscfggnngv
     iqltgvasry vgfvvalmli
 361 vlglfpavsg fvqhipepvl ggatlvmfgt iaasgvrivs
     replnrrail iialslavgl
 421 gvsqqplilq fapewlknll ssgiaaggit aivlnlifpp
     ekq
Gene Sequence (SEQ ID NO 17):
   1 atgtctgttt ccaccctcga gtcagaaaat gcgcaaccgg
     ttgcgcagac tcaaaacagc
  61 gaactgattt accgtcttga agatcgtccg ccgcttcctc
     aaaccctgtt tgccgcctgt
 121 cagcatctgc tggcgatgtt cgttgcggtg atcacgccag
     cgctattaat ctgccaggcg
 181 ctgggtttac cggcacaaga cacgcaacac attattagta
     tgtcgctgtt tgcctccggt
 241 gtggcatcga ttattcaaat taaggcctgg ggtccggttg
     gctccgggct gttgtctatt
 301 cagggcacca gcttcaactt tgttgccccg ctgattatgg
     gcggtaccgc gctgaaaacc
 361 ggtggtgctg atgttcctac catgatggcg gctttgttcg
     gcacgttgat gctggcaagt
 421 tgcaccgaga tggtgatctc ccgcgttctg catctggcgc
     gccgcattat tacgccgctg
 481 gtttctgcg ttgtggtgat gattatcggc ctgtcgctaa
     ttcaggttgg gttaacgtcc
 541 attggcggcg gttacgcagc catgagcgat aacaccttcg
     gcgcaccgaa aaatctgctg
 601 ctggcaggcg tggtcttagc cttaattatc ctgcttaacc
     gtcaacgtaa cccttactta
 661 cgcgtggcct cactggtgat tgcgatggcg gccggatatg
     cgctggcgtg gtttatgggc
 721 atgttgccag aaagcaacga accgatgacg caagaactga
     ttatggtgcc aacgccgctc
 781 tattacgtc ttggcattga atggagtctg ctgctgccgc
     tgatgctggt ctttatgatc
 841 acttcgctgg aaaccattgg cgatatcacg gcgacctctg
     acgtttccga acagccagtg
```

```
 901 tccggtccgc tgtacatgaa acgcctgaaa ggcggcgtgc
     tggcaaacgg cctgaactcg 961 tttgtttcgg cggtgtttaa caccttcccg aactcctgct
     tcgggcaaaa caacggagtg 1021 atccagttga ctggtgttgc cagccgctat gtcggttttg
     tcgtcgcgct gatgttgatc 1081 gtgctgggtc tgttcccggc agtgagcggt tttgtacaac
     acattccaga accggttctg 1141 ggcggcgcaa cgcttgtaat gtttggcacc atcgccgcct
     ccggtgtgcg tatcgtttct 1201 cgtgagccgc tgaaccgtcg ggcgattctg attatcgcgc
     tgtcgctggc ggttggtctg 1261 ggcgtgtctc agcagccgct gattttgcag tttgcccctg
     aatgctgaa aaacctgctc 1321 tcctccggga tcgccgcggg cggtattact gccatcgtgc
     tgaatctgat tttcccacca 1381 gaaaaacagt aa
```

YicH
Unknown function
hypothetical protein.

Deduced protein (569 aa) (SEQ ID NO 58):
```
mkfigkllly iliallvvia glyfllqtrw gaehisawvs          61
ensdyhlafg amdhrfsaps hivlenvtfg rdgqpatlva ksvdialssr qlteprhvdt         121
illengtlnl tdqtaplpfk adrlqlrdma fnspnsewkl saqrvnggvv pwspeagkvl         181
gtkaqiqfsa gslslndvpa tnvliegsid ndrvtltnlg adiargtltg naqrnadgsw         241
qvenlrmadi rlqseksltd ffaplrsvps lqigrlevid arlqgpdwav tdldlslrnm         301
tfskddwqtq egklsmnase fiygslhlfd piinaefspq gvalrqftsr weggmvrtsg         361
nwlrdgktli lddaaiagle ytlpknwqql wmettpgwln slqlkrfsas rnhiididpd         421
tpwqlttldg yganltlvtd hkwgvwsgsa nlnaaaatfn rvdvrrpsla ltansstvni         481
selsaftekg ileatasvsq tpqrqthisl ngrgvpvnil qqwgwpelpl tgdgniqlta         541
sgdiqanvpl kptvsgqlha vnaakqqvtq tmnagvvsss evtstepvq
```

Gene Sequence (SEQ ID NO 57):
```
atgaaattta ttgggaagct gcttctctac attctcatcg          61
ctctgttagt ggtgatcgct ggcctctatt ttcttctgca aacccgctgg ggagcagaac         121
atatcagcgc atgggtttcc gagaatagcg actatcatct ggccttcggg gcgatggatc         181
accgttttc cgcgccatct catatcgtgc tggagaacgt cacgtttggt cgtgatggtc         241
agcccgcgac cctggtggca aaaagtgtcg acattgcgct aagcagtcgc caactgaccg         301
aaccacgcca tgtcgatacc atcctgctgg aaaacgggac gctgaatctc accgaccaga         361
ccgcgccgct accgttcaaa gccgatcgtc tgcaactgcg tgatatggcg tttaatagcc         421
cgaatagcga atggaaactg agcgcgcagc gggtaaatgg cggcgtggtt ccgtggtcac         481
cagaagccgg taaagtgctg ggtacgaagg cgcagattca gtttagtgcc ggatcgcttt         541
cgctcaatga tgttcctgcc accaatgtac tgattgaagg cagtattgat aacgatcgcg         601
ttacgctgac taacctgggt gccgacatcg cccgcgggac attaaccgga aacgcgcagc         661
gtaacgccga cggcagctgg caagtggaaa atctgcgcat ggcggatatc cgtctacaaa         721
gcgaaaaatc gctaaccgac ttctttgcgc cattacgctc tgtcccgtcg ttgcagattg         781
gtcgcctgga agtgatcgat gctcgtttgc aaggtccgga ctgggcggtg accgacctcg         841
atctcagctt gcgcaacatg accttcagta aagatgactg gcagacacaa gaaggcaaac         901
tgtcgatgaa cgctagcgag ttcatttatg gttcgctgca tttatttgac ccgattataa         961
acgcggaatt ttccccgcag ggcgtagcgc tgcgccagtt caccagccgc tgggaagggg        1021
gtatggtcag aacgtcaggg aactggctgc gtgacggaaa aacgttgatc cttgatgatg        1081
cggcaattgc cgggctggaa tataccttgc cgaaaaactg gcaacagttg tggatggaaa        1141
cgacacccgg ttggttaaac agcctgcaac tgaagagatt tagcgccagc cgcaatctga        1201
tcattgatat cgaccctgac ttcccgtggc agctcaccac gctcgatggt tacggtgcca        1261
acctgacgct ggttaccgat cataaatggg gcgtctggag tggctcggcg aatctgaatg        1321
ccgccgccgc gacattcaat cgtgttgatg ttcgtcgccc gtcgctggcc ctgaccgcca        1381
acagcagcac ggtgaatatc agcgaactga gtgcatttac tgaaaaaggc attctggaag        1441
ccactgccag tgtttcacaa acgccacaac gtcagaccca tatcagcctg aatggacgcg        1501
gtgtgccggt gaatattttg caacaatggg gatggcctga attaccgttg actggcgacg        1561
gcaatattca gcttaccgcc agtggcgata ttcaggccaa tgtcccgctg aaacctacgg        1621
ttagcgggca actccatgcc gtgaacgccg caaagcagca agtgactcaa accatgaatg        1681
cgggcgtcgt ttccagtagc gaagttacat cgacagagcc ggtgcagtaa
```

2—pC-402-a
Codes for a protein of previously unknown function. It is only 68 amino acids.

=B2596 (SEQ ID NO 20)
```
  1 mscrffilsv vklkrfsryr shqiwlalry ssskktslpa
    ishkkdsltk sdkimrfssh 61 iltsgtvc
```

-continued

Gene Sequence (SEQ ID NO 19):
```
  1 ttgagctgcc gttttttat tctgtcagtt gtgaaactga
    agcgatttag tcgctatcga 61 tctcatcaaa tatggctcgc tttgagatat tcctcaagta
    aaaaaacatc tcttcctgcg 121 atttctcaca aaaagattc gttgacaaaa agtgacaaaa
    ttatgagatt ttcatcacac 181 attttgacat caggaacggt atgctga
```

There are two further genes on the same operon without a definitely assigned function.

b2595
function Unknown"
hypothetical protein"

Deduced protein: 245 aa (SEQ ID NO 60)
```
  1 mtrmkylvaa atlslflagc sgskeevpdn ppneiyataq
    qklqdgnwrq aitqlealdn 61 rypfgpysqq vqldliyayy knadiplaqa aidrfirlnp
    thpnidyvmy mrgltnmald 121 dsalqgffgv drsdrdpqha raafsdfskl vrgypnsqyt
    tdatkrlvfl kdrlakyeys 181 vaeyyterga wvavvnrveg mlrdypdtqa trdalplmen
    ayrqmqmnaq aekvakiiaa 241 nssnt
```

Gene sequence (SEQ ID NO 59)
```
  1 atgacgcgca tgaaatatct ggtggcagcc gccacactaa
    gcctgttttt ggcgggttgc 61 tcggggtcaa aggaagaagt acctgataat ccgccaaatg
    aaatttacgc gactgcacaa 121 caaaagctgc aggacggtaa ctggagacag gcaataacgc
    aactggaagc gttagataat 181 cgctatccgt ttggtccgta ttcgcagcag gtgcagctgg
    atctcatcta cgcctactat 241 aaaaacgccg atttgccgtt agcacaggct gccatcgatc
    gttttattcg ccttaacccg 301 acccatccga atatcgatta tgtcatgtac atgcgtggcc
    tgaccaatat ggcgctggat 361 gacagtcgcg tgcaagggtt cttggcgtc gatcgtagcg
    atcgcgatcc tcaacatgca 421 cgagctcgt ttagtgactt ttccaaactg gtgcgcggct
    atccgaacag tcagtacacc 481 accgatgcca ccaaacgtct ggtattcctg aaagatcgtc
    tggcgaaata tgaatactcc 541 gtggccgagt actatacaga acgtggcgca tgggttgccg
    tcgttaaccg cgtagaaggc 601 atgttgcgcg actacccgga tacccaggct acgcgtgatg
    cgctgccgct gatggaaaat 661 gcataccgtc agatgcagat gaatgcgcaa gctgaaaaag
    tagcgaaaat catcgccgca 721 aacagcagca atacataa
``` b2597 = yfiA
function = "putative regulator; belongs to the sigma (54) modulation protein family"

Deduced protein: 113 aa (SEQ ID NO 62)
```
  1 mtmnnitskqm eitpairqhv adrtaklekw qthlinphii
    lskepqgfva datintpngv 61 lvasgkhedm ytainelink lerqlnklqh kgearraats
    vkdanfveev eee
```

Gene sequence (SEQ ID NO 61)
```
  1 atgacaatga acattaccag caaacaaatg gaaattactc
    cggccatccg ccaacatgtc 61 gcagaccgtc tcgccaaact ggaaaaatgg caaacacatc
    tgattaatcc acatatcatt 121 ctgtccaaag agccacaagg gtttgttgct gacgccacaa
    tcaatacacc taacggcgtt 181 ctggttgcca gtggtaaaca tgaagatatg tacaccgcaa
    ttaacgaatt gatcaacaag 241 ctggaacggc agctcaataa actgcagcac aaaggcgaag
    cacgtcgtgc cgcaacatcg 301 gtgaaagacg ccaacttcgt cgaagaagtt gaagaagagt
    ag
```

3—pD-402

The protein has 910 amino acids. Described as NADH-Dehydrogenase I chain G: Energy metabolism, carbon: Aerobic respiration. This gene is part of a 14 gene-operon.

=NuoG (SEQ ID NO 22)
```
  1 mlmatihvdg keyevngadn lleaclslgl dipyfcwhpa
    lgsvgacrqc avkqyqnaed 61 trgrlvmscm tpasdgtfis iddeeakqfr esvvewlmtn
    hphdcpvcee ggnchlqdmt 121 vmtghsfrry rftkrthrnq dlgpfishem nrciacyrcv
    ryykdyadgt dlgvygahdn 181 vyfgrpedgt lesefsgnlv eicptgvftd kthserynrk
    wdmqfapsic qqcsigcnis 241 pgerygelrr ienryngtvn hyflcdrgrf gygyvnlkdr
    prqpvqrrgd dfitlnaeqa 301 mqgaadilrq skkvigigsp rasvesnfal relvgeenfy
    tgiahgeqer lqlalkvlre 361 ggiytpalre iesydavlvl gedvtqtgar valavrqavk
    gkaremaaaq kvadwqiaai 421 lnigqrakhp lfvtnvddtr lddiaawtyr apvedqarlg
    faiahaldns apavdgiepe 481 lqskidvivq alagakkpli isgtnagsle viqaaanvak
    alkgrgadvg itmiarsvrn 541 mglgimgggs leealtelet gradavvvle ndlhrhasai
    rvnaalakap lvmvvdhqrt 601 aimenahlvl saasfaesdg tvinnegraq rffqvydpay
    ydsktvmles wrwlhslhst 661 llsrevdwtq ldhvidavva kipelagikd aapdatfrir
    gqklarephr ysgrtamran 721 isvheprqpq didtmftfsm egnnqptahr sqvpfawapg
    wnspqawnkf qdevggklrf 781 gdpgvrlfet sengldyfts vparfqpqdg kwriapyyhl
    fgsdelsqra pvfqsrmpqp 841 yiklnpadaa klgvnagtrv sfsydgntvt lpveiaeglt
    agqvglpmgm sgiapvlaga
```

-continued 901 hledlkeaqq

Gene Sequence (SEQ ID NO 21):
    1 atgctaatgg ctacaattca gtagacggc aaagaatacg
      aggtcaacgg agcggacaac 61 ctgctggaag cttgtctgtc tctgggcctt gatattcctt
      acttttgctg gcatccggcg 121 ctggaagtg tcggtgcttg ccgccagtgt gcggtgaagc
      aataccaaaa cgcggaagac 181 acgcgtggtc gcctggtgat gtcctgtatg acaccggctt
      ccgatggcac ctttatttcc 241 attgacgacg aagaagcgaa acagttccgt gaaagcgtgg
      tcgagtggtt gatgaccaac 302 cacccgcacg actgtccggt atgtgaagag ggcggtaact
      gccatcttca ggatatgact 361 gtgatgaccg acacagctt ccgtcgctac cgtttcacca
      aacgtaccca ccgtaatcag 421 gattttgggc cattcatctc tcacgaaatg aaccgctgca
      tcgcctgcta ccgctgtgtg 481 cgttactaca aagattacgc tgacggtaca gatctgggcg
      tttacggtgc gcacgacaac 541 gtctacttcg gtcgcccgga agacggcacg ctggaaagcg
      aattttccgg taacctggtc 601 gaaatttgcc cgaccggcgt atttaccgac aaaacgcact
      ccgagcgtta caaccgtaaa 661 tgggatatgc agtttgcgcc gagcatctgc cagcaatgtt
      ccatcggctg taacatcagc 721 cccggtgaac gttacggcga actgcgtcgt atcgaaaacc
      gttacaacgg tacggtaaac 781 cactacttcc tctgcgaccg tggtcgtttc ggttacggtt
      acgtcaacct gaaggatcgt 841 ccgcgtcagc cagtacagcg tcgtggcgat gatttcatta
      ccctcaacgc cgaacaggca 901 atgcagggcg cggcagatat tctgcgtcag tcgaagaaag
      tgatcggtat tggttctccg 961 cgtgccagcg tggaaagcaa ctttgcgctg cgtgaactgg
      tgggcgaaga aaacttctac 1021 accggtatcg ctcacggtga gcaggaacgt ctgcaactgg
      cgctgaaagt gctgcgtgaa 1081 ggcggcattt atactccggc tctgcgcgaa atcgaatctt
      acgatgcggt actggtgctg 1141 ggcgaagacg ttacccagac cggcgcgcgc gtcgcgctgg
      cagtgcgtca ggctgtgaaa 1201 ggtaaagcgc gcgaaatggc ggcagcacag aaagtggctg
      actggcagat tgcggcaatc 1261 ctcaacatcg gtcaacgtgc gaagcatccg ctgtttgtta
      ccaacgttga tgacacccgt 1321 ctggatgata tcgcggcgtg gacttaccgc gcaccggttg
      aagatcaggc gcgtttaggt 1381 tttgccatcg cccatgcgct ggataactct gcaccagcgg
      ttgacggtat cgaacctgag 1441 ctgcaaagca aaatcgacgt catcgtgcag gcactggcag
      gtgcgaagaa accgttgatt 1501 atctccggga cgaacgccgg tagcttagag gtgattcagg
      cggcggctaa cgtcgcgaaa 1561 gccctgaaag gtcgcggcgc tgacgtcggt atcaccatga
      ttgcccgttc cgtcaacagc 1621 atggggctgg gcattatggg tggcggttcg cttgaagaag
      cgttaaccga actggaaacc 1681 ggacgcgccg acgcggtggt ggtgttggaa aacgatctgc
      atcgtcacgc ttctgctatc 1741 cgcgtgaatg ctgcgctggc taaagcaccg ctggtgatgg
      tggttgatca tcaacgcaca 1801 gcgattatgg aaaacgccca tctggtactt tctgctgcca
      gctttgctga aagcgacggt 1861 acggtgatca caacgaagg ccgcgcccaa cgtttcttcc
      aggtttacga tcctgcttat 1921 tacgacagca aaactgtcat gctgaaagc tggcgctggt
      tacactcgct gcacagcacc 1981 ctgctgagcc gtgaagtgga ctggacgcag ctcgaccatg
      tgattgacgc tgttgtggcg 2041 aaaatcccgg aactggcagg tatcaaagat gctgcgccgg
      atgcgacatt ccgtattcgt 2101 gggcagaaac tggcccgtga accgcaccgt tacagcggtc
      gtaccgccat gcgcgccaat 2161 atcagcgttc atgagccgcg tcagccgcag gatattgaca
      ccatgttcac cttctcgatg 2221 gaaggtaaca accagccgac tgcgcaccgt tcgcaagtgc
      cgtttgcctg ggcgccgggc 2281 tggaactccc cgcaggcgtg gaacaaattc caggacgaag
      tgggcggcaa actgcgcttt 2341 ggcgatccgg gcgtgcgtct gtttgaaacc agcgaaaatg
      gtctggatta cttcaccagc 2401 gtaccggcac gcttccagcc gcaggacggg aaatggcgta
      tcgcgccgta ttaccacctg 2461 tttggcagcg atgaattgtc acagcgtgct ccggtcttcc
      agagccgtat gccgcagccg 2521 tacatcaaac tcaacccagc ggatgccgca agttgggtg
      tgaacgcagg tacacgcgtc 2581 tcctttagtt acgatggcaa cacggtcacg ctgccggttg
      aaatcgccga aggactgacg 2641 gcagggcagg tgggcttgcc gatgggtatg tccggcattg
      ctccggtgct ggctggcgcg 2701 catcttgagg atctcaagga ggcacaacaa tga 4—pL402.

Codes for a protein of 600 amino acids that part of NADH-dehydrogenase-CD operon (14 genes).

=NuoC (SEQ ID NO 24)
    1 mvnnmtdlta qepawqtrdh lddpvigelr nrfgpdaftv
      qatrtgvpvv wikreqllev 61 gdflkklpkp yvmlfdlhgm derlrthreg lpaadfsvfy
      hlisidrnrd imlkvalaen 121 dlhvptftkl fpnanwyere twdlfgitfd ghpnlrrimm
      pqtwkghplr kdyparatef 181 spfeltkakq dlemealtfk peewgmkrgt enedfmflnl
      gpnhpsahga friviqidge 241 eivdcvpdig yhhrgaekmg erqswhsyip ytdraeylgg
      cvnempyvla veklagitvp -continued

```
301 drvnvirvml selfrinshl lyistfiqdv gamtpvffaf
    tdrqkiydlv eaitgfrmhp 361 awfriggvah dlprgwdrll refldwmpkr lasyekaalq
    ntilkgtsqg vaaygakeal 421 ewgttgaglr atgidfdvrk arpysgyenf dfeipvgggv
    sdcytrvmlk veelrqslri 481 leqclnnmpe gpfkadhplt tpppkertlq hietlithfl
    qvswgpvmpa nesfqmieat 541 kginsyylts dgstmsyrtr vrtpsfahlq qipaairgsl
    vsdlivylgs idfvmsdvdr
```

Gene Sequence (SEQ ID NO 23):
```
   1 atggtgaaca atatgaccga cttaaccgcg caagaacccg
     cctggcagac ccgcgatcat 61 cttgatgatc cggtgattgg cgaactgcgc aaccgttttg
     ggccggatgc ctttactgtt 121 caggcgactc gcaccggggt tcccgttgtg tggatcaagc
     gtgaacaatt actggaagtt 181 ggcgatttct taaagaaact gccgaaacct tacgtcatgc
     tgtttgactt acacggcatg 241 gacgaacgtc tgcgcacaca ccgcgaaggg ttacctgccg
     cggattttc cgttttctac 301 catctgattt ctatcgatcg taaccgcgac atcatgctga
     aggtggcgct ggcagaaaac 361 gacctgcacg taccgacctt caccaaactg ttcccgaacg
     ctaactggta tgagcgtgaa 421 acctgggatc tgtttggcat tactttcgac ggtcacccga
     acctgcgacg catcatgatg 481 ccgcaaacct ggaaaggtca cccgctgcgt aaagattatc
     cggcgcgcgc taccgaattc 541 tcgccgtttg agctgaccaa agccaaacag gatctggaga
     tggaagccct gaccttcaaa 601 ccggaagagt gggggatgaa gcgcggcacc gaaaacgagg
     acttcatgtt cctcaacctc 661 ggtccgaacc accgtcggc gcacggggct ttccgtatcg
     ttttgcaact cgatggcgaa 721 gagattgtcg actgcgtacc agacatcggt taccaccacc
     gtggtgcgga gaaaatgggc 781 gaacgccagt cctggcacag ctacattccg tatactgacc
     gtatcgaata cctcggcggc 841 tgcgttaacg aaatgcctta cgtgctggcg gtagagaaac
     tggccgggat caccgtgccg 901 gatcgcgtta acgtcattcg cgttatgctc tccgaactgt
     tccgcatcaa cagtcacctg 961 ctgtatatct cgacctttat tcaggacgtc ggcgcaatga
     cgccagtgtt cttcgccttt 1021 accgatcgtc agaaaattta cgatctggtg gaagcaatca
     ctggtttccg tatgcacccg 1081 gcgtggttcc gtattggcgg cgtagcgcac gacctgccgc
     gcggctggga tcgcctgctg 1141 cgtgagttcc tcgactggat gccgaaacgt ctggcgtctt
     acgagaaagc ggcgctgcaa 1201 aacaccattc tgaaaggtcg ttcccagggc gttgccgcct
     atggcgcgaa agaggcgctg
```

```
1261 gagtggggca ccactggcgc gggcctgcgt gctaccggga
     tcgacttcga cgtgcgtaag 1321 gcgcgtcctt attctggcta tgaaaacttc gactttgaaa
     tcccggtggg tggtggcgtt 1381 tctgactgct acacccgcgt aatgcttaaa gtggaagagc
     tgcgccagag tctgcgcatt 1441 cttgagcagt gcctcaacaa catgccggaa ggcccgttca
     aagcggatca cccgctgacc 1501 acgccgccgc cgaaagagcg cacgctgcaa catatcgaaa
     ccctgatcac ccacttcctg 1561 caagtgtcgt ggggtccggt gatgcctgcc aatgaatctt
     tccagatgat tgaggcgacc 1621 aaagggatca acagttacta cctgaccagc gacggcagca
     ccatgagtta ccgcacccgt 1681 gttcgtaccc cgagctttgc gcatttgcag caaattccgg
     cggcgatccg cggcagcctg 1741 gtgtctgacc tgattgttta tctgggcagt atcgattttg
     ttatgtcaga tgtggaccgc 1801 taa
```

5—pE402.

Codes for a protein of 337 amino acids implicated in protein synthesis (basic protein).

=Hnr (SEQ ID NO 26)
```
   1 mtqplvgkqi livedeqvfr slldswfssl gattvlaadg
     vdalellggf tpdlmicdia 61 mprmnglkll ehirnrgdqt pvlvisaten madiakalrl
     gvedvllkpv kdlnrlremv 121 faclypsmfn srveeeerlf rdwdamvdnp aaaakllqel
     qppvqqvish crvnyrqlva 181 adkpglvldi aalsendlaf ycldvtragh ngvlaalllr
     alfngllqeq lahqnqrlpe 121 lgallkqvnh llrqanlpgq fpllvgyyhr elknlilvsa
     glnatlntge hqvqisngvp 301 lgtlgnayln qlsqrcdawq cqiwgtggrl rlmlsae
```

Gene Sequence (SEQ ID NO 25):
```
   1 atgacgcagc cattggtcgg aaaacagatt ctcattgttg
     aagatgagca ggtatttcgc 61 tcgcttctgg attcatggtt ttcctcattg ggagcgacaa
     cggtactggc ggctgatggg 121 gtggatgccc ttgagttgct gggaggtttc actccagacc
     tgatgatatg tgatatcgcg 181 atgccacgaa tgaacgggct taaactgctg agcatatac
     gtaacagagg cgaccagacc 241 ccagttctgg tgatatctgc cactgaaaat atggcagata
     ttgccaaagc gttacgtctg 301 ggcgttgaag atgttttgct gaaaccagtt aaagatctga
     atcgcttgcg cgagatggtt 361 tttgcctgtc tctatcccag catgtttaat tcgcgcgttg
     aggaagagga aaggctttt 421 cgcgactggg atgcaatggt tgataaccct gccgcagcgg
     cgaaaattat acaggaacta 481 caaccgccgg ttcagcaggt gatttcccat tgccgggtta
     attatcgtca attggttgcc
```

```
541 gcggacaaac ccggcctggt gcttgatatt gccgcacttt
    cggaaaacga tctggcattt 601 tattgccttg atgtcacccg agctggacat aatggcgtac
    ttgctgcctt gttattacgc 661 gcattgttta acggattatt acaggaacag cttgcacacc
    aaaatcaacg gttgccagag 721 ttgggcgcgt tattgaagca ggtaaaccat ttacttcgtc
    aggccaatct gccggggcag 781 tttccgctat tagttggcta ttatcatcgc gaactgaaaa
    atctcattct ggtttctgcg 841 ggtctgaatg cgacgttaaa taccggcgaa caccaggtgc
    aaaatcagtaa tggtgttccg 901 ttaggcactt taggtaacgc ttatttgaat caattgagcc
    agcgatgcga tgcctggcaa 961 tgccaaatat ggggaaccgg tggtcgactg cgcttgatgt
    tgtctgcaga atga
```

6—pF-402.

Codes for a 232 amino acid involved in flagellar biosynthesis, basal body, outer-membrane L (liposaccharide layer) and ring protein. Part of 14 cistrones/genes operon.

```
=FlgH (SEQ ID NO 28)
  1 mqknaahtya issllvlslt gcawipstpl vqgatsaqpv
    pgptpvangs ifqsaqpiny 61 gyqplfedrr prnigdtlti vlqenvsask sssanasrdg
    ktnfgfdtvp rylqglfgna 121 radveasggn tfngkggana sntfsgtltv tvdqvlvngn
    lhvvgekqia inqgtefirf 181 sgvvnprtis gsntvpstqv adarieyvgn gyineaqnmg
    wlqrfflnls pm Gene Sequence (SEQ ID NO 27):
  1 atgcaaaaaa acgctgcgca tacttatgcc atttccagct
    tgttggtgct ttcactaacc 61 ggctgcgcct ggataccctc cacgccgctg gtgcagggg
    cgaccagtgc acaaccggtt 121 cccggtccga cgcccgtcgc caacggttct attttccagt
    ctgctcagcc gattaactat 181 ggctatcaac cgctgtttga agatcgtcga ccacgcaata
    ttggcgatac gctgaccatc 241 gtgttgcagg agaacgtcag cgccagcaaa agctcctctg
    cgaatgccag ccgtgacggt 301 aaaactaatt ttggctttga tactgtgccg cgctatttgc
    aggggctgtt tggtaacgct 361 cgtgccgatg tcgaagcctc cggtggtaac acgttcaacg
    gaaagggcgg ggccaatgcc 421 agcaataccct ttagcggcac gttgacggtg acggttgacc
    aggtactggt caacggcaac 481 ctgcatgtgg tgggtgaaaa acagattgcc attaatcagg
    gtaccgaatt tattcgcttc 541 tctgcgtgg ttaatccacg cactatcagc ggcagcaata
    ccgtaccgtc tactcaggtg 601 gcggatgcgc gcattgaata cgtaggcaat ggctacatta
    acgaagcgca aaatatgggc 661 tggttgcagc gtttcttcct taacctgtcg ccaatgtaa
```

7—pU2-414.

Codes for 365 amino acids protein that is homologous to *Salmonella* "P-ring of flagella basal body (FlgI). Part of 14 cistrons/genes operon.

It is interesting to note that this gene was discovered using a mutant α-2 (MRE414) which is defective in α-complementation while another member of the same operon (FlgH-pF402), was discovered by complementing BG2 (MRE402) indicating the common link of -conformase network.

```
=FlgI (SEQ ID NO 30)
  1 mikflsalil llvttaaqae rirdltsvqg vrqnsligyg
    lvvgldgtgd qttqtpfttq 61 tlnnmlsqlg itvptgtnmq lknvaavmvt aslppfgrqg
    qtidvvvasm gnakslrggt 121 llmtplkgvd sqvyalaqgn ilvggagasa ggssvqvnql
    nggritngav ierelpsqfg 181 vgntlnlqln dedfsmaqqi adtinrvrgy gsataldart
    iqvrvpsgns sqvrfladiq 241 nmqvnvtpqd akvvinsrtg svvmnrevtl dscavaqgnl
    svtvnrqanv sqpdtpfggg 301 qtvvtpqtqi dlrqsggslq svrssaslnn vvralnalga
    tpmdlmsilq smqsagclra 361 kleii Gene Sequence (SEQ ID NO 29);
  1 gtgattaaat ttctctctgc attaattctt ctactggtca
    cgacggcggc tcaggctgag 61 cgtattcgcg atctcaccag tgttcagggg gtaaggcaaa
    actcactgat tggctatggt 121 ctggtggtgg ggctggatgg caccggtgac cagacaaccc
    agacgccgtt taccacacaa 181 acgcttaata acatgctctc acagctggga attaccgttc
    cgacgggcac caatatgcag 241 ctaaaaaacg tcgctgcggt aatggtgaca gcgtcacttc
    ctccgtttgg acgtcagggg 301 caaaccatcg atgtggtggt ttcttccatg ggaaatgcca
    aaagcttgcg tggaggtacg 361 ttgttgatga caccgcttaa gggcgttgac agtcaggtgt
    atgcgctggc gcagggcaat 421 attctggttg gcggcgcagg agcctccgct ggcggtagca
    gtgttcaggt taaccaactg 481 aacggtgac ggatcaccaa tggtgcggtt attgaacgtg
    aattgcccag ccagtttggc 541 gtcgggaata cccttaattt gcaacttaac gacgaagatt
    tcagcatggc gcagcaaatc 601 gctgacacca tcaaccgcgt cgtggatat ggcagcgcca
    ccgcgttaga tgcgcggact 661 attcaggtgc gcgtaccgag tggcaacagt tcccaggtcc
    gcttccttgc cgatattcag 721 aatatgcagg ttaatgtcac cccgcaggac gctaaagtag
    tgattaactc gcgcaccggt 781 tcggtggtga tgaatcgcga agtgaccctc gacagctgcg
    cggtagcgca ggggaatctc 841 tcagtaacag ttaatcgtca ggccaatgtc agccagccag
    atacaccgtt tggtggtgga 901 cagactgtgg ttactccaca aacgcagatc gatttacgcc
    agagcggcg ttcgctgcaa
```

-continued

```
 961 agcgtacgtt ccagcgccag cctcaataac gtggtgcgcg
     cgctcaatgc gctgggcgct 1021 acgccgatgg atctgatgtc catactgcaa tcaatgcaaa
     gtgcgggatg tctgcgggca 1081 aaactggaaa tcatctga
```

8—pG-402.

Codes for 720 amino acid protein with unknown function.

```
=B0960 (SEQ ID NO 32)
  1 mafmlspllk rytwnsawly yarifaalcg ttafpwwlgd
    vkltipltlg mvaaaltdld 61 drlagrlrnl iitlfcffia sasvellfpw pwlfaigltl
    stsgfillgg lgqryatiaf 121 galliaiytm lgtslyehwy qqpmyllaga vwynvltlig
    hllfpvrplq dnlarcyeql 181 arylelksrm fdpdiedqsq aplydlalan gllmatlnqt
    klslltrlrg drgqrgtrrt 241 lhyyfvaqdi herasssshiq yqtlrehfrh sdvlfrfqrl
    msmqggacqq lsrcillrqp 301 yqhdphfera fthidaaler mrdngapadl lktlgfllnn
    lraidaqlat ieseqaqalp 361 hnndenelad dsphglsdiw lrlsrhftpe salfrhavrm
    slvlcfgyai iqitgmhhgy 421 willtslfvc qpnynatrhr lklriigtlv giaigipvlw
    fvpslegqlv llvitgvlff 481 afrnvqyaha tmfitllvll cfnllgegfe valprvidtl
    igcaiawaav syiwpdwqfr 541 nlprmlerat eancryldai leqyhqgrdn rlayriarrd
    ahnrdaelas vvsnmssepn 601 vtpqireaaf rllclnhtft syisalgahr eqltnpeila
    flddavcyvd dalhhqpade 661 ervnealasl kqrmqqlepr adskeplvvq qvglliallp
    eigrlqrqit qvpqetpvsa Gene Sequence (SEQ ID NO 31):
  1 atggcctta tgctaagtcc tttgctcaaa cgctatacct
    ggaacagcgc ctggctgtat 61 tacgcgcgta ttttttattgc gctttgtgga accacagcgt
    ttccgtggtg gctgggtgat 121 gtaaaactga cgattccgct aacgctgggg atggtggcag
    cggcgctgac cgatctcgat 181 gaccgactgg cgggacgttt gcgtaacctc atcattacgc
    tgttctgctt ttttatcgcc 241 tcggcctcag tagaattgct gttccctgg ccctggctat
    ttgcgattgg cttaacgctc 301 tctaccagcg gcttcatttt gctcggcggt ctgggtcaac
    gctatgcaac aattgccttc 361 ggtgcattgc tgatcgccat ttacactatg ttgggaacat
    cactgtatga gcactggtat 421 cagcagccga tgtatctgct ggccggtgcc gtctggtaca
    acgtcctgac acttattggt 481 catctgctgt tcccggtccg cccgctgcag gacaacctgg
    cgcgttgcta tgaacaactg 541 gcgcgttatc ttgagctcaa gtcgcgcatg tttgatcctg
    atattgaaga tcaaagccag
```

```
 601 gcaccgctgt acgatttggc tctcgccaac ggtctgctga
     tggcgacatt gaatcagacg 661 aaactctcgc tgctgacccg cttacgtggc gatcgtggtc
     aacggggaac gcgtcgcacg 721 ctgcattatt actttgtcgc acaggatatt cacgagcgtg
     ccagctcttc tcatattcag 781 tatcaaacat tgcgtgaaca ttttcgccac agcgacgtgc
     tgttccgttt tcagcggctg 841 atgtcgatgc agggccaggc gtgccagcaa ctgtcacgct
     gtattttgtt gcgtcagcct 901 tatcaacatg atccgcattt tgagcgcgct tttacgcata
     ttgatgctgc gctggagcgg 961 atgcgcgata acggcgcacc cgccgattta ctcaaaacac
     tgggattttt gctgaacaat 1021 ttacgcgcca ttgatgccca actggcaaca attgaatcag
     aacaggccca ggcactaccc 1081 cataataatg acgaaaatga gctcgctgat gacagcccgc
     acggggtgag tgatatctgg 1141 ctgcgtctta gccgtcactt cacgccggaa tccgccctct
     tccgtcatgc ggtaagaatg 1201 tcgctggtgt tgtgcttcgg ctacgccatc attcagataa
     ccggaatgca tcacgggtat 1261 tggatcttgc tgacaagttt gtttgtctgc cagccaaact
     ataacgccac gcgccaccgc 1321 ctgaagttaa ggattattgg tacgctggta ggtatcgcca
     ttggcattcc tgtgctgtgg 1381 tttgtgccat cactggaagg gcagctggtg ctgctggtta
     ttaccggcgt gctcttttt 1441 gccttccgta acgtgcaata cgctcatgca acgatgttca
     tcacacttttt ggtgctactg 1501 tgttttaact tactgggtga aggttttgaa gtagcgttac
     ctcgcgtaat cgatacgctg 1561 attggttgtg ccattgcgtg ggcggcagtg agctacatct
     ggcctgactg gcagtttcgc 1621 aatctgccgc gcatgctcga acgcgccaca gaggccaact
     gtcggtatct cgatgccata 1681 ctggagcaat accatcaggg gcgtgataac cgtctggcgt
     atcgtattgc ccgccgcgat 1741 gcacacaacc gtgatgctga gctggcgtcg gtggtatcaa
     atatgtccag cgagccgaac 1801 gttaccccgc aaattcgcga agccgcgttt cggttgctgt
     gccttaacca tacgtttacc 1861 agctatatct cagccctcgg tgctcaccgg gagcagttaa
     ctaatcctga aattctggcg 1921 tttcttgatg acgcagtttg ctatgttgat gacgcgttac
     atcatcaacc tgctgatgaa 1981 gaacgcgtca atgaggcatt agctagcctg aaacagcgga
     tgcagcaact tgaaccacgg 2041 gcagacagca aagaacctct ggtcgtacaa caagttggat
     tattgattgc attactgcct 2101 gagattggtc gtctgcaacg ccagattact caagttccgc
     aggaaactcc tgtttcggcg 2161 taa
```

There is a further gene, yccF, on the same operon which currently has no ascribed function.

=b0961 = yccF
function = Unknown hypothetical protein

Deduced protein: 148 aa (SEQ ID NO 64)
```
  1 mrtvlnilnf vlggfattlg wllatlvsiv liftlpltrs    60
    cweitklslv pygneaihvd elnpagknvl lntggtvlni fwliffgwwl clmhiatgia
    qcisiigipv gianfkiaai 120 alwpvgrrvv svetaqaare anarrrfe
```

Gene sequence (SEQ ID NO 63)
```
  1 atgcgtaccg ttttgaacat tctgaacttt gtgcttggcg
    gatttgccac cactctgggc 61 tggctgttgg cgactctggt cagtattgtg ctgattttta
    ccttaccgct gacacgatcc 121 tgctgggaga tcactaaact gtctctggtg ccttatggca
    atgaagctat tcatgtcgat 181 gaactgaacc cggctggcaa aaatgtgctg ctgaatactg
    gcggtacggt attgaatatt 241 ttctggctga ttttctttgg ctggtggtta tgcctgatgc
    acattgcaac gggcatcgca 301 caatgtattt caatcattgg cattcctgtc ggcattgcga
    actttaaaat tgccgctatt 361 gcactatggc cggttggtcg tcgcgtggta tcggtagaaa
    cagcgcaagc tgcgcgtgaa 421 gccaatgcac gtcgtcgttt tgaataa
```

9—pI-402.
Codes for a protein of 372 amino acids of unknown function.

=Ybdk. (SEQ ID NO 34)
```
  1 mplpdfhvse pftlgielem qvvnppgydl sqdssmlida
    vknkitagev khditesmle 61 latdvcrdin qaagqfsamq kvvlqaaadh hleicgggth
    pfqkwqrqev cdneryqrtl 121 enfgyliqqa tvfgqhvhvg casgddaiyl lhglsrfvph
    fialsaaspy mqgtdtrfas 181 srpnifsafp dngpmpwvsn wqqfealfrc lsyttmidsi
    kdlhwdirps phfgtvevrv 241 mdtpltlsha vnmagliqat ahwllterpf khkekdylly
    kfnrfqacry glegvitdpy 301 tgdrrplted tlrllekiap sahkigassa iealhrqvvs
    glneaqlmrd fvadggslig 361 lvkkhceiwa gd
```

Gene Sequence (SEQ ID NO 33):
```
  1 atgccattac ccgattttca tgtttctgaa cctttaccc
    tcggtattga actggaaatg 61 caggtggtta atccgccggg ctatgactta agccaggact
    cttcaatgct gattgacgcg 121 gttaaaaata gatcacggc cggagaggta aagcacgata
    tcaccgaaag tatgctggag 181 ctggcgacgg atgtttgccg tgatatcaac caggctgccg
    ggcaattttc agcgatgcag 241 aaagtcgtat tgcaggcagc cgcagaccat catctggaaa
    tttgcggcgg tggcacgcac 301 ccgtttcaga aatggcagcg tcaggaggta tgcgacaacg
    aacgctatca acgaacgctg
```

```
361 gaaaactttg gctatctcat ccagcaggcg accgttttg
    gtcagcatgt ccatgttggc 421 tgtgccagtg gcgatgacgc catttatttg ctgcacggct
    tgtcacggtt tgtgccgcac 481 tttatcgccc tttccgccgc gtcgccatat atgcagggaa
    cggatacgcg ttttgcctcc 541 tcacgaccga atatttttc cgcctttcct gataatggcc
    cgatgccgtg ggtcagtaac 601 tggcaacaat ttgaagccct gtttcgctgt ctgagttaca
    ccacgatgat cgacagcatt 661 aaagatctgc actgggatat tcgcccccagt cctcattttg
    gcacggtgga rgttcgggtg 721 atggataccc cgttaaccct tagcaacgcg gtaaatatgg
    cgggattaat tcaggccacc 781 gccccactggt tactgacaga acgcccgttc aaacataagg
    agaaagatta cctgctgtat 841 aaattcaacc gttttccagge ctgccgstat gggctggaag
    gcgtcattac cgatccgtac 901 actggcgatc gtcgaccact aacggaagac accttgcgat
    tgctggaaaa aatcgcccct 961 tctgcacata aaattggtgc atcgagcgcg attgaggccc
    tgcatcgcca ggtcgtcagc 1021 ggtctgaatg aagcgcagct gatgcgcgat ttcgtcgccg
     atggcggctc gctgattggg 1081 ctggtgaaaa agcattgtga gatctgggcc ggtgactaa
```

There are two further genes, ybdJ and ybdF, on the same operon which currently have no ascribed function.

=ybdJ
Unknown function
Hypothetical protein

Deduced protein: (82 aa) (SEQ ID NO 66)
```
  mkhpletltt aagillmafl sclllpapal gltlaqklvt    60
  tfhlmdlsql ytllfclwfl vlgaieyfvl rfiwrrwfsl ad
```

Gene sequence (SEQ ID NO 65)
```
atgaaacacc ctttagaaac cttgaccacc gcagcaggca     61
ttttgctgat ggctttcctc tcttgcctgc tgctgcccgc ccccgcactg gggcttacgc    121
tggcacaaaa actggtgacc acgttccatc tgatggatct tagtcagctt tacactttat    181
tgttttgtct gtggttttta gtgctgggcg ctattgagta ttttgttctg cgctttatct    241
ggcgacgctg gttctcgctg gcggattaa
``` ybdF
Unknown function
Hypothetical protein

Deduced protein (122 aa) (SEQ ID NO 68):
```
  mdkqslheta krlalelpfv elcwpfgpef dvfkiggkif    60
  mlsselrgvp finlksdpqk sllnqqiyps ikpgyhmnkk hwisvypgee iseallrdli   120
  ndswnlvvdg lakrdqkrvr
```

-continued pg

Gene sequence (SEQ ID NO 67)
```
atggataagc aatcactgca cgaaacggcg aaacgcctgg      60
cccttgagtt acccttttgtc gagctttgct ggccttttgg cccggagttc gatgttttta     120
aaattggcgg caagattttt atgctgtcgt cggagctacg cggcgtcccc tttatcaatc     180
tgaagtccga tccacaaaaa tccctgttaa atcagcaaat ataccaagc attaagccag      240
ggtatcacat gaataaaaag cactggattt cggtgtatcc cggcgaggaa atctccgaag     300
cgttacttcg cgatctgatc aacgattcgt ggaatctggt ggttgatggt ctggctaaac     360
gcgatcaaaa aagagtgcgt ccaggctaa
```

10—pA1-414.

Codes for a protein of 128 of Unknown function. It is conformase 3.
=Yjei
Gene Sequence: (see Conformase 3) (SEQ ID NO 15).

11—pC1E2-414.

Codes for a protein of 200 amino acids of unknown function.

=B1728 (SEQ ID NO 38)
```
  1 msfimtaegh llfsiacavf aknaeltpvl aqgdwwhivp
    sailtcllpd idhpksflgq 61 rlkwiskpia rafghrgfth sllavfalla tfylkvpegw
    fipadalqgm vlgylshila 121 dmltpagvpl lwpcrwrfrl pilvpqkgnq lerficmalf
    vwsvwmphsl pensavrwss 181 qmintlqiqf hrlikhqvey
```

Gene Sequence (SEQ ID NO 37):
```
  1 gtgagttta tcatgacggc ggaaggtcac cttctctttt
    ctattgcttg tgcggtattt 61 gccaaaaatg ccgagctgac gcccgtgctg gcacagggtg
    actggtggca tattgtccct 121 tccgcaatcc tgacgtgttt gttaccggac atcgatcacc
    caaagtcgtt tcttgggcag 181 cgattaaaat ggatatcaaa accgatcgcc cgcgcttttg
    ggcatcgtgg ttttacccac 241 agtctgctga cggtatttgc gctgctggca acctttttacc
    ttaaggttcc ggaaggctgg 301 ttcattccgg ctgatgcgct acaaggaatg gtgctgggtt
    atttgagcca catacttgcc 361 gatatgctga cacccgccgg tgttcccctg ctctggccat
    gccgctggcg tttccgcttg 421 cctatcctgg ttccccaaaa gggcaaccaa ctggaacgtt
    ttatctgcat ggcattattt 481 gtctggtcgg tatggatgcc ccattcatta cccgagaaca
    gcgctgttcg ttggtcatcg 541 caaatgatca ataccttgca gatccagttt catcggctta
    ttaagcatca ggttgaatac 601 taa
```

12—pD1a-M2-414.

Codes for a protein of 287 amino acids of unknown function. Part of an operon of 2 genes.

=B2475 (SEQ ID NO 40)
```
  1 mrwqgrresd nvedrrnssg gpsmggpgfr lpsgkgglil
    livvlvagyy gvdltglmtg 61 qpvsqqqstr sispnedeaa kftsvilatt edtwgqqfek
    mgktyqqpkl vmyrgmtrtg 121 cgagqsimgp fycpadgtvy idlsfyddmk dklgadgdfa
    qgyviahevg hhvqkllgie 181 pkvrqlqqna tqaevnrlsv rmelqadcfa gvwghsmqqq
    gvletgdlee alnaaqaigd 241 drlqqqsqgr vvpdsfthgt sqqryswfkr gfdsgdpaqc
    ntfgksi
```

Gene Sequence (SEQ ID NO 39):
```
  1 atgcgttggc aagggcgacg tgaaagtgac aatgttgaag
    acaggcgcaa cagctctggt 61 ggtccatcta tgggcggtcc cggttttcgc ctgccaagcg
    gtaaaggcgg gctgattta 121 ctgatagtcg tgctggttgc aggctactat ggtgttgatt
    taaccgggtt gatgaccggg 181 cagccggttt cccaacaaca atcaacgcgg tcaattagcc
    caaatgaaga cgaagccgca 241 aaattcacct cggtgattct ggcaaccacg gaagacacct
    ggggacaaca gttcgagaag 301 atgggtaaga cctatcagca accgaagctg gtcatgtacc
    gtggaatgac gcgtaccggc 361 tgcggggcgg gccagtccat aatgggccg ttctattgcc
    cggcggatgg cacggtttat 421 atcgatctct ccttctatga tgacatgaaa gacaaacttg
    gcgcggatgg cgattttgcc 481 caggggtacg ttatcgccca tgaagtcggt catcatgtgc
    agaaactgtt aggcatcgag 541 ccgaaagttc gtcaactgca acaaaacgcg acgcaggcgg
    aagtaaaccg cttatctgtg 601 cgtatggaac tccaggccga ctgttttgcc ggtgtctggg
    ggcatagtat gcagcagcaa 661 ggcgttctgg aaaccggcga tctggaagag gcgctgaacg
    cggcgcaggc catcggcgat 721 gaccgtttac aacagcaaag tcaggggcga gtagtaccag
    acagtttcac tcatggcact 781 tctcagcaac gctacagctg gtttaaacgt ggtttcgaca
    gcggcgatcc ggcacaatgc 841 aatactttg gtaaaagcat ttaa
```

The second gene of this operon is ypfI and the sequence information is given below:

="ypfI"
="b2474"
Unknown function
Hypothetical protein

Deduced protein (671 aa) (SEQ ID NO 70):
```
maeltalhtl taqmkregir rllvlsgeeg wcfehtlklr      60
dalpgdwlwi sprpdaenhc spsalqtllg refrhavfda rhgfdaaafa alsgtlkags     120
wlvlllpvwe ewenqpdads
```

-continued

```
       lrwsdcpdpi atphfvqhlk rvltadneai lwrqnqpfsl       180
       ahftprtdwy patgapqpeq qqllkqlmtm ppgvaavtaa rgrgksalag qlisriagra       240
       ivtapakast dvlaqfagek frfiapdall asdeqadwlv vdeaaaipap llhqlvsrfp       300
       rtlltttvqg yegtgrgfll kfcarfphlh rfelqqpirw aqgcplekmv sealvfdden       360
       fthtpqgniv isafeqtlwq sdpetplkvy qllsgahyrt spldlrrmmd apgqhflqaa       420
       geneiagalw lvdegglsqq lsqavwagfr rprgnlvaqs laahgnnpla atlrgrrvsr       480
       iavhparqre gtgrqliaga lqytqdldyl svsfgytgel wrfwqrcgfv lvrmgnhrea       540
       ssgcytamal lpmsdagkql aerehyrlrr daqalaqwng etlpvdplnd avlsdddwle       600
       lagfafahrp lltslgcllr llqtselalp alrgrlqkna sdaqlcttlk lsgrkmllvr       660
       qreeaaqalf alndvrterl rdritqwqlf h Gene sequence (SEQ ID NO 69)
     1 atggctgaac tgactgcgct tcacacatta acagcgcaaa
       tgaaacgtga agggatccgc 61 cgcttgctgg tgttgagcgg ggaagagggt tggtgttttg
       agcatactct taagttgcgt 121 gatgcctac ctggcgactg gctgtggatt tcgccgcggc
       cagatgctga aaaccactgt 181 tctccctcgg cactacaaac tttacttggg cgcgagttcc
       ggcatgcggt attcgacgcc 241 cgccacggct ttgatgccgc tgcctttgcc gcacttagcg
       aacgttgaa agcgggaagc 301 tggctggttt tgttactccc tgtatgggaa gagtgggaaa
       accaacctga tgccgactcg 361 ctgcgctgga gtgattgccc tgaccctatt gcgacgccgc
       attttgtcca gcatctcaaa 421 cgcgtactta cggcggataa cgaggctatc ctctggcggc
       aaaaccagcc attctcgttg 481 gcgcatttta ctccccgtac tgactggtac cccgcgactg
       gcgcaccaca accagaacaa 541 cagcaactct taaagcagct aatgaccatg ccgccgggcg
       tggcagcggt aacggctgcg 601 cgtgggcgcg gtaagtcggc gttggcaggg caactcattt
       ctcgtattgc gggcagagcg 661 attgtcaccg cgcccgcaaa agcgtcaacg gatgtactgg
       cacaatttgc gggcgagaag 721 tttcgcttta ttgcgccgga tgccttgtta gccagcgatg
       agcaagccga ctggctggtg 781 gtcgatgaag ccgcagccat acctgcgcca ttgttgcatc
       aactggtatc gcgttttcct 841 cgaacgttgt taaccactac ggtgcagggc tacgaaggca
       ccggacgtgg ttttttgctg 901 aaatttgcg ctcgctttcc gcatttacac cgttttgaac
       tgcaacagcc gatccgctgg 961 gcgcagggat gcccgctgga aaaaatggtc agcgaggcac
       tggttttgtttt cgatgaaaac
```

```
  1021 ttcacccata caccacaagg caatattgtc atttccgcat
       ttgaacagac gttatggcaa 1081 agcgatccag aaacgccgtt aaaggtttat cagctcttgt
       ctggtgcgca ctatcggact 1141 tcgccgctgg atttacgccg gatgatggat gcaccagggc
       aacatttttt acaggcggct 1201 ggcgaaaacg agattgccgg ggcgctgtgg ctggtggatg
       agggtggatt atctcaacaa 1261 ctcagtcagg cggtatgggc aggttttcgt cgcccgcggg
       gtaatctggt ggcccagtcg 1321 ctggcggcgc acggcaacaa tccactggcg gcgacattgc
       gtggacggcg ggtcagccgg 1381 atagcagttc atcccggctcg tcagcgggaa ggcacagggc
       ggcaacttat tgctggtgct 1441 ttgcaatata cgcaagacct cgactatctt tcggtgagtt
       ttggttacac cggggagtta 1501 tggcgtttct ggcaacgctg cggttttgtg ctggtgcgga
       tgggtaatca tcgggaagcc 1561 agcagcggtt gctatacggc gatggcgctg ttaccgatga
       gtgatgcggg taaacagctg 1621 gctgaacgtg agcattaccg tttacgtcgc gatgcgcaag
       ctctcgcgca gtggaatggc 1681 gaaacgcttc ctgttgatcc actaaacgat gccgtccttt
       ctgacgacga ctggcttgaa 1741 ctggccggtt ttgctttcgc tcatcgtccg ctattaacgt
       cgttaggttg cttattgcgt 1801 ctgttacaaa ccagtgaact ggcattaccg gcgctgcgtg
       ggcgtttaca gaaaaacgcc 1861 agtgatgcgc agttatgtac cacacttaaa ctttcaggcc
       gcaagatgtt actggtccgt 1921 cagcgggaag aggccgcgca ggcgctgttc gcacttaatg
       atgttcgcac tgagcgtctg 1981 cgcgatcgca taacgcaatg gcaattattt cactga
```

13—pD1b-M2b-414.

Codes for a 356 amino acid protein with unknown function.

```
=Yjfr = f356 (SEQ ID NO 42)
     1 mamskvksit reswilstfp ewgswlneei eqeqvapgtf
       amwwlgctgi wlkseggtnv 61 cvdfwcgtgk qshgnplmkq ghqmqrmagv kklqpnlrtt
       pfvldpfair qidavlathd 121 hndhidvnva aavmqncadd vpfigpktcv dlwigwgvpk
       ercivvkpgd vvkvkdieih 181 aldafdrtal itlpadqkaa gvlpdgmddr avnylfktpg
       gslyhsgdsh ysnyyakhgn 241 ehqidvalgs ygenprgitd kmtsadmlrm gealnakvvi
       pfhhdiwsnf qadpqeirvl 301 wemkkdrlky gfkpfiwqvg gkftwpldkd nfeyhyprgf
       ddcftiepdl pfksfl Gene Sequence (SEQ ID NO 41):
     1 atggcgatga gtaaagtgaa agtatcacc cgtgaatcct
       ggatcctgag cacttttccg
```

-continued

```
  61 gagtggggta gctggttgaa tgaagaaatt gaacaagaac
     aggtcgctcc tggcacattt 121 gcgatgtggt ggcttggctg caccgggatc tggttgaaat
     cggaaggtgg caccaacgtt 181 tgcgttgatt tctggtgcgg cactggcaaa caaagtcacg
     gtaacccgtt aatgaaacag 241 ggtcaccaga tgcagcgcat ggctggcgtg aaaaaactgc
     agccaaacct gcgtaccacc 301 ccgtttgttc ttgatccgtt tgcgattcgc cagatcgacg
     cggtactggc gactcacgat 361 cacaacgatc atatcgacgt taacgtcgct gctgccgtga
     tgcagaattg tgcagatgac 421 gtaccgttta tcgaccgaa aacctgtgtg gatttgtgga
     ttggctgggg cgtaccgaaa 481 gagcgttgca tcgtggtcaa accgggcgat gtagtaaaag
     tgaaagacat tgaaattcat 541 gcgcttgatg ctttcgaccg tactgcactg atcaccctgc
     ctgccgatca aaaagcggct 601 ggcgtactgc cagatggcat ggacgatcgc gcggtgaact
     acctgttcaa aacgcctggc 661 ggctccctgt atcacagcgg cgactccac tactctaact
     attatgcgaa gcacggtaac 721 gaacatcaga tcgacgtggc gttaggatcg tacggcgaaa
     acccgcgcgg tatcaccgac 781 aaaatgacca gcgccgatat gctgcgtatg ggtgaagcgc
     tgaatgcgaa agtagtgatc 841 ccgttccacc acgatatctg gtcaaacttc caggccgatc
     cgcaagagat ccgcgtgctg 901 tgggagatga aaaagatcg cctgaagtat ggcttcaagc
     cgttatctg gcaggtgggt 961 ggcaaattta cctggccgct ggataaagac aacttcgagt
     accactatcc gcgcggtttc 1021 gatgattgct tcactattga accggatctg ccgttcaagt
     cattcctgta a
```

14—pM1-414

Codes for a protein of 847 amino acids with possible role in osmotic adaptation; membrane glycosyltransferase; synthesis of membrane-derived oligosaccharide (MDO). Part of a 2 gene-operon.

```
=MdoH (SEQ ID NO 44)
   1 mnktteyida mpiaasekaa lpktdiravh qaldaehrtw
     areddspqgs vkarleqawp 61 dsladgqlik ddegrdqlka mpeakrssmf pdpwrtnpvg
     rfwdrlrgrd vtprylarlt 121 keeqeseqkw rtvgtirryi lliltlaqtv vatwymktil
     pyqgwalinp mdmvgqdlwv 181 sfmqllpyml qtgililfav lfcwvsagfw talmgflqll
     igrdkysisa stvgdeplnp 241 ehrtalimpi cnedvnrvfa glratwesvk atgnakhfdv
     yilsdsynpd icvaeqkawm 301 eliaevggeg qifyrrrrrr vkrksgnidd fcrrwgsqys
     ymvvldadsv mtgdclcglv
```

```
 361 rlmeanpnag iiqsspkasg mdtlyarcqq fatrvygplf
     taglhfwqlg eshywghnai 421 irvkpfiehc alaplpgegs fagsilshdf veaalmrrag
     wgvwiaydlp gsyeelppnl 481 ldelkrdrrw chgnlmnfrl flvkgmhpvh ravfltgvms
     ylsaplwfmf lalstalqvv 541 haltepqyfl qprqlfpvwp qwrpelaial fastmvllfl
     pkllsilliw ckgtkeyggf 601 wrvtlsllle vlfsvllapv rmlfhtvfvv saflgwevvw
     nspqrdddst swgeafkrhg 661 sqlllglvwa vgmawldlrf lfwlapivfs lilspfvsvi
     ssratvglrt krwklflipe 721 eysppqvlvd tdrflemnrq rslddgfmha vfnpsfnala
     tamatarhra skvleiardr 781 hveqalnetp eklnrdrrlv llsdpvtmar lhfrvwnspe
     rysswvsyye giklnplalr 841 kpdaasq Gene Sequence (SEQ ID NO 43):
   1 atgaataaga caactgagta cattgacgca atgcccatcg
     ccgcaagcga aaagcggca 61 ttgccgaaga ctgatatccg cgccgttcat caggcgctgg
     atgccgaaca ccgcacctgg 121 gcgcgggagg atgattcccc gcaaggctcg gtaaaggcgc
     gtctggaaca agcctggcca 181 gattcacttg ctgatggaca gttaattaaa gacgacgaag
     ggcgcgatca gctgaaggcg 241 atgccagaag caaaacgctc ctcgatgttt cccgacccgt
     ggcgtaccaa cccggtaggc 301 cgtttctggg atcgcctgcg tggacgcgat gtcacgccgc
     gctatctggc tcgtttgacc 361 aaagaagagc aggagagcga gcaaaagtgg cgtaccgtcg
     gtaccatccg ccgttacatt 421 ctgttgatcc tgacgctcgc gcaaactgtc gtcgcgacct
     ggtatatgaa gaccattctt 481 ccttatcagg gttgggcgct gattaatcct atggatatgg
     ttggtcagga tttgtgggtt 541 tcctttatgc agcttctgcc ttatatgctg caaaccggta
     tcctgatcct cttttgcggta 601 ctgttctgtt gggtgtccgc cggattctgg acggcgttaa
     tgggcttcct gcaactgctt 661 attggtcgcg ataaatacag tatatctgcg tcaacagttg
     gcgatgaacc attaaacccg 721 gagcatcgca cggcgttgat catgccctatc tgtaacgaag
     acgtgaaccg tgtttttgct 781 ggcctgcgtg caacgtggga atcagtaaaa gccaccggga
     atgccaaaca ctttgatgtc 841 tacattctta gtgacagtta taacccggat atctgcgtcg
     cagagcaaaa agcctggatg 901 gagcttatcg ctgaagtcgg tggcgaaggt cagattttct
     atcgccgccg ccgtcgccgc 961 gtgaagcgta aaagcggtaa tatcgatgac ttctgccgtC
     gctggggcag ccagtacagc 1021 tacatggtgg tgctggatgc tgactcggta atgaccggtg
     attgtttgtg cgggctggtg
```

-continued

```
1081 cgcctgatgg aagccaaccc gaacgccggg atcattcagt
     cgtcgccgaa agcgtccggt 1141 atggatacgc tgtatgcgcg ctgtcagcag ttcgcgaccc
     gcgtgtatgg gccactgttt 1201 acagccggtt tgcacttctg gcaacttggc gagtcgcact
     actgggggaca taacgcgatt 1261 atccgcgtga aaccgtttat cgagcactgc gcactggctc
     cgctgccggg cgaaggttcc 1321 tttgccggtt caatcctgtc acatgacttc gtggaagcgg
     cgttgatgcg ccgtgcaggt 1381 tgggggggtct ggattgctta cgatctcccg ggttcttatg
     aagaattgcc gcctaacttg 1441 cttgatgagc taaaacgtga ccgccgatgg tgccacggta
     acctgatgaa cttccgtctg 1501 ttcctggtga agggtatgca cccggttcac cgtgcggtgt
     tcctgacggg cgtgatgtct 1561 tatctctccg ctccgctgtg gtttatgttc ctcgcgctct
     ctactgcatt gcaggtagtg 1621 catgcgttga ccgaaccgca atacttcctg caaccacggc
     agttgttccc agtgtggccg 1681 cagtggcgtc ctgagctggc gattgcactt tttgcttcga
     ccatggtgct gttgttcctg 1741 ccgaagttat tgagcatttt gcttatctgg tgcaaaggaa
     cgaaagaata cggcggcttc 1801 tggcgcgtta cattatcgtt gctgctggaa gtgctttttt
     ccgtgctgct ggctccggta 1861 cgcatgctgt tccatacggt cttcgttgtc agcgcgttcc
     ttggctggga agtggtgtgg 1921 aattcaccgc agcgtgatga tgactccact tcctggggtg
     aagcgttcaa acgccacggc 1981 tcacagctgc tgttagggtt agtgtgggct gttgggatgg
     cgtggctgga tctgcgtttc 2041 ctgttctggc tggcaccgat tgtcttctcg ttgatcctgt
     caccgtttgt ttcggtgatt 2101 tccagccgtg ccaccgttgg tctgcgcacc aaacgctgga
     aactgttcct gatcccggaa 2161 gagtattcgc cgccgcaggt gctggttgat accgatcggt
     tccttgagat gaatcgtcaa 2221 cgctcccttg atgatggctt tatgcacgca gtgtttaacc
     cgtcatttaa cgctctggca 2281 accgcaatgg cgaccgcgcg tcaccgcgcc agtaaggtgc
     tggaaatcgc ccgtgaccgc 2341 cacgttgaac aggcgctgaa cgagacgcca gagaagctga
     atcgcgatcg tcgcctggtg 2401 ctgctaagcg atccggtgac gatggcccgt ctgcatttcc
     gtgtctggaa ttccccggag 2461 agatattctt catgggtgag ttattacgaa gggataaagc
     tcaatccact ggcattgcgt 2521 aaaccggatg cggcttcgca ataa
```

15—pO1a-414.

Codes for a protein of 434 amino acids with possible role in transport. Part of operon of 18 genes.

=Yhft (SEQ ID NO 46)

```
  1 mdlyiqiivv acltgmtsll ahrsaavfhd girpilpqli
    egymnrreag siafglsigf 61 vasvgisftl ktgllnawll flptdilgvl ainslmafgl
    gaiwgvlilt cllpvnqllt 121 alpvdvlgsl gelsspvvsa falfplvaif yqfgwkqsli
    aavvvlmtrv vvvryfphln 181 pesieifigm vmllgiaith dlrhrdendi dasglsvfee
    rtsriiknlp yiaivgalia 241 avasmkifag sevsiftlek aysagvtpeq sqtlinqaal
    aefmrglgfv pliattalat 301 gvyavagftf vyavdylspn pmvaavlgav visaevlllr
    sigkwlgryp svrnasdnir 361 namnmlmeva llvgsifaai kmagytgfsi avaiyflnes
    lgrpvqkmaa pvvavmitgi 421 llnvlywlgl fvpa
```

Gene Sequence (SEQ ID NO 45):

```
  1 atggatctgt atattcagat tatcgtggtg gcgtgcctga
    cgggtatgac atcgcttctg 61 gcgcatcgct cggcggctgt ttttcatgac ggcatccgcc
    cgatcctgcc gcaactgatt 121 gaaggctata tgaaccgtcg cgaggcgggg agtatcgctt
    ttggtctgag cattggtttt 181 gtggcctcgg tggggatctc ttttaccctg aaaaccgggc
    tgctcaacgc atggttactc 241 tttcttccta ccgatatcct cggcgtcctg gcgataaaca
    gcctgatggc gtttggtctt 301 ggcgctatct ggggcgtgtt gatccttact tgcctgttgc
    cagtaaacca gctgctgacc 361 gcgctgccgg tggatgtatt aggtagcctg ggggaattaa
    gctcgccggt ggtttcagct 421 tttgcactgt tcccgctggt ggcgattttc taccagtttg
    gctggaagca aagtctgatc 481 gccgccgtgg tggtactgat gacccgtgtg gtagtcgtgc
    gctatttccc acatcttaac 541 cctgaatcca tcgaaatctt tattggcatg gtgatgctgc
    tggggatcgc gataactcac 601 gacctgcgtc atcgtgatga aaatgacatt gatgccagcg
    ggctttcggt gttttgaagaa 661 cgcacgtcac ggattatcaa aaacttaccc tatatcgcca
    tcgtgggagc attgattgcc 721 gccgttgcca gcatgaagat ttttgctggc agtgaagtgt
    cgatcttcac actggagaaa 781 gcatattccg caggcgtaac gccggaacaa tcgcaaacgc
    tgattaatca ggcggctctg 841 gcagaattta tgcgcggact ggggtttgtg ccgttgattg
    ccaccaccgc gttagcaacg 901 ggtgtgtatg cagttgcggg ctttacctt gtttatgcgg
    tggactatct ctcgccgaat 961 ccgatggttg cagcggtatt aggcgcagtg gttatttcgg
    cggaagtctt gctgcttcgt 1021 tcgatcggca aatggctggg acgctacccg tcggtgcgta
     atgcgtcgga taacatccgt 1081 aacgccatga atatgctgat ggaagtggcg ctgctggtcg
     gttcgatttt cgcagcaatt
```

```
1141 aagatggcgg gttataccgg attctctatc gcggttgcca
     tttacttcct caacgaatcc 1201 ctgggccgtc cggtacagaa aatggcggca ccggtcgtgg
     cagtaatgat caccggtatt 1261 ctgctgaatg ttctttactg gcttggcctg ttcgttccgg
     cttaa
```

16—pO1b414.

Codes for a possible regulator 238 amino acid protein; Global regulatory functions" product="negative response regulator of genes in aerobic pathways, (sensors, ArcB and CpxA)".

```
=ArcA (SEQ ID NO 48)
  1 mqtphilive delvtrntlk sifeaegydv featdgaemh
    qilseydinl vimdinlpgk 61 nglllarelr eqanvalmfl tgrdnevdki lgleigaddy
    itkpfnprel tirarnllsr 121 tmnlgtvsee rrsvesykfn gweldinsrs ligpdgeqyk
    lprseframl hfcenpgkiq 181 sraellkkmt grelkphdrt vdvtirrirk hfestpdtpe
    iiatihgegy rfcgdled Gene Sequence (SEQ ID NO 47):
  1 atgcagaccc gcacacattct tatcgttgaa gacgagttgg
    taacacgcaa cacgttgaaa 61 agtattttcg aagcggaagg ctatgatgtt ttcgaagcga
    cagatggcgc ggaaatgcat 121 cagatcctct ctgaatatga catcaacctg gtgatcatgg
    atatcaatct gccgggtaag 181 aacggtcttc tgttagcgcg tgaactgcgc gagcaggcga
    atgttgcgtt gatgttcctg 241 actggccgtg acaacgaagt cgataaaatt ctcggcctcg
    aaatcggtgc agatgactac 301 atcaccaaac cgttcaaccc gcgtgaactg acgattcgtg
    cacgcaacct actgtcccgt 361 accatgaatc tgggtactgt cagcgaagaa cgtcgtagcg
    ttgaaagcta caagttcaat 421 ggttgggaac tggacatcaa cagccgttcg ttgatcggcc
    ctgatggcga gcagtacaag 481 ctgccgcgca gcgagttccg cgccatgctt cacttctgtg
    aaaacccagg caaaattcag 541 tcccgtgctg aactgctgaa gaaaatgacc ggccgtgagc
    tgaaaccgca cgaccgtact 601 gtagacgtga cgatccgccg tattcgtaaa catttcgaat
    ctacgccgga tacgccggaa 661 atcatcgcca ccattcacgg tgaaggttat cgcttctgcg
    gtgatctgga agattaa
```

17—pQ1-414.

Codes for a protein of 421 amino acid protein with possible involvement in outer membrane integrity and Colicin-related functions. Part of an operon of 4 genes.

```
=tolA (SEQ ID NO 50)
  1 mskateqndk lkraiiisav lhvilfaali wssfdeniea
    saggggssi davmvdsgav 61 veqykrmqsq essakrsdeq rkmkeqqaae elrekqaaeq
    erlkqleker laaqeqkkqa 121 eeaakqaelk qkqaeeaaak aaadakakae adakaaeeaa
    kkaaadakkk aeaeaakaaa 151 eaqkkaeaaa aalkkkaeaa eaaaaearkk aateaaekak
    aeaekkaaae kaaadkkaaa 241 ekaaadkkaa ekaaaekaaa dkkaaaekaa adkkaaaaka
    aaekaaaaka aaeaddifge 301 lssgknapkt gggakgnnas pagsgntknn gasgadinny
    agqiksaies kfydassyag 361 ktctlrikla pdgmlldikp eggdpalcqa alaaaklaki
    pkppsqavye vfknapldfk 421 p Gene Sequence (SEQ ID NO 49):
  1 gtgtcaaagg caaccgaaca aaacgacaag ctcaagcggg
    cgataattat ttcagcagtg 61 ctgcatgtca tcttatttgc ggcgctgatc tggagttcgt
    tcgatgagaa tatagaagct 121 tcagccggag gcggcggtgg ttcgtccatc gacgctgtca
    tggttgattc aggtgcggta 181 gttgagcagt acaaacgcat gcaaagccag gaatcaagcg
    cgaagcgttc tgatgaacag 241 cgcaagatga aggaacagca ggctgctgaa gaactccgtg
    agaaacaagc ggctgaacag 301 gaacgcctga agcaacttga gaaagagcgg ttagcggctc
    aggagcagaa aaagcaggct 361 gaagaagccg caaaacaggc cgagttaaag cagaagcaag
    ctgaagaggc ggcagcgaaa 421 gcggcggcag atgctaaagc gaaggccgaa gcagatgcta
    aagctgcgga agaagcagcg 481 aagaaagcgg ctgcagacgc aaagaaaaaa gcagaagcag
    aagccgccaa agccgcagcc 541 gaagcgcaga aaaaagccga ggcagccgct gcggcactga
    agaagaaagc ggaagcggca 601 gaagcagctg cagctgaagc aagaaagaaa gcggcaactg
    aagctgctga aaaagccaaa 661 gcagaagctg agaagaaagc ggctgctgaa aaggctgcag
    ctgataagaa agcggcagca 721 gagaaagctg cagccgacaa aaaagcagca gaaaaagcgg
    ctgctgaaaa ggcagcagct 781 gataagaaag cagcggcaga aaaagccgcc gcagacaaaa
    aagcggcagc ggcaaaagct 841 gcagctgaaa aagccgctgc agcaaaagcg gccgcagagg
    cagatgatat tttcggtgag 901 ctaagctctg gtaagaatgc accgaaaacg gggggagggg
    cgaaagggaa caatgcttcg 961 cctgccggga gtggtaatac taaaaacaat ggcgcatcag
    gggccgatat caataactat 1021 gccgggcaga ttaaatctgc tatcgaaagt aagttctatg
     acgcatcgtc ctatgcaggc 1081 aaaacctgta cgctgcgcat aaaactggca cccgatggta
     tgttactgga tatcaaacct 1141 gaaggtggcg atcccgcact tgtcaggct gcgttggcag
     cagctaaact tgcgaagatc
```

18—pB2-414.

Codes for a protein (Periplasmic protein torT) of 342 amino acids. Part of an operon of 3 genes.

```
=TorT (SEQ ID NO 52)
  1 mrvllfllls lfmlpafsad nllrwhdaqh ftvqastplk
    akrawklcal ypslkdsywl 61 slnygmqeaa rrygvdlkvl eaggysqlat qqaqidqckq
    wgaeaillgs sttsfpdlqk 121 qvaslpviel vnaidapqvk srvgvpwfqm gyqpgrylvq
    wahgkplnvl lmpgpdnagg 181 skemvegfra aiagspvriv dialgdndie iqrnhlqeml
    erhpeidvva gtaiaaeaam 241 gegrnlktpl tvvsfylshq vyrglkrgrv imaasdqmvw
    qgelaveqai rqlqgqsvsd 301 nvsppilvlt pknadrehir rslspggfrp vyfyqhtsaa
    kk Gene Sequence (SEQ ID NO 51):
  1 atgcgcgtac tgctatttt acttctttcc cttttcatgt
    tgccggcatt ttcggctgat 61 aacctgttgc gctggcatga tgcgcagcat ttcacggtgc
    aagcctctac gccgcttaaa 121 gccaaacgcg catggaaact gtgcgcgctt tatcccagcc
    tgaaagattc atattggtta 181 tcgttgaact atggtatgca ggaggctgct cgccgctacg
    gtgtggattt aaaagtgctg 241 gaggcaggcg gctacagcca gttggctacc cagcaagcac
    aaatcgacca gtgtaaacag 301 tggggcgcag aggccatttt gctcggtagt agcacgacct
    catttcccga cctgcaaaag 361 caggtagcaa gtctgccggt gatcgaactg gtaaatgcta
    ttgatgctcc ccaggtgaaa 421 agccgcgttg gtgtgccctg gtttcagatg ggctatcaac
    cggggcgata tctggtgcaa 481 tgggcgcacg gtaaaccact gaatgtgctg ttgatgcccg
    gacccgataa cgccggggc 541 agtaaggaga tggtcgaggg ttttcgcgca gccattgccg
    gaagcccggt gcgtattgtt 601 gatattgcgc ttggtgataa cgatattgaa atccagcgta
    acctgttgca ggagatgctg 661 gaacgccatc cagaaatcga cgtcgttgcc ggaacggcca
    ttgcggcaga ggcggcaatg 721 ggggaagggc gtaacctgaa aacgccgctt accgtggtgt
    cgttttatct ttcacatcag 781 gtgtatcgcg ggctgaagcg gggaagagtg attatggctg
    ccagcgatca aatggtctgg 841 caggggaac tggcggttga gcaggccatc aggcaattac
    aggggcaatc ggtttctgat 901 aatgtcagcc caccgatttt agttctgacg ccgaaaaatg
    ccgaccgtga acatattcgc
```

```
961 cgctcgctgt caccagggg atttcgtccg gtctattttt
    atcagcacac atcagcggct 1021 aagaaataa
```

19—pK2-414.

Codes for a putative alpha helix protein of 131 amino acid of unknown function. Part of an operon of 2 genes.

```
=YeeX (SEQ ID NO 54)
  1 mlaltnsgcl nesdshiirg ikmettkpsf qdvlefvrlf
    rrknklqrei qdvekkirdn 61 qkrvllldnl sdyikpgmsv eaiqgiiasm kgdyedrvdd
    yiiknaelsk errdiskklk 121 amgemkngea k Gene Sequence (SEQ ID NO 53):
  1 atgttggccc taacgaatag cggttgctta aacgaatccg
    actctcacat tatcagggt 61 ataaaaatgg aaactaccaa gccttcattc caggacgtac
    tggaatttgt tcgtctgttc 121 cgtcgtaaga acaaactgca acgtgaaatt caggacgttg
    agaaaaagat ccgtgacaac 181 cagaagcgcg tcctgctgct ggacaacctg agcgattaca
    tcaagcccgg gatgagcgtt 241 gaagcaatcc agggcatcat cgccagcatg aaaggtgact
    atgaagatcg cgttgacgat 301 tacatcatca aaaatgccga gctctccaaa gaacgccgcg
    atatctccaa aaagctgaaa 361 gctatgggcg aaatgaaaaa cggcgaagcg aagtaa
```

20—pK2b-414.

Codes for a protein of 352 amino acid of unknown function. Part of an operon of 2 genes.

```
=YeeA (SEQ ID NO 56)
  1 mradkslspf eirvyrhyri vhgtrvalaf litfliirlf
    tipestwplv tmvvimgpis 61 fwgnvvpraf eriggtvlgs ilglailqle lislplmlvw
    caaamflcgw lalgkkpyqg 121 lligvtlaiv vgsptgeidt alwrsgdvil gsllamlftg
    iwpqrafihw riqlakslte 181 ynrvyqsafs pnllerprle shlqklltda vkmrgliapa
    sketripksi yegiqtinrn 241 lvcmlelqin aywatrpshf vllnaqklrd tqhmmqqill
    slvhalyegn pqpvfantek 301 lndaveelrq llnnhhdlkv vetpiygyvw lnmetahqle
    llsnlicral rk Gene Sequence (SEQ ID NO 55):
  1 gtgcgtgccg ataagtcatt aagcccgttt gaaatccggg
    tataccgcca ttaccgcatt 61 gtgcatggta ctcgggtcgc gctggcattc ctgctcactt
    ttctcattat ccgcctgttt 121 actatcccgg aaagcacctg gccgctggtc accatggtgg
    tgattatggg gccaatctcg 181 ttctgggta acgttgtccc tcgcgccttt gagcgtattg
    gcggtacggt gttgggtcg
```

-continued

```
241 attttaggtc ttatcgctct gcaactggag ttaatctcgt
    taccgctgat gttagtctgg 301 tgcgcggcgg ccatgttcct ttgcggttgg ctggcgctgg
    gcaagaaacc gtatcaaggt 361 ttattgattg gggtgacgct ggcaattgtt gtgggttccc
    cgacaggtga aattgatacg 421 gcgttatggc gaagcggcga tgtgatcctc ggctctttac
    tggcaatgtt gtttaccggt 481 atctggccac aacgggcgtt catccactgg cgcattcaac
    tggcgaaaag tctgaccgag 541 tataatcggg tctatcaatc tgcattctca ccgaacttac
    tcgaacgccc acgtctggaa 601 agccatctac aaaaactcct gaccgatgcc gtgaaaatgc
    gtggactgat tgcgcccgcc 661 agcaaagaaa cccgtattcc aaaatcgata tatgaaggta
    tccagaccat taaccgcaat 721 ctggtttgta tgctggagtt gcaaatcaat gcatactggg
    ccacgcgccc cagccatttc 781 gtgttattga acgcgcaaaa acttcgtgat acccagcaca
    tgatgcagca aatactgctg 841 agccttgttc atgcgctgta cgaaggtaat ccgcagccgg
    tttttgccaa tacggaaaaa 901 ttgaacgatg ctgtggaaga gctgcgtcag ttgctcaata
    accaccatga cctgaaggtt 951 gtggaaacac caatctatgg ttatgtgtgg ctgaacatgg
    aaacggcgca tcagcttgag 1021 ttgctataga atctgatttg ccgggccttg cgcaaataa
```

Example 4

Figure 6:
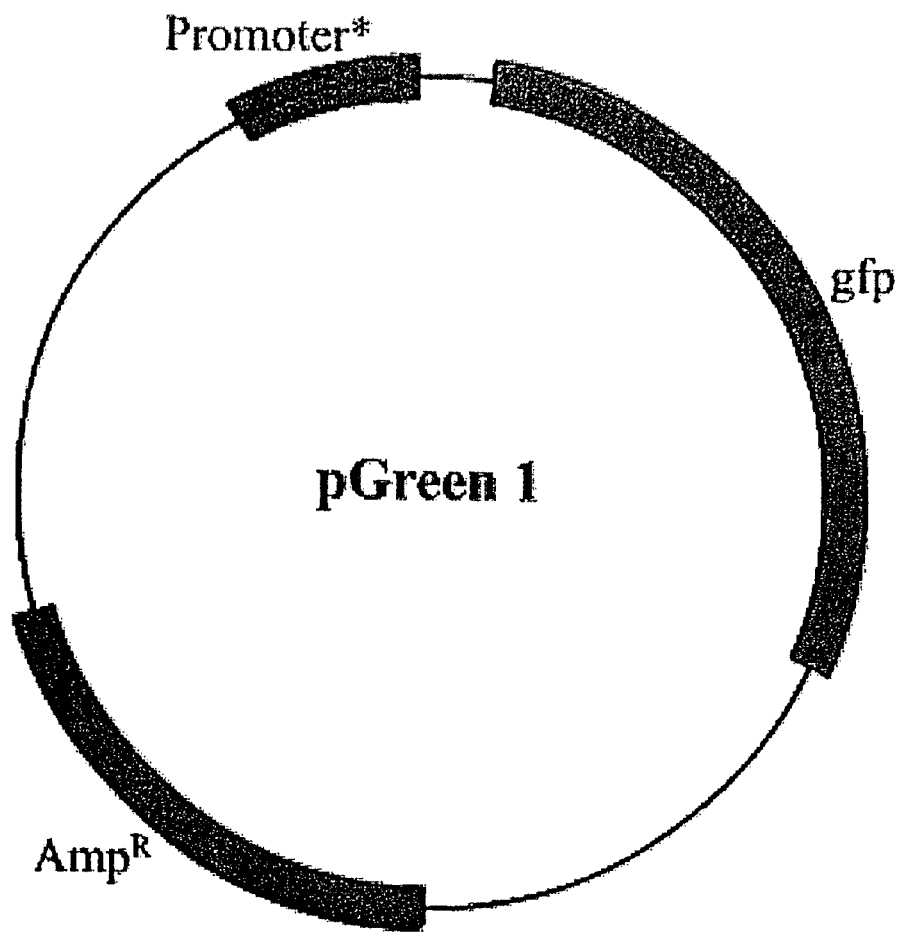
FIG. 6 is a diagrammatic representation of the reporter-3 plasmid that expresses green fluorescent protein constitutively. This plasmid (pGreen1) was isolated from bacterial cells expressing the green fluorescence protein without the IPTG induction.
Figure 7:
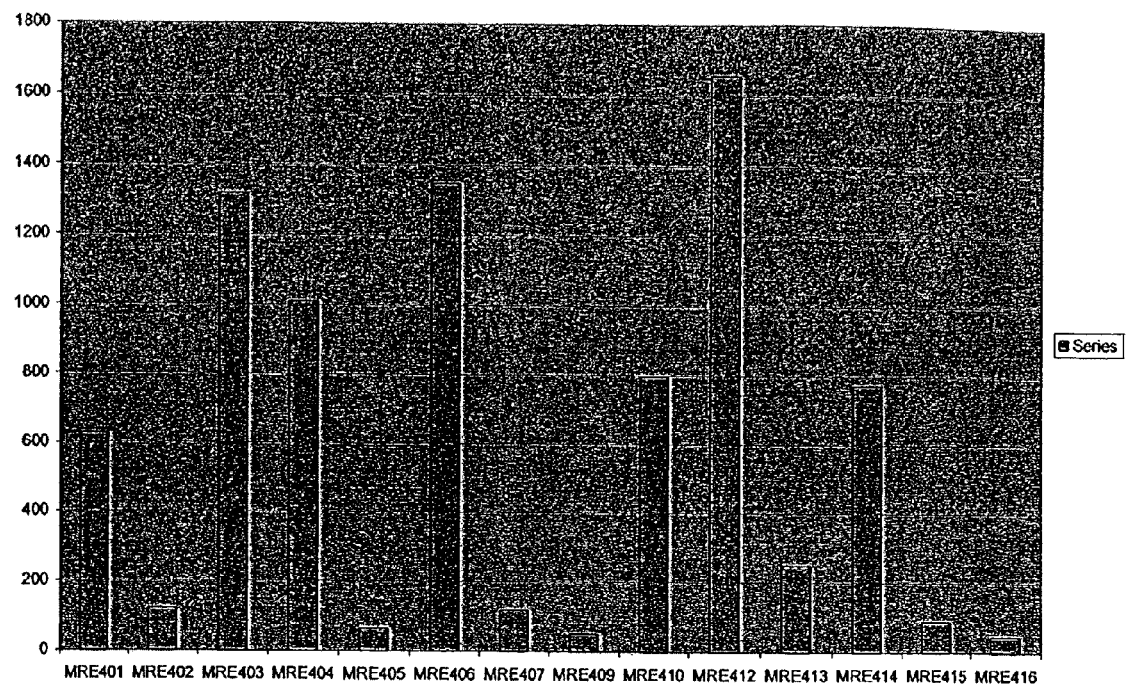
FIG. 7 is a graph showing folding potential of different strains using reporter-3 (GFP) as an indicator. The y axis in this graph shows the relative fluorescent intensity at 510 nm per $10^9$ cells.

Evaluation of the Folding Ability of Our Engineered Folding-Compromised Mutants as Well as Some Other Lab Strains We have used a visual as well as a quantitative assay to measure the efficiency of folding by measuring the quantitative fluorescence of a folding reporter (reporter 3), using pGreen1 (FIG. 6). We isolated pGreen1 as a constitutive variant of pGreen-TIR (Miller and Lindow, 1997 Gene 191 (2): 149-153). The reporter plasmid, pGreen1 uses the fluorescence emitting from green fluorescence protein as indication of the folding ability of the strain.
The Protocol is as Described by Miller and Lindow, Supra.
By transforming pGreen-1 in some of our characterized mutants that were moved to the K37 background, we managed to evaluate the fluorescence in these mutants relative to the wild type strain (K37), identified herein as MRE403.
As expected, our mutants (MRE401, MRE402 and MRE414) gave lower fluorescence than the wild type strain background they were moved into (see FIG. 7).
Also, several lab-strains were compared and they exhibited a wide range of activity. Interestingly some of the E. coli strains used routinely in protein expression were very poor in their folding potential. Commercially available strains which on our testing appeared to have compromised folding ability include BL21 (Novagen), BL21.DE3 (Novagen) and XL1-Blue (Stratagene): referred to in our tests as MRE408, MRE409 and MRE411 respectively.

Example 5

Strategy to Generate New Constitutive Expression Vectors With Compatible Replication Origin These vectors will allow the expression of conformases without the need to use expensive inducers (e.g. IPTG). They will also have more general utility in research into protein-protein interactions and as a low copy number plasmid providing constitutive expression.

This new plasmid has the following important features:

1—Strong constitutive promoter, making it cheaper to use, avoiding any clash with the induction of the recombinant protein (e.g. if both require IPTG) and by having conformase(s) expressed all the time, even before the induction of the target protein, the system would be ready with enough conformase(s) before the induction and after induction of the target gene/protein.

2—Replication origin compatible with wide a range of plasmids. Thus making the coexpression of conformases together with any plasmid that is used to express a recombinant protein possible.

3—The plasmid was made sure not to have any "scars", sequence of other promoters in the opposite direction of the promoter that will be used to express the conformases. T7 promoter for example was deleted.

4—The encoded antibiotics, e.g. gentamicin, do not interfere with other antibiotic markers used for gene expression.

Basic Strategy:

1—Isolate the strong constitutive promoter from pKK232-8-AmpC (Caroff et al, J. Antimicrob Chemother. 2000 June; 45(6):783-8).

2—Include a transcription terminator from the same pKK232-8-AmpC plasmid.

3—Use the replication origin and drug resistant marker (gentamicin) from plasmid pBBR1MCS-5 (Kovach et al., Gene. 1995 Dec. 1; 166(1):175-6)

4—Have TIR (Transcription enhancing region) containing a ribosome binding site (Miller and Lindow 1997. Gene 191(2):149-53).

5—Contain cloning sites that would be easy to clone any desired gene and express from the above promoters and signals, sarting from its encoded ATG by using NdeI site at the 5' end.

A plasmid prepared according to these principles is pConstEx4 shown in FIG. 8. Conformases 1, 2 and 3 and the full operons incorporating conformases 1 and 2 have been cloned in this new vector.

Example 6

The PROSITE Database was used to perform protein signature analysis of all the conformases identified herein and an equivalent analysis was performed for chaperones, DNAK, DNAJ, DSB and cis-trans peptide isomerase (PDI). The results of this analysis are shown in the tables below.

TABLE 3

Protein Motifs for Conformases 1, 2, 3 and the further Conformases listed in Table 2

| Fold. NO. | Putative name | How Strong | Gene name | Gene or Section Accession no. | Protein ID | Operon? (Judged by linkage/co-transcription) | MOTIFS Accession Number |
|---|---|---|---|---|---|---|---|
| 1- | F1 | v.strong | YcfU | AE005321 | AAG55862.1 | Yes (5) YcfV, YcfW, YcfX, CoB | PS00001, PS00005 PS00006, PS00008 PS00016, PS00029 |
| 2- | F2 | v.strong | Crp | AP002564 | AAG58465.1 | Yes (2) YhfK | PS00005, PS00006 PS00008, PS00888 PS00889, PS00042 |
| 3- | F3 | strong | Yjei | AE005648 | AAG59343.1 | No | PS00005, PS00006 PS00008, PS00013 |
| 4- | Pab-402 | v.strong | YicE | AE005593 | AAG58799.1 | (2) genes (+YicH) | PS00006, PS00008 PS00013, PS0116 |
| 5- | Pc-402 | v.strong | B2596 | AE000346.1 | AAC75645.1 | Yes (3) +B2595, B2597 | PS00004, PS00005 PS00006 |
| 6- | Pd-402 | Med. | NuoG | AE000317 | AAC75343.1 | Yes (14) +Nuoa, b, c, d, e, f, h, i, j, k, l, m, n | PS00001, PS00005 PS00006, PS00007 PS00008, PS00013 PS00016, PS00641 PS00642, PS00643 |
| 7- | PL-402 | Strong | NuoC | AE000317 | AAC75346.1 | Yes (14) Nuoa, b, d, e, f, g, h, i, j, k, l, m, n | PS00001, PS00004 PS00005, PS00006 PS00008, PS00542 PS00535 |
| 8- | Pe-402 | v.strong | Hnr | AE000222 | AAC74317.1 | ? | PS00001, PS00005 PS00006, PS00008 PS00016, PS00029 |
| 9- | Pf-402 | Strong | FlgH | AE000208 | AAC74163.1 | Yes (14) Flga, b, c, d, e, f, g, i, j, k, l, m, n | PS00001, PS00008 PS00013 |
| 10- | PU2-414 | Strong | FlgI | AE000208.1 | AAC74164.1 | Yes (14) Flga, b, c, d, e, f, g, h, j, k, l, m, n | PS00001, PS00005 PS00006, PS00007 PS00008 |
| 11- | Pg-402 | Strong | B0960 | AE000198 | AAC74046.1 | Yes (2) +YccF | PS00001, PS00004 PS00005, PS00006 PS00008, PS00016 PS00029, PS00217 |
| 12- | Pi-402 | Strong | Ybdk | AE005237 | AAG54914.1 | ? 2-5? | PS00005, PS00006 PS00007, PS00008 |
| 13- | PAI-414 | Strong | Yjei | AE005648 | AAG59343.1 | No | PS00005, PS00006 PS00008, PS00013 |
| 14- | PCIE2-414 | Strong | B1728 | AE000268.1 | AAC74798.1 | No | PS00006, PS00008 |
| 15- | PD1a-M2-414 | Strong | B2475 | AE000334.1 | AAC75528.1 | 2 genes? YpfI | PS00001, PS00002 PS00004, PS00005 PS00006, PS00008 PS00009, PS00142 |
| 16- | PD1b-M2b-414 | Strong | YjfR? | AE000491.1 | AAC77149.1 | No | PS00005, PS00006 PS00007, PS00008 PS00013 |
| 17- | PM1-414 | Strong | MdoH | AE000206.1 | AAC74133.1 | 2 genes MdoG | PS00001, PS00004 PS00005, PS00006 PS00008, PS00213 |
| 18- | PO1a414 | Strong | Yhft | AE000413.1 | AAC76402.1 | 15 genes +YhfL, m, n, o, p, q, r, s, u, v, w, x, y, z | PS00001, PS00005 PS00006, PS00008 PS00030 |
| 19- | PO1b414 | Strong | ArcA | AE000510.1 | AAC77354.1 | No | PS00004, PS00005 PS00006, PS00007 PS00008, PS00029 |
| 20- | PQ1-414 | Strong | TolA | AE000177.1 | AAC73833.1 | 4 genes +tolQ, r, b | PS00005, PS00006 PS00007, PS00008 PS00017 |
| 21- | PB2-d2-414 | Strong | TorT | D90737.1 | BAA35761.1 | >3 genes +torR, torS | PS00005, PS00006 PS00007, PS00008 |
| 22- | PK2-414 | Strong | YeeX | AE000292.1 | AAC75068.1 | 2? +YeeA | PS00001, PS00005 PS00006, PS00008 |
| 23- | PK2b414 | Strong | YeeA | AE000292.1 | AAC75069.1 | 2? +YeeX | PS00005, PS00006 PS00007, PS00008 PS00009 |

TABLE 4

Protein Motifs for Known Chaperones & Heat Shock Proteins
(*Escherichia coli*).

| NO. | Name | Gene or Section Accession no. | Protein ID | MOTIFS (Prosite) Accession Number |
|---|---|---|---|---|
| 1- | GroEL | AE005648 | AAG59342.1 | PS00004, PS00005 PS00006, PS00007 PS00008, PS00296 |
| 2- | GroES | AE005648 | AAG59341.1 | PS00005, PS00006 PS00008, PS00681 |
| 3- | DNAK | AE000112 | AAC73125.1 | PS00001, PS00005 PS00006, PS00008 PS00009, PS00297 PS00329, PS01036 |
| 4- | DNAJ | AE000112 | AAC73126.1 | PS00005, PS00006 PS00007, PS00008 PS00190, PS00636 PS00637 |
| 5- | DsbA | AE005616 | AAG59049.1 | PS00005, PS00006 PS00008, PS00194 |
| 6- | DsbB | L03721 | AAA23711.1 | PS00008, PS00029 |
| 7- | DsbC | AE005519 | AAG58021.1 | PS00001, PS00005 PS00006, PS00008 PS00190, PS00194 |
| 8- | DsbD | AE005647 | AAG59335.1 | PS00001, PS00005 PS00006, PS00008 PS00194 |
| 9- | DsbE | AE005452 | AAG57330.1 | PS00005, PS00006 PS00008, PS00194 |
| 10- | DsbG | AF000956 | AAC45785.1 | PS00001, PS00005 PS00006, PS00008 PS00009 |
| 11- | PPI | AE005653 | AAG59405.1 | PS00001, PS00005 PS00006, PS00008 PS00453, PS00454 |

TABLE 5

MOTIFS Amino Acids Signatures in 23 Conformases identified to date

| No | Accession Number | Description | Pattern | Frequency/23 | % protein |
|---|---|---|---|---|---|
| 1 | PS00001 | N-Glycosylation | N-{P}-[ST]-{P} | 11 | 47.8 |
| 2 | PS00002 | Glycosaminoglycan attachement site | S-G-x-G | 1 | 4.3 |
| 3 | PS00004 | CAMP- and cGMP-dependent protein kinase phosphorylation site | [RK](2)-X-[ST] | 6 | 26.1 |
| 4 | PS00005 | Protein kinase C Phosphorylation site | [ST]-x- [RK] | 20 | 87.0 |
| 5 | PS00006 | Casine kinase II phosphorylation site | [ST]-x(2)- [DE] | 22 | 95.7 |
| 6 | PS00007 | Tyrosine kinase Phosphorylation site | [RK]-x(2,3)-[DE]-x(2,3)-Y | 8 | 34.8 |
| 7 | PS00008 | N-Myristylation site | G-{EDRKHPFYW}-x(2)-[STAGCN]- {P} | 22 | 95.7 |
| 8 | PS00009 | Amidation site | x-G-[RK]-[RK] | 2 | 8.7 |
| 9 | PS00013 | Prokaryotic membrane lipoprotein lipid attachement | {DER} (6)-[LIVMFWSTAG] (2)-[LIVMFYSTAGCQ]-[AGS]-C | 6 | 26.1 |
| 10 | PS00016 | Cell attachment sequence | R-G-D | 4 | 17.4 |
| 11 | PS00017 | ATP/GTP binding site motif A (P-loop) | [AG]-x-(4)-G-K-[ST] | 1 | 4.3 |
| 12 | PS00029 | Leucine-Zipper pattern | L-x(6)-L-x(6)-L-x(6)-L | 4 | 17.4 |
| 13 | PS00030 | Eukaryotic putative RNA-binding region RNP-I signature | [RK]-G-[EDRKHPCG]-[AGSCI]-[FY]-[LIVA]-x-[FYLM] | 1 | 4.3 |
| 14 | PS00042 | Bacterial regulatory proteins, crp family signature | [LIVM]-[STAG]-[RHNW]-x(2)-[LIM]-[GA]-x-[LIVMFYA]-[LIVSC]-[GA]-x-[STACN]-x(2)- [MST]-x-[GSTN]-R-x-[LIVMF]-x-(2)- [LIVMF] | 1 | 4.3 |
| 15 | PS00142 | Neutral zinc metallopeptidases, zinc-binding region signature | [GSTALIVN]-x-(2)-H-E-[LIVFMFYW]-{DEHRKP}-H-x-[LIVFYWGSPQ] | 1 | 4.3 |
| 16 | PS00213 | Lipocalin Signature | [DENG]-x-[DENQGSTARK]-x-(0, 2)-[DENQARK]-[LIVFY]- {CP}-G-{C}-W- [FYWLRH]-[LIVMTA] | 1 | 4.3 |
| 17 | PS00217 | Sugar transport protein signature-2 | [LIVMF]-x-G- [LIVMFA]-x(2)-G-x-(8)-[LIFY]-x(2)-[EQ]-x(6)-[RK] | 1 | 4.3 |
| 18 | PS00535 | Respiratory chain NADH dehydrogenase 49 kd subunit signature | [LIVMH]-H-[RT]-[GA]-x-E-K-[LIVMT]-x-E-x-[KRQ] | 1 | 4.3 |
| 19 | PS00542 | Respiratory chain NADH dehydrogenase 30 kd subunit signature | E-R-E-x- (2)-x(6)-[HK]-x(3)-[KRP]-[LIVM]- [LIVMS] | 1 | 4.3 |
| 20 | PS00641 | Respiratory chain NADH dehydrogenase 75 kd subunit signature-1 | P-x- (2)-C-[YWS]-x (7) -G-x-C-R-x-C | 1 | 4.3 |
| 21 | PS00642 | Respiratory chain NADH dehydrogenase 75 kd subunit signature-2 | C-P-x-C-[DE]-x-[GS] (2)-x-C-x-L-Q | 1 | 4.3 |

TABLE 5-continued

MOTIFS Amino Acids Signatures in 23 Conformases identified to date

| No | Accession Number | Description | Pattern | Frequency/23 | % protein |
|---|---|---|---|---|---|
| 22 | PS00643 | Respiratory chain NADH dehydrogenase 75 kd subunit signature-3 | R-C-[LIVM]-x-C-x-R-C-[LIVM]-x-[FY] | 1 | 4.3 |
| 23 | PS00888 | Cyclic nucleotide-binding domain signature-1 | [LIVM]-[VIC]-x(2)-G-[DENQTA]-x-[GAC]-x(2)- [LIVMFY] (4)-x(2)-G | 1 | 4.3 |
| 24 | PS00889 | Cyclic nucleotide-binding domain signature-2 | [LIVMF]-GEX-[GAS]-[LIVM]-x(5,11)-R-[STAQ]-A-x- [LIVMA]-X-[STACV] | 1 | 4.3 |
| 25 | PS01116 | Xanthine/uracil permeases family signature | [LIVM]-P-x[PASIF]-V-[LIVM]-G-G-x (4) -[LIVM]- [FY]-[GSA]-x-[LIVM]-x(3)-G | 1 | 4.3 |

TABLE 6

MOTIFS Amino Acids Signatures found in Chaperones and the like proteins:

| No | Accession Number | Description | Pattern | Frequency/11 | % |
|---|---|---|---|---|---|
| 1 | PS00001 | N-Glycosylation | N-{P}-(ST)-{P} | 5 | 45.5 |
| 2 | PS00004 | CAMP- and cGMP-dependent protein kinase phosphorylation site | [RK](2)-X-[ST] | 1 | 9.1 |
| 3 | PS00005 | Protein kinase C Phosphorylation site | [ST]-x- [RK] | 10 | 90.9 |
| 4 | PS00006 | Casine kinase II phosphorylation site | [ST]-x(2)- [DE] | 10 | 90.9 |
| 5 | PS00007 | Tyrosine kinase Phosphorylation site | [RK]-x(2,3)-[DE]-x(2,3)-Y | 2 | 18.2 |
| 6 | PS00008 | N-Myristylation site | G-{EDRKHPFYW}-x(2)-[STAGCN]- {P} | 11 | 100 |
| 7 | PS00009 | Amidation site | x-G-[RK]-[RK] | 2 | 18.2 |
| 8 | PS00029 | Leucine-Zipper pattern | L-x(6)-L-x(6)-L-x(6)-L | 1 | 9.1 |
| 9 | PS00190 | Cytochrome c family heme-binding site signature | C-{CPWHF}-{CPWR}-C-H-{CFYW} | 2 | 18.2 |
| 10 | PS00194[4] | Thioredoxin family active site | [LIVMF]-[LIVMSTA] -x-[LIVMFYC]-[FYWSTHE]- x-(2)-[FYWGTN] -C-[GATPLVE]-[PHYWSTA]- C- x (6)-[LIVMFYWT] | 4 | 36.4 |
| 11 | PS00296[1] | Chaperonins cpn60 signature | A-[AS]-x-[DEQ]-E-x-(4) -G-G-[GA] | 1 | 9.1 |
| 12 | PS00297[2] | Heat shock hsp70 proteins family signature 1 | [IV]-D-L-G-T-[ST]-x-[SC] | 1 | 9.1 |
| 13 | PS00329[2] | Heat shock hsp70 proteins family signature 2 | [LIVMF]-[LIVMFY]- [DN]- [LIVMFS]- G-[GSH]-[GS]-[AST]-x- (3)- [LIVM]-[LIVMFC] | 1 | 9.1 |
| 14 | PS00453[5] | FKBP-type peptidyl-prolyl cis-trans isomerase signature 1 | [LIVMC]-x-[YF]-x-[GVL] -x- (1,2)- [LFT]-x-(2)-G-x(3)-[DE]-[STAEQK]-[STAN] | 1 | 9.1 |
| 15 | PS00454[5] | FKBP-type peptidyl-prolyl cis-trans isomerase signature 2 | [LIVMFY]- x (2)- [GA]-x- (3, 4) [LIVMF]- x (2)-[LIVMFHK]-x (2)-G-x (4)- [LIVMF]-x(3)-[PSGAQ]-x(2)-[AG]- [FY]-G | 1 | 9.1 |
| 16 | PS00636[3] | dnaj domain signature | [FY]-x-(2)-[LIVMA] -x(3) -[FYWHNT]-[DENQSA]-x-L-x[DN]-x (3)- [KR]-x-(2)-[FYI] | 1 | 9.1 |
| 17 | PS00637[3] | CXXCXGX dnaj domain signature | C-[DEGSTHKR]-x-C-x-G-x[GK]-[AGSDM]- x (2)-[GSNKR]-x- (4, 6)-C-x- (2, 3)-C-x-G-x-G | 1 | 9.1 |
| 18 | PS00681[1] | Chaperonins cpn10 signature | [LIVMFY]-x-P-[ILT]-x-[DEN]-[KR]- [LIVMFA] (3)- | 1 | 9.1 |
| 19 | PS01036[2] | Heat shock hsp70 proteins family signature 3 | [LIVMY]- [LIVMF]-x-G-G-x-[ST]-x-[LIVM]-x-[DEQKRSTA] | 1 | 9.1 |

[1]Chaperone
[2]Heat Shock
[3]DNAJ patteren
[4]Thioredoxin pattern
[5]Cis-trans isomerase Motif numbers 10-19 in Table 6 are known signatures dealing directly with the chaperone/heat shock function and none of these signature sequences are found in the newly identified conformase family of molecules. Thus while some motifs may be found in both groups of proteins, e.g. the N-glycosylation signature, the characteristic signatures dealing directly with the chaperone and heat shock functions are not found in the conformases.

Example 7

Construction of Vector for Constitutive Expression

We constructed a vector with a constitutive promoter that does not require any added inducer such as IPTG.

The vector used for this and for subsequent modifications is pACT3 (Dykxhoorn D M, St Pierre R, Linn T. 1996. A set of compatible tac promoter expression vectors. Gene 177 (1-2): 133-6.). The original multiple cloning site (MCS) downstream of the tac promoter (Ptac) suitated on this plasmid contains the following restriction sites in the following order: EcoRI, SacI, KpnI, SmaI, BamHI, XbaI, SalI, PstI, SphI, HindIII. The vector has a Cam$^R$ (Chloramphenicol resistance) gene and the p15 replication origin. This replication origin is compatible with most replication origins typically used in protein expression. This allows the bacterial host strain to contain both a plasmid encoding the gene/protein to be also expressed and this vector, i.e. this vector of the present invention can co-exist with many other types of vectors in a host cell.

Constitutive expression of the protein of interest encoded by the vector (e.g. a conformase) was achieved by deleting the LacO sequence. LacO is the binding site of the lac-repressor. By deleting the LacO, the expression can no longer be repressed by the lac-repressor. Consequently, no inducer such as IPTG (isopropyl thiogalactoside) is required in order to de-repress/induce gene expression. IPTG is an artificial inducer of the Lac operon. It induces genes by strongly binding and inhibiting the lac repressor.

The resulting plasmid was named pACT3-Δlaco, but is also referred to as pMRE200. A map of pMRE200 is shown in FIG. 9. The sequence (SEQ ID NO 71) and main features of pMRE200 are shown below.

```
DEFINITION    Expression vector pMRE200

SOURCE        Constitutive expression vector pMRE200

FEATURES      Location/Qualifiers
misc_feature  34 . . . 61
              /note="-10 through -35 region."
              /standard_name="tac promoter"

misc_feature  order (652 . . . 701, 651)
              /note="lac repressor."
              /standard_name="lacI"

misc_feature  2745 . . . 3404
              /note="chloramphenicol acetyl transferase."
              /standard_name="CamR"

misc_feature  4020 . . . 4022
              /note="P15 ori from pACYC184."
              /standard_name="P15 ori"

misc_feature  4817 . . . 4870
              /note="Multiple cloning site:
              HindIII-PstI-SalI-XbaI-BamHI-XmaI-SmaI-KpnI-
              SacI
              /standard_name="MCS"

terminator    4701 . . . 4786
              /note="rrnBT2 terminator-containing segment."
              /standard_name="terminator"

misc_feature  72 . . . 96
              /note="sequencing primer designed for pACT to
              check out the deletion of lacO. It can anneal
              to the upper chain."
              /standard_name="pACTfor primer"

misc_feature  4749 . . . 4773
              /note="sequencing primer designed for pACT to
              check out the deletion of lacO. It is in the
              upper chain."
              /standard_name="pACT-reverse primer"

misc_feature  23 . . . 43
              /note="primer designed for the deletion of
              lacO from pACT3. It is in the upper chain."
              /standard_name="ACT3-laco-1"

misc_feature  3 . . . 22
              /note="primer designed to delete lacO from
              pACT3. It can aneal to the upper-chain."
              /standard_name="ACT3-laco-2"

COMMENT:      Low copy number constitutive expression
              vector under tac promoter.

f1 fragment was cut out by NarI from our
              previous modified plasmid "pACT (f1+) delLacO".

Resistant Marker: CAM
```

Origin of Replication: p15 ori from pACYC184.
The lac repressor lacI, is partially deleted.

BASE COUNT     1168 a    1294 c    1256 g    1152 t (SEQ ID NO 71)

ORIGIN
```
   1 ttctgtttcc tgtgtgaaat tgcaattcca cacattatac
     gagccgatga ttaattgtca
  61 acagctcatt tcagaatatt tgccagaacc gttatgatgt
     cggcgcaaaa aacattatcc
 121 agaacgggag tgcgccttga gcgacacgaa ttatgcagtg
     atttacgacc tgcacagcca
 181 taccacagct tccgatggct gcctgacgcc agaagcattg
     gtgcaccgtg cagtcgataa
 241 gctccgccga tgcccttgag agccttcaac ccagtcagct
     ccttccggtg ggcgcggggc
 301 atgactatcg tcgccgcact tatgactgtc ttctttatca
     tgcaactcgt aggacaggtg
 361 ccggcagcgc tctgggtcat tttcggcgag gaccgctttc
     gctggagcgc gacgatgatc
 421 ggcctgtcgc ttgcggtatt cggaatcttg cacgccctcg
     ctcaagcctt cgtcactggt
 481 cccgccacca aacgtttcgg cgagaagcag gccattatcg
     ccggcatggc ggccaattcg
 541 cgcgcgaagg cgaagcggca tgcatttacg ttgacaccat
     cgaatggtgc aaaacctttc
 601 gcggtatggc atgatagcgc ccggaagaga gtcaattcag
     ggtggtgaat atgaaaccag
 661 taacgttata cgatgtcgca gagtatgccg gtgtctctta
     tcagaccgtt tcccgcgtgg
 721 tgaaccaggc cagccacgtt tctgcgaaaa cgcgggaaaa
     agtggaagcg gcgatggcgg
 781 agctgaatta cattcccaac cgcgtggcac aacaactggc
     gggcaaacag tcgttgctga
 841 ttggcgttgc cacctccagt ctggccctgc acgcgccgtc
     gcaaattgtc gcggcgatta
 901 aatctcgcgc cgatcaactg ggtgccagcg tggtggtgtc
     gatggtagaa cgaagcggcg
 961 tcgaagcctg taaagcggcg gtgcacaatc ttctcgcgca
     acgcgtcagt gggctgatca
1021 ttaactatcc gctggatgac caggatgcca ttgctgtgga
     agctgcctgc actaatgttc
1081 cggcgttatt tcttgatgtc tctgaccaga cacccatcaa
     cagtattatt ttctcccatg
1141 aagacggtac gcgactgggc gtggagcatc tggtcgcatt
     gggtcaccag caaatcgcgc
1201 tgttagcggg cccattaagt tctgtctcgg cgcgtctgcg
     tctggctggc tggcataaat
1261 atctcactcg caatcaaatt cagccgatag cggaacggga
     aggcgactgg agtgccatgt
1321 ccggttttca acaaaccatg caaatgctga atgagggcat
     cgttcccact gcgatgctgg
1381 ttgccaacga tcagatggcg ctgggcgcaa tgcgcgccat
     taccgagtcc gggctgcgcg
1441 ttggtgcgga tatctcggta gtgggatacg acgataccga
     agacagctca tgttatatcc
```

-continued

```
1501  cgccgtcaac caccatcaaa caggattttc gcctgctggg
      gcaaaccagc gtggaccgct 1561  tgctgcaact ctctcagggc caggcggtga agggcaatca
      gctgttgccc gtctcactgg 1621  tgaaagaaa aaccaccctg gcgccgccct ataccttgtc
      tgcctccccg cgttgcgtcg 1681  cggtgcatgg agccgggcca cctcgacctg aatggaagcc
      ggcggcacct cgctaacgga 1741  ttcaccactc caagaattgg agccaatcaa ttcttgcgga
      gaactgtgaa tgcgcaaacc 1801  aaccccttggc agaacatatc catcgcgtcc gccatctcca
      gcagccgcac gcggcgcatc 1861  tcgggcagcg ttgggtcctg gccacgggtg cgcatgatcg
      tgctcctgtc gttgaggacc 1921  cggctaggct ggcggggttg ccttactggt tagcagaatg
      aatcaccgat acgcgagcga 1981  acgtgaagcg actgctgctg caaaacgtct gcgacctgag
      caacaacatg aatggtcttc 2041  ggtttccgtg tttcgtaaag tctggaaacg cggaagtccc
      ctacgtgctg ctgaagttgc 2101  ccgcaacaga gagtggaacc aaccggtgat accacgatac
      tatgactgag agtcaacgcc 2161  atgagcggcc tcatttctta ttctgagtta caacagtccg
      caccgctgtc cggtagctcc 2221  ttccggtggg cgcggggcat gactatcgtc gccgcactta
      tgactgtctt ctttatcatg 2281  caactcgtag acaggtgcc ggcagcgccc aacagtcccc
      cggccacggg gcctgccacc 2341  atacccacgc cgaaacaagc gccctgcacc attatgttcc
      ggatctgcat cgcaggatgc 2401  tgctggctac cctgtggaac acctacatct gtattaacga
      agcgctaacc gtttttatca 2461  ggctctggga ggcagaataa atgatcatat cgtcaaitat
      tacctccacg gggagagcct 2521  gagcaaactg gcctcaggca tttgagaagc acacggtcac
      actgcttccg gtagtcaata 2581  aaccggtaaa ccagcaatag acataagcgg ctatttaacg
      accctgccct gaaccgacga 2641  ccgggtcgaa tttgctttcg aatttctgcc attcatccgc
      ttattatcac ttattcaggc 2701  gtagcaccag gcgtttaagg gcaccaataa ctgccttaaa
      aaaattacgc cccgccctgc 2161  cactcatcgc agtactgttg taattcatta agcattctgc
      cgacatggaa gccatcacag 2821  acggcatgat gaacctgaat cgccagcggc atcagcacct
      tgtcgccttg cgtataatat 2881  ttgcccatgg tgaaaacggg ggcgaagaag ttgtccatat
      tggccacgtt taaatcaaaa 2941  ctggtgaaac tcacccaggg attggctgag acgaaaaaca
      tattctcaat aaacccttta 3001  gggaaatagg ccaggttttc accgtaacac gccacatctt
      gcgaatatat gtgtagaaac 3061  tgccggaaat cgtcgtggta ttcactccag agcgatgaaa
      acgtttcagt ttgctcatgg
```

-continued

```
3121  aaaacggtgt aacaagggtg aacactatcc catatcacca
      gctcaccgtc tttcattgcc 3181  atacggaatt ccgatgagc attcatcagg cgggcaagaa
      tgtgaataaa ggccggataa 3241  aacttgtgct tattttctt tacggtcttt aaaaaggccg
      taatatccag ctgaacggtc 3301  tggttatagg tacattgagc aactgactga aatgcctcaa
      aatgttcttt acgatgccat 3361  tgggatatat caacggtggt atatccagtg attttttct
      ccattttagc ttccttagct 3421  cctgaaaatc tcgataactc aaaaaatacg cccggtagtg
      atcttatttc attatggtga 3481  aagttggaac ctcttacgtg ccgatcaacg tctcattttc
      gccaaaagit ggcccagggc 3541  ttcccggtat caacagggac accaggattt atttattctg
      cgaagtgatc ttccgtcaca 3601  ggtatttatt cggcgcaaag tgcgtcgggt gatgctgcca
      acttactgat ttagtgtatg 3661  atggtgtttt tgaggtgctc cagtggcttc tgtttctatc
      agctgtccct cctgttcagc 3721  tactgacggg gtggtgcgta acggcaaaag caccgccgga
      catcagcgct agcggagtgt 3781  atactggctt actatgttgg cactgatgag ggtgtcagtg
      aagtgcttca tgtggcagga 3841  gaaaaaggc tgcaccggtg cgtcagcaga atatgtcata
      caggatatat tccgcttcct 3901  cgctcactga ctcgctacgc tcggtcgttc gactgcggcg
      agcggaaatg gcttacgaac 3961  ggggcggaga tttcctggaa gatgccagga agatacttaa
      cagggaagtg agagggccgc 4021  ggcaaagccg tttttccata ggctccgccc ccctgacaag
      catcacgaaa tctgacgctc 4081  aaatcagtgg tggcgaaacc cgacaggact ataaagatac
      caggcgtttc ccctggcggc 4141  tccctcgtgc gctctcctgt tcctgccttt cggtttaccg
      gtgtcattcc gctgttatgg 4201  ccgcgtttgt ctcattccac gcctgacact cagttccggg
      taggcagttc gctccaagct 4261  ggactgtatg cacgaacccc ccgttcagtc cgaccgctgc
      gccttatccg gtaactatcg 4321  tcttgagtcc aacccggaaa gacatgcaaa agcaccactg
      gcagcagcca ctggtaattg 4381  atttagagga gttagtcttg aagtcatgcg ccggttaagg
      ctaaactgaa aggacaagtt 4441  ttggtgactg cgctcctcca agccagttac ctcggttcaa
      agagttggta gctcagagaa 4501  ccttcgaaaa accgccctgc aaggcggttt tttcgttttc
      agagcaagag attacgcgca 4561  gaccaaaacg atctcaagaa gatcatctta ttaatcagat
      aaaatatttc tagcatgagc 4621  ggatacatat ttgaatgtat ttagaaaaat aaacaaatag
      gggttccgcg cacatttccc 4681  cgaaaagtgc cacctgctag acaggaagag tttgtagaaa
      cgcaaaaagg ccatccgtca
```

```
4741   ggatggcctt ctgcttaatt tgatgcctgg cagtttatgg
       cgggcgacga atttcttctc 4801   tcatccgcca aaacagaagc ttgcatgcct gcaggtcgac
       tctagaggat ccccgggtac 4861   cgagctcgaa
```

The vector was tested to confirm that expression of any gene introduced into the vector at the appropriate site is indeed constitutive.

The expression of β-galactosidase was tested by first inserting the entire lacZ gene (BamHI DNA fragment) cleaved from pMRE101 downstream from the engineered constitutive tac promoter. Only dark blue colonies were selected, indicating the correct orientation relative to the promoter, on plates containing chloramphenicol and X-gal without the IPTG inducer. The resulting plasmid containing the lacZ gene was named pMRE201.

Example 8

Construction of a Vector Containing Rare tRNA Genes

Selected tRNA genes which encode codons which are rare in prokaryotic cells and can therefore have a rate limiting effect on the expression of heterologous proteins, especially eukaryotic proteins, were added to vector pMRE201. The tRNA genes used were ArgU, ArgW and Ilex. The sequences of the rare tRNA genes are shown below:

```
ArgU (SEQ ID NO 72)
gtcgttcacttgttagcaaccagatcaaaagccattgactcagcaagggt
tgaccgtataattcacgcgattacaccgcattgcggtatcaacgcgccct
tagctcagttggatagagcaacgaccttctaagtcgtgggccgcaggttc
gaatcctgcagggcgcgccattacaattcaatcagttacgccttctttat
atcctccataatttcagagtgggacatatttgggacattatcaccaaaaa
tgtcgtctattttcctcgcatgc ArgW (SEQ ID NO 73)
cgtacttacccgcactccattagcgggtatactcatgccgcattgtcct
cttagttaaatggatataacgagcccctcctaagggctaattgcaggttc
gattcctgcagggacaccatttatcagttcgctcccatccgtaccagtc
cgcaaaatcccctgaatatcaagcattccgtagatttacagttcgtcatg
gttcgctt Ilex (SEQ ID NO 74)
gctggattgcgacacggagttactttataatccgctaccatggcccctta
gctcagtggttagagcaggcgactcataatcgcttggtcgctggttcaag
tccagcaggggccaccagatatagcaaaggctgacgagaaatcgtcagcc
tttttctttttatatatcagttactttgcgtgccag
```

The combined Sequence of the engineered t-RNA gene-cluster is as follows: (SEQ ID NO 75)

```
gtcgttcacttgttagcaaccagatcaaaagccattgactcagcaagggt tgaccgtataattcacgcgattacaccgcattgcggtatcaacgcgccct tagctcagttggatagagcaacgaccttctaagtcgtgggccgcaggttc gaatcctgcagggcgcgccattacaattcaatcagttacgccttctttat atcctccataatttcagagtgggacatatttgggacattatcaccaaaaa tgtcgtctattttcctcgcatgccgtacttacccgcactccattagcgg gtatactcatgccgcattgtcctcttagttaaatggatataacgagcccc tcctaagggctaattgcaggttcgattcctgcagggacaccatttatca gttcgctcccatccgtaccagtccgcaaaatcccctgaatatcaagcatt ccgtagatttacagttcgtcatggttcgcttgctggattgcgacacggag ttactttataatccgctaccatggcccttagctcagtggttagagcagg cgactcataatcgcttggtcgctggttcaagtccagcaggggccaccaga tatagcaaaggctgacgagaaatcgtcagcctttttcttttatatatca gttactttgcgtgccag
```

The following primers were used to design a polynucleotide sequence encoding the three rare tRNA genes

TABLE 7

PCR primers used in order to combine, in tandem the three tRNA genes.

| No | Primer | Restric Enzymes | Gene |
|---|---|---|---|
| T1-1 | AACCGCGGTCGTTCACTTGTTCAGCAAC (SEQ ID NO 76) | SacII | ArgU |
| T1-2 | GGAGTGCGGGGTAAGTACGGCATGCGAG GAAAATAGACG (SEQ ID NO 77) | | ArgU/ ArgW |
| T2-1 | CGTCTATTTTCCTCGCATGCCGTACTTA CCCCGCACTCC (SEQ ID NO 78) | | ArgU/ ArgW |
| T2-2 | CTCCGTGTCGCAATCCAGCAAGCGAACC ATGACGAACTGT (SEQ ID NO 79) | | ArgW/ IleX |
| T3-1 | ACAGTTCGTCATGGTTCGCTTGCTGGAT TGCGACACGGAG (SEQ ID NO 80) | | Argw/ IleX |
| T3-2 | AACCGCGGCTGGCACGCAAAGTAACTGA (SEQ ID NO 81) | SacII | IleX |

PCR using DNA of *E. coli* as a Template

Genomic DNA was prepared from *E. coli* strains MRE403, MRE406 and MV1190. Best results were obtained with isolated-genomic DNA from strain MRE406 for the ArgU gene fragment, while genomic DNA from strain MV1190 gave the best results for the IleX (T1 & T3) and for ArgW (T2) gene fragments.

Using the above primers-pairs and Turbo pfu DNA polymerase (Stratagene) the expected three different DNA fragments by PCR were obtained.

It should be noted that best results were obtained when the following cycles were used:
For T1:
PCR Cycles:
1 cycle
94° C. 3 min
40 cycles:
94° C. for 1 min 56° C. for 1 min
70° C. for 1 min
1 cycle
70° C. for 5 min
Store at 4° C.
For T2
  PCR Cycles:
  1 cycle
  95° C. 5 min
  40 cycles:
  94° C. for 1 min
  56° C. for 1 min
  70° C. for 1 min
  1 cycle
  70° C. for 5 min
  Store at 4° C.
For T3
  PCR Cycles:
  1 cycle
  95° C. 10 min
  40 cycles:
  94° C. for 1 min
  56° C. for 1 min
  1 cycle
  70° C. for 5 min
  Store at 4° C.

The following PCR products were obtained:

T1=274 bp: contains ArgU with a small overlap of Arg W genes. SacII site is designed at the 5'-end T2=208 bp: contains Arg W, preceded with a small overlap with ArgU, and followed by small overlap with IleX T3=186 bp: contains IleX, preceded by a small overlap with ArgW, and followed by transcription terminator and SacII as designed.

These fragments were purified from 1.5 agarose gel electrophoresis.

PCR to Combine T1 & T2:

By mixing equal molar ratio of T1+T2 product (5 ng and 6.5ng respectively) as potential overlapping template, and adding the primers T1-1 and T2-2 (50 pmol each) in the PCR reaction the expected combined fragment of 482 bp was obtained.

PCR Cycles for Combining T1 & T2
1 cycle
95° C. 3 min
1 cycle
94° C. 1 min
56° C. 1 min
72° C. 1 min
33 cycles:
94° C. for 1 min
72° C. for 1 min
1 cycle
72° C. for 5 min
Store at 4° C.

PCR to Combine T1-T2 &T3

Similarly by combining equal molar ratio of the purified T1-T2 fragment and the purified T3 fragment (13 and 5 ng) in the presence of primers T1-1 and T3-2 (50 pmol each), the expected fragment of 668 bp was obtained and purified. DNA sequence verification was also made.

PCR Cycles for Combining T1 & T2
1 cycle
95° C. 3 min
1 cycle
94° C. 1 min
56° C. 1 min
72° C. 1 min
33 cycles:
94° C. for 1 min
72° C. for 1 min
1 cycle
72° C. for 5 min
Store at 4° C.

Cloning of the Engineered Rare tRNA Gene Cluster:

The vector pMRE201 (described above) designed for the constitutive expression of a protein of interest such as a conformases is linearized by NarI restriction enzyme and then blunted by T4 DNA polymerase. The SacII DNA fragment containing the engineered tRNA genes cluster was also blunted by T4 DNA polymerase. Both fragments were ligated, generating pMRE403.

The SacII fragment containing the tRNA gene-cluster was also cloned into pMRE102 (a slightly shorter version of pMRE101) in the blunted NheI-site, giving rise to pMRE103. A map of pMRE103 is shown in FIG. 10.

Test for the Expression of the Cloned tRNA Genes

After transforming pMRE103 into *E. Coli*, XL1-Blue strain, the total RNA was isolated using the RNeasy Mini Kit (Qiagen). In these experiments 1.5 ml of cell cultures at 0.6 OD were used. All the experiments were done simultaneously. Host strain cells (XL1-Blue), with the cloning vector pMRE102 that does not have the engineered tRNA gene-cluster was used as a control.

| Primer design for expression of the cloned tRNA genes |
|---|
| Combined sequence of the cluster as double stranded DNA |
| AACCGCGGTCGTTCACTTGTTAGCAACCAGATCAAAAGCCATTGACTCAGCAAGGGTTGA |
| TTGGCGCCAGCAAGTGAACAATCGTTGGTCTAGTTTTCGGTAACTGAGTCGTTCCCAACT |
| |
| CCGTATAATTCACGCGATTACACCGCATTGCGGTATCAACGCGCCCTTAGCTCAGTTGGA |
| GGCATATTAAGTGCGCTAATGTGGCGTAACGCCATAGTTGCGCGGGAATCGAGTCAACCT |
| |
| TAGAGCAACGACCTTCTAAGTCGTGGGCCGCAGGTTCGAATCCTGCAGGGCGCGCCATTA |
| ATCTCGTTGCTGGAAGATTCAGCACCCGGCGTCCAAGCTTAGGACGTCCCGCGCGGTAAT |
| |
| CAATTCAATCAGTTACGCCTTCTTTATATCCTCCATAATTTCAGAGTGGGACATATTTGG |
| GTTAAGTTAGTCAATGCGGAAGAAATATAGGAGGTATTAAAGTCTCACCCTGTATAAACC |
| |
| GACATTATCACCAAAAATGTCGTCTATTTTCCTCGCATGCCGTACTTACCCCGCACTCCA |
| CTGTAATAGTGGTTTTTACAGCAGATAAAAGGAGCGTACGGCATGAATGGGGCGTGAGGT |
| |
| TTAGCGGGTATACTCATGCCGCATTGTCCTCTTAGTTAAATGGATATAACGAGCCCCTCC |
| AATCGCCCATATGAGTACGGCGTAACAGGAGAATCAATTTACCTATATTGCTCGGGGAGG |

Primer design for expression of the cloned tRNA genes

```
TAAGGGCTAATTGCAGGTTCGATTCCTGCAGGGGACACCATTTATCAGTTCGCTCCCATC
ATTCCCGATTAACGTCCAAGCTAAGGACGTCCCCTGTGGTAAATAGTCAAGCGAGGGTAG

CGTACCAGTCCGCAAAATCCCCTGAATATCAAGCATTCCGTAGATTTACAGTTCGTCATG
GCATGGTCAGGCGTTTTAGGGGACTTATAGTTCGTAAGGCATCTAAATGTCAAGCAGTAC

GTTCGCTTGCTGGATTGCGACACGGAGTTACTTTATAATCCGCTACCATGGCCCCTTAGC
CAAGCGAACGACCTAACGCTGTGCCTCAATGAAATATTAGGCGATGGTACCGGGGAATCG

TCAGTGGTTAGAGCAGGCGACTCATAATCGCTTGGTCGCTGGTTCAAGTCCAGCAGGGGC
AGTCACCAATCTCGTCCGCTGAGTATTAGCGAACCAGCGACCAAGTTCAGGTCGTCCCCG

CACCAGATATAGCAAAGGCTGACGAGAAATCGTCAGCCTTTTTCTTTTTATATATCAGTT
GTGGTCTATATCGTTTCCGACTGCTCTTTAGCAGTCGGAAAAAGAAAAATATATAGTCAA

ACTTTGCGTGCCAGCCGCGGTT (SEQ ID NO 82)
TGAAACGCACGGTCGGCGCCAA (SEQ ID NO 83)
```

Restriction enzyme analysis of the engineered tRNA gene-cluster DNA as generated by PCR was carried out. The following sites were found: AscI, BfuA1, Bpu10, Bam1, BspM1, BarD1, BssH2, BstB1, BstZ1, Bsu36, Nco1, Psi1, Pst1, Sac2, Sbf1, Sph1. Of these, AscI, Bsm1, BsrD1, BssH2, BstB1, BstZ1, Bsu36, Nco1, Psi1 and Sph1 were unique.

TABLE 8

Sequences of primers used to monitor tRNA-genes expression:

| No | Name of primer | Primer Sequence |
|---|---|---|
| 1 | ArgU-Forward | CGCGCCCTTAGCTCAGTT (SEQ ID NO 84) |
| 2 | ArgU-Reverse | GCCCTGCAGGATTCGAAC (SEQ ID NO 85) |
| 3 | ArgW-Forward | CCTCTTAGTTAAATGGATA (SEQ ID NO 86) |
| 4 | ArgW-Reverse | TGCAGGAATCGAACC (SEQ ID NO 87) |
| 5 | IleX-Forward | GCCCCTTAGCTCAGTGGT (SEQ ID NO 88) |
| 6 | IleX-Reverse | GGCCCCTGCTGGACTT (SEQ ID NO 89) |
| 7 | Cam Forward* | TCCGGCCTTTATTCACATTC (SEQ ID NO 90) |
| 8 | Cam Reverse* | ACGGCATGATGAACCTGAAT (SEQ ID NO 91) |

*Control primers to make RT-PCR on the isolated chloramphenicol resistance gene (CAT) transcripts/mRNA in the isolated total RNA.
RT-PCR to monitor tRNA expression First strand cDNA of the each corresponding tRNA was prepared using the reverse transcriptase, SuperscriptII RT (Life Technologies, Inc.). Samples of total RNA (500 ng; 1.5 µL) were mixed with 1 µL of 10 µM of the corresponding reverse tRNA primer in a small microfuge tube. Samples were heated at 70° C. for 5 min. in order to denature the secondary structure of tRNA. Samples were chilled on ice immediately. The following master mix was prepared and 5 µL was added to each sample:

| Reagent | Volume (µL) |
|---|---|
| 5x first strand-buffer | 32 |
| 20 mM-DTT | 16 |
| 10 mM dNTP | 16 |
| SuperscriptII (200 U/µL) | 16 |
| Total | 80 |

Tubes were mixed, centrifuged and incubated at 42° C. for 1 hour. To each tube, 40 µL $H_2O$ was added and tubes were heated at 72° C. for 7 min then frozen at −70° C. until RT-PCR.

RT-PCR reactions were made in a total volume of 25 µL using 0.5 µL of a stock of 50 µM of each primer. For the RT-PCR for each tRNA the Forward & Reverse primers were added (0.5 µL+0.5 µL)+1 µL of the corresponding cDNA, 2.5 µL 10×PCR buffer, 0.5 µL 10 mMdNTP, 0.25 µL Hot Start Taq DNA Polymerase (Qiagen) and 19.75 µL $H_2O$. Chloramphenicol RT-PCR control is done similarly.

PCR Cycles:
1 cycle
95° C. 15 min
40 cycles:
94° C. for 30 sec
50° C. for 30 sec
72° C. for 30 sec
1 cycle
72° C. for 3 min
Store at 4° C.

Acrylamide gel Electrophoresis of the RT-PCR products is shown in FIG. 12. The above the RT-PCR experiment shows that cells with the plasmid containing the tRNA gene cluster (pMRE103) expressed more ArgU, ArgW and IleX than cells with the empty vector, but total RNA amounts are similar, as judged by similar Cloramphenicol (CAM) bands.

Example 9

Further Improvement to the Vector pMRE403 in Order to Improve the Expression of Proteins, in Particular Conformases pMRE403 is a low copy number plasmid with multiple cloning sites to clone downstream of a constitutive tac promoter. A strong Shine-Dalgarno (SD) as well as transcription enhancer sequence (ENH) (Miller and Lindow, 1997) were added to improve protein expression.

Plasmid pGreen-TIR (Miller and Lindow, 1997) contains Green Fluorescent Protein gene (gfp) under the control of lac promoter (plac) with a strong SD and ENH. The SD and ENH comprise the TIR region (translation initiation region). In this vector the TIR sequence is TTAACTTTATAAGGAG-GAAAAACAT (SEQ ID NO 92).

In this Experiment, this sequence was inserted into pMRE403 upstream of the site into which a gene encoding a protein of interest can be introduced.

Example 10

Cloning of Conformase 2

Conformase-2 was cloned into the modified vector pMRE403 described above in Example 9. The sequence of this conformase is preceded by SacI, TIR (ENH, SD) and a start (ATG) followed by the rest of the sequence until the natural stop codon followed by the anti-"UAA" stop codon and then XbaI site for cloning in the engineered vector between SacI and XbaI sites. Primers used to clone Conformase-2 (F2):

```
Forward: (SEQ ID NO 93)
5' AAGAGCTCTGATTAACCTTTATAAGGAGGAAAAACATATGGTGCTTG
GCAAACCGCAA Reverse: (SEQ ID NO 94)
5' CTTCTAGATTATTAACGAGTGCCGTAAACGAC
```

The resulting vector expressing Coformase.2 (F2), was termed pMRE205. A map of this vector is shown in FIG. 11. Some important features of this plasmid are given below.

Resulting vector pMRE205 has a working NdeI site at the ATG initiation site (cat'ATG) that can also used for cloning. For example by inserting fragments with NdeI-xbaI or NdeI-HindIII Successful cloning of the conformase was verified by transforming pMRE205 into one of the *E. coli* strains with compromised conformases but with complete copy of lac z gene such as MRE201, MRE202 or MRE214. Plasmid DNA was prepared from the resulting dark-blue colonies (in the presence of IPTG and X-gal) indicating correct conformation of the expressed β-galactosidase due to the correct expression of conformase-2 (F2).

The skilled man will appreciate that other conformases can be cloned in a similar way. If any conformase has an amino acid following the first Met that would clash with the N-End Rule (Varshavsky, 1996), an additional Met is inserted before the natural second amino acid.

In order to verify conformase activity, the results of transformation with the conformase-containing vector can be compared to the results of a transformation with a similar but empty vector (i.e. a vector without any conformases). A significantly higher activity of reporter protein such as β-galactosidase would reflect the successful cloning of the designated conformase. Empty vector would reflect a significantly lower reporter protein (e.g. β-galactosidase) activity. Other reporter systems such as pG1 can also be used. In this system, the fluorescence of green fluorescencent protein is measured.

Example 11

Cloning of Conformases 2, 1 and 3 (F-2-1-3)

The cloning of the engineered artificial operon comprising conformases 1, 2 & 3 in tandem and expressed constitutively in the a above described system was done as follows:

pMRE205 (described in Example 10) was digested with restriction enzymes SacI & XbaI. The vector band was

| Features: | | |
|---|---|---|
| Promoter | 34 ... 61 | /note = "−10 through −35 region." |
| | | /standard_name = "tac promoter" |
| TIR | 6151 ... 6178 | /note = "translation enhancer" |
| | | /standard_name = "TIR" |
| Conformase 2(F2) | 5520 ... 6150 | (F2) as amplified by PCR from *E. coli* genomic DNA. The entire sequence, including the TIR, is between SacI and XbaI |
| MCS (remaining) | 5490 to 5513 | HindIII-PstI-SalI" |
| Terminator | 5374 ... 5459 | /note = "rrnBT2 terminator-containing segment." |
| | | /standard_name = "terminator" |
| NdeI | 6148 ... 6153 | /note = "TIR-PCR (F2) fragment was re-inserted into SacI and XbaI sites, and the resulting vector has a working NdeI site." |
| SacI | 6179 ... 6184 | /note = "restriction site used to insert TIR-F2 fragment" |
| XbaI | 5514 ... 5519 | /note = "restriction site used to insert TIR-F2 fragment" |
| Blunted NarI | order(1640 ... 1643 & 2315 ... 2318) | /note = "NarI site from pMRE203 is blunted in pMRE204 by T4 DNA polymerase" |
| tRNA ArgU | 1739 ... 1815 | ACCESSION: M27155, VERSION: M27155.1, GI: 146494" |
| tRNA ArgW | 1964 ... 2038 | /note = "*E. coli* argW gene for tRNA-Arg. ACCESSION: X52794, VERSION: X52794.1, GI: 43160" |
| tRNA IleX | 2168 ... 2240 | /note = "*E. coli* ileX gene for tRNA-Ile. ACCESSION: X52800, VERSION: X52800.1, GI: 43152" |
| Selection marker | 3418 ... 4077 | /note = "chloramphenicol acetyl transferase." |
| | | /standard_name = "CamR" |
| Origin | 4693 ... 4695 | /note = "P15 ori from pACYC184." |
| misc_feature | 651 ... 701 | /note = "lac repressor." |
| | | /standard_name = "lacI" | removed and purified from the agarose gel. PCR was used to include a strong Shine-Dalgarno (SD) sequence as well as transcription enhancer sequence (ENH) in the TIR sequence as described above. The PCR product was also designed to include the SacI & XbaI site to facilitate the insertion of the PCR product (after digestion with these enzymes) into a modified pMRE205. (pMRE205 was modified by removing F2 and the vector was then cleaved with SacI and XbaI). The template used for the PCR reaction was plasmid pF213 engineered previously to expresse the conformase cluster from pAlter2 plasmid. In pAlter2, the expression of these conformases was subject to IPTG induction.

The Sequence of PCR primers to generate DNA fragment TIR, SacI, XbaI to clone Confarmases cluster F2-1-3 was as follows:

```
Forward: (SEQ ID NO 95)
5' AAGAGCTCTGATTAACCTTTATAAGGAGGAAAAACATATGGTGCTTG
GCAAACCGCAA Reverse: (SEQ ID NO 96)
5' CTTCTAGATTATCAGTTCGGGCACTTATAAA
```

The PCR DNA fragment was treated with SacI & XbaI and then purified and ligated to the enzyme treated vector. The plasmid was termed pMRE410.

Mini plasmid DNA preparations from the resulting colonies were screened by restriction with SacI & XbaI and agarose electrophoresis. Plasmid DNA and colonies that revealed the correct size were selected.

Successful cloning was verified as described above by transforming the constructed plasmid in one of the *E. coli* strains with compromised conformases but with complete copy of lac z gene such as MRE201. Plasmid DNA was prepared from the resulting dark-blue colonies indicating correct conformation of the expressed β-galactosidase due to the correct expression of conformases2-1-3. Empty vector without the any conformase did not reflect good β-galactosidase activity. Similar strategy is being followed to clone and express the conformases in this described constitutive system, which also express rate limiting tRNA genes.

The following linker/adaptor is designed to be inserted between NdeI site and XbaI:

Linker "MRE205-Linker" Restriction Enzyme Strings:

NdeI-NotI-SpeI-SmaI XhoI-XbaI

By cloning this adaptor between NdeI and XbaI in plasmid pMRE205 restricted with NdeI and XbaI a new plasmid, pMRE205-link is generated. In this plasmid sites SalI, PstI and HindIII sites, down of XbaI, is also available for potential use for cloning other conformases. However, PstI site could not be used since the engineered tRNA gene cluster has also a PstI site in the middle.

The sequence of the two complementary primers is as follows. The gg bases at each end of Primer1 and the cc at each end of Primer2 are designed to protect the sites as well as making the restriction digestion more efficient.

```
Primer1: (SEQ ID NO 97)
5' ggCATATGGCGGCCGCACTAGTCCCGGGCTCGAGTCTAGAgg

Primer2: (SEQ ID NO 98)
5' ccTCTAGACTCGAGCCCGGGACTAGTGCGGCCGCCATATGcc
```

Restriction Enzyme Analysis of the Linker/Adaptor:

```
        NotI              XhoI
Ndel   EagI    SpeI   SmaI   |   XbaI
 |      |       |       |    |    |
ggCATATGGCGGCCGCACTAGTCCCGGGCTCGAGTCTAGAgg
1---------+---------+---------+---------+--   42
ccGTATACCGCCGGCGTGATCAGGGCCCGAGCTCAGATCTcc
```

---

The invention claimed is:

1. A method of producing a target protein in a host cell, said method comprising:

(a) introducing a recombinant nucleic acid molecule encoding a target protein into said host cell;

(b) introducing a recombinanat nucleic acid molecule encoding a catalyst of protein folding comprising SEQ ID NO: 2, 12 or 16 into said host cell;

(c) culturing the said host cell, wherein the catalyst of protein folding comprising SEQ ID NO: 2, 12 or 16 assists in the correct folding of the target protein; and (d) harvesting the target protein.

2. A method of producing a target protein in a host cell, said method comprising:

(a) introducing a recombinanat nucleic acid molecule encoding a catalyst of protein folding comprising SEQ ID NO: 2, 12 or 16 into said host cell;

(b) introducing a recombinant nucleic acid molecule encoding a target protein into said host cell;
(c) culturing said host cell, wherein the catalyst of protein folding comprising SEQ ID NO: 2, 12 or 16 assists in the correct folding of the target protein; and
(d) harvesting the target protein.

* * * * *

UNITED STATES PATENT AND TRADEMARK OFFICE
CERTIFICATE OF CORRECTION

PATENT NO.        : 8,586,326 B2                              Page 1 of 1
APPLICATION NO. : 11/569304
DATED             : November 19, 2013
INVENTOR(S)       : Raafat El-Gewely It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1816 days.

Signed and Sealed this
Twenty-second Day of September, 2015

Michelle K. Lee
*Director of the United States Patent and Trademark Office*

SEQUENCE LISTING

<160> NUMBER OF SEQ ID NOS: 98

<210> SEQ ID NO 1
<211> LENGTH: 1200
<212> TYPE: DNA
<213> ORGANISM: Escherichia coli

<400> SEQUENCE: 1

```
atgtaccaac ctgtcgctct atttattggc ctgcgttaca tgcgtgggcg tgcagcggat    60
cgcttcggtc gtttcgtctc ctggctttct accatcggca ttaccctcgg ggtgatggcg   120
ctggtcacag tattgtcagt gatgaacggc tttgagcgcg agctgcaaaa caacatcctt   180
ggcctgatgc cacaggcaat tctctcttct gagcatggct ctcttaaccc gcagcaactc   240
ccggaaacgg cagtcaaact ggacggcgtt aatcgcgtcg cacctattac taccggtgat   300
gtggtactgc aaagcgcgcg cagcgtggcg gtcggggtga tgctgggtat cgatccggcg   360
caaaaagatc cactaacgcc gtatctggtc aatgtgaaac aaactgacct cgagccgggg   420
aaatataatg tcatcctcgg cgaacaactt gcctcacagc taggcgttaa tcgcggtgat   480
caaatccgcg tgatggtgcc atctgccagc cagttcacgc cgatggggcg tattccaagt   540
cagcgcctgt tcaatgtgat tggtactttt gccgctaaca gtgaagtcga tggctatgaa   600
atgctggtga atattgagga tgcctcgcgt ctgatgcgtt atccggcagg caatattacc   660
```

```
ggctggcgtt tgtggctgga tgagccgctg aaagttgact ctttaagtca gcaaaaactg    720
cctgaaggca gcaaatggca ggactggcgt gatcgtaaag gcgagctgtt ccaggccgta    780
cgcatggaaa aaatatgat gggcttactg ctgagcctga ttgtcgccgt tgcggcgttt    840
aacattatta cctcgctggg gctgatggtg atggagaagc agggcgaagt agcgatcctg    900
caaacgcaag gcttaactcc gcacaaatc atgatggtct ttatggtgca agggccagc    960 gccgggatta tcggtgcgat cctcggagcg gcgcttggcg cactgcttgc cagccagtta   1020
aataatctga tgccgataat cggcgtcctg cttgatggcg cggcgctgcc ggtggctatc   1080
gaacctttac aggtcattgt tattgcgctg gtggcgatgg ctatcgcgct gctgtctacg   1140 ctttacccttc atggcgcgc tgccgccaca caacccgctg aggctttacg ttatgaataa   1200
```

<210> SEQ ID NO 2
<211> LENGTH: 399
<212> TYPE: PRT
<213> ORGANISM: Escherichia coli

<400> SEQUENCE: 2

```
Met Tyr Gln Pro Val Ala Leu Phe Ile Gly Leu Arg Tyr Met Arg Gly
1               5                   10                  15

Arg Ala Ala Asp Arg Phe Gly Arg Phe Val Ser Trp Leu Ser Thr Ile
            20                  25                  30

Gly Ile Thr Leu Gly Val Met Ala Leu Val Thr Val Leu Ser Val Met
        35                  40                  45

Asn Gly Phe Glu Arg Glu Leu Gln Asn Asn Ile Leu Gly Leu Met Pro
    50                  55                  60

Gln Ala Ile Leu Ser Ser Glu His Gly Ser Leu Asn Pro Gln Gln Leu
65                  70                  75                  80

Pro Glu Thr Ala Val Lys Leu Asp Gly Val Asn Arg Val Ala Pro Ile
                85                  90                  95

Thr Thr Gly Asp Val Val Leu Gln Ser Ala Arg Ser Val Ala Val Gly
            100                 105                 110

Val Met Leu Gly Ile Asp Pro Ala Gln Lys Asp Pro Leu Thr Pro Tyr
        115                 120                 125

Leu Val Asn Val Lys Gln Thr Asp Leu Glu Pro Gly Lys Tyr Asn Val
    130                 135                 140

Ile Leu Gly Glu Gln Leu Ala Ser Gln Leu Gly Val Asn Arg Gly Asp
145                 150                 155                 160

Gln Ile Arg Val Met Val Pro Ser Ala Ser Gln Phe Thr Pro Met Gly
                165                 170                 175

Arg Ile Pro Ser Gln Arg Leu Phe Asn Val Ile Gly Thr Phe Ala Ala
            180                 185                 190

Asn Ser Glu Val Asp Gly Tyr Glu Met Leu Val Asn Ile Glu Asp Ala
        195                 200                 205

Ser Arg Leu Met Arg Tyr Pro Ala Gly Asn Ile Thr Gly Trp Arg Leu
    210                 215                 220

Trp Leu Asp Glu Pro Leu Lys Val Asp Ser Leu Ser Gln Gln Lys Leu
225                 230                 235                 240

Pro Glu Gly Ser Lys Trp Gln Asp Trp Arg Asp Arg Lys Gly Glu Leu
                245                 250                 255

Phe Gln Ala Val Arg Met Glu Lys Asn Met Met Gly Leu Leu Leu Ser
            260                 265                 270

Leu Ile Val Ala Val Ala Ala Phe Asn Ile Ile Thr Ser Leu Gly Leu
        275                 280                 285
```

```
Met Val Met Glu Lys Gln Gly Glu Val Ala Ile Leu Gln Thr Gln Gly
    290                 295                 300
Leu Thr Pro Arg Gln Ile Met Met Val Phe Met Val Gln Gly Ala Ser
305                 310                 315                 320
Ala Gly Ile Ile Gly Ala Ile Leu Gly Ala Ala Leu Gly Ala Leu Leu
                325                 330                 335
Ala Ser Gln Leu Asn Asn Leu Met Pro Ile Ile Gly Val Leu Leu Asp
            340                 345                 350
Gly Ala Ala Leu Pro Val Ala Ile Glu Pro Leu Gln Val Ile Val Ile
                355                 360                 365
Ala Leu Val Ala Met Ala Ile Ala Leu Leu Ser Thr Leu Tyr Pro Ser
    370                 375                 380
Trp Arg Ala Ala Ala Thr Gln Pro Ala Glu Ala Leu Arg Tyr Glu
385                 390                 395
```

<210> SEQ ID NO 3
<211> LENGTH: 687
<212> TYPE: DNA
<213> ORGANISM: Escherichia coli

<400> SEQUENCE: 3

```
ttgcaatgcg acaacctgtg caaacgctat caggaaggca gtgtgcaaac cgatgtactg      60
cacaatgtca gtttcagcgt gggcgaaggt gaaatgatgg cgatcgtcgg tagctctggt     120
tccggtaaaa gtaccttgct gcacctgctg ggcgggctgg ataccaacc ctccggcgat      180
gtgatcttta acggtcaacc gatgagcaaa ctgtcttcgg cggcgaaagc agaactgcgc     240
aaccagaagc tgggctttat ttatcagttt caccacctgc tgccggattt tactgccctg     300
gaaaacgtgg ctatgccgct gctgattggc aagaaaaagc ccgctgaaat caacagccgt     360
gcacttgaga tgttaaaagc ggtggggctg agcatcgtg cgaatcaccg cccatctgaa      420
ctttctggcg gcgaacgcca gcgtgtggcg attcccgtg cgctggtcaa taacccgtgg      480
ctggtactgg cggatgaacc taccggtaac ctcgatgcgc gtaacgcaga cagcatcttc     540
cagttgcttg gggaattgaa tcgcttgcag ggcaccgcct tcctggtggt tactcacgac     600
ctgcaactgg cgaaacgtat gagccgccaa ctggagatgc gtgatggtcg tctgacggcg     660
gaactgagcc tgatgggggc ggagtaa                                          687
```

<210> SEQ ID NO 4
<211> LENGTH: 228
<212> TYPE: PRT
<213> ORGANISM: Escherichia coli

<400> SEQUENCE: 4

```
Met Gln Cys Asp Asn Leu Cys Lys Arg Tyr Gln Glu Gly Ser Val Gln
1               5                   10                  15
Thr Asp Val Leu His Asn Val Ser Phe Ser Val Gly Glu Gly Glu Met
                20                  25                  30
Met Ala Ile Val Gly Ser Ser Gly Ser Gly Lys Ser Thr Leu Leu His
            35                  40                  45
Leu Leu Gly Gly Leu Asp Thr Pro Thr Ser Gly Asp Val Ile Phe Asn
    50                  55                  60
Gly Gln Pro Met Ser Lys Leu Ser Ser Ala Ala Lys Ala Glu Leu Arg
65                  70                  75                  80
Asn Gln Lys Leu Gly Phe Ile Tyr Gln Phe His His Leu Leu Pro Asp
                85                  90                  95
```

Phe Thr Ala Leu Glu Asn Val Ala Met Pro Leu Leu Ile Gly Lys Lys
                100                 105                 110

Lys Pro Ala Glu Ile Asn Ser Arg Ala Leu Glu Met Leu Lys Ala Val
            115                 120                 125

Gly Leu Glu His Arg Ala Asn His Arg Pro Ser Glu Leu Ser Gly Gly
        130                 135                 140

Glu Arg Gln Arg Val Ala Ile Ala Arg Ala Leu Val Asn Asn Pro Trp
145                 150                 155                 160

Leu Val Leu Ala Asp Glu Pro Thr Gly Asn Leu Asp Ala Arg Asn Ala
                165                 170                 175

Asp Ser Ile Phe Gln Leu Leu Gly Glu Leu Asn Arg Leu Gln Gly Thr
            180                 185                 190

Ala Phe Leu Val Val Thr His Asp Leu Gln Leu Ala Lys Arg Met Ser
        195                 200                 205

Arg Gln Leu Glu Met Arg Asp Gly Arg Leu Thr Ala Glu Leu Ser Leu
210                 215                 220

Met Gly Ala Glu
225

<210> SEQ ID NO 5
<211> LENGTH: 1245
<212> TYPE: DNA
<213> ORGANISM: Escherichia coli

<400> SEQUENCE: 5
atggcgatgc ctttatcgtt attgattggc ctgcgtttta gccgcggacg gcgacgcggc    60
ggcatggtgt cgctgatctc cgtcatttct accattggca ttgcccttgg cgtggcggta   120
ttgatcgtcg gcttaagcgc gatgaacggc tttgaacgcg aactgaataa ccgcattctg   180
gcggtggtgc cgcatggcga aatagaggcg gtggatcaac cgtggactaa ctggcaggaa   240
gcactggata cgtgcaaaa agtgccaggt attgccgccg ctgcgccgta tatcaatttc   300
accgggctgg tggaaagtgg agcgaatctg cgcgcaatcc aggtgaaggg cgttaacccg   360
caacaggaac agcgtctgag cgcattaccc tcgtttgttc aggggatgc ctggcgcaat    420 tttaaagcgg gcgaacagca aattatcatc ggcaaaggcg tggcggatgc gctgaaagtg   480
aagcagggcg attgggtgtc gattatgatc cccaactcga atcctgagca taaactgatg   540
cagccaaaac gtgtgcgttt gcacgttgcc ggtattttgc agttgagtgg tcaactcgat   600
cacagttttg ccatgatccc gctggcggat gcccaacaat atcttgatat gggttccagc   660
gtgtcaggta ttgcccttaa atgacggat gtttttcaacg ccaataagct ggtacgcgat    720
gcgggtgaag tgaccaacag ctatgtttat attaaaagct ggattggtac ttacggctat   780
atgtatcgcg atatccagat gatccgcgcc attatgtatc tggcgatggt actggtgatt   840
ggcgtggcct gtttcaacat cgtctccacc ttagtgatgg cggtgaaaga caagagtggc   900
gatatcgcag tattaagaac gctgggggcg aaagatggtt taattcgcgc catctttgtc   960
tggtatggat tgctggcagg gctattcggt agcctgtgtg gtgtgattat cggcgtagtt  1020
gtttcactgc aacttacccc gattattgag cggattgaaa agctgatcgg tcatcagttc  1080
ctctccagcg atatctattt tattgacttc ctgccatcgg aattgcactg gctggacgtc  1140
ttctacgtac tggtcacagc attgttgctg agtcttttgg caagttggta tccggcgcgg  1200
cgcgccagta atattgaccc tgcgcgagtc cttagcggcc agtaa                 1245

<210> SEQ ID NO 6
<211> LENGTH: 414

```
<212> TYPE: PRT
<213> ORGANISM: Escherichia coli

<400> SEQUENCE: 6

Met Ala Met Pro Leu Ser Leu Leu Ile Gly Leu Arg Phe Ser Arg Gly
1               5                   10                  15

Arg Arg Arg Gly Gly Met Val Ser Leu Ile Ser Val Ile Ser Thr Ile
            20                  25                  30

Gly Ile Ala Leu Gly Val Ala Val Leu Ile Val Gly Leu Ser Ala Met
            35                  40                  45

Asn Gly Phe Glu Arg Glu Leu Asn Asn Arg Ile Leu Ala Val Val Pro
50                  55                  60

His Gly Glu Ile Glu Ala Val Asp Gln Pro Trp Thr Asn Trp Gln Glu
65                  70                  75                  80

Ala Leu Asp Asn Val Gln Lys Val Pro Gly Ile Ala Ala Ala Ala Pro
                85                  90                  95

Tyr Ile Asn Phe Thr Gly Leu Val Glu Ser Gly Ala Asn Leu Arg Ala
            100                 105                 110

Ile Gln Val Lys Gly Val Asn Pro Gln Gln Glu Gln Arg Leu Ser Ala
        115                 120                 125

Leu Pro Ser Phe Val Gln Gly Asp Ala Trp Arg Asn Phe Lys Ala Gly
130                 135                 140

Glu Gln Gln Ile Ile Gly Lys Gly Val Ala Asp Ala Leu Lys Val
145                 150                 155                 160

Lys Gln Gly Asp Trp Val Ser Ile Met Ile Pro Asn Ser Asn Pro Glu
                165                 170                 175

His Lys Leu Met Gln Pro Lys Arg Val Arg Leu His Val Ala Gly Ile
            180                 185                 190

Leu Gln Leu Ser Gly Gln Leu Asp His Ser Phe Ala Met Ile Pro Leu
        195                 200                 205

Ala Asp Ala Gln Gln Tyr Leu Asp Met Gly Ser Val Ser Gly Ile
210                 215                 220

Ala Leu Lys Met Thr Asp Val Phe Asn Ala Asn Lys Leu Val Arg Asp
225                 230                 235                 240

Ala Gly Glu Val Thr Asn Ser Tyr Val Tyr Ile Lys Ser Trp Ile Gly
                245                 250                 255

Thr Tyr Gly Tyr Met Tyr Arg Asp Ile Gln Met Ile Arg Ala Ile Met
            260                 265                 270

Tyr Leu Ala Met Val Leu Val Ile Gly Val Ala Cys Phe Asn Ile Val
        275                 280                 285

Ser Thr Leu Val Met Ala Val Lys Asp Lys Ser Gly Asp Ile Ala Val
290                 295                 300

Leu Arg Thr Leu Gly Ala Lys Asp Gly Leu Ile Arg Ala Ile Phe Val
305                 310                 315                 320

Trp Tyr Gly Leu Leu Ala Gly Leu Phe Gly Ser Leu Cys Gly Val Ile
                325                 330                 335

Ile Gly Val Val Val Ser Leu Gln Leu Thr Pro Ile Ile Glu Arg Ile
            340                 345                 350

Glu Lys Leu Ile Gly His Gln Phe Leu Ser Ser Asp Ile Tyr Phe Ile
        355                 360                 365

Asp Phe Leu Pro Ser Glu Leu His Trp Leu Asp Val Phe Tyr Val Leu
370                 375                 380

Val Thr Ala Leu Leu Leu Ser Leu Leu Ala Ser Trp Tyr Pro Ala Arg
385                 390                 395                 400
```

```
          Arg Ala Ser Asn Ile Asp Pro Ala Arg Val Leu Ser Gly Gln
                      405                 410

<210> SEQ ID NO 7
<211> LENGTH: 912
<212> TYPE: DNA
<213> ORGANISM: Escherichia coli

<400> SEQUENCE: 7
atgtattacg ggtttgatat tggtggaaca aaaattgcgc ttggcgtgtt tgatagcggt    60
cggcagttgc agtgggaaaa gcgggtgccg acaccgcgtg acagctatga cgcattttta   120
gatgcagtgt gcgagctggt agccgaagct gatcaacgtt tggctgtaa aggctctgtc    180 ggcatcggta ttccgggaat gccggaaaca gaagatggta cgctgtatgc cgccaatgtc   240
cctgctgcca gcggtaaacc gctgcgtgcc gacctgagcg cacgtcttga tcgcgatgta   300
cgccttgata cgatgccaa ctgttttgcc ctttcagaag cctgggatga cgaatttacg    360
caatatccgt tggtgatggg gttgattctc ggcaccggcg ttggcggcgg gctgattttc   420
aacggcaaac cgattaccgg gaaaagctac attaccggcg agtttggcca tatgcgtctg   480
ccggttgatg cgttaaccat gatggggctg gatttcccgt acgccgctg cggctgtggt    540 cagcatggct gcattgaaaa ttatctgtct ggtcgcggtt ttgcgtggct gtatcaacac   600
tattatcatc aaccgttgcc ggctcccgaa attattgcgc tttatgatca aggcgatgag   660
caggcaaggg cgcacgttga gcgttatctg gatttattag cggtttgtct gggaaatatc   720
ctgaccattg ttgaccctga cctggtcgtc attggtggtg gcttatcgaa tttcccggca   780
atcacaacgc aactggcgga caggctgcct cgtcatctct acctgtagc tcgtgttccg    840 cgcattgaac gcgcgcgcca cggtgatgcg ggaggaatgc gtggtgcggc cttcctacat   900
ctaaccgatt aa                                                       912

<210> SEQ ID NO 8
<211> LENGTH: 303
<212> TYPE: PRT
<213> ORGANISM: Escherichia coli

<400> SEQUENCE: 8

Met Tyr Tyr Gly Phe Asp Ile Gly Gly Thr Lys Ile Ala Leu Gly Val
1               5                   10                  15

Phe Asp Ser Gly Arg Gln Leu Gln Trp Glu Lys Arg Val Pro Thr Pro
            20                  25                  30

Arg Asp Ser Tyr Asp Ala Phe Leu Asp Ala Val Cys Glu Leu Val Ala
        35                  40                  45

Glu Ala Asp Gln Arg Phe Gly Cys Lys Gly Ser Val Gly Ile Gly Ile
    50                  55                  60

Pro Gly Met Pro Glu Thr Glu Asp Gly Thr Leu Tyr Ala Ala Asn Val
65                  70                  75                  80

Pro Ala Ala Ser Gly Lys Pro Leu Arg Ala Asp Leu Ser Ala Arg Leu
                85                  90                  95

Asp Arg Asp Val Arg Leu Asp Asn Asp Ala Asn Cys Phe Ala Leu Ser
            100                 105                 110

Glu Ala Trp Asp Asp Glu Phe Thr Gln Tyr Pro Leu Val Met Gly Leu
        115                 120                 125

Ile Leu Gly Thr Gly Val Gly Gly Gly Leu Ile Phe Asn Gly Lys Pro
    130                 135                 140

Ile Thr Gly Lys Ser Tyr Ile Thr Gly Glu Phe Gly His Met Arg Leu
145                 150                 155                 160
```

```
Pro Val Asp Ala Leu Thr Met Met Gly Leu Asp Phe Pro Leu Arg Arg
                165                 170                 175

Cys Gly Cys Gly Gln His Gly Cys Ile Glu Asn Tyr Leu Ser Gly Arg
            180                 185                 190

Gly Phe Ala Trp Leu Tyr Gln His Tyr Tyr His Gln Pro Leu Pro Ala
        195                 200                 205

Pro Glu Ile Ile Ala Leu Tyr Asp Gln Gly Asp Glu Gln Ala Arg Ala
    210                 215                 220

His Val Glu Arg Tyr Leu Asp Leu Leu Ala Val Cys Leu Gly Asn Ile
225                 230                 235                 240

Leu Thr Ile Val Asp Pro Leu Val Val Ile Gly Gly Leu Ser
                245                 250                 255

Asn Phe Pro Ala Ile Thr Thr Gln Leu Ala Asp Arg Leu Pro Arg His
                260                 265                 270

Leu Leu Pro Val Ala Arg Val Pro Arg Ile Glu Arg Ala Arg His Gly
            275                 280                 285

Asp Ala Gly Gly Met Arg Gly Ala Ala Phe Leu His Leu Thr Asp
    290                 295                 300
```

<210> SEQ ID NO 9
<211> LENGTH: 822
<212> TYPE: DNA
<213> ORGANISM: Escherichia coli

<400> SEQUENCE: 9

```
atgctgtcgc gtcggggtca tcggttaagt cgttttcgta aaataaacg ccgcctgcgc      60
gagcgtttgc gtcagcgtat ttttttcaga gataaagtgg tgccggaagc aatggaaaaa    120
ccaagagtac tcgtactgac aggggcagga atttctgcgg aatcaggtat tcgtaccttt    180
cgcgccgcag atggcctgtg gaagaacat  cgggttgaag atgtggcaac gccgaaggt     240
ttcgatcgcg atcctgaact ggtgcaagcg ttttataacg cccgtcgtcg acagctgcag    300
cagccagaaa ttcagcctaa cgccgcgcat cttgcgctgg ctaaactgca agatgctctc    360
ggcgatcgct ttttgctggt gacgcagaat atagacaacc tgcatgaacg cgcaggtaat    420
accaatgtga ttcatatgca tggggaactg ctgaaagttc gttgttcaca agtggtcag    480
gttctcgact ggaccggaga cgttacccca gaagataaat gccattgctg ccagttcccg    540
gccccctgc gcccacacgt agtatggttt ggcgaaatgc cactcggcat ggatgaaatt    600
tatatggcgt tgtcgatggc cgatattttc attgccattg gtacttccgg gcatgtttat    660
ccggcggctg ggtttgttca cgaagcgaaa ctgcatggcg cgcacaccgt ggagctgaat    720
cttgaaccaa gtcaggtcgg taatgaattt gccgagaaat attacggccc ggcaagccag    780
gtggtgccag aatttgttga aaagttgctg aagggattat aa                       822
```

<210> SEQ ID NO 10
<211> LENGTH: 273
<212> TYPE: PRT
<213> ORGANISM: Escherichia coli

<400> SEQUENCE: 10

```
Met Leu Ser Arg Arg Gly His Arg Leu Ser Arg Phe Arg Lys Asn Lys
1               5                   10                  15

Arg Arg Leu Arg Glu Arg Leu Arg Gln Arg Ile Phe Phe Arg Asp Lys
            20                  25                  30

Val Val Pro Glu Ala Met Glu Lys Pro Arg Val Leu Val Leu Thr Gly
        35                  40                  45
```

```
Ala Gly Ile Ser Ala Glu Ser Gly Ile Arg Thr Phe Arg Ala Ala Asp
         50                  55                  60

Gly Leu Trp Glu Glu His Arg Val Glu Asp Val Ala Thr Pro Glu Gly
 65                  70                  75                  80

Phe Asp Arg Asp Pro Glu Leu Val Gln Ala Phe Tyr Asn Ala Arg Arg
                 85                  90                  95

Arg Gln Leu Gln Gln Pro Glu Ile Gln Pro Asn Ala Ala His Leu Ala
            100                 105                 110

Leu Ala Lys Leu Gln Asp Ala Leu Gly Asp Arg Phe Leu Leu Val Thr
        115                 120                 125

Gln Asn Ile Asp Asn Leu His Glu Arg Ala Gly Asn Thr Asn Val Ile
130                 135                 140

His Met His Gly Glu Leu Leu Lys Val Arg Cys Ser Gln Ser Gly Gln
145                 150                 155                 160

Val Leu Asp Trp Thr Gly Asp Val Thr Pro Glu Asp Lys Cys His Cys
                165                 170                 175

Cys Gln Phe Pro Ala Pro Leu Arg Pro His Val Val Trp Phe Gly Glu
            180                 185                 190

Met Pro Leu Gly Met Asp Glu Ile Tyr Met Ala Leu Ser Met Ala Asp
        195                 200                 205

Ile Phe Ile Ala Ile Gly Thr Ser Gly His Val Tyr Pro Ala Ala Gly
210                 215                 220

Phe Val His Glu Ala Lys Leu His Gly Ala His Thr Val Glu Leu Asn
225                 230                 235                 240

Leu Glu Pro Ser Gln Val Gly Asn Glu Phe Ala Glu Lys Tyr Tyr Gly
                245                 250                 255

Pro Ala Ser Gln Val Val Pro Glu Phe Val Glu Lys Leu Leu Lys Gly
            260                 265                 270

Leu

<210> SEQ ID NO 11
<211> LENGTH: 633
<212> TYPE: DNA
<213> ORGANISM: Escherichia coli

<400> SEQUENCE: 11
atggtgcttg gcaaaccgca acagacccg actctcgaat ggttcttgtc tcattgccac      60
attcataagt acccatccaa gagcacgctt attcaccagg gtgaaaaagc ggaaacgctg    120
tactacatcg ttaaaggctc tgtggctgtg ctgatcaaag acgaagaggg taaagaaatg    180
atcctctcct atctgaatca gggtgatttt attggcgaac tgggcctgtt tgaagagggc    240
caggaacgta gcgcatgggt acgtgcgaaa accgcctgtg aagtggctga aatttcgtac    300
aaaaaatttc gccaattgat tcaggtaaac ccggacattc tgatgcgtct gtctgcacag    360
atggcgcgtc gtctgcaagt cacttcagag aaagtgggca acctggcgtt cctcgacgtg    420
acgggccgca ttgcacagac tctgctcaat ctggcaaaac aaccagacgc tatgactcac    480
ccggacggta tgcaaatcaa aattacccgt caggaaatcg gtcagattgt cggctgttct    540
cgtgaaaccg tgggacgcat tctgaagatg cttgaagatc agaacctgat ctccgcacac    600
ggtaaaacca tcgtcgttta cggcactcgt taa                                 633

<210> SEQ ID NO 12
<211> LENGTH: 210
<212> TYPE: PRT
<213> ORGANISM: Escherichia coli
```

<400> SEQUENCE: 12

```
Met Val Leu Gly Lys Pro Gln Thr Asp Pro Thr Leu Glu Trp Phe Leu
1               5                   10                  15

Ser His Cys His Ile His Lys Tyr Pro Ser Lys Ser Thr Leu Ile His
            20                  25                  30

Gln Gly Glu Lys Ala Glu Thr Leu Tyr Tyr Ile Val Lys Gly Ser Val
        35                  40                  45

Ala Val Leu Ile Lys Asp Glu Gly Lys Glu Met Ile Leu Ser Tyr
    50                  55                  60

Leu Asn Gln Gly Asp Phe Ile Gly Glu Leu Gly Leu Phe Glu Glu Gly
65                  70                  75                  80

Gln Glu Arg Ser Ala Trp Val Arg Ala Lys Thr Ala Cys Glu Val Ala
                85                  90                  95

Glu Ile Ser Tyr Lys Lys Phe Arg Gln Leu Ile Gln Val Asn Pro Asp
            100                 105                 110

Ile Leu Met Arg Leu Ser Ala Gln Met Ala Arg Arg Leu Gln Val Thr
        115                 120                 125

Ser Glu Lys Val Gly Asn Leu Ala Phe Leu Asp Val Thr Gly Arg Ile
    130                 135                 140

Ala Gln Thr Leu Leu Asn Leu Ala Lys Gln Pro Asp Ala Met Thr His
145                 150                 155                 160

Pro Asp Gly Met Gln Ile Lys Ile Thr Arg Gln Glu Ile Gly Gln Ile
                165                 170                 175

Val Gly Cys Ser Arg Glu Thr Val Gly Arg Ile Leu Lys Met Leu Glu
            180                 185                 190

Asp Gln Asn Leu Ile Ser Ala His Gly Lys Thr Ile Val Val Tyr Gly
        195                 200                 205

Thr Arg
    210
```

<210> SEQ ID NO 13
<211> LENGTH: 2091
<212> TYPE: DNA
<213> ORGANISM: Escherichia coli

<400> SEQUENCE: 13

```
atgtggcgca gactgattta tcaccccgat atcaactatg cacttcgaca aacgctggtg      60
ctatgtttgc ccgtggccgt tgggttaatg cttggcgaat tacgattcgg tctgctcttc     120
tccctcgttc ctgcctgttg caatattgcg ggccttgata cgcctcataa acgtttttc      180 aaacgcttaa tcattggtgc gtcgctgttt gccacctgta gcttgctgac acagctacta     240
ctggcaaaag atgttcccct gccctttttg ctgaccggat taacgctggt acttggcgtc     300
actgctgagc tggggccatt gcacgcaaaa ttgcttcctg catcgctgct cgccgccatt     360
tttaccctca gtttggcggg atacatgccg gtctgggaac cgttgctcat ctatgcgttg     420
ggcactctct ggtacggatt gtttaactgg ttttggttct ggatctggcg cgaacaaccg     480
ctgcgcgagt cactaagtct gctgtaccgt gaactggcag attattgtga agccaaatac     540
agcctgctta cccagcacac cgaccctgaa aaagcgctgc cgccgctgct ggtgcgccag     600
caaaaagcgg tcgatctaat tacccagtgc tatcagcaaa tgcatatgct tccgcgcaa      660 aataatactg actacaagcg gatgctgcgt attttccagg aggcgctgga tttacaggaa     720
catatttcgg tcagtttgca tcagccggaa gaggtgcaaa gctggtcga gcgtagccat      780 gcggaagaag ttatccgctg gaatgcgcaa accgtcgccg ctcgcctgcg cgtgctggct     840
```

```
gatgacattc tttaccatcg cctgccaacg cgttttacga tggaaaagca aattggcgca      900
ctggaaaaaa tcgcccgcca gcatccggat aatccggttg ggcaattctg ctactggcat      960
ttcagccgca tcgcccgcgt gctgcgcacc caaaaaccgc tctatgcccg tgacttactg     1020
gccgataaac agcggcgaat gccattactt ccggcgctga aaagttatct gtcactaaag     1080
tctccggcgc tacgcaatgc cggacgactc agtgtgatgt taagcgttgc cagcctgatg     1140
ggcaccgcgc tgcatctgcc gaagtcgtac tggatcctga tgacggtatt gctggtgaca     1200
caaaatggct atggcgcaac ccgtctgagg attgtgaatc gctccgtggg aaccgtggtc     1260
gggttaatca ttgcgggcgt ggcgctgcac tttaaaattc ccgaaggtta cccctgacg      1320
ttgatgctga ttaccaccct cgccagctac ctgatattgc gcaaaaacta cggctgggcg     1380
acggtcggtt ttactattac cgcagtgtat accctgcaac tattgtggtt gaacggcgag     1440
caatacatcc ttccgcgtct tatcgatacc attattggtt gtttaattgc tttcggcggt     1500
actgtctggc tgtggccgca gtggcagagc gggttattgc gtaaaaacgc ccatgatgct     1560
ttagaagcct atcaggaagc gattcgcttg attcttagcg aggatccgca acctacgcca     1620
ctggcctgga gcgaatgcg ggtaaatcag gcacataaca ctctgtataa ctcattgaat     1680
caggcgatgc aggaaccggc gtttaacagc cattatctgg cagatatgaa actgtgggta     1740
acgcacagcc agtttattgt tgagcatatt aatgccatga ccacgctggc gcgggaacac     1800
cgggcattgc cacctgaact ggcacaagag tatttacagt cttgtgaaat cgccattcag     1860
cgttgtcagc agcgactgga gtatgacgaa ccgggtagtt ctggcgatgc caatatcatg     1920
gatgcgccgg agatgcagcc gcacgaaggc gcggcaggta cgctggagca gcatttacag     1980
cgggttattg gtcatctgaa caccatgcac accatttcgt cgatggcatg cgtcagcga     2040
ccgcatcacg ggatttggct gagtcgcaag ttgcgggatt cgaaggcgta a             2091

<210> SEQ ID NO 14
<211> LENGTH: 696
<212> TYPE: PRT
<213> ORGANISM: Escherichia coli

<400> SEQUENCE: 14

Met Trp Arg Arg Leu Ile Tyr His Pro Asp Ile Asn Tyr Ala Leu Arg
1               5                   10                  15

Gln Thr Leu Val Leu Cys Leu Pro Val Ala Val Gly Leu Met Leu Gly
            20                  25                  30

Glu Leu Arg Phe Gly Leu Leu Phe Ser Leu Val Pro Ala Cys Cys Asn
        35                  40                  45

Ile Ala Gly Leu Asp Thr Pro His Lys Arg Phe Phe Lys Arg Leu Ile
    50                  55                  60

Ile Gly Ala Ser Leu Phe Ala Thr Cys Ser Leu Leu Thr Gln Leu Leu
65                  70                  75                  80

Leu Ala Lys Asp Val Pro Leu Pro Phe Leu Leu Thr Gly Leu Thr Leu
                85                  90                  95

Val Leu Gly Val Thr Ala Glu Leu Gly Pro Leu His Ala Lys Leu Leu
            100                 105                 110

Pro Ala Ser Leu Leu Ala Ala Ile Phe Thr Leu Ser Leu Ala Gly Tyr
        115                 120                 125

Met Pro Val Trp Glu Pro Leu Leu Ile Tyr Ala Leu Gly Thr Leu Trp
    130                 135                 140

Tyr Gly Leu Phe Asn Trp Phe Trp Phe Trp Ile Trp Arg Glu Gln Pro
145                 150                 155                 160
```

```
Leu Arg Glu Ser Leu Ser Leu Leu Tyr Arg Glu Leu Ala Asp Tyr Cys
            165                 170                 175
Glu Ala Lys Tyr Ser Leu Leu Thr Gln His Thr Asp Pro Glu Lys Ala
            180                 185                 190
Leu Pro Pro Leu Leu Val Arg Gln Gln Lys Ala Val Asp Leu Ile Thr
            195                 200                 205
Gln Cys Tyr Gln Gln Met His Met Leu Ser Ala Gln Asn Asn Thr Asp
            210                 215                 220
Tyr Lys Arg Met Leu Arg Ile Phe Gln Glu Ala Leu Asp Leu Gln Glu
225                 230                 235                 240
His Ile Ser Val Ser Leu His Gln Pro Glu Glu Val Gln Lys Leu Val
                    245                 250                 255
Glu Arg Ser His Ala Glu Glu Val Ile Arg Trp Asn Ala Gln Thr Val
                    260                 265                 270
Ala Ala Arg Leu Arg Val Leu Ala Asp Asp Ile Leu Tyr His Arg Leu
                    275                 280                 285
Pro Thr Arg Phe Thr Met Glu Lys Gln Ile Gly Ala Leu Glu Lys Ile
            290                 295                 300
Ala Arg Gln His Pro Asp Asn Pro Val Gly Gln Phe Cys Tyr Trp His
305                 310                 315                 320
Phe Ser Arg Ile Ala Arg Val Leu Arg Thr Gln Lys Pro Leu Tyr Ala
                    325                 330                 335
Arg Asp Leu Leu Ala Asp Lys Gln Arg Arg Met Pro Leu Leu Pro Ala
                    340                 345                 350
Leu Lys Ser Tyr Leu Ser Leu Lys Ser Pro Ala Leu Arg Asn Ala Gly
            355                 360                 365
Arg Leu Ser Val Met Leu Ser Val Ala Ser Leu Met Gly Thr Ala Leu
            370                 375                 380
His Leu Pro Lys Ser Tyr Trp Ile Leu Met Thr Val Leu Leu Val Thr
385                 390                 395                 400
Gln Asn Gly Tyr Gly Ala Thr Arg Leu Arg Ile Val Asn Arg Ser Val
                    405                 410                 415
Gly Thr Val Val Gly Leu Ile Ile Ala Gly Val Ala Leu His Phe Lys
                    420                 425                 430
Ile Pro Glu Gly Tyr Thr Leu Thr Leu Met Leu Ile Thr Thr Leu Ala
            435                 440                 445
Ser Tyr Leu Ile Leu Arg Lys Asn Tyr Gly Trp Ala Thr Val Gly Phe
450                 455                 460
Thr Ile Thr Ala Val Tyr Thr Leu Gln Leu Leu Trp Leu Asn Gly Glu
465                 470                 475                 480
Gln Tyr Ile Leu Pro Arg Leu Ile Asp Thr Ile Gly Cys Leu Ile
                    485                 490                 495
Ala Phe Gly Gly Thr Val Trp Leu Trp Pro Gln Trp Gln Ser Gly Leu
            500                 505                 510
Leu Arg Lys Asn Ala His Asp Ala Leu Glu Ala Tyr Gln Glu Ala Ile
            515                 520                 525
Arg Leu Ile Leu Ser Glu Asp Pro Gln Pro Thr Pro Leu Ala Trp Gln
            530                 535                 540
Arg Met Arg Val Asn Gln Ala His Asn Thr Leu Tyr Asn Ser Leu Asn
545                 550                 555                 560
Gln Ala Met Gln Glu Pro Ala Phe Asn Ser His Tyr Leu Ala Asp Met
                    565                 570                 575
Lys Leu Trp Val Thr His Ser Gln Phe Ile Val Glu His Ile Asn Ala
```

|   |   | 580 |   |   |   | 585 |   |   |   | 590 |   |
|---|---|---|---|---|---|---|---|---|---|---|---|

Met Thr Thr Leu Ala Arg Glu His Arg Ala Leu Pro Pro Glu Leu Ala
              595                 600                 605

Gln Glu Tyr Leu Gln Ser Cys Glu Ile Ala Ile Gln Arg Cys Gln Gln
              610                 615                 620

Arg Leu Glu Tyr Asp Glu Pro Gly Ser Ser Gly Asp Ala Asn Ile Met
625                 630                 635                 640

Asp Ala Pro Glu Met Gln Pro His Glu Gly Ala Ala Gly Thr Leu Glu
              645                 650                 655

Gln His Leu Gln Arg Val Ile Gly His Leu Asn Thr Met His Thr Ile
              660                 665                 670

Ser Ser Met Ala Trp Arg Gln Arg Pro His His Gly Ile Trp Leu Ser
              675                 680                 685

Arg Lys Leu Arg Asp Ser Lys Ala
              690                 695

<210> SEQ ID NO 15
<211> LENGTH: 387
<212> TYPE: DNA
<213> ORGANISM: Escherichia coli

<400> SEQUENCE: 15
gtggcgtcca gctcattgat tatggggaat aacatgcacg taaaatactt agcagggatt      60
gtcggtgccg cgctactgat ggcgggttgt agctccagca acgaattgag tgctgccggt     120
cagagtgtac gcattgtgga cgagcagcca ggcgcagagt gccagctgat tggtactgcg     180
acaggtaagc aaagcaactg gctttccggg caacacggag aagagggcgg ttctatgcgc     240
ggcgcagcaa acgatctgcg caaccaggcg ctgcaatgg gcggtaacgt gatttatggc      300
atcagtagcc cgtcgcaggg aatgttgtcc agttttgtcc cgacggatag ccagattatc     360
ggccaggtat ataagtgccc gaactga                                         387

<210> SEQ ID NO 16
<211> LENGTH: 128
<212> TYPE: PRT
<213> ORGANISM: Escherichia coli

<400> SEQUENCE: 16

Met Ala Ser Ser Ser Leu Ile Met Gly Asn Asn Met His Val Lys Tyr
1               5                   10                  15

Leu Ala Gly Ile Val Gly Ala Ala Leu Leu Met Ala Gly Cys Ser Ser
              20                  25                  30

Ser Asn Glu Leu Ser Ala Ala Gly Gln Ser Val Arg Ile Val Asp Glu
              35                  40                  45

Gln Pro Gly Ala Glu Cys Gln Leu Ile Gly Thr Ala Thr Gly Lys Gln
        50                  55                  60

Ser Asn Trp Leu Ser Gly Gln His Gly Glu Glu Gly Ser Met Arg
65                  70                  75                  80

Gly Ala Ala Asn Asp Leu Arg Asn Gln Ala Ala Ala Met Gly Gly Asn
              85                  90                  95

Val Ile Tyr Gly Ile Ser Ser Pro Ser Gln Gly Met Leu Ser Ser Phe
              100                 105                 110

Val Pro Thr Asp Ser Gln Ile Ile Gly Gln Val Tyr Lys Cys Pro Asn
              115                 120                 125

<210> SEQ ID NO 17
<211> LENGTH: 1392

-continued

<212> TYPE: DNA
<213> ORGANISM: Escherichia coli

<400> SEQUENCE: 17

```
atgtctgttt ccaccctcga gtcagaaaat gcgcaaccgg ttgcgcagac tcaaaacagc    60
gaactgattt accgtcttga agatcgtccg ccgcttcctc aaaccctgtt tgccgcctgt   120
cagcatctgc tggcgatgtt cgttgcggtg atcacgccag cgctattaat ctgccaggcg   180
ctgggtttac cggcacaaga cacgcaacac attattagta tgtcgctgtt tgcctccggt   240
gtggcatcga ttattcaaat taaggcctgg ggtccggttg gctccgggct gttgtctatt   300
cagggcacca gcttcaactt tgttgccccg ctgattatgg gcggtaccgc gctgaaaacc   360
ggtggtgctg atgttcctac catgatggcg gctttgttcg gcacgttgat gctggcaagt   420
tgcaccgaga tggtgatctc ccgcgttctg catctggcgc gccgcattat tacgccgctg   480
gtttctggcg ttgtggtgat gattatcggc ctgtcgctaa ttcaggttgg gttaacgtcc   540
attggcggcg ttacgcagc catgagcgat aacaccttcg cgcaccgaa aaatctgctg   600
ctggcaggcg tggtcttagc cttaattatc ctgcttaacc gtcaacgtaa cccttactta   660
cgcgtggcct cactggtgat tgcgatggcg gccggatatg cgctggcgtg gtttatgggc   720
atgttgccag aaagcaacga accgatgacg caagaactga ttatggtgcc aacgccgctc   780
tattacggtc ttggcattga atggagtctg ctgctgccgc tgatgctggt ctttatgatc   840
acttcgctgg aaaccattgg cgatatcacg gcgacctctg acgtttccga acagccagtg   900
tccggtccgc tgtacatgaa acgcctgaaa ggcggcgtgc tggcaaacgg cctgaactcg   960
tttgtttcgg cggtgtttaa caccttcccg aactcctgct cgggcaaaaa caacggagtg  1020
atccagttga ctggtgttgc cagccgctat gtcggttttg tcgtcgcgct gatgttgatc  1080
gtgctgggtc tgttcccggc agtgagcggt tttgtacaac acattccaga accggttctg  1140
ggcggcgcaa cgcttgtaat gtttggcacc atcgccgcct ccggtgtgcg tatcgtttct  1200
cgtgagccgc tgaaccgtcg ggcgattctg attatcgcgc tgtcgctggc ggttggtctg  1260
ggcgtgtctc agcagccgct gattttgcag tttgccccctg aatggctgaa aaacctgctc  1320
tcctccggga tcgccgcggg cggtattact gccatcgtgc tgaatctgat tttcccacca  1380
gaaaaacagt aa                                                      1392
```

<210> SEQ ID NO 18
<211> LENGTH: 463
<212> TYPE: PRT
<213> ORGANISM: Escherichia coli

<400> SEQUENCE: 18

```
Met Ser Val Ser Thr Leu Glu Ser Glu Asn Ala Gln Pro Val Ala Gln
1               5                   10                  15

Thr Gln Asn Ser Glu Leu Ile Tyr Arg Leu Glu Asp Arg Pro Pro Leu
            20                  25                  30

Pro Gln Thr Leu Phe Ala Ala Cys Gln His Leu Leu Ala Met Phe Val
        35                  40                  45

Ala Val Ile Thr Pro Ala Leu Leu Ile Cys Gln Ala Leu Gly Leu Pro
    50                  55                  60

Ala Gln Asp Thr Gln His Ile Ile Ser Met Ser Leu Phe Ala Ser Gly
65                  70                  75                  80

Val Ala Ser Ile Ile Gln Ile Lys Ala Trp Gly Pro Val Gly Ser Gly
                85                  90                  95

Leu Leu Ser Ile Gln Gly Thr Ser Phe Asn Phe Val Ala Pro Leu Ile
```

Met Gly Gly Thr Ala Leu Lys Thr Gly Ala Asp Val Pro Thr Met
            115                 120                 125

Met Ala Ala Leu Phe Gly Thr Leu Met Leu Ala Ser Cys Thr Glu Met
130                 135                 140

Val Ile Ser Arg Val Leu His Leu Ala Arg Arg Ile Ile Thr Pro Leu
145                 150                 155                 160

Val Ser Gly Val Val Met Ile Ile Gly Leu Ser Leu Ile Gln Val
                165                 170                 175

Gly Leu Thr Ser Ile Gly Gly Tyr Ala Ala Met Ser Asp Asn Thr
                180                 185                 190

Phe Gly Ala Pro Lys Asn Leu Leu Ala Gly Val Val Leu Ala Leu
            195                 200                 205

Ile Ile Leu Leu Asn Arg Gln Arg Asn Pro Tyr Leu Arg Val Ala Ser
210                 215                 220

Leu Val Ile Ala Met Ala Ala Gly Tyr Ala Leu Ala Trp Phe Met Gly
225                 230                 235                 240

Met Leu Pro Glu Ser Asn Glu Pro Met Thr Gln Glu Leu Ile Met Val
                245                 250                 255

Pro Thr Pro Leu Tyr Tyr Gly Leu Gly Ile Glu Trp Ser Leu Leu Leu
                260                 265                 270

Pro Leu Met Leu Val Phe Met Ile Thr Ser Leu Glu Thr Ile Gly Asp
            275                 280                 285

Ile Thr Ala Thr Ser Asp Val Ser Glu Gln Pro Val Ser Gly Pro Leu
            290                 295                 300

Tyr Met Lys Arg Leu Lys Gly Gly Val Leu Ala Asn Gly Leu Asn Ser
305                 310                 315                 320

Phe Val Ser Ala Val Phe Asn Thr Phe Pro Asn Ser Cys Phe Gly Gln
                325                 330                 335

Asn Asn Gly Val Ile Gln Leu Thr Gly Val Ala Ser Arg Tyr Val Gly
                340                 345                 350

Phe Val Val Ala Leu Met Leu Ile Val Leu Gly Leu Phe Pro Ala Val
                355                 360                 365

Ser Gly Phe Val Gln His Ile Pro Glu Pro Val Leu Gly Gly Ala Thr
370                 375                 380

Leu Val Met Phe Gly Thr Ile Ala Ala Ser Gly Val Arg Ile Val Ser
385                 390                 395                 400

Arg Glu Pro Leu Asn Arg Arg Ala Ile Leu Ile Ile Ala Leu Ser Leu
                405                 410                 415

Ala Val Gly Leu Gly Val Ser Gln Gln Pro Leu Ile Leu Gln Phe Ala
                420                 425                 430

Pro Glu Trp Leu Lys Asn Leu Leu Ser Ser Gly Ile Ala Ala Gly Gly
            435                 440                 445

Ile Thr Ala Ile Val Leu Asn Leu Ile Phe Pro Pro Glu Lys Gln
            450                 455                 460

<210> SEQ ID NO 19
<211> LENGTH: 207
<212> TYPE: DNA
<213> ORGANISM: Escherichia coli

<400> SEQUENCE: 19
ttgagctgcc gttttttat tctgtcagtt gtgaaactga agcgatttag tcgctatcga    60
tctcatcaaa tatggctcgc tttgagatat tcctcaagta aaaaaacatc tcttcctgcg   120

-continued

| atttctcaca aaaaagattc gttgacaaaa agtgacaaaa ttatgagatt ttcatcacac | 180 |
| attttgacat caggaacggt atgctga | 207 |

```
<210> SEQ ID NO 20
<211> LENGTH: 68
<212> TYPE: PRT
<213> ORGANISM: Escherichia coli

<400> SEQUENCE: 20
```

Met Ser Cys Arg Phe Phe Ile Leu Ser Val Val Lys Leu Lys Arg Phe
1               5                   10                  15

Ser Arg Tyr Arg Ser His Gln Ile Trp Leu Ala Leu Arg Tyr Ser Ser
            20                  25                  30

Ser Lys Lys Thr Ser Leu Pro Ala Ile Ser His Lys Lys Asp Ser Leu
        35                  40                  45

Thr Lys Ser Asp Lys Ile Met Arg Phe Ser Ser His Ile Leu Thr Ser
    50                  55                  60

Gly Thr Val Cys
65

```
<210> SEQ ID NO 21
<211> LENGTH: 2733
<212> TYPE: DNA
<213> ORGANISM: Escherichia coli

<400> SEQUENCE: 21
```

| atgctaatgg ctacaattca tgtagacggc aaagaatacg aggtcaacgg agcggacaac | 60 |
| ctgctggaag cttgtctgtc tctgggcctt gatattcctt acttttgctg gcatccggcg | 120 |
| ctgggaagtg tcggtgcttg ccgccagtgt gcggtgaagc aataccaaaa cgcggaagac | 180 |
| acgcgtggtc gcctggtgat gtcctgtatg acaccggctt ccgatggcac ctttatttcc | 240 |
| attgacgaca agaagcgaa acagttccgt gaaagcgtgg tcgagtggtt gatgaccaac | 300 |
| cacccgcacg actgtccggt atgtgaagag ggcggtaact gccatcttca ggatatgact | 360 |
| gtgatgaccg acacagcttc cgtcgctac cgtttcacca aacgtaccca ccgtaatcag | 420 |
| gatttggggc cattcatctc tcacgaaatg aaccgctgca tcgcctgcta ccgctgtgtg | 480 |
| cgttactaca agattacgc tgaccggtaca gatctgggcg tttacggtgc gcacgacaac | 540 |
| gtctacttcg gtcgcccgga agacggcacg ctggaaagcg aatttttccgg taacctggtc | 600 |
| gaaatttgcc cgaccggcgt atttaccgac aaaacgcact ccgagcgtta caaccgtaaa | 660 |
| tgggatatgc agtttgcgcc gagcatctgc cagcaatgtt ccatcggctg taacatcagc | 720 |
| cccggtgaac gttacggcga actgcgtcgt atcgaaaacc gttacaacgg tacggtaaac | 780 |
| cactacttcc tctgcgaccg tggtcgtttc ggttacggtt acgtcaacct gaaggatcgt | 840 |
| ccgcgtcagc cagtacagcg tcgtggcgat gatttcatta ccctcaacgc cgaacaggca | 900 |
| atgcagggcg cggcagatat tctgcgtcag tcgaagaaag tgatcggtat tggttctccg | 960 |
| cgtgccagcg tggaaagcaa ctttgcgctg cgtgaactgg tgggcgaaga aaacttctac | 1020 |
| accggtatcg ctcacggtga gcaggaacgt ctgcaactgg cgctgaaagt gctgcgtgaa | 1080 |
| ggcggcattt atactccggc tctgcgcgaa atcgaatctt acgatgcggt actggtgctg | 1140 |
| ggcgaagacg ttacccagac cggcgcgcgc gtcgcgctgg cagtgcgtca ggctgtgaaa | 1200 |
| ggtaaagcgc gcgaaatggg ggcagcacag aaagtggctg actggcagat tgcggcaatc | 1260 |
| ctcaacatcg gtcaacgtgc gaagcatccg ctgtttgtta ccaacgttga tgacacccgt | 1320 |
| ctggatgata tcgcggcgtg gacttaccgc gcaccggttg aagatcaggc gcgtttaggt | 1380 |

```
tttgccatcg cccatgcgct ggataactct gcaccagcgg ttgacggtat cgaacctgag    1440
ctgcaaagca aaatcgacgt catcgtgcag gcactggcag gtgcgaagaa accgttgatt    1500
atctccggga cgaacgccgg tagcttagag gtgattcagg cggcggctaa cgtcgcgaaa    1560
gccctgaaag gtcgcggcgc tgacgtcggt atcaccatga ttgcccgttc cgtcaacagc    1620
atggggctgg gcattatggg tggcggttcg cttgaagaag cgttaaccga actggaaacc    1680
ggacgcgccg acgcggtggt ggtgttggaa acgatctgc atcgtcacgc ttctgctatc     1740
cgcgtgaatg ctgcgctggc taaagcaccg ctggtgatgg tggttgatca tcaacgcaca    1800
gcgattatgg aaaacgccca tctggtactt tctgctgcca gctttgctga aagcgacggt    1860
acggtgatca caacgaagg ccgcgcccaa cgtttcttcc aggtttacga tcctgcttat     1920
tacgacagca aaactgtcat gctggaaagc tggcgctggt acactcgct gcacagcacc     1980 ctgctgagcc gtgaagtgga ctggacgcag ctcgaccatg tgattgacgc tgttgtggcg    2040
aaaatcccgg aactggcagg tatcaaagat gctgcgccgg atgcgacatt ccgtattcgt    2100
gggcagaaac tggcccgtga accgcaccgt tacagcggtc gtaccgccat gcgcgccaat    2160
atcagcgttc atgagccgcg tcagccgcag gatattgaca ccatgttcac cttctcgatg    2220
gaaggtaaca accagccgac tgcgcaccgt tcgcaagtgc cgtttgcctg ggcgccgggc    2280
tggaactccc cgcaggcgtg gaacaaattc caggacgaag tgggcggcaa actgcgcttt    2340
ggcgatccgg gcgtgcgtct gtttgaaacc agcgaaaatg gtctggatta cttcaccagc    2400
gtaccggcac gcttccagcc gcaggacggg aaatggcgta tcgcgccgta ttaccacctg    2460
tttggcagcg atgaattgtc acagcgtgct ccggtcttcc agagccgtat gccgcagccg    2520
tacatcaaac tcaacccagc ggatgccgcg aagttgggtg tgaacgcagg tacacgcgtc    2580
tcctttagtt acgatggcaa cacggtcacg ctgccggttg aaatcgccga aggactgacg    2640
gcagggcagg tgggcttgcc gatgggtatg tccggcattg ctccggtgct ggctggcgcg    2700
catcttgagg atctcaagga ggcacaacaa tga                                 2733
```

<210> SEQ ID NO 22
<211> LENGTH: 910
<212> TYPE: PRT
<213> ORGANISM: Escherichia coli

<400> SEQUENCE: 22

```
Met Leu Met Ala Thr Ile His Val Asp Gly Lys Glu Tyr Glu Val Asn
1               5                   10                  15

Gly Ala Asp Asn Leu Leu Glu Ala Cys Leu Ser Leu Gly Leu Asp Ile
                20                  25                  30

Pro Tyr Phe Cys Trp His Pro Ala Leu Gly Ser Val Gly Ala Cys Arg
            35                  40                  45

Gln Cys Ala Val Lys Gln Tyr Gln Asn Ala Glu Asp Thr Arg Gly Arg
        50                  55                  60

Leu Val Met Ser Cys Met Thr Pro Ala Ser Asp Gly Thr Phe Ile Ser
65                  70                  75                  80

Ile Asp Asp Glu Glu Ala Lys Gln Phe Arg Glu Ser Val Val Glu Trp
                85                  90                  95

Leu Met Thr Asn His Pro His Asp Cys Pro Val Cys Glu Glu Gly Gly
                100                 105                 110

Asn Cys His Leu Gln Asp Met Thr Val Met Thr Gly His Ser Phe Arg
            115                 120                 125

Arg Tyr Arg Phe Thr Lys Arg Thr His Arg Asn Gln Asp Leu Gly Pro
```

-continued

```
        130                 135                 140
Phe Ile Ser His Glu Met Asn Arg Cys Ile Ala Cys Tyr Arg Cys Val
145                 150                 155                 160

Arg Tyr Tyr Lys Asp Tyr Ala Asp Gly Thr Asp Leu Gly Val Tyr Gly
                165                 170                 175

Ala His Asp Asn Val Tyr Phe Gly Arg Pro Glu Asp Gly Thr Leu Glu
                180                 185                 190

Ser Glu Phe Ser Gly Asn Leu Val Glu Ile Cys Pro Thr Gly Val Phe
                195                 200                 205

Thr Asp Lys Thr His Ser Glu Arg Tyr Asn Arg Lys Trp Asp Met Gln
210                 215                 220

Phe Ala Pro Ser Ile Cys Gln Gln Cys Ser Ile Gly Cys Asn Ile Ser
225                 230                 235                 240

Pro Gly Glu Arg Tyr Gly Glu Leu Arg Arg Ile Glu Asn Arg Tyr Asn
                245                 250                 255

Gly Thr Val Asn His Tyr Phe Leu Cys Asp Arg Gly Arg Phe Gly Tyr
                260                 265                 270

Gly Tyr Val Asn Leu Lys Asp Arg Pro Arg Gln Pro Val Gln Arg Arg
                275                 280                 285

Gly Asp Asp Phe Ile Thr Leu Asn Ala Glu Gln Ala Met Gln Gly Ala
                290                 295                 300

Ala Asp Ile Leu Arg Gln Ser Lys Lys Val Ile Gly Ile Gly Ser Pro
305                 310                 315                 320

Arg Ala Ser Val Glu Ser Asn Phe Ala Leu Arg Glu Leu Val Gly Glu
                325                 330                 335

Glu Asn Phe Tyr Thr Gly Ile Ala His Gly Glu Gln Glu Arg Leu Gln
                340                 345                 350

Leu Ala Leu Lys Val Leu Arg Glu Gly Gly Ile Tyr Thr Pro Ala Leu
                355                 360                 365

Arg Glu Ile Glu Ser Tyr Asp Ala Val Leu Val Leu Gly Glu Asp Val
                370                 375                 380

Thr Gln Thr Gly Ala Arg Val Ala Leu Ala Val Arg Gln Ala Val Lys
385                 390                 395                 400

Gly Lys Ala Arg Glu Met Ala Ala Ala Gln Lys Val Ala Asp Trp Gln
                405                 410                 415

Ile Ala Ala Ile Leu Asn Ile Gly Gln Arg Ala Lys His Pro Leu Phe
                420                 425                 430

Val Thr Asn Val Asp Asp Thr Arg Leu Asp Asp Ile Ala Ala Trp Thr
                435                 440                 445

Tyr Arg Ala Pro Val Glu Asp Gln Ala Arg Leu Gly Phe Ala Ile Ala
                450                 455                 460

His Ala Leu Asp Asn Ser Ala Pro Ala Val Asp Gly Ile Glu Pro Glu
465                 470                 475                 480

Leu Gln Ser Lys Ile Asp Val Ile Val Gln Ala Leu Ala Gly Ala Lys
                485                 490                 495

Lys Pro Leu Ile Ile Ser Gly Thr Asn Ala Gly Ser Leu Glu Val Ile
                500                 505                 510

Gln Ala Ala Ala Asn Val Ala Lys Ala Leu Lys Gly Arg Gly Ala Asp
                515                 520                 525

Val Gly Ile Thr Met Ile Ala Arg Ser Val Asn Ser Met Gly Leu Gly
                530                 535                 540

Ile Met Gly Gly Gly Ser Leu Glu Glu Ala Leu Thr Glu Leu Glu Thr
545                 550                 555                 560
```

Gly Arg Ala Asp Ala Val Val Leu Glu Asn Asp Leu His Arg His
               565                 570                 575
Ala Ser Ala Ile Arg Val Asn Ala Ala Leu Ala Lys Ala Pro Leu Val
            580                 585                 590
Met Val Val Asp His Gln Arg Thr Ala Ile Met Glu Asn Ala His Leu
        595                 600                 605
Val Leu Ser Ala Ala Ser Phe Ala Glu Ser Asp Gly Thr Val Ile Asn
    610                 615                 620
Asn Glu Gly Arg Ala Gln Arg Phe Phe Gln Val Tyr Asp Pro Ala Tyr
625                 630                 635                 640
Tyr Asp Ser Lys Thr Val Met Leu Glu Ser Trp Arg Trp Leu His Ser
                645                 650                 655
Leu His Ser Thr Leu Leu Ser Arg Glu Val Asp Trp Thr Gln Leu Asp
            660                 665                 670
His Val Ile Asp Ala Val Val Ala Lys Ile Pro Glu Leu Ala Gly Ile
        675                 680                 685
Lys Asp Ala Ala Pro Asp Ala Thr Phe Arg Ile Arg Gly Gln Lys Leu
    690                 695                 700
Ala Arg Glu Pro His Arg Tyr Ser Gly Arg Thr Ala Met Arg Ala Asn
705                 710                 715                 720
Ile Ser Val His Glu Pro Arg Gln Pro Gln Asp Ile Asp Thr Met Phe
                725                 730                 735
Thr Phe Ser Met Glu Gly Asn Asn Gln Pro Thr Ala His Arg Ser Gln
            740                 745                 750
Val Pro Phe Ala Trp Ala Pro Gly Trp Asn Ser Pro Gln Ala Trp Asn
        755                 760                 765
Lys Phe Gln Asp Glu Val Gly Gly Lys Leu Arg Phe Gly Asp Pro Gly
    770                 775                 780
Val Arg Leu Phe Glu Thr Ser Glu Asn Gly Leu Asp Tyr Phe Thr Ser
785                 790                 795                 800
Val Pro Ala Arg Phe Gln Pro Gln Asp Gly Lys Trp Arg Ile Ala Pro
                805                 810                 815
Tyr Tyr His Leu Phe Gly Ser Asp Glu Leu Ser Gln Arg Ala Pro Val
            820                 825                 830
Phe Gln Ser Arg Met Pro Gln Pro Tyr Ile Lys Leu Asn Pro Ala Asp
        835                 840                 845
Ala Ala Lys Leu Gly Val Asn Ala Gly Thr Arg Val Ser Phe Ser Tyr
    850                 855                 860
Asp Gly Asn Thr Val Thr Leu Pro Val Glu Ile Ala Glu Gly Leu Thr
865                 870                 875                 880
Ala Gly Gln Val Gly Leu Pro Met Gly Met Ser Gly Ile Ala Pro Val
                885                 890                 895
Leu Ala Gly Ala His Leu Glu Asp Leu Lys Glu Ala Gln Gln
            900                 905                 910

<210> SEQ ID NO 23
<211> LENGTH: 1803
<212> TYPE: DNA
<213> ORGANISM: Escherichia coli

<400> SEQUENCE: 23
atggtgaaca atatgaccga cttaaccgcg caagaacccg cctggcagac ccgcgatcat      60
cttgatgatc cggtgattgg cgaactgcgc aaccgttttg ggccggatgc ctttactgtt     120
caggcgactc gcaccggggt tcccgttgtg tggatcaagc gtgaacaatt actggaagtt     180

```
ggcgatttct taaagaaact gccgaaacct tacgtcatgc tgtttgactt acacggcatg    240
gacgaacgtc tgcgcacaca ccgcgaaggg ttacctgccg cggattttc cgttttctac    300 catctgattt ctatcgatcg taaccgcgac atcatgctga aggtggcgct ggcagaaaac    360
gacctgcacg taccgacctt caccaaactg ttcccgaacg ctaactggta tgagcgtgaa    420
acctgggatc tgtttggcat tactttcgac ggtcacccga acctgcgacg catcatgatg    480
ccgcaaacct ggaaaggtca cccgctgcgt aaagattatc cggcgcgcgc taccgaattc    540
tcgccgtttg agctgaccaa agccaaacag gatctggaga tggaagccct gaccttcaaa    600
ccggaagagt ggggatgaa gcgcggcacc gaaaacgagg acttcatgtt cctcaacctc    660
ggtccgaacc acccgtcggc gcacgggct ttccgtatcg ttttgcaact cgatggcgaa    720
gagattgtcg actgcgtacc agacatcggt taccaccacc gtggtgcgga aaaatgggc    780 gaacgccagt cctggcacag ctacattccg tatactgacc gtatcgaata cctcggcggc    840
tgcgttaacg aaatgcctta cgtgctggcg gtagagaaac tggccgggat caccgtgccg    900
gatcgcgtta acgtcattcg cgttatgctc tccgaactgt tccgcatcaa cagtcacctg    960
ctgtatatct cgaccttta tcaggacgtc ggcgcaatga cgccagtgtt cttcgccttt   1020
accgatcgtc agaaaattta cgatctggtg gaagcaatca ctggtttccg tatgcacccg   1080
gcgtggttcc gtattggcgg cgtagcgcac gacctgccgc gcggctggga tcgcctgctg   1140
cgtgagttcc tcgactggat gccgaaacgt ctggcgtctt acgagaaagc ggcgctgcaa   1200
aacaccattc tgaaaggtcg ttcccagggc gttgccgcct atggcgcgaa agaggcgctg   1260
gagtggggca ccactggcgc gggcctgcgt gctaccggga tcgacttcga cgtgcgtaag   1320
gcgcgtcctt attctggcta tgaaaacttc gactttgaaa tcccggtggg tggtggcgtt   1380
tctgactgct acacccgcgt aatgcttaaa gtggaagagc tgcgccagag tctgcgcatt   1440
cttgagcagt gcctcaacaa catgccggaa ggcccgttca agcggatca cccgctgacc   1500 acgccgccgc cgaaagagcg cacgctgcaa catatcgaaa ccctgatcac ccacttcctg   1560
caagtgtcgt ggggtccggt gatgcctgcc aatgaatctt tccagatgat tgaggcgacc   1620
aaagggatca acagttacta cctgaccagc gacggcagca ccatgagtta ccgcacccgt   1680
gttcgtaccc cgagctttgc gcatttgcag caaattccgg cggcgatccg cggcagcctg   1740
gtgtctgacc tgattgttta tctgggcagt atcgattttg ttatgtcaga gtgtggaccgc   1800 taa                                                                1803
```

<210> SEQ ID NO 24
<211> LENGTH: 600
<212> TYPE: PRT
<213> ORGANISM: Escherichia coli

<400> SEQUENCE: 24

```
Met Val Asn Asn Met Thr Asp Leu Thr Ala Gln Glu Pro Ala Trp Gln
1               5                   10                  15

Thr Arg Asp His Leu Asp Asp Pro Val Ile Gly Glu Leu Arg Asn Arg
                20                  25                  30

Phe Gly Pro Asp Ala Phe Thr Val Gln Ala Thr Arg Thr Gly Val Pro
            35                  40                  45

Val Val Trp Ile Lys Arg Glu Gln Leu Leu Glu Val Gly Asp Phe Leu
        50                  55                  60

Lys Lys Leu Pro Lys Pro Tyr Val Met Leu Phe Asp Leu His Gly Met
65                  70                  75                  80

Asp Glu Arg Leu Arg Thr His Arg Glu Gly Leu Pro Ala Ala Asp Phe
```

```
                    85                  90                  95
Ser Val Phe Tyr His Leu Ile Ser Ile Asp Arg Asn Arg Asp Ile Met
                100                 105                 110
Leu Lys Val Ala Leu Ala Glu Asn Asp Leu His Val Pro Thr Phe Thr
                115                 120                 125
Lys Leu Phe Pro Asn Ala Asn Trp Tyr Glu Arg Glu Thr Trp Asp Leu
                130                 135                 140
Phe Gly Ile Thr Phe Asp Gly His Pro Asn Leu Arg Arg Ile Met Met
145                 150                 155                 160
Pro Gln Thr Trp Lys Gly His Pro Leu Arg Lys Asp Tyr Pro Ala Arg
                165                 170                 175
Ala Thr Glu Phe Ser Pro Phe Glu Leu Thr Lys Ala Lys Gln Asp Leu
                180                 185                 190
Glu Met Glu Ala Leu Thr Phe Lys Pro Glu Glu Trp Gly Met Lys Arg
                195                 200                 205
Gly Thr Glu Asn Glu Asp Phe Met Phe Leu Asn Leu Gly Pro Asn His
                210                 215                 220
Pro Ser Ala His Gly Ala Phe Arg Ile Val Leu Gln Leu Asp Gly Glu
225                 230                 235                 240
Glu Ile Val Asp Cys Val Pro Asp Ile Gly Tyr His His Arg Gly Ala
                245                 250                 255
Glu Lys Met Gly Glu Arg Gln Ser Trp His Ser Tyr Ile Pro Tyr Thr
                260                 265                 270
Asp Arg Ile Glu Tyr Leu Gly Gly Cys Val Asn Glu Met Pro Tyr Val
                275                 280                 285
Leu Ala Val Glu Lys Leu Ala Gly Ile Thr Val Pro Asp Arg Val Asn
                290                 295                 300
Val Ile Arg Val Met Leu Ser Glu Leu Phe Arg Ile Asn Ser His Leu
305                 310                 315                 320
Leu Tyr Ile Ser Thr Phe Ile Gln Asp Val Gly Ala Met Thr Pro Val
                325                 330                 335
Phe Phe Ala Phe Thr Asp Arg Gln Lys Ile Tyr Asp Leu Val Glu Ala
                340                 345                 350
Ile Thr Gly Phe Arg Met His Pro Ala Trp Phe Arg Ile Gly Gly Val
                355                 360                 365
Ala His Asp Leu Pro Arg Gly Trp Asp Arg Leu Leu Arg Glu Phe Leu
                370                 375                 380
Asp Trp Met Pro Lys Arg Leu Ala Ser Tyr Glu Lys Ala Ala Leu Gln
385                 390                 395                 400
Asn Thr Ile Leu Lys Gly Arg Ser Gln Gly Val Ala Ala Tyr Gly Ala
                405                 410                 415
Lys Glu Ala Leu Glu Trp Gly Thr Thr Gly Ala Gly Leu Arg Ala Thr
                420                 425                 430
Gly Ile Asp Phe Asp Val Arg Lys Ala Arg Pro Tyr Ser Gly Tyr Glu
                435                 440                 445
Asn Phe Asp Phe Glu Ile Pro Val Gly Gly Gly Val Ser Asp Cys Tyr
                450                 455                 460
Thr Arg Val Met Leu Lys Val Glu Glu Leu Arg Gln Ser Leu Arg Ile
465                 470                 475                 480
Leu Glu Gln Cys Leu Asn Asn Met Pro Glu Gly Pro Phe Lys Ala Asp
                485                 490                 495
His Pro Leu Thr Thr Pro Pro Lys Glu Arg Thr Leu Gln His Ile
                500                 505                 510
```

```
Glu Thr Leu Ile Thr His Phe Leu Gln Val Ser Trp Gly Pro Val Met
        515                 520                 525

Pro Ala Asn Glu Ser Phe Gln Met Ile Glu Ala Thr Lys Gly Ile Asn
    530                 535                 540

Ser Tyr Tyr Leu Thr Ser Asp Gly Ser Thr Met Ser Tyr Arg Thr Arg
545                 550                 555                 560

Val Arg Thr Pro Ser Phe Ala His Leu Gln Gln Ile Pro Ala Ala Ile
                565                 570                 575

Arg Gly Ser Leu Val Ser Asp Leu Ile Val Tyr Leu Gly Ser Ile Asp
            580                 585                 590

Phe Val Met Ser Asp Val Asp Arg
            595                 600

<210> SEQ ID NO 25
<211> LENGTH: 1014
<212> TYPE: DNA
<213> ORGANISM: Escherichia coli

<400> SEQUENCE: 25
atgacgcagc cattggtcgg aaaacagatt ctcattgttg aagatgagca ggtatttcgc      60
tcgcttctgg attcatggtt ttcctcattg ggagcgacaa cggtactggc ggctgatggg     120
gtggatgccc ttgagttgct gggaggtttc actccagacc tgatgatatg tgatatcgcg     180
atgccacgaa tgaacgggct aaactgctg gagcatatac gtaacagagg cgaccagacc      240
ccagttctgg tgtatctgc cactgaaaat atggcagata ttgccaaagc gttacgtctg     300
ggcgttgaag atgttttgct gaaaccagtt aaagatctga atcgcttgcg cgagatggtt     360
tttgcctgtc tctatcccag catgtttaat tcgcgcgttg aggaagagga aaggcttttt     420
cgcgactggg atgcaatggt tgataaccct gccgcagcgg cgaaattatt acaggaacta     480
caaccgccgg ttcagcaggt gatttcccat tgccgggtta attatcgtca attggttgcc     540
gcggacaaac ccggcctggt gcttgatatt gccgcacttt cggaaaacga tctggcattt     600
tattgccttg atgtcacccg agctggacat aatggcgtac ttgctgcctt gttattacgc     660
gcattgttta acggattatt acaggaacag cttgcacacc aaaatcaacg gttgccagag     720
ttgggcgcgt tattgaagca ggtaaaccat ttacttcgtc aggccaatct gccggggcag     780
tttccgctat tagttggcta ttatcatcgc gaactgaaaa atctcattct ggtttctgcg     840
ggtctgaatg cgacgttaaa taccggcgaa caccaggtgc aaatcagtaa tggtgttccg     900
ttaggcactt taggtaacgc ttatttgaat caattgagcc agcgatgcga tgcctggcaa     960
tgccaaatat ggggaaccgg tggtcgactg cgcttgatgt tgtctgcaga atga          1014

<210> SEQ ID NO 26
<211> LENGTH: 337
<212> TYPE: PRT
<213> ORGANISM: Escherichia coli

<400> SEQUENCE: 26

Met Thr Gln Pro Leu Val Gly Lys Gln Ile Leu Ile Val Glu Asp Glu
1               5                   10                  15

Gln Val Phe Arg Ser Leu Leu Asp Ser Trp Phe Ser Ser Leu Gly Ala
                20                  25                  30

Thr Thr Val Leu Ala Ala Asp Gly Val Asp Ala Leu Glu Leu Leu Gly
            35                  40                  45

Gly Phe Thr Pro Asp Leu Met Ile Cys Asp Ile Ala Met Pro Arg Met
        50                  55                  60
```

```
Asn Gly Leu Lys Leu Leu Glu His Ile Arg Asn Arg Gly Asp Gln Thr
 65                  70                  75                  80

Pro Val Leu Val Ile Ser Ala Thr Glu Asn Met Ala Asp Ile Ala Lys
                 85                  90                  95

Ala Leu Arg Leu Gly Val Glu Asp Val Leu Leu Lys Pro Val Lys Asp
            100                 105                 110

Leu Asn Arg Leu Arg Glu Met Val Phe Ala Cys Leu Tyr Pro Ser Met
        115                 120                 125

Phe Asn Ser Arg Val Glu Glu Glu Arg Leu Phe Arg Asp Trp Asp
130                 135                 140

Ala Met Val Asp Asn Pro Ala Ala Ala Lys Leu Leu Gln Glu Leu
145                 150                 155                 160

Gln Pro Pro Val Gln Gln Val Ile Ser His Cys Arg Val Asn Tyr Arg
                165                 170                 175

Gln Leu Val Ala Ala Asp Lys Pro Gly Leu Val Leu Asp Ile Ala Ala
            180                 185                 190

Leu Ser Glu Asn Asp Leu Ala Phe Tyr Cys Leu Asp Val Thr Arg Ala
        195                 200                 205

Gly His Asn Gly Val Leu Ala Ala Leu Leu Arg Ala Leu Phe Asn
210                 215                 220

Gly Leu Leu Gln Glu Gln Leu Ala His Gln Asn Gln Arg Leu Pro Glu
225                 230                 235                 240

Leu Gly Ala Leu Leu Lys Gln Val Asn His Leu Leu Arg Gln Ala Asn
                245                 250                 255

Leu Pro Gly Gln Phe Pro Leu Leu Val Gly Tyr Tyr His Arg Glu Leu
            260                 265                 270

Lys Asn Leu Ile Leu Val Ser Ala Gly Leu Asn Ala Thr Leu Asn Thr
        275                 280                 285

Gly Glu His Gln Val Gln Ile Ser Asn Gly Val Pro Leu Gly Thr Leu
    290                 295                 300

Gly Asn Ala Tyr Leu Asn Gln Leu Ser Gln Arg Cys Asp Ala Trp Gln
305                 310                 315                 320

Cys Gln Ile Trp Gly Thr Gly Gly Arg Leu Arg Leu Met Leu Ser Ala
                325                 330                 335

Glu

<210> SEQ ID NO 27
<211> LENGTH: 699
<212> TYPE: DNA
<213> ORGANISM: Escherichia coli

<400> SEQUENCE: 27
atgcaaaaaa acgctgcgca tacttatgcc atttccagct tgttggtgct ttcactaacc      60
ggctgcgcct ggatacccatc cacgccgctg gtgcagggg cgaccagtgc acaaccggtt     120
cccggtccga cgcccgtcgc caacggttct attttccagt ctgctcagcc gattaactat     180
ggctatcaac cgctgtttga agatcgtcga ccacgcaata ttggcgatac gctgaccatc     240
gtgttgcagg agaacgtcag cgccagcaaa agctcctctg cgaatgccag ccgtgacggt     300
aaaactaatt ttggctttga tactgtgccg cgctatttgc aggggctgtt tggtaacgct     360
cgtgccgatg tcgaagcctc cggtggtaac acgttcaacg aaagggcgg ggccaatgcc     420 agcaatacct ttagcggcac gttgacggtg acggttgacc aggtactggt caacggcaac     480
ctgcatgtgg tgggtgaaaa acagattgcc attaatcagg gtaccgaatt tattcgcttc     540
tctggcgtgg ttaatccacg cactatcagc ggcagcaata ccgtaccgtc tactcaggtg     600
```

```
gcggatgcgc gcattgaata cgtaggcaat ggctacatta cgaagcgca aaatatgggc      660 tggttgcagc gtttcttcct taacctgtcg ccaatgtaa                            699
```

<210> SEQ ID NO 28
<211> LENGTH: 232
<212> TYPE: PRT
<213> ORGANISM: Escherichia coli

<400> SEQUENCE: 28

```
Met Gln Lys Asn Ala Ala His Thr Tyr Ala Ile Ser Ser Leu Leu Val
1               5                   10                  15

Leu Ser Leu Thr Gly Cys Ala Trp Ile Pro Ser Thr Pro Leu Val Gln
            20                  25                  30

Gly Ala Thr Ser Ala Gln Pro Val Pro Gly Pro Thr Pro Val Ala Asn
        35                  40                  45

Gly Ser Ile Phe Gln Ser Ala Gln Pro Ile Asn Tyr Gly Tyr Gln Pro
    50                  55                  60

Leu Phe Glu Asp Arg Arg Pro Arg Asn Ile Gly Asp Thr Leu Thr Ile
65                  70                  75                  80

Val Leu Gln Glu Asn Val Ser Ala Ser Lys Ser Ser Ala Asn Ala
                85                  90                  95

Ser Arg Asp Gly Lys Thr Asn Phe Gly Phe Asp Thr Val Pro Arg Tyr
            100                 105                 110

Leu Gln Gly Leu Phe Gly Asn Ala Arg Ala Asp Val Glu Ala Ser Gly
        115                 120                 125

Gly Asn Thr Phe Asn Gly Lys Gly Gly Ala Asn Ala Ser Asn Thr Phe
    130                 135                 140

Ser Gly Thr Leu Thr Val Thr Val Asp Gln Val Leu Val Asn Gly Asn
145                 150                 155                 160

Leu His Val Val Gly Glu Lys Gln Ile Ala Ile Asn Gln Gly Thr Glu
                165                 170                 175

Phe Ile Arg Phe Ser Gly Val Val Asn Pro Arg Thr Ile Ser Gly Ser
            180                 185                 190

Asn Thr Val Pro Ser Thr Gln Val Ala Asp Ala Arg Ile Glu Tyr Val
        195                 200                 205

Gly Asn Gly Tyr Ile Asn Glu Ala Gln Asn Met Gly Trp Leu Gln Arg
    210                 215                 220

Phe Phe Leu Asn Leu Ser Pro Met
225                 230
```

<210> SEQ ID NO 29
<211> LENGTH: 1098
<212> TYPE: DNA
<213> ORGANISM: Escherichia coli

<400> SEQUENCE: 29

```
gtgattaaat ttctctctgc attaattctt ctactggtca cgacggcggc tcaggctgag      60
cgtattcgcg atctcaccag tgttcagggg gtaaggcaaa actcactgat tggctatggt     120
ctggtggtgg ggctggatgg caccggtgac agacaaccc agacgccgtt taccacacaa      180
acgcttaata acatgctctc acagctggga attaccgttc cgacgggcac caatatgcag     240
ctaaaaaacg tcgctgcggt aatggtgaca gcgtcacttc ctccgtttgg acgtcagggg     300
caaaccatcg atgtggtggt ttcttccatg ggaaatgcca aaagcttgcg tggaggtacg     360
ttgttgatga caccgcttaa gggcgttgac agtcaggtgt atgcgctggc gcagggcaat     420
```

-continued

```
attctggttg cggcgcagg agcctccgct ggcggtagca gtgttcaggt taaccaactg    480
aacggtggac ggatcaccaa tggtgcggtt attgaacgtg aattgcccag ccagtttggc    540
gtcgggaata cccttaattt gcaacttaac gacgaagatt tcagcatggc gcagcaaatc    600
gctgacacca tcaaccgcgt gcgtggatat ggcagcgcca ccgcgttaga tgcgcggact    660
attcaggtgc gcgtaccgag tggcaacagt tcccaggtcc gcttccttgc cgatattcag    720
aatatgcagg ttaatgtcac cccgcaggac gctaaagtag tgattaactc gcgcaccggt    780
tcggtggtga tgaatcgcga agtgaccctc gacagctgcg cggtagcgca ggggaatctc    840
tcagtaacag ttaatcgtca ggccaatgtc agccagccag atacaccgtt tggtggtgga    900
cagactgtgg ttactccaca aacgcagatc gatttacgcc agagcggcgg ttcgctgcaa    960
agcgtacgtt ccagcgccag cctcaataac gtggtgcgcg cgctcaatgc gctgggcgct   1020
acgccgatgg atctgatgtc catactgcaa tcaatgcaaa gtgcgggatg tctgcgggca   1080
aaactggaaa tcatctga                                                 1098
```

<210> SEQ ID NO 30
<211> LENGTH: 365
<212> TYPE: PRT
<213> ORGANISM: Escherichia coli

<400> SEQUENCE: 30

```
Met Ile Lys Phe Leu Ser Ala Leu Ile Leu Leu Val Thr Thr Ala
1               5                   10                  15

Ala Gln Ala Glu Arg Ile Arg Asp Leu Thr Ser Val Gln Gly Val Arg
            20                  25                  30

Gln Asn Ser Leu Ile Gly Tyr Gly Leu Val Val Gly Leu Asp Gly Thr
        35                  40                  45

Gly Asp Gln Thr Thr Gln Thr Pro Phe Thr Thr Gln Thr Leu Asn Asn
    50                  55                  60

Met Leu Ser Gln Leu Gly Ile Thr Val Pro Thr Gly Thr Asn Met Gln
65                  70                  75                  80

Leu Lys Asn Val Ala Ala Val Met Val Thr Ala Ser Leu Pro Pro Phe
                85                  90                  95

Gly Arg Gln Gly Gln Thr Ile Asp Val Val Val Ser Ser Met Gly Asn
            100                 105                 110

Ala Lys Ser Leu Arg Gly Gly Thr Leu Leu Met Thr Pro Leu Lys Gly
        115                 120                 125

Val Asp Ser Gln Val Tyr Ala Leu Ala Gln Gly Asn Ile Leu Val Gly
    130                 135                 140

Gly Ala Gly Ala Ser Ala Gly Gly Ser Ser Val Gln Val Asn Gln Leu
145                 150                 155                 160

Asn Gly Gly Arg Ile Thr Asn Gly Ala Val Ile Glu Arg Glu Leu Pro
                165                 170                 175

Ser Gln Phe Gly Val Gly Asn Thr Leu Asn Leu Gln Leu Asn Asp Glu
            180                 185                 190

Asp Phe Ser Met Ala Gln Gln Ile Ala Asp Thr Ile Asn Arg Val Arg
        195                 200                 205

Gly Tyr Gly Ser Ala Thr Ala Leu Asp Ala Arg Thr Ile Gln Val Arg
    210                 215                 220

Val Pro Ser Gly Asn Ser Ser Gln Val Arg Phe Leu Ala Asp Ile Gln
225                 230                 235                 240

Asn Met Gln Val Asn Val Thr Pro Gln Asp Ala Lys Val Val Ile Asn
                245                 250                 255
```

```
Ser Arg Thr Gly Ser Val Val Met Asn Arg Glu Val Thr Leu Asp Ser
            260                 265                 270

Cys Ala Val Ala Gln Gly Asn Leu Ser Val Thr Val Asn Arg Gln Ala
                275                 280                 285

Asn Val Ser Gln Pro Asp Thr Pro Phe Gly Gly Gln Thr Val Val
            290                 295                 300

Thr Pro Gln Thr Gln Ile Asp Leu Arg Gln Ser Gly Gly Ser Leu Gln
305                 310                 315                 320

Ser Val Arg Ser Ser Ala Ser Leu Asn Asn Val Val Arg Ala Leu Asn
                325                 330                 335

Ala Leu Gly Ala Thr Pro Met Asp Leu Met Ser Ile Leu Gln Ser Met
                340                 345                 350

Gln Ser Ala Gly Cys Leu Arg Ala Lys Leu Glu Ile Ile
                355                 360                 365

<210> SEQ ID NO 31
<211> LENGTH: 2163
<212> TYPE: DNA
<213> ORGANISM: Escherichia coli

<400> SEQUENCE: 31
atggccttta tgctaagtcc tttgctcaaa cgctatacct ggaacagcgc ctggctgtat      60
tacgcgcgta tttttattgc ctttgtgga accacagcgt ttccgtggtg ctgggtgat      120 gtaaaactga cgattccgct aacgctgggg atggtggcag cggcgctgac cgatctcgat     180
gaccgactgg cgggacgttt gcgtaacctc atcattacgc tgttctgctt ttttatcgcc     240
tcggcctcag tagaattgct gttttccctgg ccctggctat ttgcgattgg cttaacgctc    300
tctaccagcg gcttcatttt gctcggcggt ctgggtcaac gctatgcaac aattgccttc    360
ggtgcattgc tgatcgccat ttacactatg ttgggaacat cactgtatga gcactggtat    420
cagcagccga tgtatctgct ggccggtgcc gtctggtaca cgtcctgac acttattggt    480 catctgctgt ccccggtccg cccgctgcag acaacctgg cgcgttgcta tgaacaactg    540
gcgcgttatc ttgagctcaa gtcgcgcatg tttgatcctg atattgaaga tcaaagccag    600
gcaccgctgt acgatttggc tctcgccaac ggtctgctga tggcgacatt gaatcagacg    660
aaactctcgc tgctgacccg cttacgtggc gatcgtggtc aacggggaac gcgtcgcacg    720
ctgcattatt actttgtcgc acaggatatt cacgagcgtg ccagctcttc tcatattcag    780
tatcaaacat gcgtgaaaca ttttcgccac agcgacgtgc tgttccgttt tcagcggctg    840
atgtcgatgc agggccaggc gtgccagcaa ctgtcacgct gtattttgtt gcgtcagcct    900
tatcaacatg atccgcattt tgagcgcgct tttacgcata ttgatgctgc gctggagcgg    960
atgcgcgata acggcgcacc cgccgattta ctcaaaacac tgggatttt gctgaacaat    1020 ttacgcgcca ttgatgccca actggcaaca attgaatcag aacaggccca ggcactaccc    1080
cataataatg acgaaaatga gctcgctgat gacagcccgc acgggttgag tgatatctgg    1140
ctgcgtctta gccgtcactt cacgccggaa tccgccctct ccgtcatgc ggtaagaatg     1200 tcgctggtgt tgtgcttcgg ctacgccatc attcagataa ccggaatgca tcacgggtat    1260
tggatcttgc tgacaagttt gtttgtctgc cagccaaact ataacgccac gcgccaccgc    1320
ctgaagttaa ggattattgg tacgctggta ggtatcgcca ttggcattcc tgtgctgtgg    1380
tttgtgccat cactggaagg gcagctggtg ctgctggtta ttaccggcgt gctctttttt    1440
gccttccgta acgtgcaata cgctcatgca acgatgttca tcacactttt ggtgctactg    1500
tgttttaact tactgggtga aggttttgaa gtagcgttac ctcgcgtaat cgatacgctg    1560
```

-continued

```
attggttgtg ccattgcgtg ggcggcagtg agctacatct ggcctgactg gcagtttcgc    1620
aatctgccgc gcatgctcga acgcgccaca gaggccaact gtcggtatct cgatgccata    1680
ctggagcaat accatcaggg gcgtgataac cgtctggcgt atcgtattgc ccgccgcgat    1740
gcacacaacc gtgatgctga gctggcgtcg gtggtatcaa atatgtccag cgagccgaac    1800
gttaccccgc aaattcgcga agccgcgttt cggttgctgt gccttaacca tacgtttacc    1860
agctatatct cagccctcgg tgctcaccgg gagcagttaa ctaatcctga aattctggcg    1920
tttcttgatg acgcagtttg ctatgttgat gacgcgttac atcatcaacc tgctgatgaa    1980
gaacgcgtca atgaggcatt agctagcctg aaacagcgga tgcagcaact tgaaccacgg    2040
gcagacagca agaacctct ggtcgtacaa caagttggat tattgattgc attactgcct    2100
gagattggtc gtctgcaacg ccagattact caagttccgc aggaaactcc tgtttcggcg    2160
taa                                                                   2163
```

<210> SEQ ID NO 32
<211> LENGTH: 720
<212> TYPE: PRT
<213> ORGANISM: Escherichia coli

<400> SEQUENCE: 32

```
Met Ala Phe Met Leu Ser Pro Leu Leu Lys Arg Tyr Thr Trp Asn Ser
1               5                   10                  15

Ala Trp Leu Tyr Tyr Ala Arg Ile Phe Ile Ala Leu Cys Gly Thr Thr
            20                  25                  30

Ala Phe Pro Trp Trp Leu Gly Asp Val Lys Leu Thr Ile Pro Leu Thr
        35                  40                  45

Leu Gly Met Val Ala Ala Leu Thr Asp Leu Asp Asp Arg Leu Ala
    50                  55                  60

Gly Arg Leu Arg Asn Leu Ile Ile Thr Leu Phe Cys Phe Phe Ile Ala
65                  70                  75                  80

Ser Ala Ser Val Glu Leu Leu Phe Pro Trp Pro Trp Leu Phe Ala Ile
                85                  90                  95

Gly Leu Thr Leu Ser Thr Ser Gly Phe Ile Leu Leu Gly Gly Leu Gly
            100                 105                 110

Gln Arg Tyr Ala Thr Ile Ala Phe Gly Ala Leu Leu Ile Ala Ile Tyr
        115                 120                 125

Thr Met Leu Gly Thr Ser Leu Tyr Glu His Trp Tyr Gln Gln Pro Met
    130                 135                 140

Tyr Leu Leu Ala Gly Ala Val Trp Tyr Asn Val Leu Thr Leu Ile Gly
145                 150                 155                 160

His Leu Leu Phe Pro Val Arg Pro Leu Gln Asp Asn Leu Ala Arg Cys
                165                 170                 175

Tyr Glu Gln Leu Ala Arg Tyr Leu Glu Leu Lys Ser Arg Met Phe Asp
            180                 185                 190

Pro Asp Ile Glu Asp Gln Ser Gln Ala Pro Leu Tyr Asp Leu Ala Leu
        195                 200                 205

Ala Asn Gly Leu Leu Met Ala Thr Leu Asn Gln Thr Lys Leu Ser Leu
    210                 215                 220

Leu Thr Arg Leu Arg Gly Asp Arg Gly Gln Arg Gly Thr Arg Arg Thr
225                 230                 235                 240

Leu His Tyr Tyr Phe Val Ala Gln Asp Ile His Glu Arg Ala Ser Ser
                245                 250                 255

Ser His Ile Gln Tyr Gln Thr Leu Arg Glu His Phe Arg His Ser Asp
```

-continued

```
            260                 265                 270
Val Leu Phe Arg Phe Gln Arg Leu Met Ser Met Gln Gly Gln Ala Cys
        275                 280                 285

Gln Gln Leu Ser Arg Cys Ile Leu Leu Arg Gln Pro Tyr Gln His Asp
        290                 295                 300

Pro His Phe Glu Arg Ala Phe Thr His Ile Asp Ala Ala Leu Glu Arg
305                 310                 315                 320

Met Arg Asp Asn Gly Ala Pro Ala Asp Leu Leu Lys Thr Leu Gly Phe
                325                 330                 335

Leu Leu Asn Asn Leu Arg Ala Ile Asp Ala Gln Leu Ala Thr Ile Glu
                340                 345                 350

Ser Glu Gln Ala Gln Ala Leu Pro His Asn Asn Asp Glu Asn Glu Leu
                355                 360                 365

Ala Asp Asp Ser Pro His Gly Leu Ser Asp Ile Trp Leu Arg Leu Ser
                370                 375                 380

Arg His Phe Thr Pro Glu Ser Ala Leu Phe Arg His Ala Val Arg Met
385                 390                 395                 400

Ser Leu Val Leu Cys Phe Gly Tyr Ala Ile Ile Gln Ile Thr Gly Met
                405                 410                 415

His His Gly Tyr Trp Ile Leu Leu Thr Ser Leu Phe Val Cys Gln Pro
                420                 425                 430

Asn Tyr Asn Ala Thr Arg His Arg Leu Lys Leu Arg Ile Ile Gly Thr
                435                 440                 445

Leu Val Gly Ile Ala Ile Gly Ile Pro Val Leu Trp Phe Val Pro Ser
                450                 455                 460

Leu Glu Gly Gln Leu Val Leu Val Ile Thr Gly Val Leu Phe Phe
465                 470                 475                 480

Ala Phe Arg Asn Val Gln Tyr Ala His Ala Thr Met Phe Ile Thr Leu
                485                 490                 495

Leu Val Leu Leu Cys Phe Asn Leu Leu Gly Glu Gly Phe Glu Val Ala
                500                 505                 510

Leu Pro Arg Val Ile Asp Thr Leu Ile Gly Cys Ala Ile Ala Trp Ala
                515                 520                 525

Ala Val Ser Tyr Ile Trp Pro Asp Trp Gln Phe Arg Asn Leu Pro Arg
                530                 535                 540

Met Leu Glu Arg Ala Thr Glu Ala Asn Cys Arg Tyr Leu Asp Ala Ile
545                 550                 555                 560

Leu Glu Gln Tyr His Gln Gly Arg Asp Asn Arg Leu Ala Tyr Arg Ile
                565                 570                 575

Ala Arg Arg Asp Ala His Asn Arg Asp Ala Glu Leu Ala Ser Val Val
                580                 585                 590

Ser Asn Met Ser Ser Glu Pro Asn Val Thr Pro Gln Ile Arg Glu Ala
                595                 600                 605

Ala Phe Arg Leu Leu Cys Leu Asn His Thr Phe Thr Ser Tyr Ile Ser
                610                 615                 620

Ala Leu Gly Ala His Arg Glu Gln Leu Thr Asn Pro Glu Ile Leu Ala
625                 630                 635                 640

Phe Leu Asp Asp Ala Val Cys Tyr Val Asp Asp Ala Leu His His Gln
                645                 650                 655

Pro Ala Asp Glu Glu Arg Val Asn Glu Ala Leu Ala Ser Leu Lys Gln
                660                 665                 670

Arg Met Gln Gln Leu Glu Pro Arg Ala Asp Ser Lys Glu Pro Leu Val
                675                 680                 685
```

Val Gln Gln Val Gly Leu Leu Ile Ala Leu Leu Pro Glu Ile Gly Arg
690                 695                 700

Leu Gln Arg Gln Ile Thr Gln Val Pro Gln Glu Thr Pro Val Ser Ala
705                 710                 715                 720

<210> SEQ ID NO 33
<211> LENGTH: 1119
<212> TYPE: DNA
<213> ORGANISM: Escherichia coli

<400> SEQUENCE: 33

| | | | | | |
|---|---|---|---|---|---|
| atgccattac | ccgattttca | tgtttctgaa | ccttttaccc | tcggtattga | actggaaatg | 60 |
| caggtggtta | atccgccggg | ctatgactta | agccaggact | cttcaatgct | gattgacgcg | 120 |
| gttaaaaata | agatcacggc | cggagaggta | aagcacgata | tcaccgaaag | tatgctggag | 180 |
| ctggcgacgg | atgtttgccg | tgatatcaac | caggctgccg | ggcaattttc | agcgatgcag | 240 |
| aaagtcgtat | tgcaggcagc | cgcagaccat | catctggaaa | tttgcggcgg | tggcacgcac | 300 |
| ccgtttcaga | atggcagcg | tcaggaggta | tgcgacaacg | aacgctatca | acgaacgctg | 360 |
| gaaaactttg | gctatctcat | ccagcaggcg | accgttttg | gtcagcatgt | ccatgttggc | 420 |
| tgtgccagtg | gcgatgacgc | catttatttg | ctgcacggct | tgtcacggtt | tgtgccgcac | 480 |
| tttatcgccc | tttccgccgc | gtcgccatat | atgcagggaa | cggatacgcg | ttttgcctcc | 540 |
| tcacgaccga | atattttttc | cgcctttcct | gataatggcc | cgatgccgtg | ggtcagtaac | 600 |
| tgcaacaat | ttgaagccct | gtttcgctgt | ctgagttaca | ccacgatgat | cgacagcatt | 660 |
| aaagatctgc | actgggatat | tcgccccagt | cctcattttg | gcacggtgga | rgttcgggtg | 720 |
| atggatcccc | cgttaaccct | tagccacgcg | gtaaatatgg | cgggattaat | tcaggccacc | 780 |
| gcccactggt | tactgacaga | acgcccgttc | aaacataagg | agaaagatta | cctgctgtat | 840 |
| aaattcaacc | gtttccaggc | ctgccgstat | gggctggaag | gcgtcattac | cgatccgtac | 900 |
| actggcgatc | gtcgaccact | aacggaagac | accttgcgat | tgctgaaaaa | aatcgcccct | 960 |
| tctgcacata | aaattggtgc | atcgagcgcg | attgaggccc | tgcatcgcca | ggtcgtcagc | 1020 |
| ggtctgaatg | aagcgcagct | gatgcgcgat | ttcgtcgccg | atggcggctc | gctgattggg | 1080 |
| ctggtgaaaa | agcattgtga | gatctgggcc | ggtgactaa | | | 1119 |

<210> SEQ ID NO 34
<211> LENGTH: 372
<212> TYPE: PRT
<213> ORGANISM: Escherichia coli

<400> SEQUENCE: 34

Met Pro Leu Pro Asp Phe His Val Ser Glu Pro Phe Thr Leu Gly Ile
1               5                   10                  15

Glu Leu Glu Met Gln Val Val Asn Pro Pro Gly Tyr Asp Leu Ser Gln
                20                  25                  30

Asp Ser Ser Met Leu Ile Asp Ala Val Lys Asn Lys Ile Thr Ala Gly
            35                  40                  45

Glu Val Lys His Asp Ile Thr Glu Ser Met Leu Glu Leu Ala Thr Asp
        50                  55                  60

Val Cys Arg Asp Ile Asn Gln Ala Ala Gly Gln Phe Ser Ala Met Gln
65                  70                  75                  80

Lys Val Val Leu Gln Ala Ala Ala Asp His His Leu Glu Ile Cys Gly
                85                  90                  95

Gly Gly Thr His Pro Phe Gln Lys Trp Gln Arg Gln Glu Val Cys Asp
                100                 105                 110

Asn Glu Arg Tyr Gln Arg Thr Leu Glu Asn Phe Gly Tyr Leu Ile Gln
            115                 120                 125

Gln Ala Thr Val Phe Gly Gln His Val His Val Gly Cys Ala Ser Gly
        130                 135                 140

Asp Asp Ala Ile Tyr Leu Leu His Gly Leu Ser Arg Phe Val Pro His
145                 150                 155                 160

Phe Ile Ala Leu Ser Ala Ala Ser Pro Tyr Met Gln Gly Thr Asp Thr
                165                 170                 175

Arg Phe Ala Ser Ser Arg Pro Asn Ile Phe Ser Ala Phe Pro Asp Asn
            180                 185                 190

Gly Pro Met Pro Trp Val Ser Asn Trp Gln Gln Phe Glu Ala Leu Phe
        195                 200                 205

Arg Cys Leu Ser Tyr Thr Thr Met Ile Asp Ser Ile Lys Asp Leu His
    210                 215                 220

Trp Asp Ile Arg Pro Ser Pro His Phe Gly Thr Val Glu Val Arg Val
225                 230                 235                 240

Met Asp Thr Pro Leu Thr Leu Ser His Ala Val Asn Met Ala Gly Leu
                245                 250                 255

Ile Gln Ala Thr Ala His Trp Leu Leu Thr Glu Arg Pro Phe Lys His
            260                 265                 270

Lys Glu Lys Asp Tyr Leu Leu Tyr Lys Phe Asn Arg Phe Gln Ala Cys
        275                 280                 285

Arg Tyr Gly Leu Glu Gly Val Ile Thr Asp Pro Tyr Thr Gly Asp Arg
    290                 295                 300

Arg Pro Leu Thr Glu Asp Thr Leu Arg Leu Leu Glu Lys Ile Ala Pro
305                 310                 315                 320

Ser Ala His Lys Ile Gly Ala Ser Ala Ile Glu Ala Leu His Arg
                325                 330                 335

Gln Val Val Ser Gly Leu Asn Glu Ala Gln Leu Met Arg Asp Phe Val
            340                 345                 350

Ala Asp Gly Gly Ser Leu Ile Gly Leu Val Lys Lys His Cys Glu Ile
        355                 360                 365

Trp Ala Gly Asp
    370

<210> SEQ ID NO 35
<211> LENGTH: 387
<212> TYPE: DNA
<213> ORGANISM: Escherichia coli

<400> SEQUENCE: 35
gtggcgtcca gctcattgat tatgggaat aacatgcacg taaaatactt agcagggatt    60
gtcggtgccg cgctactgat ggcgggttgt agctccagca acgaattgag tgctgccggt   120
cagagtgtac gcattgtgga cgagcagcca ggcgcagagt gccagctgat tggtactgcg   180
acaggtaagc aaagcaactg gctttccggg caacacggag aagagggcgg ttctatgcgc   240
ggcgcagcaa acgatctgcg caaccaggcg gctgcaatgg gcggtaacgt gatttatggc   300
atcagtagcc cgtcgcaggg aatgttgtcc agttttgtcc cgacggatag ccagattatc   360
ggccaggtat ataagtgccc gaactga                                       387

<210> SEQ ID NO 36
<211> LENGTH: 128
<212> TYPE: PRT
<213> ORGANISM: Escherichia coli

<400> SEQUENCE: 36

Met Ala Ser Ser Ser Leu Ile Met Gly Asn Asn Met His Val Lys Tyr
1               5                   10                  15

Leu Ala Gly Ile Val Gly Ala Ala Leu Leu Met Ala Gly Cys Ser Ser
            20                  25                  30

Ser Asn Glu Leu Ser Ala Ala Gly Gln Ser Val Arg Ile Val Asp Glu
        35                  40                  45

Gln Pro Gly Ala Glu Cys Gln Leu Ile Gly Thr Ala Thr Gly Lys Gln
    50                  55                  60

Ser Asn Trp Leu Ser Gly Gln His Gly Glu Glu Gly Gly Ser Met Arg
65                  70                  75                  80

Gly Ala Ala Asn Asp Leu Arg Asn Gln Ala Ala Ala Met Gly Gly Asn
                85                  90                  95

Val Ile Tyr Gly Ile Ser Ser Pro Ser Gln Gly Met Leu Ser Ser Phe
            100                 105                 110

Val Pro Thr Asp Ser Gln Ile Ile Gly Gln Val Tyr Lys Cys Pro Asn
        115                 120                 125

<210> SEQ ID NO 37
<211> LENGTH: 603
<212> TYPE: DNA
<213> ORGANISM: Escherichia coli

<400> SEQUENCE: 37
gtgagtttta tcatgacggc ggaaggtcac cttctctttt ctattgcttg tgcggtattt      60
gccaaaaatg ccgagctgac gcccgtgctg cacagggtg actggtggca tattgtccct     120
tccgcaatcc tgacgtgttt gttaccggac atcgatcacc caaagtcgtt tcttgggcag    180
cgattaaaat ggatatcaaa accgatcgcc cgcgcttttg gcatcgtgg ttttacccac     240
agtctgctgg cggtatttgc gctgctggca accttttacc ttaaggttcc ggaaggctgg    300
ttcattccgg ctgatgcgct acaaggaatg gtgctgggtt atttgagcca catacttgcc    360
gatatgctga cacccgccgg tgttcccctg ctctggccat gccgctggcg tttccgcttg    420
cctatcctgg ttccccaaaa gggcaaccaa ctggaacgtt tatctgcat ggcattattt     480
gtctggtcgg tatggatgcc ccattcatta cccgagaaca gcgctgttcg ttggtcatcg    540
caaatgatca ataccttgca gatccagttt catcggctta ttaagcatca ggttgaatac    600
taa                                                                  603

<210> SEQ ID NO 38
<211> LENGTH: 200
<212> TYPE: PRT
<213> ORGANISM: Escherichia coli

<400> SEQUENCE: 38

Met Ser Phe Ile Met Thr Ala Glu Gly His Leu Leu Phe Ser Ile Ala
1               5                   10                  15

Cys Ala Val Phe Ala Lys Asn Ala Glu Leu Thr Pro Val Leu Ala Gln
            20                  25                  30

Gly Asp Trp Trp His Ile Val Pro Ser Ala Ile Leu Thr Cys Leu Leu
        35                  40                  45

Pro Asp Ile Asp His Pro Lys Ser Phe Leu Gly Gln Arg Leu Lys Trp
    50                  55                  60

Ile Ser Lys Pro Ile Ala Arg Ala Phe Gly His Arg Gly Phe Thr His
65                  70                  75                  80

Ser Leu Leu Ala Val Phe Ala Leu Leu Ala Thr Phe Tyr Leu Lys Val

```
                        85                  90                  95
Pro Glu Gly Trp Phe Ile Pro Ala Asp Ala Leu Gln Gly Met Val Leu
                100                 105                 110

Gly Tyr Leu Ser His Ile Leu Ala Asp Met Leu Thr Pro Ala Gly Val
            115                 120                 125

Pro Leu Leu Trp Pro Cys Arg Trp Arg Phe Arg Leu Pro Ile Leu Val
        130                 135                 140

Pro Gln Lys Gly Asn Gln Leu Glu Arg Phe Ile Cys Met Ala Leu Phe
145                 150                 155                 160

Val Trp Ser Val Trp Met Pro His Ser Leu Pro Glu Asn Ser Ala Val
                165                 170                 175

Arg Trp Ser Ser Gln Met Ile Asn Thr Leu Gln Ile Gln Phe His Arg
            180                 185                 190

Leu Ile Lys His Gln Val Glu Tyr
        195                 200

<210> SEQ ID NO 39
<211> LENGTH: 864
<212> TYPE: DNA
<213> ORGANISM: Escherichia coli

<400> SEQUENCE: 39
atgcgttggc aagggcgacg tgaaagtgac aatgttgaag acaggcgcaa cagctctggt      60
ggtccatcta tgggcggtcc cggttttcgc ctgccaagcg gtaaaggcgg gctgatttta     120
ctgatagtcg tgctggttgc aggctactat ggtgttgatt taaccgggtt gatgaccggg     180
cagccggttt cccaacaaca atcaacgcgg tcaattagcc caaatgaaga cgaagccgca     240
aaattcacct cggtgattct ggcaaccacg gaagacacct ggggacaaca gttcgagaag     300
atgggtaaga cctatcagca accgaagctg gtcatgtacc gtggaatgac gcgtaccggc     360
tgcggggcgg gccagtccat aatggggccg ttctattgcc cggcgatgg cacggtttat     420 atcgatctct ccttctatga tgacatgaaa gacaaacttg gcgcggatgg cgattttgcc     480
cagggggtac gttatcgccc tgaagtcggt catcatgtgc agaaactgtt aggcatcgag     540
ccgaaagttc gtcaactgca acaaaacgcg acgcaggcgg aagtaaaccg cttatctgtg     600
cgtatggaac tccaggccga ctgttttgcc ggtgtctggg gcatagtat gcagcagcaa      660 ggcgttctgg aaaccggcga tctggaagag gcgctgaacg cggcgcaggc catcggcgat     720
gaccgtttac aacagcaaag tcaggggcga gtagtaccag acagtttcac tcatggcact     780
tctcagcaac gctacagctg gtttaaacgt ggtttcgaca gcggcgatcc ggcacaatgc     840 aatactttg gtaaaagcat ttaa                                             864

<210> SEQ ID NO 40
<211> LENGTH: 287
<212> TYPE: PRT
<213> ORGANISM: Escherichia coli

<400> SEQUENCE: 40

Met Arg Trp Gln Gly Arg Arg Glu Ser Asp Asn Val Glu Asp Arg Arg
1               5                   10                  15

Asn Ser Ser Gly Gly Pro Ser Met Gly Gly Pro Gly Phe Arg Leu Pro
            20                  25                  30

Ser Gly Lys Gly Gly Leu Ile Leu Leu Ile Val Val Leu Val Ala Gly
        35                  40                  45

Tyr Tyr Gly Val Asp Leu Thr Gly Leu Met Thr Gly Gln Pro Val Ser
    50                  55                  60
```

Gln Gln Gln Ser Thr Arg Ser Ile Ser Pro Asn Glu Asp Glu Ala Ala
 65                  70                  75                  80

Lys Phe Thr Ser Val Ile Leu Ala Thr Thr Glu Asp Thr Trp Gly Gln
                 85                  90                  95

Gln Phe Glu Lys Met Gly Lys Thr Tyr Gln Gln Pro Lys Leu Val Met
            100                 105                 110

Tyr Arg Gly Met Thr Arg Thr Gly Cys Gly Ala Gly Gln Ser Ile Met
        115                 120                 125

Gly Pro Phe Tyr Cys Pro Ala Asp Gly Thr Val Tyr Ile Asp Leu Ser
130                 135                 140

Phe Tyr Asp Asp Met Lys Asp Lys Leu Gly Ala Asp Gly Asp Phe Ala
145                 150                 155                 160

Gln Gly Tyr Val Ile Ala His Glu Val Gly His His Val Gln Lys Leu
                165                 170                 175

Leu Gly Ile Glu Pro Lys Val Arg Gln Leu Gln Gln Asn Ala Thr Gln
            180                 185                 190

Ala Glu Val Asn Arg Leu Ser Val Arg Met Glu Leu Gln Ala Asp Cys
        195                 200                 205

Phe Ala Gly Val Trp Gly His Ser Met Gln Gln Gln Gly Val Leu Glu
210                 215                 220

Thr Gly Asp Leu Glu Glu Ala Leu Asn Ala Ala Gln Ala Ile Gly Asp
225                 230                 235                 240

Asp Arg Leu Gln Gln Gln Ser Gln Gly Arg Val Val Pro Asp Ser Phe
                245                 250                 255

Thr His Gly Thr Ser Gln Gln Arg Tyr Ser Trp Phe Lys Arg Gly Phe
            260                 265                 270

Asp Ser Gly Asp Pro Ala Gln Cys Asn Thr Phe Gly Lys Ser Ile
        275                 280                 285

<210> SEQ ID NO 41
<211> LENGTH: 1071
<212> TYPE: DNA
<213> ORGANISM: Escherichia coli

<400> SEQUENCE: 41
atggcgatga gtaaagtgaa aagtatcacc cgtgaatcct ggatcctgag cactttcccg    60
gagtggggta gctggttgaa tgaagaaatt gaacaagaac aggtcgctcc tggcacattt   120
gcgatgtggt ggcttggctg caccgggatc tggttgaaat cggaaggtgg caccaacgtt   180
tgcgttgatt tctggtgcgg cactggcaaa caaagtcacg gtaacccgtt aatgaaacag   240
ggtcaccaga tgcagcgcat ggctggcgtg aaaaaaactg cagccaaacct gcgtaccacc   300 ccgtttgttc ttgatccgtt tgcgattcgc cagatcgacg cggtactggc gactcacgat   360
cacaacgatc atatcgacgt taacgtcgct gctgccgtga tgcagaattg tgcagatgac   420 gtaccgtttta tcggaccgaa aacctgtgtg gatttgtgga ttggctgggg cgtaccgaaa   480
gagcgttgca tcgtggtcaa accgggcgat gtagtaaaag tgaaagacat tgaaattcat   540
gcgcttgatg ctttcgaccg tactgcactg atcaccctgc tgccgatca aaaagcggct    600 ggcgtactgc cagatggcat ggacgatcgc gcggtgaact acctgttcaa acgcctggc    660 ggctccctgt atcacagcgg cgactcccac tactctaact attatgcgaa gcacggtaac   720
gaacatcaga tcgacgtggc gttaggatcg tacggcgaaa accgcgcgg tatcaccgac    780 aaaatgacca cgccgatat gctgcgtatg ggtgaagcgc tgaatgcgaa agtagtgatc    840
ccgttccacc acgatatctg gtcaaacttc caggccgatc cgcaagagat ccgcgtgctg   900

-continued

```
tgggagatga aaaaagatcg cctgaagtat ggcttcaagc cgtttatctg gcaggtgggt    960
ggcaaattta cctggccgct ggataaagac aacttcgagt accactatcc gcgcggtttc   1020
gatgattgct tcactattga accggatctg ccgttcaagt cattcctgta a            1071
```

<210> SEQ ID NO 42
<211> LENGTH: 356
<212> TYPE: PRT
<213> ORGANISM: Escherichia coli

<400> SEQUENCE: 42

```
Met Ala Met Ser Lys Val Lys Ser Ile Thr Arg Glu Ser Trp Ile Leu
1               5                   10                  15

Ser Thr Phe Pro Glu Trp Gly Ser Trp Leu Asn Glu Ile Glu Gln
            20                  25                  30

Glu Gln Val Ala Pro Gly Thr Phe Ala Met Trp Trp Leu Gly Cys Thr
        35                  40                  45

Gly Ile Trp Leu Lys Ser Glu Gly Gly Thr Asn Val Cys Val Asp Phe
    50                  55                  60

Trp Cys Gly Thr Gly Lys Gln Ser His Gly Asn Pro Leu Met Lys Gln
65                  70                  75                  80

Gly His Gln Met Gln Arg Met Ala Gly Val Lys Lys Leu Gln Pro Asn
                85                  90                  95

Leu Arg Thr Thr Pro Phe Val Leu Asp Pro Phe Ala Ile Arg Gln Ile
            100                 105                 110

Asp Ala Val Leu Ala Thr His Asp His Asn Asp His Ile Asp Val Asn
        115                 120                 125

Val Ala Ala Ala Val Met Gln Asn Cys Ala Asp Val Pro Phe Ile
    130                 135                 140

Gly Pro Lys Thr Cys Val Asp Leu Trp Ile Gly Trp Gly Val Pro Lys
145                 150                 155                 160

Glu Arg Cys Ile Val Val Lys Pro Gly Asp Val Val Lys Val Lys Asp
                165                 170                 175

Ile Glu Ile His Ala Leu Asp Ala Phe Asp Arg Thr Ala Leu Ile Thr
            180                 185                 190

Leu Pro Ala Asp Gln Lys Ala Ala Gly Val Leu Pro Asp Gly Met Asp
        195                 200                 205

Asp Arg Ala Val Asn Tyr Leu Phe Lys Thr Pro Gly Gly Ser Leu Tyr
    210                 215                 220

His Ser Gly Asp Ser His Tyr Ser Asn Tyr Tyr Ala Lys His Gly Asn
225                 230                 235                 240

Glu His Gln Ile Asp Val Ala Leu Gly Ser Tyr Gly Glu Asn Pro Arg
                245                 250                 255

Gly Ile Thr Asp Lys Met Thr Ser Ala Asp Met Leu Arg Met Gly Glu
            260                 265                 270

Ala Leu Asn Ala Lys Val Val Ile Pro Phe His His Asp Ile Trp Ser
        275                 280                 285

Asn Phe Gln Ala Asp Pro Gln Glu Ile Arg Val Leu Trp Glu Met Lys
    290                 295                 300

Lys Asp Arg Leu Lys Tyr Gly Phe Lys Pro Phe Ile Trp Gln Val Gly
305                 310                 315                 320

Gly Lys Phe Thr Trp Pro Leu Asp Lys Asp Asn Phe Glu Tyr His Tyr
                325                 330                 335

Pro Arg Gly Phe Asp Asp Cys Phe Thr Ile Glu Pro Asp Leu Pro Phe
            340                 345                 350
```

Lys Ser Phe Leu
        355

<210> SEQ ID NO 43
<211> LENGTH: 2544
<212> TYPE: DNA
<213> ORGANISM: Escherichia coli

<400> SEQUENCE: 43

| | | | | | | |
|---|---|---|---|---|---|---|
| atgaataaga | caactgagta | cattgacgca | atgcccatcg | ccgcaagcga | gaaagcggca | 60 |
| ttgccgaaga | ctgatatccg | cgccgttcat | caggcgctgg | atgccgaaca | ccgcacctgg | 120 |
| gcgcgggagg | atgattcccc | gcaaggctcg | gtaaaggcgc | gtctggaaca | agcctggcca | 180 |
| gattcacttg | ctgatggaca | gttaattaaa | gacgacgaag | ggcgcgatca | gctgaaggcg | 240 |
| atgccagaag | caaaacgctc | ctcgatgttt | cccgacccgt | ggcgtaccaa | cccggtaggc | 300 |
| cgtttctggg | atcgcctgcg | tggacgcgat | gtcacgccgc | gctatctggc | tcgtttgacc | 360 |
| aaagaagagc | aggagagcga | gcaaaagtgg | cgtaccgtcg | gtaccatccg | ccgttacatt | 420 |
| ctgttgatcc | tgacgctcgc | gcaaactgtc | gtcgcgacct | ggtatatgaa | gaccattctt | 480 |
| ccttatcagg | gttgggcgct | gattaatcct | atggatatgg | ttggtcagga | tttgtgggtt | 540 |
| tcctttatgc | agcttctgcc | ttatatgctg | caaaccggta | tcctgatcct | ctttgcggta | 600 |
| ctgttctgtt | gggtgtccgc | cggattctgg | acggcgttaa | tgggcttcct | gcaactgctt | 660 |
| attggtcgcg | ataaatacag | tatatctgcg | tcaacagttg | gcgatgaacc | attaaacccg | 720 |
| gagcatcgca | cggcgttgat | catgcctatc | tgtaacgaag | acgtgaaccg | tgtttttgct | 780 |
| ggcctgcgtg | caacgtggga | atcagtaaaa | gccaccggga | atgccaaaca | ctttgatgtc | 840 |
| tacattctta | gtgacagtta | taacccggat | atctgcgtcg | cagagcaaaa | agcctggatg | 900 |
| gagcttatcg | ctgaagtcgg | tggcgaaggt | cagattttct | atcgccgccg | ccgtcgccgc | 960 |
| gtgaagcgta | aaagcggtaa | tatcgatgac | ttctgccgtc | gctggggcag | ccagtacagc | 1020 |
| tacatggtgg | tgctggatgc | tgactcggta | atgaccggtg | attgtttgtg | cgggctggtg | 1080 |
| cgcctgatgg | aagccaaccc | gaacgccggg | atcattcagt | cgtcgccgaa | agcgtccggt | 1140 |
| atggatacgc | tgtatgcgcg | ctgtcagcag | ttcgcgaccc | gcgtgtatgg | gccactgttt | 1200 |
| acagccggtt | tgcacttctg | gcaacttggc | gagtcgcact | actggggaca | taacgcgatt | 1260 |
| atccgcgtga | aaccgtttat | cgagcactgc | gcactggctc | cgctgccggg | cgaaggttcc | 1320 |
| tttgccggtt | caatcctgtc | acatgacttc | gtggaagcgg | cgttgatgcg | ccgtgcaggt | 1380 |
| tgggggggtct | ggattgctta | cgatctcccg | ggttcttatg | aagaattgcc | gcctaacttg | 1440 |
| cttgatgagc | taaaacgtga | ccgccgatgg | tgccacggta | acctgatgaa | cttccgtctg | 1500 |
| ttcctggtga | agggtatgca | cccggttcac | cgtgcggtgt | tcctgacggg | cgtgatgtct | 1560 |
| tatctctccg | ctccgctgtg | gtttatgttc | ctcgcgctct | ctactgcatt | gcaggtagtg | 1620 |
| catgcgttga | ccgaaccgca | atacttcctg | caaccacggc | agttgttccc | agtgtggccg | 1680 |
| cagtggcgtc | ctgagctggc | gattgcactt | tttgcttcga | ccatggtgct | gttgttcctg | 1740 |
| ccgaagttat | tgagcatttt | gcttatctgg | tgcaaaggaa | cgaaagaata | cggcggcttc | 1800 |
| tggcgcgtta | cattatcgtt | gctgctggaa | gtgcttttttt | ccgtgctgct | ggctccggta | 1860 |
| cgcatgctgt | tccatacggt | cttcgttgtc | agcgcgttcc | ttggctggga | agtggtgtgg | 1920 |
| aattcaccgc | agcgtgatga | tgactccact | tcctggggtg | aagcgttcaa | acgccacggc | 1980 |
| tcacagctgc | tgttagggtt | agtgtgggct | gttgggatgg | cgtggctgga | tctgcgtttc | 2040 |

-continued

```
ctgttctggc tggcaccgat tgtcttctcg ttgatcctgt caccgtttgt ttcggtgatt    2100
tccagccgtg ccaccgttgg tctgcgcacc aaacgctgga aactgttcct gatcccggaa    2160
gagtattcgc cgccgcaggt gctggttgat accgatcggt tccttgagat gaatcgtcaa    2220
cgctcccttg atgatggctt tatgcacgca gtgtttaacc cgtcatttaa cgctctggca    2280
accgcaatgg cgaccgcgcg tcaccgcgcc agtaaggtgc tggaaatcgc ccgtgaccgc    2340
cacgttgaac aggcgctgaa cgagacgcca gagaagctga atcgcgatcg tcgcctggtg    2400
ctgctaagcg atccggtgac gatggcccgt ctgcatttcc gtgtctggaa ttccccggag    2460
agatattctt catgggtgag ttattacgaa gggataaagc tcaatccact ggcattgcgt    2520
aaaccggatg cggcttcgca ataa                                          2544
```

<210> SEQ ID NO 44
<211> LENGTH: 847
<212> TYPE: PRT
<213> ORGANISM: Escherichia coli

<400> SEQUENCE: 44

```
Met Asn Lys Thr Thr Glu Tyr Ile Asp Ala Met Pro Ile Ala Ala Ser
1               5                   10                  15

Glu Lys Ala Ala Leu Pro Lys Thr Asp Ile Arg Ala Val His Gln Ala
            20                  25                  30

Leu Asp Ala Glu His Arg Thr Trp Ala Arg Glu Asp Asp Ser Pro Gln
        35                  40                  45

Gly Ser Val Lys Ala Arg Leu Glu Gln Ala Trp Pro Asp Ser Leu Ala
    50                  55                  60

Asp Gly Gln Leu Ile Lys Asp Glu Gly Arg Asp Gln Leu Lys Ala
65                  70                  75                  80

Met Pro Glu Ala Lys Arg Ser Ser Met Phe Pro Asp Pro Trp Arg Thr
                85                  90                  95

Asn Pro Val Gly Arg Phe Trp Asp Arg Leu Arg Gly Arg Asp Val Thr
            100                 105                 110

Pro Arg Tyr Leu Ala Arg Leu Thr Lys Glu Glu Gln Glu Ser Glu Gln
        115                 120                 125

Lys Trp Arg Thr Val Gly Thr Ile Arg Arg Tyr Ile Leu Leu Ile Leu
    130                 135                 140

Thr Leu Ala Gln Thr Val Val Ala Thr Trp Tyr Met Lys Thr Ile Leu
145                 150                 155                 160

Pro Tyr Gln Gly Trp Ala Leu Ile Asn Pro Met Asp Met Val Gly Gln
                165                 170                 175

Asp Leu Trp Val Ser Phe Met Gln Leu Leu Pro Tyr Met Leu Gln Thr
            180                 185                 190

Gly Ile Leu Ile Leu Phe Ala Val Leu Phe Cys Trp Val Ser Ala Gly
        195                 200                 205

Phe Trp Thr Ala Leu Met Gly Phe Leu Gln Leu Ile Gly Arg Asp
    210                 215                 220

Lys Tyr Ser Ile Ser Ala Ser Thr Val Gly Asp Glu Pro Leu Asn Pro
225                 230                 235                 240

Glu His Arg Thr Ala Leu Ile Met Pro Ile Cys Asn Glu Asp Val Asn
                245                 250                 255

Arg Val Phe Ala Gly Leu Arg Ala Thr Trp Glu Ser Val Lys Ala Thr
            260                 265                 270

Gly Asn Ala Lys His Phe Asp Val Tyr Ile Leu Ser Asp Ser Tyr Asn
        275                 280                 285
```

```
Pro Asp Ile Cys Val Ala Glu Gln Lys Ala Trp Met Glu Leu Ile Ala
        290                 295                 300

Glu Val Gly Gly Glu Gly Gln Ile Phe Tyr Arg Arg Arg Arg Arg Arg
305                 310                 315                 320

Val Lys Arg Lys Ser Gly Asn Ile Asp Asp Phe Cys Arg Arg Trp Gly
                325                 330                 335

Ser Gln Tyr Ser Tyr Met Val Val Leu Asp Ala Asp Ser Val Met Thr
                340                 345                 350

Gly Asp Cys Leu Cys Gly Leu Val Arg Leu Met Glu Ala Asn Pro Asn
                355                 360                 365

Ala Gly Ile Ile Gln Ser Pro Lys Ala Ser Gly Met Asp Thr Leu
        370                 375                 380

Tyr Ala Arg Cys Gln Gln Phe Ala Thr Arg Val Tyr Gly Pro Leu Phe
385                 390                 395                 400

Thr Ala Gly Leu His Phe Trp Gln Leu Gly Glu Ser His Tyr Trp Gly
                405                 410                 415

His Asn Ala Ile Ile Arg Val Lys Pro Phe Ile Glu His Cys Ala Leu
                420                 425                 430

Ala Pro Leu Pro Gly Glu Gly Ser Phe Ala Gly Ser Ile Leu Ser His
        435                 440                 445

Asp Phe Val Glu Ala Ala Leu Met Arg Arg Ala Gly Trp Gly Val Trp
450                 455                 460

Ile Ala Tyr Asp Leu Pro Gly Ser Tyr Glu Glu Leu Pro Pro Asn Leu
465                 470                 475                 480

Leu Asp Glu Leu Lys Arg Asp Arg Arg Trp Cys His Gly Asn Leu Met
                485                 490                 495

Asn Phe Arg Leu Phe Leu Val Lys Gly Met His Pro Val His Arg Ala
        500                 505                 510

Val Phe Leu Thr Gly Val Met Ser Tyr Leu Ser Ala Pro Leu Trp Phe
        515                 520                 525

Met Phe Leu Ala Leu Ser Thr Ala Leu Gln Val Val His Ala Leu Thr
        530                 535                 540

Glu Pro Gln Tyr Phe Leu Gln Pro Arg Gln Leu Phe Pro Val Trp Pro
545                 550                 555                 560

Gln Trp Arg Pro Glu Leu Ala Ile Ala Leu Phe Ala Ser Thr Met Val
                565                 570                 575

Leu Leu Phe Leu Pro Lys Leu Leu Ser Ile Leu Leu Ile Trp Cys Lys
                580                 585                 590

Gly Thr Lys Glu Tyr Gly Gly Phe Trp Arg Val Thr Leu Ser Leu Leu
                595                 600                 605

Leu Glu Val Leu Phe Ser Val Leu Leu Ala Pro Val Arg Met Leu Phe
        610                 615                 620

His Thr Val Phe Val Val Ser Ala Phe Leu Gly Trp Glu Val Val Trp
625                 630                 635                 640

Asn Ser Pro Gln Arg Asp Asp Asp Ser Thr Ser Trp Gly Glu Ala Phe
                645                 650                 655

Lys Arg His Gly Ser Gln Leu Leu Leu Gly Leu Val Trp Ala Val Gly
                660                 665                 670

Met Ala Trp Leu Asp Leu Arg Phe Leu Phe Trp Leu Ala Pro Ile Val
                675                 680                 685

Phe Ser Leu Ile Leu Ser Pro Phe Val Ser Val Ile Ser Ser Arg Ala
        690                 695                 700

Thr Val Gly Leu Arg Thr Lys Arg Trp Lys Leu Phe Leu Ile Pro Glu
705                 710                 715                 720
```

```
Glu Tyr Ser Pro Pro Gln Val Leu Val Asp Thr Asp Arg Phe Leu Glu
                725                 730                 735

Met Asn Arg Gln Arg Ser Leu Asp Asp Gly Phe Met His Ala Val Phe
            740                 745                 750

Asn Pro Ser Phe Asn Ala Leu Ala Thr Ala Met Ala Thr Ala Arg His
                755                 760                 765

Arg Ala Ser Lys Val Leu Glu Ile Ala Arg Asp Arg His Val Glu Gln
        770                 775                 780

Ala Leu Asn Glu Thr Pro Glu Lys Leu Asn Arg Asp Arg Arg Leu Val
785                 790                 795                 800

Leu Leu Ser Asp Pro Val Thr Met Ala Arg Leu His Phe Arg Val Trp
                805                 810                 815

Asn Ser Pro Glu Arg Tyr Ser Ser Trp Val Ser Tyr Tyr Glu Gly Ile
            820                 825                 830

Lys Leu Asn Pro Leu Ala Leu Arg Lys Pro Asp Ala Ala Ser Gln
        835                 840                 845

<210> SEQ ID NO 45
<211> LENGTH: 1305
<212> TYPE: DNA
<213> ORGANISM: Escherichia coli

<400> SEQUENCE: 45
atggatctgt atattcagat tatcgtggtg gcgtgcctga cgggtatgac atcgcttctg      60
gcgcatcgct cggcggctgt ttttcatgac ggcatccgcc cgatcctgcc gcaactgatt     120
gaaggctata tgaaccgtcg cgaggcgggg agtatcgctt ttggtctgag cattggtttt     180
gtggcctcgg tggggatctc ttttacccct aaaaccgggc tgctcaacgc atggttactc     240
tttcttccta ccgatatcct cggcgtcctg gcgataaaca gcctgatggc gtttggtctt     300
ggcgctatct ggggcgtgtt gatccttact tgcctgttgc cagtaaaacca gctgctgacc     360 gcgctgccgg tggatgtatt aggtagcctg ggggaattaa gctcgccggt ggtttcagct     420
tttgcactgt tcccgctggt ggcgattttc taccagtttg ctggaagca agtctgatc     480 gccgccgtgg tggtactgat gacccgtgtg gtagtcgtgc gctatttccc acatcttaac     540
cctgaatcca tcgaaatctt tattggcatg gtgatgctgc tggggatcgc gataactcac     600
gacctgcgtc atcgtgatga aaatgacatt gatgccagcg ggctttcggt gtttgaagaa     660
cgcacgtcac ggattatcaa aaacttaccc tatatcgcca tcgtgggagc attgattgcc     720
gccgttgcca gcatgaagat ttttgctggc agtgaagtgt cgatcttcac actggagaaa     780
gcatattccg caggcgtaac gccggaacaa tcgcaaacgc tgattaatca ggcggctctg     840
gcagaattta tgcgcggact ggggtttgtg ccgttgattg ccaccaccgc gttagcaacg     900
ggtgtgtatg cagttgcggg ctttacctt gtttatgcgg tggactatct ctcgccgaat     960
ccgatggttg cagcggtatt aggcgcagtg gttatttcgg cggaagtctt gctgcttcgt    1020
tcgatcggca atggctggga cgctacccg tcggtgcgta atgcgtcgga taacatccgt    1080
aacgccatga atatgctgat ggaagtggcg ctgctggtcg gttcgatttt cgcagcaatt    1140
aagatggcgg ttataccgg attctctatc gcggttgcca tttacttcct caacgaatcc    1200
ctgggccgtc cggtacagaa aatggcggca ccggtcgtgg cagtaatgat caccggtatt    1260
ctgctgaatg ttctttactg gcttggcctg ttcgttccgg cttaa                    1305

<210> SEQ ID NO 46
<211> LENGTH: 434
```

```
<212> TYPE: PRT
<213> ORGANISM: Escherichia coli

<400> SEQUENCE: 46

Met Asp Leu Tyr Ile Gln Ile Val Val Ala Cys Leu Thr Gly Met
1               5                   10                  15

Thr Ser Leu Leu Ala His Arg Ser Ala Val Phe His Asp Gly Ile
                20                  25                  30

Arg Pro Ile Leu Pro Gln Leu Ile Glu Gly Tyr Met Asn Arg Arg Glu
            35                  40                  45

Ala Gly Ser Ile Ala Phe Gly Leu Ser Ile Gly Phe Val Ala Ser Val
        50                  55                  60

Gly Ile Ser Phe Thr Leu Lys Thr Gly Leu Leu Asn Ala Trp Leu Leu
65                  70                  75                  80

Phe Leu Pro Thr Asp Ile Leu Gly Val Leu Ala Ile Asn Ser Leu Met
                85                  90                  95

Ala Phe Gly Leu Gly Ala Ile Trp Gly Val Leu Ile Leu Thr Cys Leu
            100                 105                 110

Leu Pro Val Asn Gln Leu Leu Thr Ala Leu Pro Val Asp Val Leu Gly
        115                 120                 125

Ser Leu Gly Glu Leu Ser Ser Pro Val Val Ser Ala Phe Ala Leu Phe
130                 135                 140

Pro Leu Val Ala Ile Phe Tyr Gln Phe Gly Trp Lys Gln Ser Leu Ile
145                 150                 155                 160

Ala Ala Val Val Val Leu Met Thr Arg Val Val Val Arg Tyr Phe
            165                 170                 175

Pro His Leu Asn Pro Glu Ser Ile Glu Ile Phe Ile Gly Met Val Met
        180                 185                 190

Leu Leu Gly Ile Ala Ile Thr His Asp Leu Arg His Arg Asp Glu Asn
            195                 200                 205

Asp Ile Asp Ala Ser Gly Leu Ser Val Phe Glu Glu Arg Thr Ser Arg
        210                 215                 220

Ile Ile Lys Asn Leu Pro Tyr Ile Ala Ile Val Gly Ala Leu Ile Ala
225                 230                 235                 240

Ala Val Ala Ser Met Lys Ile Phe Ala Gly Ser Glu Val Ser Ile Phe
            245                 250                 255

Thr Leu Glu Lys Ala Tyr Ser Ala Gly Val Thr Pro Glu Gln Ser Gln
        260                 265                 270

Thr Leu Ile Asn Gln Ala Ala Leu Ala Glu Phe Met Arg Gly Leu Gly
        275                 280                 285

Phe Val Pro Leu Ile Ala Thr Thr Ala Leu Ala Thr Gly Val Tyr Ala
290                 295                 300

Val Ala Gly Phe Thr Phe Val Tyr Ala Val Asp Tyr Leu Ser Pro Asn
305                 310                 315                 320

Pro Met Val Ala Ala Val Leu Gly Ala Val Val Ile Ser Ala Glu Val
            325                 330                 335

Leu Leu Leu Arg Ser Ile Gly Lys Trp Leu Gly Arg Tyr Pro Ser Val
        340                 345                 350

Arg Asn Ala Ser Asp Asn Ile Arg Asn Ala Met Asn Met Leu Met Glu
        355                 360                 365

Val Ala Leu Leu Val Gly Ser Ile Phe Ala Ala Ile Lys Met Ala Gly
        370                 375                 380

Tyr Thr Gly Phe Ser Ile Ala Val Ala Ile Tyr Phe Leu Asn Glu Ser
385                 390                 395                 400
```

```
Leu Gly Arg Pro Val Gln Lys Met Ala Ala Pro Val Val Ala Val Met
            405                 410                 415

Ile Thr Gly Ile Leu Leu Asn Val Leu Tyr Trp Leu Gly Leu Phe Val
            420                 425                 430

Pro Ala

<210> SEQ ID NO 47
<211> LENGTH: 717
<212> TYPE: DNA
<213> ORGANISM: Escherichia coli

<400> SEQUENCE: 47
atgcagaccc cgcacattct tatcgttgaa gacgagttgg taacacgcaa cacgttgaaa     60
agtattttcg aagcggaagg ctatgatgtt ttcgaagcga cagatggcgc ggaaatgcat    120
cagatcctct ctgaatatga catcaacctg gtgatcatgg atatcaatct gccgggtaag    180
aacggtcttc tgttagcgcg tgaactgcgc gagcaggcga atgttgcgtt gatgttcctg    240
actggccgtg acaacgaagt cgataaaatt ctcggcctcg aaatcggtgc agatgactac    300
atcaccaaac cgttcaaccc gcgtgaactg acgattcgtg cacgcaacct actgtcccgt    360
accatgaatc tgggtactgt cagcgaagaa cgtcgtagcg ttgaaagcta caagttcaat    420
ggttgggaac tggacatcaa cagccgttcg ttgatcggcc ctgatggcga gcagtacaag    480
ctgccgcgca gcgagttccg cgccatgctt cacttctgtg aaacccagg caaaattcag     540 tcccgtgctg aactgctgaa gaaaatgacc ggccgtgagc tgaaccgca cgaccgtact     600 gtagacgtga cgatccgccg tattcgtaaa catttcgaat ctacgccgga tacgccggaa    660
atcatcgcca ccattcacgg tgaaggttat cgcttctgcg gtgatctgga agattaa       717

<210> SEQ ID NO 48
<211> LENGTH: 238
<212> TYPE: PRT
<213> ORGANISM: Escherichia coli

<400> SEQUENCE: 48

Met Gln Thr Pro His Ile Leu Ile Val Glu Asp Glu Leu Val Thr Arg
1               5                   10                  15

Asn Thr Leu Lys Ser Ile Phe Glu Ala Glu Gly Tyr Asp Val Phe Glu
                20                  25                  30

Ala Thr Asp Gly Ala Glu Met His Gln Ile Leu Ser Glu Tyr Asp Ile
            35                  40                  45

Asn Leu Val Ile Met Asp Ile Asn Leu Pro Gly Lys Asn Gly Leu Leu
        50                  55                  60

Leu Ala Arg Glu Leu Arg Glu Gln Ala Asn Val Ala Leu Met Phe Leu
65                  70                  75                  80

Thr Gly Arg Asp Asn Glu Val Asp Lys Ile Leu Gly Leu Glu Ile Gly
                85                  90                  95

Ala Asp Asp Tyr Ile Thr Lys Pro Phe Asn Pro Arg Glu Leu Thr Ile
            100                 105                 110

Arg Ala Arg Asn Leu Leu Ser Arg Thr Met Asn Leu Gly Thr Val Ser
        115                 120                 125

Glu Glu Arg Arg Ser Val Glu Ser Tyr Lys Phe Asn Gly Trp Glu Leu
    130                 135                 140

Asp Ile Asn Ser Arg Ser Leu Ile Gly Pro Asp Gly Glu Gln Tyr Lys
145                 150                 155                 160

Leu Pro Arg Ser Glu Phe Arg Ala Met Leu His Phe Cys Glu Asn Pro
                165                 170                 175
```

```
Gly Lys Ile Gln Ser Arg Ala Glu Leu Leu Lys Lys Met Thr Gly Arg
            180                 185                 190

Glu Leu Lys Pro His Asp Arg Thr Val Asp Val Thr Ile Arg Arg Ile
        195                 200                 205

Arg Lys His Phe Glu Ser Thr Pro Asp Thr Pro Glu Ile Ile Ala Thr
    210                 215                 220

Ile His Gly Glu Gly Tyr Arg Phe Cys Gly Asp Leu Glu Asp
225                 230                 235

<210> SEQ ID NO 49
<211> LENGTH: 1266
<212> TYPE: DNA
<213> ORGANISM: Escherichia coli

<400> SEQUENCE: 49
gtgtcaaagg caaccgaaca aaacgacaag ctcaagcggg cgataattat ttcagcagtg      60
ctgcatgtca tcttatttgc ggcgctgatc tggagttcgt tcgatgagaa tatagaagct     120
tcagccggag cggcggtgg ttcgtccatc gacgctgtca tggttgattc aggtgcggta      180
gttgagcagt acaaacgcat gcaaagccag gaatcaagcg cgaagcgttc tgatgaacag     240
cgcaagatga aggaacagca ggctgctgaa gaactgcgtg agaaacaagc ggctgaacag     300
gaacgcctga gcaacttgaa aagagcggt tagcggctc aggagcagaa aaagcaggct      360
gaagaagccg caaacaggc cgagttaaag cagaagcaag ctgaagaggc ggcagcgaaa     420
gcggcggcag atgctaaagc gaaggccgaa gcagatgcta agctgcgga agaagcagcg     480 aagaaagcgg ctgcagacgc aaagaaaaaa gcagaagcag aagccgccaa agccgcagcc     540
gaagcgcaga aaaagccga ggcagccgct gcggcactga agaagaaagc ggaagcggca      600
gaagcagctg cagctgaagc aagaaagaaa gcggcaactg aagctgctga aaaagccaaa     660
gcagaagctg agaagaaagc ggctgctgaa aaggctgcag ctgataagaa agcggcagca     720
gagaaagctg cagccgacaa aaaagcagca gaaaaagcgg ctgctgaaaa ggcagcagct     780
gataagaaag cagcggcaga aaaagccgcc gcagacaaaa aagcggcagc ggcaaaagct     840
gcagctgaaa aagccgctgc agcaaaagcg gccgcagagg cagatgatat tttcggtgag     900
ctaagctctg gtaagaatgc accgaaaacg ggggagggg cgaaagggaa caatgcttcg      960
cctgccggga gtggtaatac taaaaacaat ggcgcatcag gggccgatat caataactat    1020
gccgggcaga ttaaatctgc tatcgaaagt aagttctatg acgcatcgtc ctatgcaggc    1080
aaaacctgta cgctgcgcat aaaactggca cccgatggta tgttactgga tatcaaacct    1140
gaaggtggcg atcccgcact tgtcaggct gcgttggcag cagctaaact tgcgaagatc      1200
ccgaaaccac caagccaggc agtatatgaa gtgttcaaaa acgcgccatt ggacttcaaa    1260
ccgtaa                                                               1266

<210> SEQ ID NO 50
<211> LENGTH: 421
<212> TYPE: PRT
<213> ORGANISM: Escherichia coli

<400> SEQUENCE: 50

Met Ser Lys Ala Thr Glu Gln Asn Asp Lys Leu Lys Arg Ala Ile Ile
1               5                   10                  15

Ile Ser Ala Val Leu His Val Ile Leu Phe Ala Ala Leu Ile Trp Ser
            20                  25                  30

Ser Phe Asp Glu Asn Ile Glu Ala Ser Ala Gly Gly Gly Gly Gly Ser
```

```
                35                  40                  45
Ser Ile Asp Ala Val Met Val Asp Ser Gly Ala Val Glu Gln Tyr
    50                  55                  60
Lys Arg Met Gln Ser Gln Glu Ser Ser Ala Lys Arg Ser Asp Glu Gln
65                  70                  75                  80
Arg Lys Met Lys Glu Gln Gln Ala Ala Glu Glu Leu Arg Glu Lys Gln
                85                  90                  95
Ala Ala Glu Gln Glu Arg Leu Lys Gln Leu Glu Lys Glu Arg Leu Ala
            100                 105                 110
Ala Gln Glu Gln Lys Lys Gln Ala Glu Glu Ala Lys Gln Ala Glu
        115                 120                 125
Leu Lys Gln Lys Gln Ala Glu Glu Ala Ala Lys Ala Ala Ala Asp
    130                 135                 140
Ala Lys Ala Lys Ala Glu Ala Asp Ala Lys Ala Ala Glu Glu Ala Ala
145                 150                 155                 160
Lys Lys Ala Ala Ala Asp Ala Lys Lys Lys Ala Glu Ala Glu Ala Ala
                165                 170                 175
Lys Ala Ala Ala Glu Ala Gln Lys Lys Ala Glu Ala Ala Ala Ala
            180                 185                 190
Leu Lys Lys Lys Ala Glu Ala Ala Glu Ala Ala Ala Glu Ala Arg
        195                 200                 205
Lys Lys Ala Ala Thr Glu Ala Glu Lys Ala Lys Ala Glu Ala Glu
    210                 215                 220
Lys Lys Ala Ala Ala Glu Lys Ala Ala Ala Asp Lys Lys Ala Ala
225                 230                 235                 240
Glu Lys Ala Ala Ala Asp Lys Lys Ala Ala Glu Lys Ala Ala Ala Glu
                245                 250                 255
Lys Ala Ala Ala Asp Lys Lys Ala Ala Ala Glu Lys Ala Ala Ala Asp
            260                 265                 270
Lys Lys Ala Ala Ala Ala Lys Ala Ala Ala Glu Lys Ala Ala Ala Ala
        275                 280                 285
Lys Ala Ala Ala Glu Ala Asp Asp Ile Phe Gly Glu Leu Ser Ser Gly
    290                 295                 300
Lys Asn Ala Pro Lys Thr Gly Gly Gly Ala Lys Gly Asn Asn Ala Ser
305                 310                 315                 320
Pro Ala Gly Ser Gly Asn Thr Lys Asn Asn Gly Ala Ser Gly Ala Asp
                325                 330                 335
Ile Asn Asn Tyr Ala Gly Gln Ile Lys Ser Ala Ile Glu Ser Lys Phe
            340                 345                 350
Tyr Asp Ala Ser Ser Tyr Ala Gly Lys Thr Cys Thr Leu Arg Ile Lys
        355                 360                 365
Leu Ala Pro Asp Gly Met Leu Leu Asp Ile Lys Pro Glu Gly Gly Asp
    370                 375                 380
Pro Ala Leu Cys Gln Ala Ala Leu Ala Ala Ala Lys Leu Ala Lys Ile
385                 390                 395                 400
Pro Lys Pro Pro Ser Gln Ala Val Tyr Glu Val Phe Lys Asn Ala Pro
                405                 410                 415
Leu Asp Phe Lys Pro
            420

<210> SEQ ID NO 51
<211> LENGTH: 1029
<212> TYPE: DNA
<213> ORGANISM: Escherichia coli
```

<400> SEQUENCE: 51

```
atgcgcgtac tgctatttt  acttctttcc cttttcatgt tgccggcatt ttcggctgat    60
aacctgttgc gctggcatga tgcgcagcat ttcacggtgc aagcctctac gccgcttaaa   120
gccaaacgcg catggaaact gtgcgcgctt tatcccagcc tgaaagattc atattggtta   180
tcgttgaact atggtatgca ggaggctgct cgccgctacg gtgtggattt aaaagtgctg   240
gaggcaggcg gctacagcca gttggctacc cagcaagcac aaatcgacca gtgtaaacag   300
tggggcgcag aggccatttt gctcggtagt agcacgacct catttcccga cctgcaaaag   360
caggtagcaa gtctgccggt gatcgaactg gtaaatgcta ttgatgctcc ccaggtgaaa   420
agccgcgttg gtgtgccctg gtttcagatg ggctatcaac cggggcgata tctggtgcaa   480
tgggcgcacg gtaaaccact gaatgtgctg ttgatgcccg acccgataa  cgccgggggc   540
agtaaggaga tggtcgaggg ttttcgcgca gccattgccg aagcccggt  gcgtattgtt   600
gatattgcgc ttggtgataa cgatattgaa atccagcgta acctgttgca ggagatgctg   660
gaacgccatc cagaaatcga cgtcgttgcc ggaacggcca ttgcggcaga ggcggcaatg   720
ggggaagggc gtaacctgaa acgccgcgtt accgtggtgt cgttttatct ttcacatcag   780
gtgtatcgcg ggctgaagcg gggaagagtg attatggctg ccagcgatca aatggtctgg   840
caggggaac  tggcggttga gcaggccatc aggcaattac aggggcaatc ggtttctgat   900
aatgtcagcc caccgatttt agttctgacg ccgaaaaatg ccgaccgtga acatattcgc   960
cgctcgctgt caccaggggg atttcgtccg gtctattttt atcagcacac atcagcggct  1020
aagaaataa                                                          1029
```

<210> SEQ ID NO 52
<211> LENGTH: 342
<212> TYPE: PRT
<213> ORGANISM: Escherichia coli

<400> SEQUENCE: 52

```
Met Arg Val Leu Leu Phe Leu Leu Leu Ser Leu Phe Met Leu Pro Ala
1               5                   10                  15

Phe Ser Ala Asp Asn Leu Leu Arg Trp His Asp Ala Gln His Phe Thr
                20                  25                  30

Val Gln Ala Ser Thr Pro Leu Lys Ala Lys Arg Ala Trp Lys Leu Cys
            35                  40                  45

Ala Leu Tyr Pro Ser Leu Lys Asp Ser Tyr Trp Leu Ser Leu Asn Tyr
        50                  55                  60

Gly Met Gln Glu Ala Ala Arg Arg Tyr Gly Val Asp Leu Lys Val Leu
65                  70                  75                  80

Glu Ala Gly Gly Tyr Ser Gln Leu Ala Thr Gln Gln Ala Gln Ile Asp
                85                  90                  95

Gln Cys Lys Gln Trp Gly Ala Glu Ala Ile Leu Leu Gly Ser Ser Thr
            100                 105                 110

Thr Ser Phe Pro Asp Leu Gln Lys Gln Val Ala Ser Leu Pro Val Ile
        115                 120                 125

Glu Leu Val Asn Ala Ile Asp Ala Pro Gln Val Lys Ser Arg Val Gly
    130                 135                 140

Val Pro Trp Phe Gln Met Gly Tyr Gln Pro Gly Arg Tyr Leu Val Gln
145                 150                 155                 160

Trp Ala His Gly Lys Pro Leu Asn Val Leu Leu Met Pro Gly Pro Asp
                165                 170                 175

Asn Ala Gly Gly Ser Lys Glu Met Val Glu Gly Phe Arg Ala Ala Ile
```

```
                  180                 185                 190
Ala Gly Ser Pro Val Arg Ile Val Asp Ile Ala Leu Gly Asp Asn Asp
            195                 200                 205

Ile Glu Ile Gln Arg Asn Leu Leu Gln Glu Met Leu Glu Arg His Pro
210                 215                 220

Glu Ile Asp Val Val Ala Gly Thr Ala Ile Ala Glu Ala Ala Met
225                 230                 235                 240

Gly Glu Gly Arg Asn Leu Lys Thr Pro Leu Thr Val Val Ser Phe Tyr
            245                 250                 255

Leu Ser His Gln Val Tyr Arg Gly Leu Lys Arg Gly Arg Val Ile Met
                260                 265                 270

Ala Ala Ser Asp Gln Met Val Trp Gln Gly Glu Leu Ala Val Glu Gln
            275                 280                 285

Ala Ile Arg Gln Leu Gln Gly Gln Ser Val Ser Asp Asn Val Ser Pro
        290                 295                 300

Pro Ile Leu Val Leu Thr Pro Lys Asn Ala Asp Arg Glu His Ile Arg
305                 310                 315                 320

Arg Ser Leu Ser Pro Gly Gly Phe Arg Pro Val Tyr Phe Tyr Gln His
                325                 330                 335

Thr Ser Ala Ala Lys Lys
                340

<210> SEQ ID NO 53
<211> LENGTH: 396
<212> TYPE: DNA
<213> ORGANISM: Escherichia coli

<400> SEQUENCE: 53
atgttggccc taacgaatag cggttgctta acgaatccg actctcacat tatcagggt      60 ataaaaatgg aaactaccaa gccttcattc caggacgtac tggaatttgt tcgtctgttc    120
cgtcgtaaga acaaactgca acgtgaaatt caggacgttg agaaaaagat ccgtgacaac    180
cagaagcgcg tcctgctgct ggacaacctg agcgattaca tcaagccggg gatgagcgtt    240
gaagcaatcc aggcatcat cgccagcatg aaaggtgact atgaagatcg cgttgacgat    300
tacatcatca aaaatgccga gctctccaaa gaacgccgcg atatctccaa aaagctgaaa    360
gctatgggcg aaatgaaaaa cggcgaagcg aagtaa                             396

<210> SEQ ID NO 54
<211> LENGTH: 131
<212> TYPE: PRT
<213> ORGANISM: Escherichia coli

<400> SEQUENCE: 54

Met Leu Ala Leu Thr Asn Ser Gly Cys Leu Asn Glu Ser Asp Ser His
1               5                   10                  15

Ile Ile Arg Gly Ile Lys Met Glu Thr Thr Lys Pro Ser Phe Gln Asp
                20                  25                  30

Val Leu Glu Phe Val Arg Leu Phe Arg Arg Lys Asn Lys Leu Gln Arg
            35                  40                  45

Glu Ile Gln Asp Val Glu Lys Lys Ile Arg Asp Asn Gln Lys Arg Val
        50                  55                  60

Leu Leu Leu Asp Asn Leu Ser Asp Tyr Ile Lys Pro Gly Met Ser Val
65                  70                  75                  80

Glu Ala Ile Gln Gly Ile Ile Ala Ser Met Lys Gly Asp Tyr Glu Asp
                85                  90                  95
```

Arg Val Asp Asp Tyr Ile Ile Lys Asn Ala Glu Leu Ser Lys Glu Arg
            100                 105                 110

Arg Asp Ile Ser Lys Lys Leu Lys Ala Met Gly Glu Met Lys Asn Gly
        115                 120                 125

Glu Ala Lys
    130

<210> SEQ ID NO 55
<211> LENGTH: 1059
<212> TYPE: DNA
<213> ORGANISM: Escherichia coli

<400> SEQUENCE: 55

```
gtgcgtgccg ataagtcatt aagcccgttt gaaatccggg tataccgcca ttaccgcatt    60
gtgcatggta ctcgggtcgc gctggcattc ctgctcactt ttctcattat ccgcctgttt   120
actatcccgg aaagcacctg gccgctggtc accatggtgg tgattatggg gccaatctcg   180
ttctgggta acgttgtccc tcgcgccttt gagcgtattg cggtacggt gttgggttcg    240
attttaggtc ttatcgctct gcaactggag ttaatctcgt taccgctgat gttagtctgg   300
tgcgcggcgg ccatgttcct ttgcggttgg ctggcgctgg caagaaacc gtatcaaggt   360
ttattgattg gggtgacgct ggcaattgtt gtgggttccc cgacaggtga aattgatacg   420
gcgttatggc gaagcggcga tgtgatcctc ggctctttac tggcaatgtt gtttaccggt   480
atctggccac aacgggcgtt catccactgg cgcattcaac tggcgaaaag tctgaccgag   540
tataatcggg tctatcaatc tgcattctca ccgaacttac tcgaacgccc acgtctggaa   600
agccatctac aaaaactcct gaccgatgcc gtgaaaatgc gtggactgat tgcgcccgcc   660
agcaaagaaa cccgtattcc aaaatcgata tatgaaggta tccagaccat taaccgcaat   720
ctggtttgta tgctggagtt gcaaatcaat gcatactggg ccacgcgccc cagccatttc   780
gtgttattga acgcgcaaaa acttcgtgat acccagcaca tgatgcagca atactgctg   840
agccttgttc atgcgctgta cgaaggtaat ccgcagccgg tttttgccaa tacggaaaaa   900
ttgaacgatg ctgtggaaga gctgcgtcag ttgctcaata accaccatga cctgaaggtt   960
gtggaaacac caatctatgg ttatgtgtgg ctgaacatgg aaacggcgca tcagcttgag  1020
ttgctatcga atctgatttg ccgggccttg cgcaaataa                         1059
```

<210> SEQ ID NO 56
<211> LENGTH: 352
<212> TYPE: PRT
<213> ORGANISM: Escherichia coli

<400> SEQUENCE: 56

Met Arg Ala Asp Lys Ser Leu Ser Pro Phe Glu Ile Arg Val Tyr Arg
1               5                  10                  15

His Tyr Arg Ile Val His Gly Thr Arg Val Ala Leu Ala Phe Leu Leu
            20                  25                  30

Thr Phe Leu Ile Ile Arg Leu Phe Thr Ile Pro Glu Ser Thr Trp Pro
        35                  40                  45

Leu Val Thr Met Val Val Ile Met Gly Pro Ile Ser Phe Trp Gly Asn
    50                  55                  60

Val Val Pro Arg Ala Phe Glu Arg Ile Gly Gly Thr Val Leu Gly Ser
65                  70                  75                  80

Ile Leu Gly Leu Ile Ala Leu Gln Leu Glu Leu Ile Ser Leu Pro Leu
                85                  90                  95

Met Leu Val Trp Cys Ala Ala Ala Met Phe Leu Cys Gly Trp Leu Ala

|  |  |  | 100 |  |  |  | 105 |  |  |  | 110 |  |  |
|---|---|---|---|---|---|---|---|---|---|---|---|---|---|

Leu Gly Lys Lys Pro Tyr Gln Gly Leu Leu Ile Gly Val Thr Leu Ala
            115                    120                    125

Ile Val Val Gly Ser Pro Thr Gly Glu Ile Asp Thr Ala Leu Trp Arg
130                    135                    140

Ser Gly Asp Val Ile Leu Gly Ser Leu Leu Ala Met Leu Phe Thr Gly
145                    150                    155                    160

Ile Trp Pro Gln Arg Ala Phe Ile His Trp Arg Ile Gln Leu Ala Lys
            165                    170                    175

Ser Leu Thr Glu Tyr Asn Arg Val Tyr Gln Ser Ala Phe Ser Pro Asn
        180                    185                    190

Leu Leu Glu Arg Pro Arg Leu Glu Ser His Leu Gln Lys Leu Leu Thr
        195                    200                    205

Asp Ala Val Lys Met Arg Gly Leu Ile Ala Pro Ala Ser Lys Glu Thr
210                    215                    220

Arg Ile Pro Lys Ser Ile Tyr Glu Gly Ile Gln Thr Ile Asn Arg Asn
225                    230                    235                    240

Leu Val Cys Met Leu Glu Leu Gln Ile Asn Ala Tyr Trp Ala Thr Arg
            245                    250                    255

Pro Ser His Phe Val Leu Leu Asn Ala Gln Lys Leu Arg Asp Thr Gln
        260                    265                    270

His Met Met Gln Gln Ile Leu Leu Ser Leu Val His Ala Leu Tyr Glu
        275                    280                    285

Gly Asn Pro Gln Pro Val Phe Ala Asn Thr Glu Lys Leu Asn Asp Ala
290                    295                    300

Val Glu Glu Leu Arg Gln Leu Leu Asn Asn His His Asp Leu Lys Val
305                    310                    315                    320

Val Glu Thr Pro Ile Tyr Gly Tyr Val Trp Leu Asn Met Glu Thr Ala
            325                    330                    335

His Gln Leu Glu Leu Leu Ser Asn Leu Ile Cys Arg Ala Leu Arg Lys
        340                    345                    350

<210> SEQ ID NO 57
<211> LENGTH: 1710
<212> TYPE: DNA
<213> ORGANISM: Escherichia coli

<400> SEQUENCE: 57

| atgaaattta ttgggaagct gcttctctac attctcatcg ctctgttagt ggtgatcgct | 60 |
|---|---|
| ggcctctatt ttcttctgca aacccgctgg ggagcagaac atatcagcgc atgggtttcc | 120 |
| gagaatagcg actatcatct ggccttcggg gcgatggatc accgttttc cgcgccatct | 180 |
| catatcgtgc tggagaacgt cacgtttggt cgtgatggtc agcccgcgac cctggtggca | 240 |
| aaaagtgtcg acattgcgct aagcagtcgg caactgaccg aaccacgcca tgtcgatacc | 300 |
| atcctgctgg aaaacgggac gctgaatctc accgaccaga ccgcgccgct accgttcaaa | 360 |
| gccgatcgtc tgcaactgcg tgatatggcg tttaatagcc cgaatagcga atggaaactg | 420 |
| agcgcgcagc gggtaaatgg cggcgtggtt ccgtggtcac cagaagccgg taaagtgctg | 480 |
| ggtacgaagg cgcagattca gtttagtgcc ggatcgcttt cgctcaatga tgttcctgcc | 540 |
| accaatgtac tgattgaagg cagtattgat aacgatcgcg ttacgctgac taacctgggt | 600 |
| gccgacatcg cccgcgggac attaaccgga aacgcgcagc gtaacgccga cggcagctgg | 660 |
| caagtggaaa atctgcgcat ggcggatatc cgtctacaaa gcgaaaaatc gctaaccgac | 720 |
| ttctttgcgc cattacgctc tgtcccgtcg ttgcagattg gtcgcctgga agtgatcgat | 780 |

```
gctcgtttgc aaggtccgga ctgggcggtg accgacctcg atctcagctt gcgcaacatg    840
accttcagta aagatgactg gcagacacaa gaaggcaaac tgtcgatgaa cgctagcgag    900
ttcatttatg gttcgctgca tttatttgac ccgattataa acgcggaatt ttccccgcag    960
ggcgtagcgc tgcgccagtt caccagccgc tgggaagggg gtatggtcag aacgtcaggg   1020
aactggctgc gtgacgggaa aacgttgatc cttgatgatg cggcaattgc cgggctggaa   1080
tataccttgc cgaaaaactg gcaacagttg tggatggaaa cgacaccgg ttggttaaac    1140 agcctgcaac tgaagagatt tagcgccagc cgcaatctga tcattgatat cgaccctgac   1200
ttcccgtggc agctcaccac gctcgatggt tacggtgcca acctgacgct ggttaccgat   1260
cataaatggg gcgtctggag tggctcggcg aatctgaatg ccgccgccgc gacattcaat   1320
cgtgttgatg ttcgtcgccc gtcgctgcg ctgaccgcca acagcagcac ggtgaatatc    1380
agcgaactga gtgcatttac tgaaaaaggc attctggaag ccactgccag tgtttcacaa   1440
acgccacaac gtcagaccca tatcagcctg aatggacgcg gtgtgccggt gaatattttg   1500
caacaatggg gatggcctga attaccgttg actggcgacg gcaatattca gcttaccgcc   1560
agtggcgata ttcaggccaa tgtcccgctg aaacctacgg ttagcgggca actccatgcc   1620
gtgaacgccg caaagcagca agtgactcaa accatgaatg cgggcgtcgt ttccagtagc   1680
gaagttacat cgacagagcc ggtgcagtaa                                    1710
```

<210> SEQ ID NO 58
<211> LENGTH: 569
<212> TYPE: PRT
<213> ORGANISM: Escherichia coli

<400> SEQUENCE: 58

```
Met Lys Phe Ile Gly Lys Leu Leu Leu Tyr Ile Leu Ile Ala Leu Leu
1               5                   10                  15

Val Val Ile Ala Gly Leu Tyr Phe Leu Leu Gln Thr Arg Trp Gly Ala
            20                  25                  30

Glu His Ile Ser Ala Trp Val Ser Glu Asn Ser Asp Tyr His Leu Ala
        35                  40                  45

Phe Gly Ala Met Asp His Arg Phe Ser Ala Pro Ser His Ile Val Leu
    50                  55                  60

Glu Asn Val Thr Phe Gly Arg Asp Gly Gln Pro Ala Thr Leu Val Ala
65                  70                  75                  80

Lys Ser Val Asp Ile Ala Leu Ser Ser Arg Gln Leu Thr Glu Pro Arg
                85                  90                  95

His Val Asp Thr Ile Leu Leu Glu Asn Gly Thr Leu Asn Leu Thr Asp
            100                 105                 110

Gln Thr Ala Pro Leu Pro Phe Lys Ala Asp Arg Leu Gln Leu Arg Asp
        115                 120                 125

Met Ala Phe Asn Ser Pro Asn Ser Glu Trp Lys Leu Ser Ala Gln Arg
    130                 135                 140

Val Asn Gly Gly Val Val Pro Trp Ser Pro Glu Ala Gly Lys Val Leu
145                 150                 155                 160

Gly Thr Lys Ala Gln Ile Gln Phe Ser Ala Gly Ser Leu Ser Leu Asn
                165                 170                 175

Asp Val Pro Ala Thr Asn Val Leu Ile Glu Gly Ser Ile Asp Asn Asp
            180                 185                 190

Arg Val Thr Leu Thr Asn Leu Gly Ala Asp Ile Ala Arg Gly Thr Leu
        195                 200                 205
```

```
Thr Gly Asn Ala Gln Arg Asn Ala Asp Gly Ser Trp Gln Val Glu Asn
            210                 215                 220
Leu Arg Met Ala Asp Ile Arg Leu Gln Ser Glu Lys Ser Leu Thr Asp
225                 230                 235                 240
Phe Phe Ala Pro Leu Arg Ser Val Pro Ser Leu Gln Ile Gly Arg Leu
                245                 250                 255
Glu Val Ile Asp Ala Arg Leu Gln Gly Pro Asp Trp Ala Val Thr Asp
            260                 265                 270
Leu Asp Leu Ser Leu Arg Asn Met Thr Phe Ser Lys Asp Asp Trp Gln
        275                 280                 285
Thr Gln Glu Gly Lys Leu Ser Met Asn Ala Ser Glu Phe Ile Tyr Gly
290                 295                 300
Ser Leu His Leu Phe Asp Pro Ile Ile Asn Ala Glu Phe Ser Pro Gln
305                 310                 315                 320
Gly Val Ala Leu Arg Gln Phe Thr Ser Arg Trp Glu Gly Gly Met Val
                325                 330                 335
Arg Thr Ser Gly Asn Trp Leu Arg Asp Gly Lys Thr Leu Ile Leu Asp
            340                 345                 350
Asp Ala Ala Ile Ala Gly Leu Glu Tyr Thr Leu Pro Lys Asn Trp Gln
        355                 360                 365
Gln Leu Trp Met Glu Thr Thr Pro Gly Trp Leu Asn Ser Leu Gln Leu
370                 375                 380
Lys Arg Phe Ser Ala Ser Arg Asn Leu Ile Ile Asp Ile Asp Pro Asp
385                 390                 395                 400
Phe Pro Trp Gln Leu Thr Thr Leu Asp Gly Tyr Gly Ala Asn Leu Thr
                405                 410                 415
Leu Val Thr Asp His Lys Trp Gly Val Trp Ser Gly Ser Ala Asn Leu
            420                 425                 430
Asn Ala Ala Ala Thr Phe Asn Arg Val Asp Val Arg Arg Pro Ser
        435                 440                 445
Leu Ala Leu Thr Ala Asn Ser Ser Thr Val Asn Ile Ser Glu Leu Ser
450                 455                 460
Ala Phe Thr Glu Lys Gly Ile Leu Glu Ala Thr Ala Ser Val Ser Gln
465                 470                 475                 480
Thr Pro Gln Arg Gln Thr His Ile Ser Leu Asn Gly Arg Gly Val Pro
                485                 490                 495
Val Asn Ile Leu Gln Gln Trp Gly Trp Pro Glu Leu Pro Leu Thr Gly
            500                 505                 510
Asp Gly Asn Ile Gln Leu Thr Ala Ser Gly Asp Ile Gln Ala Asn Val
        515                 520                 525
Pro Leu Lys Pro Thr Val Ser Gly Gln Leu His Ala Val Asn Ala Ala
530                 535                 540
Lys Gln Gln Val Thr Gln Thr Met Asn Ala Gly Val Val Ser Ser Ser
545                 550                 555                 560
Glu Val Thr Ser Thr Glu Pro Val Gln
                565
```

<210> SEQ ID NO 59
<211> LENGTH: 738
<212> TYPE: DNA
<213> ORGANISM: Escherichia coli

<400> SEQUENCE: 59

```
atgacgcgca tgaaatatct ggtggcagcc gccacactaa gcctgttttt ggcgggttgc      60
tcggggtcaa aggaagaagt acctgataat ccgccaaatg aaatttacgc gactgcacaa     120
```

```
caaaagctgc aggacggtaa ctggagacag gcaataacgc aactggaagc gttagataat    180
cgctatccgt ttggtccgta ttcgcagcag gtgcagctgg atctcatcta cgcctactat    240
aaaaacgccg atttgccgtt agcacaggct gccatcgatc gttttattcg ccttaacccg    300
acccatccga atatcgatta tgtcatgtac atgcgtggcc tgaccaatat ggcgctggat    360
gacagtgcgc tgcaagggtt ctttggcgtc gatcgtagcg atcgcgatcc tcaacatgca    420
cgagctgcgt ttagtgactt ttccaaactg gtgcgcggct atccgaacag tcagtacacc    480
accgatgcca ccaaacgtct ggtattcctg aaagatcgtc tggcgaaata tgaatactcc    540
gtggccgagt actatacaga acgtggcgca tgggttgccg tcgttaaccg cgtagaaggc    600
atgttgcgcg actacccgga tacccaggct acgcgtgatg cgctgccgct gatggaaaat    660
gcataccgtc agatgcagat gaatgcgcaa gctgaaaaag tagcgaaaat catcgccgca    720
aacagcagca atacataa                                                 738
```

<210> SEQ ID NO 60
<211> LENGTH: 245
<212> TYPE: PRT
<213> ORGANISM: Escherichia coli

<400> SEQUENCE: 60

```
Met Thr Arg Met Lys Tyr Leu Val Ala Ala Thr Leu Ser Leu Phe
 1               5                  10                  15

Leu Ala Gly Cys Ser Gly Ser Lys Glu Glu Val Pro Asp Asn Pro
                20                  25                  30

Asn Glu Ile Tyr Ala Thr Ala Gln Gln Lys Leu Gln Asp Gly Asn Trp
                35                  40                  45

Arg Gln Ala Ile Thr Gln Leu Glu Ala Leu Asp Asn Arg Tyr Pro Phe
 50                  55                  60

Gly Pro Tyr Ser Gln Gln Val Gln Leu Asp Leu Ile Tyr Ala Tyr Tyr
 65                  70                  75                  80

Lys Asn Ala Asp Leu Pro Leu Ala Gln Ala Ala Ile Asp Arg Phe Ile
                85                  90                  95

Arg Leu Asn Pro Thr His Pro Asn Ile Asp Tyr Val Met Tyr Met Arg
                100                 105                 110

Gly Leu Thr Asn Met Ala Leu Asp Asp Ser Ala Leu Gln Gly Phe Phe
                115                 120                 125

Gly Val Asp Arg Ser Asp Arg Asp Pro Gln His Ala Arg Ala Ala Phe
                130                 135                 140

Ser Asp Phe Ser Lys Leu Val Arg Gly Tyr Pro Asn Ser Gln Tyr Thr
145                 150                 155                 160

Thr Asp Ala Thr Lys Arg Leu Val Phe Leu Lys Asp Arg Leu Ala Lys
                165                 170                 175

Tyr Glu Tyr Ser Val Ala Glu Tyr Tyr Thr Glu Arg Gly Ala Trp Val
                180                 185                 190

Ala Val Val Asn Arg Val Glu Gly Met Leu Arg Asp Tyr Pro Asp Thr
                195                 200                 205

Gln Ala Thr Arg Asp Ala Leu Pro Leu Met Glu Asn Ala Tyr Arg Gln
                210                 215                 220

Met Gln Met Asn Ala Gln Ala Glu Lys Val Ala Lys Ile Ile Ala Ala
225                 230                 235                 240

Asn Ser Ser Asn Thr
                245
```

<210> SEQ ID NO 61
<211> LENGTH: 342
<212> TYPE: DNA
<213> ORGANISM: Escherichia coli

<400> SEQUENCE: 61

```
atgacaatga acattaccag caaacaaatg gaaattactc cggccatccg ccaacatgtc      60
gcagaccgtc tcgccaaact ggaaaaatgg caaacacatc tgattaatcc acatatcatt     120
ctgtccaaag agccacaagg gtttgttgct gacgccacaa tcaatacacc taacggcgtt     180
ctggttgcca gtggtaaaca tgaagatatg tacaccgcaa ttaacgaatt gatcaacaag     240
ctggaacggc agctcaataa actgcagcac aaaggcgaag cacgtcgtgc cgcaacatcg     300
gtgaaagacg ccaacttcgt cgaagaagtt gaagaagagt ag                        342
```

<210> SEQ ID NO 62
<211> LENGTH: 113
<212> TYPE: PRT
<213> ORGANISM: Escherichia coli

<400> SEQUENCE: 62

```
Met Thr Met Asn Ile Thr Ser Lys Gln Met Glu Ile Thr Pro Ala Ile
1               5                   10                  15

Arg Gln His Val Ala Asp Arg Leu Ala Lys Leu Glu Lys Trp Gln Thr
            20                  25                  30

His Leu Ile Asn Pro His Ile Ile Leu Ser Lys Glu Pro Gln Gly Phe
        35                  40                  45

Val Ala Asp Ala Thr Ile Asn Thr Pro Asn Gly Val Leu Val Ala Ser
    50                  55                  60

Gly Lys His Glu Asp Met Tyr Thr Ala Ile Asn Glu Leu Ile Asn Lys
65                  70                  75                  80

Leu Glu Arg Gln Leu Asn Lys Leu Gln His Lys Gly Glu Ala Arg Arg
                85                  90                  95

Ala Ala Thr Ser Val Lys Asp Ala Asn Phe Val Glu Val Glu Glu
            100                 105                 110

Glu
```

<210> SEQ ID NO 63
<211> LENGTH: 447
<212> TYPE: DNA
<213> ORGANISM: Escherichia coli

<400> SEQUENCE: 63

```
atgcgtaccg ttttgaacat tctgaacttt gtgcttggcg atttgccac cactctgggc       60 tggctgttgg cgactctggt cagtattgtg ctgattttta ccttaccgct gacacgatcc     120
tgctgggaga tcactaaact gtctctggtg ccttatggca atgaagctat tcatgtcgat     180
gaactgaacc cggctggcaa aaatgtgctg ctgaatactg cggtacggt attgaatatt     240 ttctggctga ttttctttgg ctggtggtta tgcctgatgc acattgcaac gggcatcgca     300
caatgtattt caatcattgg cattcctgtc ggcattgcga actttaaaat tgccgctatt     360
gcactatggc cggttggtcg tcgcgtggta tcggtagaaa cagcgcaagc tgcgcgtgaa     420
gccaatgcac gtcgtcgttt tgaataa                                         447
```

<210> SEQ ID NO 64
<211> LENGTH: 148
<212> TYPE: PRT
<213> ORGANISM: Escherichia coli

<400> SEQUENCE: 64

Met Arg Thr Val Leu Asn Ile Leu Asn Phe Val Leu Gly Gly Phe Ala
1               5                   10                  15

Thr Thr Leu Gly Trp Leu Leu Ala Thr Leu Val Ser Ile Val Leu Ile
            20                  25                  30

Phe Thr Leu Pro Leu Thr Arg Ser Cys Trp Glu Ile Thr Lys Leu Ser
        35                  40                  45

Leu Val Pro Tyr Gly Asn Glu Ala Ile His Val Asp Glu Leu Asn Pro
    50                  55                  60

Ala Gly Lys Asn Val Leu Leu Asn Thr Gly Gly Thr Val Leu Asn Ile
65                  70                  75                  80

Phe Trp Leu Ile Phe Phe Gly Trp Trp Leu Cys Leu Met His Ile Ala
                85                  90                  95

Thr Gly Ile Ala Gln Cys Ile Ser Ile Ile Gly Ile Pro Val Gly Ile
            100                 105                 110

Ala Asn Phe Lys Ile Ala Ala Ile Ala Leu Trp Pro Val Gly Arg Arg
        115                 120                 125

Val Val Ser Val Glu Thr Ala Gln Ala Ala Arg Glu Ala Asn Ala Arg
    130                 135                 140

Arg Arg Phe Glu
145

<210> SEQ ID NO 65
<211> LENGTH: 249
<212> TYPE: DNA
<213> ORGANISM: Escherichia coli

<400> SEQUENCE: 65
atgaaacacc ctttagaaac cttgaccacc gcagcaggca ttttgctgat ggctttcctc      60
tcttgcctgc tgctgcccgc ccccgcactg gggcttacgc tggcacaaaa actggtgacc     120
acgttccatc tgatggatct tagtcagctt tacactttat tgttttgtct gtggttttta     180
gtgctgggcg ctattgagta ttttgttctg cgctttatct ggcgacgctg gttctcgctg     240
gcggattaa                                                              249

<210> SEQ ID NO 66
<211> LENGTH: 82
<212> TYPE: PRT
<213> ORGANISM: Escherichia coli

<400> SEQUENCE: 66

Met Lys His Pro Leu Glu Thr Leu Thr Thr Ala Ala Gly Ile Leu Leu
1               5                   10                  15

Met Ala Phe Leu Ser Cys Leu Leu Leu Pro Ala Pro Ala Leu Gly Leu
            20                  25                  30

Thr Leu Ala Gln Lys Leu Val Thr Thr Phe His Leu Met Asp Leu Ser
        35                  40                  45

Gln Leu Tyr Thr Leu Leu Phe Cys Leu Trp Phe Leu Val Leu Gly Ala
    50                  55                  60

Ile Glu Tyr Phe Val Leu Arg Phe Ile Trp Arg Arg Trp Phe Ser Leu
65                  70                  75                  80

Ala Asp

<210> SEQ ID NO 67
<211> LENGTH: 369
<212> TYPE: DNA
<213> ORGANISM: Escherichia coli

<400> SEQUENCE: 67

```
atggataagc aatcactgca cgaaacggcg aaacgcctgg cccttgagtt acccttttgtc    60
gagctttgct ggccttttgg cccggagttc gatgttttta aaattggcgg caagattttt   120
atgctgtcgt cggagctacg cggcgtcccc tttatcaatc tgaagtccga tccacaaaaa   180
tccctgttaa atcagcaaat atcccaagc attaagccag gtatcacat gaataaaaag    240
cactggattt cggtgtatcc cggcgaggaa atctccgaag cgttacttcg cgatctgatc   300
aacgattcgt ggaatctggt ggttgatggt ctggctaaac gcgatcaaaa aagagtgcgt   360
ccaggctaa                                                           369
```

<210> SEQ ID NO 68
<211> LENGTH: 122
<212> TYPE: PRT
<213> ORGANISM: Escherichia coli

<400> SEQUENCE: 68

```
Met Asp Lys Gln Ser Leu His Glu Thr Ala Lys Arg Leu Ala Leu Glu
1               5                   10                  15
Leu Pro Phe Val Glu Leu Cys Trp Pro Phe Gly Pro Glu Phe Asp Val
            20                  25                  30
Phe Lys Ile Gly Gly Lys Ile Phe Met Leu Ser Ser Glu Leu Arg Gly
        35                  40                  45
Val Pro Phe Ile Asn Leu Lys Ser Asp Pro Gln Lys Ser Leu Leu Asn
    50                  55                  60
Gln Gln Ile Tyr Pro Ser Ile Lys Pro Gly Tyr His Met Asn Lys Lys
65                  70                  75                  80
His Trp Ile Ser Val Tyr Pro Gly Glu Glu Ile Ser Glu Ala Leu Leu
                85                  90                  95
Arg Asp Leu Ile Asn Asp Ser Trp Asn Leu Val Val Asp Gly Leu Ala
            100                 105                 110
Lys Arg Asp Gln Lys Arg Val Arg Pro Gly
        115                 120
```

<210> SEQ ID NO 69
<211> LENGTH: 2016
<212> TYPE: DNA
<213> ORGANISM: Escherichia coli

<400> SEQUENCE: 69

```
atggctgaac tgactgcgct tcacacatta acagcgcaaa tgaacgtga agggatccgc     60
cgcttgctgg tgttgagcgg ggaagagggt tggtgttttg agcatactct taagttgcgt   120
gatgccttac ctggcgactg gctgtggatt tcgccgcggc cagatgctga aaaccactgt   180
tctccctcgg cactacaaac tttacttggg cgcgagttcc ggcatgcggt attcgacgcc   240
cgccacggct ttgatgccgc tgcctttgcc gcacttagcg gaacgttgaa agcgggaagc   300
tggctggttt tgttactccc tgtatgggaa gagtgggaaa accaacctga tgccgactcg   360
ctgcgctgga gtgattgccc tgaccctatt gcgacgccgc attttgtcca gcatctcaaa   420
cgcgtactta cggcggataa cgaggctatc ctctggcggc aaaaccagcc attctcgttg   480
gcgcatttta ctccccgtac tgactggtac cccgcgactg cgcaccaca accagaacaa   540
cagcaactct aaagcagct aatgaccatg ccgccgggcg tggcagcggt aacggctgcg   600
cgtgggcgcg gtaagtcggc gttggcaggg caactcattt ctcgtattgc gggcagagcg   660
attgtcaccg cgcccgcaaa agcgtcaacg gatgtactgg cacaatttgc gggcgagaag   720
```

```
tttcgcttta ttgcgccgga tgccttgtta gccagcgatg agcaagccga ctggctggtg    780
gtcgatgaag ccgcagccat acctgcgcca ttgttgcatc aactggtatc gcgttttcct    840
cgaacgttgt taaccactac ggtgcagggc tacgaaggca ccggacgtgg tttttttgctg   900 aaattttgcg ctcgctttcc gcatttacac cgttttgaac tgcaacagcc gatccgctgg    960
gcgcagggat gcccgctgga aaaaatggtc agcgaggcac tggttttga cgatgaaaac    1020 ttcacccata caccacaagg caatattgtc atttccgcat ttgaacagac gttatggcaa    1080
agcgatccag aaacgccgtt aaaggtttat cagctcttgt ctggtgcgca ctatcggact    1140
tcgccgctgg atttacgccg gatgatggat gcaccagggc aacattttt acaggcggct     1200 ggcgaaaacg agattgccgg ggcgctgtgg ctggtggatg agggtggatt atctcaacaa    1260
ctcagtcagg cggtatgggc aggttttcgt cgcccgcggg gtaatctggt ggcccagtcg    1320
ctggcggcgc acggcaacaa tccactggcg gcgacattgc gtggacggcg gtcagccgg    1380 atagcagttc atccggctcg tcagcgggaa ggcacagggc ggcaacttat tgctggtgct    1440
ttgcaatata cgcaagacct cgactatctt tcggtgagtt ttggttacac cggggagtta    1500
tggcgtttct ggcaacgctg cggttttgtg ctggtgcgga tgggtaatca tcgggaagcc    1560
agcagcggtt gctatacggc gatggcgctg ttaccgatga gtgatgcggg taaacagctg    1620
gctgaacgtg agcattaccg tttacgtcgc gatgcgcaag ctctcgcgca gtggaatggc    1680
gaaacgcttc ctgttgatcc actaaacgat gccgtccttt ctgacgacga ctggcttgaa    1740
ctggccggtt ttgctttcgc tcatcgtccg ctattaacgt cgttaggttg cttattgcgt    1800
ctgttacaaa ccagtgaact ggcattaccg gcgctgcgtg ggcgtttaca gaaaaacgcc    1860
agtgatgcgc agttatgtac cacacttaaa ctttcaggcc gcaagatgtt actggtccgt    1920
cagcgggaag aggccgcgca ggcgctgttc gcacttaatg atgttcgcac tgagcgtctg    1980
cgcgatcgca taacgcaatg gcaattattt cactga                              2016
```

<210> SEQ ID NO 70
<211> LENGTH: 671
<212> TYPE: PRT
<213> ORGANISM: Escherichia coli

<400> SEQUENCE: 70

```
Met Ala Glu Leu Thr Ala Leu His Thr Leu Thr Ala Gln Met Lys Arg
1               5                   10                  15

Glu Gly Ile Arg Arg Leu Leu Val Leu Ser Gly Glu Glu Gly Trp Cys
            20                  25                  30

Phe Glu His Thr Leu Lys Leu Arg Asp Ala Leu Pro Gly Asp Trp Leu
        35                  40                  45

Trp Ile Ser Pro Arg Pro Asp Ala Glu Asn His Cys Ser Pro Ser Ala
    50                  55                  60

Leu Gln Thr Leu Leu Gly Arg Glu Phe Arg His Ala Val Phe Asp Ala
65                  70                  75                  80

Arg His Gly Phe Asp Ala Ala Ala Phe Ala Ala Leu Ser Gly Thr Leu
                85                  90                  95

Lys Ala Gly Ser Trp Leu Val Leu Leu Pro Val Trp Glu Glu Trp
            100                 105                 110

Glu Asn Gln Pro Asp Ala Asp Ser Leu Arg Trp Ser Asp Cys Pro Asp
        115                 120                 125

Pro Ile Ala Thr Pro His Phe Val Gln His Leu Lys Arg Val Leu Thr
    130                 135                 140
```

```
                                      -continued

Ala Asp Asn Glu Ala Ile Leu Trp Arg Gln Asn Gln Pro Phe Ser Leu
145                 150                 155                 160

Ala His Phe Thr Pro Arg Thr Asp Trp Tyr Pro Ala Thr Gly Ala Pro
                165                 170                 175

Gln Pro Glu Gln Gln Leu Leu Lys Gln Leu Met Thr Met Pro Pro
            180                 185                 190

Gly Val Ala Ala Val Thr Ala Ala Arg Gly Arg Gly Lys Ser Ala Leu
        195                 200                 205

Ala Gly Gln Leu Ile Ser Arg Ile Ala Gly Arg Ala Ile Val Thr Ala
210                 215                 220

Pro Ala Lys Ala Ser Thr Asp Val Leu Ala Gln Phe Ala Gly Glu Lys
225                 230                 235                 240

Phe Arg Phe Ile Ala Pro Asp Ala Leu Leu Ala Ser Asp Glu Gln Ala
                245                 250                 255

Asp Trp Leu Val Val Asp Glu Ala Ala Ala Ile Pro Ala Pro Leu Leu
            260                 265                 270

His Gln Leu Val Ser Arg Phe Pro Arg Thr Leu Leu Thr Thr Thr Val
        275                 280                 285

Gln Gly Tyr Glu Gly Thr Gly Arg Gly Phe Leu Leu Lys Phe Cys Ala
290                 295                 300

Arg Phe Pro His Leu His Arg Phe Glu Leu Gln Gln Pro Ile Arg Trp
305                 310                 315                 320

Ala Gln Gly Cys Pro Leu Glu Lys Met Val Ser Glu Ala Leu Val Phe
                325                 330                 335

Asp Asp Glu Asn Phe Thr His Thr Pro Gln Gly Asn Ile Val Ile Ser
            340                 345                 350

Ala Phe Glu Gln Thr Leu Trp Gln Ser Asp Pro Glu Thr Pro Leu Lys
        355                 360                 365

Val Tyr Gln Leu Leu Ser Gly Ala His Tyr Arg Thr Ser Pro Leu Asp
370                 375                 380

Leu Arg Arg Met Met Asp Ala Pro Gly Gln His Phe Leu Gln Ala Ala
385                 390                 395                 400

Gly Glu Asn Glu Ile Ala Gly Ala Leu Trp Leu Val Asp Glu Gly Gly
                405                 410                 415

Leu Ser Gln Gln Leu Ser Gln Ala Val Trp Ala Gly Phe Arg Arg Pro
            420                 425                 430

Arg Gly Asn Leu Val Ala Gln Ser Leu Ala Ala His Gly Asn Asn Pro
        435                 440                 445

Leu Ala Ala Thr Leu Arg Gly Arg Val Ser Arg Ile Ala Val His
450                 455                 460

Pro Ala Arg Gln Arg Glu Gly Thr Gly Arg Gln Leu Ile Ala Gly Ala
465                 470                 475                 480

Leu Gln Tyr Thr Gln Asp Leu Asp Tyr Leu Ser Val Ser Phe Gly Tyr
                485                 490                 495

Thr Gly Glu Leu Trp Arg Phe Trp Gln Arg Cys Gly Phe Val Leu Val
            500                 505                 510

Arg Met Gly Asn His Arg Glu Ala Ser Ser Gly Cys Tyr Thr Ala Met
        515                 520                 525

Ala Leu Leu Pro Met Ser Asp Ala Gly Lys Gln Leu Ala Glu Arg Glu
530                 535                 540

His Tyr Arg Leu Arg Arg Asp Ala Gln Ala Leu Ala Gln Trp Asn Gly
545                 550                 555                 560

Glu Thr Leu Pro Val Asp Pro Leu Asn Asp Ala Val Leu Ser Asp Asp
                565                 570                 575
```

```
Asp Trp Leu Glu Leu Ala Gly Phe Ala Phe Ala His Arg Pro Leu Leu
            580                 585                 590

Thr Ser Leu Gly Cys Leu Leu Arg Leu Leu Gln Thr Ser Glu Leu Ala
            595                 600                 605

Leu Pro Ala Leu Arg Gly Arg Leu Gln Lys Asn Ala Ser Asp Ala Gln
        610                 615                 620

Leu Cys Thr Thr Leu Lys Leu Ser Gly Arg Lys Met Leu Leu Val Arg
625                 630                 635                 640

Gln Arg Glu Glu Ala Ala Gln Ala Leu Phe Ala Leu Asn Asp Val Arg
                645                 650                 655

Thr Glu Arg Leu Arg Asp Arg Ile Thr Gln Trp Gln Leu Phe His
            660                 665                 670

<210> SEQ ID NO 71
<211> LENGTH: 4870
<212> TYPE: DNA
<213> ORGANISM: Escherichia coli

<400> SEQUENCE: 71
ttctgtttcc tgtgtgaaat tgcaattcca cacattatac gagccgatga ttaattgtca      60
acagctcatt tcagaatatt tgccagaacc gttatgatgt cggcgcaaaa acattatcc     120 agaacgggag tgcgccttga gcgacacgaa ttatgcagtg atttcgacc tgcacagcca     180 taccacagct tccgatggct gcctgacgcc agaagcattg gtgcaccgtg cagtcgataa     240
gctccgccga tgcccttgag agccttcaac ccagtcagct ccttccggtg ggcgcggggc     300
atgactatcg tcgccgcact tatgactgtc ttctttatca tgcaactcgt aggacaggtg     360
ccggcagcgc tctgggtcat tttcggcgag gaccgctttc gctggagcgc gacgatgatc     420
ggcctgtcgc ttgcggtatt cggaatcttg cacgccctcg ctcaagcctt cgtcactggt     480
cccgccacca aacgtttcgg cgagaagcag gccattatcg ccggcatggc ggccaattcg     540
cgcgcgaagg cgaagcggca tgcatttacg ttgacaccat cgaatggtgc aaaacctttc     600
gcggtatggc atgatagcgc ccggaagaga gtcaattcag ggtggtgaat atgaaaccag     660
taacgttata cgatgtcgca gagtatgccg gtgtctctta tcagaccgtt tcccgcgtgg     720
tgaaccaggc cagccacgtt tctgcgaaaa cgcgggaaaa agtggaagcg gcgatggcgg     780
agctgaatta cattcccaac cgcgtggcac aacaactggc gggcaaacag tcgttgctga     840
ttggcgttgc cacctccagt ctggccctgc acgcgccgtc gcaaattgtc gcggcgatta     900
aatctcgcgc cgatcaactg ggtgccagcg tggtggtgtc gatggtagaa cgaagcggcg     960
tcgaagcctg taaagcggcg gtgcacaatc ttctcgcgca acgcgtcagt gggctgatca    1020
ttaactatcc gctggatgac caggatgcca ttgctgtgga agctgcctgc actaatgttc    1080
cggcgttatt tcttgatgtc tctgaccaga cacccatcaa cagtattatt ttctcccatg    1140
aagacggtac gcgactgggc gtggagcatc tggtcgcatt gggtcaccag caaatcgcgc    1200
tgttagcggg cccattaagt tctgtctcgg cgcgtctgcg tctggctggc tggcataaat    1260
atctcactcg caatcaaatt cagccgatag cggaacggga aggcgactgg agtgccatgt    1320
ccggttttca acaaaccatg caaatgctga atgagggcat cgttcccact gcgatgctgg    1380
ttgccaacga tcagatggcg ctgggcgcaa tgcgcgccat taccgagtcc gggctgcgcg    1440
ttggtgcgga tatctcggta gtgggatacg acgataccga agacagctca tgttatatcc    1500
cgccgtcaac caccatcaaa caggattttc gcctgctggg gcaaaccagc gtggaccgct    1560
tgctgcaact ctctcagggc caggcggtga agggcaatca gctgttgccc gtctcactgg    1620
```

```
tgaaaagaaa aaccaccctg gcgccgccct ataccttgtc tgcctcccg  cgttgcgtcg   1680
cggtgcatgg agccgggcca cctcgacctg aatggaagcc ggcggcacct cgctaacgga   1740
ttcaccactc caagaattgg agccaatcaa ttcttgcgga gaactgtgaa tgcgcaaacc   1800
aaccttggc  agaacatatc catcgcgtcc gccatctcca gcagccgcac gcggcgcatc   1860
tcggcagcg  ttgggtcctg gccacgggtg cgcatgatcg tgctcctgtc gttgaggacc   1920
cggctaggct ggcggggttg ccttactggt tagcagaatg aatcaccgat acgcgagcga   1980
acgtgaagcg actgctgctg caaaacgtct gcgacctgag caacaacatg aatggtcttc   2040
ggtttccgtg tttcgtaaag tctggaaacg cggaagtccc ctacgtgctg ctgaagttgc   2100
ccgcaacaga gagtggaacc aaccggtgat accacgatac tatgactgag agtcaacgcc   2160
atgagcggcc tcatttctta ttctgagtta caacagtccg caccgctgtc cggtagctcc   2220
ttccggtggg cgcggggcat gactatcgtc gccgcactta tgactgtctt ctttatcatg   2280
caactcgtag gacaggtgcc ggcagcgccc aacagtcccc cggccacggg gcctgccacc   2340
atcccacgc  cgaaacaagc gccctgcacc attatgttcc ggatctgcat cgcaggatgc   2400
tgctggctac cctgtggaac acctacatct gtattaacga agcgctaacc gttttttatca  2460
ggctctggga ggcagaataa atgatcatat cgtcaattat tacctccacg gggagagcct   2520
gagcaaactg gcctcaggca tttgagaagc acacggtcac actgcttccg gtagtcaata   2580
aaccggtaaa ccagcaatag acataagcgg ctatttaacg accctgccct gaaccgacga   2640
ccgggtcgaa tttgctttcg aatttctgcc attcatccgc ttattatcac ttattcaggc   2700
gtagcaccag gcgtttaagg gcaccaataa ctgccttaaa aaaattacgc cccgccctgc   2760
cactcatcgc agtactgttg taattcatta agcattctgc cgacatggaa gccatcacag   2820
acggcatgat gaacctgaat cgccagcggc atcagcacct tgtcgccttg cgtataatat   2880
ttgcccatgt tgaaaacggg ggcgaagaag ttgtccatat tggccacgtt taaatcaaaa   2940
ctggtgaaac tcacccaggg attggctgag acgaaaaaca tattctcaat aaacccttta   3000
gggaaatagg ccaggttttc accgtaacac gccacatctt gcgaatatat gtgtagaaac   3060
tgccggaaat cgtcgtggta ttcactccag agcgatgaaa acgtttcagt ttgctcatgg   3120
aaaacggtgt aacaagggtg aacactatcc catatccacca gctcaccgtc tttcattgcc   3180
atacggaatt ccggatgagc attcatcagg cgggcaagaa tgtgaataaa ggccggataa   3240
aacttgtgct tattttttctt tacggtcttt aaaaaggccg taatatccag ctgaacggtc   3300
tggttatagg tacattgagc aactgactga atgcctcaa  aatgttcttt acgatgccat   3360
tgggatatat caacggtggt atatccagtg atttttttct ccattttagc ttccttagct   3420
cctgaaaatc tcgataactc aaaaaatacg cccggtagtg atcttatttc attatggtga   3480
aagttggaac ctcttacgtg ccgatcaacg tctcatttc  gccaaaagtt ggcccagggc   3540
ttcccggtat caacagggac accaggattt atttattctg cgaagtgatc ttccgtcaca   3600
ggtatttatt cggcgcaaag tgcgtcgggt gatgctgcca acttactgat ttagtgtatg   3660
atggtgtttt tgaggtgctc cagtggcttc tgtttctatc agctgtccct cctgttcagc   3720
tactgacggg gtggtgcgta acggcaaaag caccgccgga catcagcgct agcggagtgt   3780
atactggctt actatgttgg cactgatgag ggtgtcagtg aagtgcttca tgtggcagga   3840
gaaaaaaggc tgcaccggtg cgtcagcaga atatgtgata caggatatat tccgcttcct   3900
cgctcactga ctcgctacgc tcggtcgttc gactgcggcg agcggaaatg gcttacgaac   3960
ggggcggaga tttcctggaa gatgccagga agatacttaa cagggaagtg agagggccgc   4020
```

```
ggcaaagccg ttttccata ggctccgccc ccctgacaag catcacgaaa tctgacgctc    4080
aaatcagtgg tggcgaaacc cgacaggact ataaagatac caggcgtttc cctggcggc    4140 tccctcgtgc gctctcctgt tcctgccttt cggtttaccg gtgtcattcc gctgttatgg    4200
ccgcgtttgt ctcattccac gcctgacact cagttccggg taggcagttc gctccaagct    4260
ggactgtatg cacgaacccc ccgttcagtc cgaccgctgc gccttatccg gtaactatcg    4320
tcttgagtcc aacccggaaa gacatgcaaa agcaccactg gcagcagcca ctggtaattg    4380
atttagagga gttagtcttg aagtcatgcg ccggttaagg ctaaactgaa aggacaagtt    4440
ttggtgactg cgctcctcca agccagttac ctcggttcaa agagttggta gctcagagaa    4500
ccttcgaaaa accgccctgc aaggcggttt tttcgttttc agagcaagag attacgcgca    4560
gaccaaaacg atctcaagaa gatcatctta ttaatcagat aaaatatttc tagcatgagc    4620
ggatacatat ttgaatgtat ttagaaaaat aaacaaatag gggttccgcg cacatttccc    4680
cgaaaagtgc cacctgctag acaggaagag tttgtagaaa cgcaaaaagg ccatccgtca    4740
ggatggcctt ctgcttaatt tgatgcctgg cagtttatgg cgggcgacga atttcttctc    4800
tcatccgcca aaacagaagc ttgcatgcct gcaggtcgac tctagaggat ccccgggtac    4860
cgagctcgaa                                                          4870

<210> SEQ ID NO 72
<211> LENGTH: 273
<212> TYPE: DNA
<213> ORGANISM: Escherichia coli

<400> SEQUENCE: 72
gtcgttcact tgttagcaac cagatcaaaa gccattgact cagcaagggt tgaccgtata     60
attcacgcga ttacaccgca ttgcggtatc aacgcgccct tagctcagtt ggatagagca    120
acgaccttct aagtcgtggg ccgcaggttc gaatcctgca gggcgcgcca ttacaattca    180
atcagttacg ccttctttat atcctccata atttcagagt gggacatatt tgggacatta    240
tcaccaaaaa tgtcgtctat tttcctcgca tgc                                273

<210> SEQ ID NO 73
<211> LENGTH: 208
<212> TYPE: DNA
<213> ORGANISM: Escherichia coli

<400> SEQUENCE: 73
cgtacttacc ccgcactcca ttagcgggta tactcatgcc gcattgtcct cttagttaaa     60
tggatataac gagcccctcc taagggctaa ttgcaggttc gattcctgca ggggacacca    120
tttatcagtt cgctcccatc cgtaccagtc cgcaaaatcc cctgaatatc aagcattccg    180
tagatttaca gttcgtcatg gttcgctt                                      208

<210> SEQ ID NO 74
<211> LENGTH: 186
<212> TYPE: DNA
<213> ORGANISM: Escherichia coli

<400> SEQUENCE: 74
gctggattgc gacacggagt tactttataa tccgctacca tggccccta gctcagtggt     60 tagagcaggc gactcataat cgcttggtcg ctggttcaag tccagcaggg gccaccagat    120
atagcaaagg ctgacgagaa atcgtcagcc ttttctttt tatatatcag ttactttgcg    180
tgccag                                                              186
```

<210> SEQ ID NO 75
<211> LENGTH: 667
<212> TYPE: DNA
<213> ORGANISM: Escherichia coli

<400> SEQUENCE: 75

| | | | | | |
|---|---|---|---|---|---|
| gtcgttcact | tgttagcaac | cagatcaaaa | gccattgact | cagcaagggt | tgaccgtata | 60 |
| attcacgcga | ttacaccgca | ttgcggtatc | aacgcgccct | tagctcagtt | ggatagagca | 120 |
| acgaccttct | aagtcgtggg | ccgcaggttc | gaatcctgca | gggcgcgcca | ttacaattca | 180 |
| atcagttacg | ccttctttat | atcctccata | atttcagagt | gggacatatt | tgggacatta | 240 |
| tcaccaaaaa | tgtcgtctat | tttcctcgca | tgccgtactt | accccgcact | ccattagcgg | 300 |
| gtatactcat | gccgcattgt | cctcttagtt | aaatggatat | aacgagcccc | tcctaagggc | 360 |
| taattgcagg | ttcgattcct | gcaggggaca | ccatttatca | gttcgctccc | atccgtacca | 420 |
| gtccgcaaaa | tcccctgaat | atcaagcatt | ccgtagattt | acagttcgtc | atggttcgct | 480 |
| tgctggattg | cgacacggag | ttactttata | atccgctacc | atggccccctt | agctcagtgg | 540 |
| ttagagcagg | cgactcataa | tcgcttggtc | gctggttcaa | gtccagcagg | ggccaccaga | 600 |
| tatagcaaag | gctgacgaga | aatcgtcagc | cttttctttt | ttatatatca | gttactttgc | 660 |
| gtgccag | | | | | | 667 |

<210> SEQ ID NO 76
<211> LENGTH: 28
<212> TYPE: DNA
<213> ORGANISM: artificial sequence
<220> FEATURE:
<221> NAME/KEY: misc_feature
<222> LOCATION: (1)..(28)
<223> OTHER INFORMATION: primer

<400> SEQUENCE: 76
aaccgcggtc gttcacttgt tcagcaac        28

<210> SEQ ID NO 77
<211> LENGTH: 39
<212> TYPE: DNA
<213> ORGANISM: artificial sequence
<220> FEATURE:
<221> NAME/KEY: misc_feature
<222> LOCATION: (1)..(39)
<223> OTHER INFORMATION: primer

<400> SEQUENCE: 77
ggagtgcggg gtaagtacgg catgcgagga aaatagacg        39

<210> SEQ ID NO 78
<211> LENGTH: 39
<212> TYPE: DNA
<213> ORGANISM: artificial sequence
<220> FEATURE:
<221> NAME/KEY: misc_feature
<222> LOCATION: (1)..(39)
<223> OTHER INFORMATION: primer

<400> SEQUENCE: 78
cgtctatttt cctcgcatgc cgtacttacc ccgcactcc        39

<210> SEQ ID NO 79
<211> LENGTH: 40
<212> TYPE: DNA
<213> ORGANISM: artificial sequence

```
<220> FEATURE:
<221> NAME/KEY: misc_feature
<222> LOCATION: (1)..(40)
<223> OTHER INFORMATION: primer

<400> SEQUENCE: 79
ctccgtgtcg caatccagca agcgaaccat gacgaactgt                              40

<210> SEQ ID NO 80
<211> LENGTH: 40
<212> TYPE: DNA
<213> ORGANISM: artificial sequence
<220> FEATURE:
<221> NAME/KEY: misc_feature
<222> LOCATION: (1)..(40)
<223> OTHER INFORMATION: primer

<400> SEQUENCE: 80
acagttcgtc atggttcgct tgctggattg cgacacggag                              40

<210> SEQ ID NO 81
<211> LENGTH: 28
<212> TYPE: DNA
<213> ORGANISM: artificial sequence
<220> FEATURE:
<221> NAME/KEY: misc_feature
<222> LOCATION: (1)..(28)
<223> OTHER INFORMATION: primer

<400> SEQUENCE: 81
aaccgcggct ggcacgcaaa gtaactga                                          28

<210> SEQ ID NO 82
<211> LENGTH: 682
<212> TYPE: DNA
<213> ORGANISM: Escherichia coli

<400> SEQUENCE: 82
aaccgcggtc gttcacttgt tagcaaccag atcaaaagcc attgactcag caagggttga        60
ccgtataatt cacgcgatta caccgcattg cggtatcaac gcgcccttag ctcagttgga       120
tagagcaacg accttctaag tcgtgggccg caggttcgaa tcctgcaggg cgcgccatta       180
caattcaatc agttacgcct tctttatatc ctccataatt tcagagtggg acatatttgg       240
gacattatca ccaaaaatgt cgtctatttt cctcgcatgc cgtacttacc ccgcactcca       300
ttagcgggta tactcatgcc gcattgtcct cttagttaaa tggatataac gagcccctcc       360
taagggctaa ttgcaggttc gattcctgca ggggacacca tttatcagtt cgctcccatc       420
cgtaccagtc cgcaaaatcc cctgaatatc aagcattccg tagatttaca gttcgtcatg       480
gttcgcttgc tggattgcga cacggagtta ctttataatc cgctaccatg gccccttagc       540
tcagtggtta gagcaggcga ctcataatcg cttggtcgct ggttcaagtc agcaggggc        600 caccagatat agcaaaggct gacgagaaat cgtcagcctt tttctttta tatatcagtt       660 actttgcgtg ccagccgcgg tt                                                 682

<210> SEQ ID NO 83
<211> LENGTH: 682
<212> TYPE: DNA
<213> ORGANISM: Escherichia coli

<400> SEQUENCE: 83
ttggcgccag caagtgaaca atcgttggtc tagttttcgg taactgagtc gttcccaact        60
ggcatattaa gtgcgctaat gtggcgtaac gccatagttg cgcgggaatc gagtcaacct       120
```

```
atctcgttgc tggaagattc agcacccggc gtccaagctt aggacgtccc gcgcggtaat      180
gttaagttag tcaatgcgga agaaatatag gaggtattaa agtctcaccc tgtataaacc      240
ctgtaatagt ggtttttaca gcagataaaa ggagcgtacg gcatgaatgg ggcgtgaggt      300
aatcgcccat atgagtacgg cgtaacagga gaatcaattt acctatattg ctcggggagg      360
attcccgatt aacgtccaag ctaaggacgt cccctgtggt aaatagtcaa gcgagggtag      420
gcatggtcag gcgttttagg ggacttatag ttcgtaaggc atctaaatgt caagcagtac      480
caagcgaacg acctaacgct gtgcctcaat gaaatattag gcgatggtac cggggaatcg      540
agtcaccaat ctcgtccgct gagtattagc gaaccagcga ccaagttcag gtcgtccccg      600
gtggtctata tcgtttccga ctgctctttta gcagtcggaa aaagaaaaat atatagtcaa      660
tgaaacgcac ggtcggcgcc aa                                                682
```

<210> SEQ ID NO 84
<211> LENGTH: 18
<212> TYPE: DNA
<213> ORGANISM: artificial sequence
<220> FEATURE:
<221> NAME/KEY: misc_feature
<222> LOCATION: (1)..(18)
<223> OTHER INFORMATION: primer

<400> SEQUENCE: 84 cgcgcccta gctcagtt                                                      18

<210> SEQ ID NO 85
<211> LENGTH: 18
<212> TYPE: DNA
<213> ORGANISM: artificial sequence
<220> FEATURE:
<221> NAME/KEY: misc_feature
<222> LOCATION: (1)..(18)
<223> OTHER INFORMATION: primer

<400> SEQUENCE: 85
gccctgcagg attcgaac                                                     18

<210> SEQ ID NO 86
<211> LENGTH: 19
<212> TYPE: DNA
<213> ORGANISM: artificial sequence
<220> FEATURE:
<221> NAME/KEY: misc_feature
<222> LOCATION: (1)..(19)
<223> OTHER INFORMATION: primer

<400> SEQUENCE: 86
cctcttagtt aaatggata                                                    19

<210> SEQ ID NO 87
<211> LENGTH: 15
<212> TYPE: DNA
<213> ORGANISM: artificial sequence
<220> FEATURE:
<221> NAME/KEY: misc_feature
<222> LOCATION: (1)..(15)
<223> OTHER INFORMATION: primer

<400> SEQUENCE: 87
tgcaggaatc gaacc                                                        15

<210> SEQ ID NO 88
<211> LENGTH: 18

-continued

```
<212> TYPE: DNA
<213> ORGANISM: artificial sequence
<220> FEATURE:
<221> NAME/KEY: misc_feature
<222> LOCATION: (1)..(18)
<223> OTHER INFORMATION: primer

<400> SEQUENCE: 88 gcccttagc tcagtggt                                                  18

<210> SEQ ID NO 89
<211> LENGTH: 16
<212> TYPE: DNA
<213> ORGANISM: artificial sequence
<220> FEATURE:
<221> NAME/KEY: misc_feature
<222> LOCATION: (1)..(16)
<223> OTHER INFORMATION: primer

<400> SEQUENCE: 89
ggcccctgct ggactt                                                   16

<210> SEQ ID NO 90
<211> LENGTH: 20
<212> TYPE: DNA
<213> ORGANISM: artificial sequence
<220> FEATURE:
<221> NAME/KEY: misc_feature
<222> LOCATION: (1)..(20)
<223> OTHER INFORMATION: primer

<400> SEQUENCE: 90
tccggccttt attcacattc                                               20

<210> SEQ ID NO 91
<211> LENGTH: 20
<212> TYPE: DNA
<213> ORGANISM: artificial sequence
<220> FEATURE:
<221> NAME/KEY: misc_feature
<222> LOCATION: (1)..(20)
<223> OTHER INFORMATION: primer

<400> SEQUENCE: 91
acggcatgat gaacctgaat                                               20

<210> SEQ ID NO 92
<211> LENGTH: 25
<212> TYPE: DNA
<213> ORGANISM: Escherichia coli

<400> SEQUENCE: 92
ttaactttat aaggaggaaa aacat                                         25

<210> SEQ ID NO 93
<211> LENGTH: 58
<212> TYPE: DNA
<213> ORGANISM: artificial sequence
<220> FEATURE:
<221> NAME/KEY: misc_feature
<222> LOCATION: (1)..(58)
<223> OTHER INFORMATION: primer

<400> SEQUENCE: 93
aagagctctg attaaccttt ataaggagga aaaacatatg gtgcttggca aaccgcaa     58

<210> SEQ ID NO 94
<211> LENGTH: 32
```

```
<212> TYPE: DNA
<213> ORGANISM: artificial sequence
<220> FEATURE:
<221> NAME/KEY: misc_feature
<222> LOCATION: (1)..(32)
<223> OTHER INFORMATION: primer

<400> SEQUENCE: 94
cttctagatt attaacgagt gccgtaaacg ac                              32

<210> SEQ ID NO 95
<211> LENGTH: 58
<212> TYPE: DNA
<213> ORGANISM: artificial sequence
<220> FEATURE:
<221> NAME/KEY: misc_feature
<222> LOCATION: (1)..(58)
<223> OTHER INFORMATION: primer

<400> SEQUENCE: 95
aagagctctg attaaccttt ataaggagga aaaacatatg gtgcttggca aaccgcaa   58

<210> SEQ ID NO 96
<211> LENGTH: 31
<212> TYPE: DNA
<213> ORGANISM: artificial sequence
<220> FEATURE:
<221> NAME/KEY: misc_feature
<222> LOCATION: (1)..(31)
<223> OTHER INFORMATION: primer

<400> SEQUENCE: 96
cttctagatt atcagttcgg gcacttataa a                               31

<210> SEQ ID NO 97
<211> LENGTH: 42
<212> TYPE: DNA
<213> ORGANISM: artificial sequence
<220> FEATURE:
<221> NAME/KEY: misc_feature
<222> LOCATION: (1)..(42)
<223> OTHER INFORMATION: primer

<400> SEQUENCE: 97
ggcatatggc ggccgcacta gtcccgggct cgagtctaga gg                   42

<210> SEQ ID NO 98
<211> LENGTH: 42
<212> TYPE: DNA
<213> ORGANISM: artificial sequence
<220> FEATURE:
<221> NAME/KEY: misc_feature
<222> LOCATION: (1)..(42)
<223> OTHER INFORMATION: primer

<400> SEQUENCE: 98
cctctagact cgagcccggg actagtgcgg ccgccatatg cc                   42
```